US012780868B2

(12) United States Patent
Dyer et al.

(10) Patent No.: US 12,780,868 B2
(45) Date of Patent: Nov. 3, 2026

(54) METHODS OF PREPARING SAMPLES FOR MULTIPLEX POLYPEPTIDE SEQUENCING

(71) Applicant: Quantum-Si Incorporated, Guilford, CT (US)

(72) Inventors: Matthew Dyer, Heber City, UT (US); Brian Reed, Madison, CT (US)

(73) Assignee: Quantum-Si Incorporated, Branford, CT (US)

(*) Notice: Subject to any disclaimer, the term of this patent is extended or adjusted under 35 U.S.C. 154(b) by 189 days.

(21) Appl. No.: 17/082,906

(22) Filed: Oct. 28, 2020

(65) Prior Publication Data

US 2021/0147474 A1 May 20, 2021

Related U.S. Application Data

(60) Provisional application No. 62/926,975, filed on Oct. 28, 2019.

(51) Int. Cl.

| | |
|---|---|
| ***C07K 1/02*** | (2006.01) |
| ***C07K 1/04*** | (2006.01) |
| ***C07K 1/113*** | (2006.01) |
| ***C12Q 1/6813*** | (2018.01) |
| ***G01N 33/68*** | (2006.01) |

(52) U.S. Cl.

CPC .............. *C07K 1/023* (2013.01); *C07K 1/045* (2013.01); *C07K 1/1136* (2013.01); *C12Q 1/6813* (2013.01); *G01N 33/6818* (2013.01)

(58) Field of Classification Search

CPC ...... C07K 1/023; C07K 1/045; C07K 1/1136; C12Q 1/6813; C12Q 2525/205; C12Q 2563/179; G01N 33/6818; G01N 33/54366

See application file for complete search history.

(56) References Cited

U.S. PATENT DOCUMENTS

| | | | |
|---|---|---|---|
| 5,707,804 | A | 1/1998 | Mathies et al. |
| 5,851,840 | A | 12/1998 | Sluka et al. |
| 5,961,924 | A | 10/1999 | Reichert et al. |
| 6,153,442 | A | 11/2000 | Pirio et al. |
| 6,248,518 | B1 | 6/2001 | Parkhurst et al. |
| 6,255,083 | B1 | 7/2001 | Williams |
| 6,762,048 | B2 | 7/2004 | Williams |
| 6,787,308 | B2 | 9/2004 | Balasubramanian et al. |
| 6,846,638 | B2 | 1/2005 | Shipwash |
| 6,869,764 | B2 | 3/2005 | Williams et al. |
| 6,917,726 | B2 | 7/2005 | Levene et al. |

(Continued)

FOREIGN PATENT DOCUMENTS

| | | |
|---|---|---|
| AU | 2003-282832 A1 | 5/2004 |
| AU | 2009-251881 A1 | 12/2009 |

(Continued)

OTHER PUBLICATIONS

International Search Report and Written Opinion for Application No. PCT/US2019/061831, mailed Mar. 23, 2020.

(Continued)

*Primary Examiner* — Kathryn Elizabeth Limbaugh

(74) *Attorney, Agent, or Firm* — Wolf, Greenfield & Sacks, P.C.

(57) ABSTRACT

Aspects of the application provide methods of preparing a multiplexed sample for polypeptide sequencing, and compositions, kits and devices useful for the same.

20 Claims, 9 Drawing Sheets

Specification includes a Sequence Listing.

(56) References Cited

U.S. PATENT DOCUMENTS

| | | | |
|---|---|---|---|
| 6,936,702 | B2 | 8/2005 | Williams et al. |
| 7,052,847 | B2 | 5/2006 | Korlach et al. |
| 7,056,661 | B2 | 6/2006 | Korlach et al. |
| 7,175,811 | B2 | 2/2007 | Bach et al. |
| 7,229,799 | B2 | 6/2007 | Williams |
| 7,361,466 | B2 | 4/2008 | Korlach et al. |
| 7,426,322 | B2 | 9/2008 | Hyde |
| 7,738,086 | B2 | 6/2010 | Shepard et al. |
| 7,820,983 | B2 | 10/2010 | Lundquist et al. |
| 7,834,329 | B2 | 11/2010 | Lundquist et al. |
| 7,838,847 | B2 | 11/2010 | Lundquist et al. |
| 7,968,702 | B2 | 6/2011 | Wegener et al. |
| 8,034,623 | B2 | 10/2011 | Oh et al. |
| 8,053,742 | B2 | 11/2011 | Lundquist et al. |
| 8,084,734 | B2 | 12/2011 | Vertes et al. |
| 8,153,375 | B2 | 4/2012 | Travers et al. |
| 8,192,961 | B2 | 6/2012 | Williams |
| 8,207,509 | B2 | 6/2012 | Lundquist et al. |
| 8,252,910 | B2 | 8/2012 | Korlach et al. |
| 8,257,954 | B2 | 9/2012 | Clark et al. |
| 8,274,040 | B2 | 9/2012 | Zhong et al. |
| 8,278,728 | B2 | 10/2012 | Murshid |
| 8,309,330 | B2 | 11/2012 | Travers et al. |
| 8,354,252 | B2 | 1/2013 | Wegener et al. |
| 8,420,366 | B2 | 4/2013 | Clark et al. |
| 8,455,193 | B2 | 6/2013 | Travers et al. |
| 8,465,699 | B2 | 6/2013 | Fehr et al. |
| 8,471,219 | B2 | 6/2013 | Lundquist et al. |
| 8,471,230 | B2 | 6/2013 | Zhong et al. |
| 8,502,169 | B2 | 8/2013 | Rigneault et al. |
| 8,530,154 | B2 | 9/2013 | Williams |
| 8,581,179 | B2 | 11/2013 | Franzen |
| 8,586,006 | B2 | 11/2013 | Hood |
| 8,608,929 | B2 | 12/2013 | Marziali et al. |
| 8,618,507 | B1 | 12/2013 | Lundquist et al. |
| 8,846,881 | B2 | 9/2014 | Korlach et al. |
| 8,906,614 | B2 | 12/2014 | Wegener et al. |
| 8,927,212 | B2 | 1/2015 | Kong et al. |
| 8,980,584 | B2 | 3/2015 | Williams |
| 9,029,802 | B2 | 5/2015 | Lundquist et al. |
| 9,062,091 | B2 | 6/2015 | Bjornson et al. |
| 9,157,864 | B2 | 10/2015 | Fehr et al. |
| 9,222,123 | B2 | 12/2015 | Zhong et al. |
| 9,222,133 | B2 | 12/2015 | Lundquist et al. |
| 9,223,084 | B2 | 12/2015 | Grot et al. |
| 9,238,822 | B2 | 1/2016 | Baum et al. |
| 9,372,308 | B1 | 6/2016 | Saxena et al. |
| 9,404,146 | B2 | 8/2016 | Travers et al. |
| 9,435,810 | B2 | 9/2016 | Havranek et al. |
| 9,464,107 | B2 | 10/2016 | Wegener et al. |
| 9,542,527 | B2 | 1/2017 | Travers et al. |
| 9,551,031 | B2 | 1/2017 | Korlach et al. |
| 9,551,660 | B2 | 1/2017 | Kong et al. |
| 9,566,335 | B1 | 2/2017 | Emili et al. |
| 9,582,640 | B2 | 2/2017 | Travers et al. |
| 9,587,276 | B2 | 3/2017 | Lundquist et al. |
| 9,600,626 | B2 | 3/2017 | Travers et al. |
| 9,606,060 | B2 | 3/2017 | Chen et al. |
| 9,658,161 | B2 | 5/2017 | Saxena et al. |
| 9,666,748 | B2 | 5/2017 | Leobandung |
| 9,678,080 | B2 | 6/2017 | Bjornson et al. |
| 9,719,073 | B2 | 8/2017 | Emig et al. |
| 9,719,138 | B2 | 8/2017 | Zhong et al. |
| 9,759,658 | B2 | 9/2017 | Rothberg et al. |
| 9,765,395 | B2 | 9/2017 | Goldsmith |
| 9,845,501 | B2 | 12/2017 | Williams |
| 9,879,319 | B2 | 1/2018 | Korlach et al. |
| 9,885,657 | B2 | 2/2018 | Rothberg et al. |
| 9,910,956 | B2 | 3/2018 | Travers et al. |
| 9,946,017 | B2 | 4/2018 | Saxena et al. |
| 9,957,291 | B2 | 5/2018 | Sebo et al. |
| 9,995,739 | B2 | 6/2018 | Dunaway |
| 10,018,764 | B2 | 7/2018 | Grot et al. |
| 10,023,605 | B2 | 7/2018 | Bjornson et al. |
| 10,048,208 | B2 | 8/2018 | Rothberg et al. |
| 10,066,258 | B2 | 9/2018 | Kong et al. |
| 10,090,429 | B2 | 10/2018 | Leobandung |
| 10,138,291 | B2 | 11/2018 | Chhabra et al. |
| 10,138,515 | B2 | 11/2018 | Fehr et al. |
| 10,150,872 | B2 | 12/2018 | Zheng et al. |
| 10,161,002 | B2 | 12/2018 | Korlach et al. |
| 10,174,363 | B2 | 1/2019 | Rothberg et al. |
| 10,246,742 | B2 | 4/2019 | Rothberg et al. |
| 10,266,874 | B2 | 4/2019 | Weissleder et al. |
| 10,280,457 | B2 | 5/2019 | Zhong et al. |
| 10,310,178 | B2 | 6/2019 | Saxena et al. |
| 10,481,162 | B2 | 11/2019 | Emili et al. |
| 10,487,356 | B2 | 11/2019 | Lundquist et al. |
| 10,544,449 | B2 | 1/2020 | Shen et al. |
| 10,545,153 | B2 | 1/2020 | Marcotte et al. |
| 10,551,624 | B2 | 2/2020 | Rothberg et al. |
| 10,570,445 | B2 | 2/2020 | Kong et al. |
| 10,578,788 | B2 | 3/2020 | Grot et al. |
| 10,592,121 | B2 | 3/2020 | Malladi et al. |
| 10,640,816 | B2 | 5/2020 | Beechem et al. |
| 10,655,172 | B2 | 5/2020 | Rank et al. |
| 10,676,788 | B2 | 6/2020 | Shen et al. |
| 10,724,090 | B2 | 7/2020 | McCaffrey et al. |
| 10,745,750 | B2 | 8/2020 | Korlach et al. |
| 10,787,573 | B2 | 9/2020 | Zheng et al. |
| 10,845,308 | B2 | 11/2020 | Rothberg et al. |
| 10,876,177 | B2 | 12/2020 | Koussa et al. |
| 11,237,326 | B2 | 2/2022 | Rothberg et al. |
| 11,573,238 | B2 | 2/2023 | Callewaert et al. |
| 11,959,920 | B2 | 4/2024 | Reed et al. |
| 12,000,835 | B2 | 6/2024 | Reed et al. |
| 12,055,548 | B2 | 8/2024 | Reed et al. |
| 12,065,466 | B2 | 8/2024 | Reed et al. |
| 12,174,196 | B2 | 12/2024 | Reed et al. |
| 12,259,391 | B2 | 3/2025 | Reed et al. |
| 2002/0182716 | A1 | 12/2002 | Weisbuch et al. |
| 2003/0174992 | A1 | 9/2003 | Levene et al. |
| 2005/0042633 | A1 | 2/2005 | Williams |
| 2005/0266456 | A1 | 12/2005 | Williams et al. |
| 2006/0014212 | A1 | 1/2006 | Benkovic et al. |
| 2007/0072196 | A1 | 3/2007 | Xu et al. |
| 2007/0219367 | A1 | 9/2007 | Shchepinov et al. |
| 2009/0028832 | A1 | 1/2009 | Chung et al. |
| 2009/0105341 | A1 | 4/2009 | Stanton |
| 2009/0263802 | A1 | 10/2009 | Drmanac |
| 2010/0009872 | A1 | 1/2010 | Eid et al. |
| 2010/0029494 | A1 | 2/2010 | Cherkasov et al. |
| 2010/0035254 | A1 | 2/2010 | Williams |
| 2010/0065726 | A1 | 3/2010 | Zhong et al. |
| 2010/0311098 | A1 | 12/2010 | Heck et al. |
| 2011/0003343 | A1 | 1/2011 | Nikiforov et al. |
| 2011/0151451 | A1 | 6/2011 | Lemaire et al. |
| 2011/0281776 | A1 | 11/2011 | Eshoo et al. |
| 2012/0178676 | A1 | 7/2012 | Barrack et al. |
| 2012/0322692 | A1 | 12/2012 | Pham et al. |
| 2013/0116153 | A1 | 5/2013 | Bowen et al. |
| 2013/0316912 | A1 | 11/2013 | Bjornson et al. |
| 2014/0031243 | A1 | 1/2014 | Cai et al. |
| 2014/0273004 | A1 | 9/2014 | Havranek et al. |
| 2014/0356389 | A1 | 12/2014 | Masignani et al. |
| 2016/0169903 | A1 | 6/2016 | Dai et al. |
| 2017/0037462 | A1 | 2/2017 | Turner et al. |
| 2017/0052194 | A1 | 2/2017 | Havranek et al. |
| 2017/0114356 | A1 | 4/2017 | Li et al. |
| 2017/0136433 | A1 | 5/2017 | Sun et al. |
| 2017/0146479 | A1 | 5/2017 | Levine et al. |
| 2017/0204401 | A1 | 7/2017 | Brevnova et al. |
| 2017/0212126 | A1 | 7/2017 | Emili et al. |
| 2017/0276686 | A1 | 9/2017 | Marcotte et al. |
| 2017/0336419 | A1 | 11/2017 | Tran et al. |
| 2018/0105808 | A1 | 4/2018 | Mikkelsen et al. |
| 2018/0172906 | A1 | 6/2018 | Rothberg et al. |
| 2018/0211003 | A1 | 7/2018 | Travers et al. |
| 2018/0273933 | A1 | 9/2018 | Gunderson et al. |
| 2018/0299460 | A1 | 10/2018 | Emili |
| 2018/0320224 | A1 | 11/2018 | Guablomme et al. |
| 2018/0326412 | A1 | 11/2018 | Rothberg et al. |
| 2018/0346507 | A1 | 12/2018 | Sebo et al. |
| 2019/0010183 | A1 | 1/2019 | Bjornson et al. |

(56) References Cited

U.S. PATENT DOCUMENTS

| | | | |
|---|---|---|---|
| 2019/0024168 | A1 | 1/2019 | Rothberg et al. |
| 2019/0025511 | A1 | 1/2019 | Rothberg et al. |
| 2019/0145982 | A1 | 5/2019 | Chee et al. |
| 2019/0194709 | A1 | 6/2019 | Church et al. |
| 2019/0249153 | A1 | 8/2019 | Kamtekar et al. |
| 2019/0285644 | A1 | 9/2019 | Regev et al. |
| 2019/0292590 | A1 | 9/2019 | Zhong et al. |
| 2020/0141944 | A1 | 5/2020 | Emili et al. |
| 2020/0148727 | A1 | 5/2020 | Tullman et al. |
| 2020/0209249 | A1 | 7/2020 | Reed et al. |
| 2020/0209253 | A1 | 7/2020 | Reed et al. |
| 2020/0209254 | A1 | 7/2020 | Reed et al. |
| 2020/0209255 | A1 | 7/2020 | Reed et al. |
| 2020/0209256 | A1 | 7/2020 | Reed et al. |
| 2020/0209257 | A1 | 7/2020 | Reed et al. |
| 2020/0217853 | A1 | 7/2020 | Estandian et al. |
| 2020/0219590 | A1 | 7/2020 | Reed et al. |
| 2020/0231956 | A1 | 7/2020 | Callewaert et al. |
| 2020/0300861 | A1 | 9/2020 | Mena et al. |
| 2020/0348307 | A1 | 11/2020 | Beierle et al. |
| 2020/0348308 | A1 | 11/2020 | Chee et al. |
| 2020/0395099 | A1 | 12/2020 | Meyer et al. |
| 2020/0400677 | A1 | 12/2020 | Boyden et al. |
| 2021/0071162 | A1 | 3/2021 | Franzetti et al. |
| 2021/0139973 | A1 | 5/2021 | Dyer et al. |
| 2021/0148921 | A1 | 5/2021 | Reed et al. |
| 2021/0148922 | A1 | 5/2021 | Dyer et al. |
| 2021/0354134 | A1 | 11/2021 | Rothberg et al. |
| 2021/0364527 | A1 | 11/2021 | Reed et al. |
| 2021/0396762 | A1 | 12/2021 | Chee et al. |
| 2022/0186295 | A1 | 6/2022 | Ad et al. |
| 2022/0186305 | A1 | 6/2022 | Webster |
| 2022/0221467 | A1 | 7/2022 | Kirschner et al. |
| 2022/0235145 | A1 | 7/2022 | Tsourkas et al. |
| 2023/0021352 | A1 | 1/2023 | Callewaert et al. |
| 2023/0213527 | A1 | 7/2023 | Reed et al. |
| 2023/0321146 | A1 | 10/2023 | Yang et al. |
| 2024/0003886 | A1 | 1/2024 | Ribezzi-Crivellari et al. |
| 2024/0272169 | A1 | 8/2024 | Reed et al. |
| 2024/0272170 | A1 | 8/2024 | Reed et al. |
| 2024/0295562 | A1 | 9/2024 | Reed et al. |
| 2024/0344122 | A1 | 10/2024 | Dyer et al. |
| 2025/0035639 | A1 | 1/2025 | Ribezzi-Crivellari et al. |
| 2025/0130238 | A1 | 4/2025 | Reed et al. |
| 2026/0029406 | A1 | 1/2026 | Reed |

FOREIGN PATENT DOCUMENTS

| | | | | | |
|---|---|---|---|---|---|
| AU | 2013-226090 | A1 | | 9/2014 | |
| CN | 109923216 | A | | 6/2019 | |
| CN | 110199019 | A | | 9/2019 | |
| EP | 3008094 | A1 | | 4/2016 | |
| JP | 2019-531715 | A | | 11/2019 | |
| WO | WO 2000/057183 | A1 | | 9/2000 | |
| WO | WO 2005/044836 | A2 | | 5/2005 | |
| WO | WO 2007/070572 | A2 | | 6/2007 | |
| WO | WO 2007/123708 | A1 | | 11/2007 | |
| WO | WO 2009/065635 | A1 | | 5/2009 | |
| WO | WO 2010/044892 | A1 | | 4/2010 | |
| WO | WO 2010/065322 | A1 | | 6/2010 | |
| WO | WO 2010/065531 | A1 | | 6/2010 | |
| WO | WO 2010/115016 | A2 | | 10/2010 | |
| WO | WO 2011/153962 | A1 | | 12/2011 | |
| WO | WO 2013/003555 | A1 | | 1/2012 | |
| WO | WO 2013/112745 | A1 | | 8/2013 | |
| WO | WO 2013/130683 | A2 | | 9/2013 | |
| WO | WO 2014/014347 | A1 | | 1/2014 | |
| WO | WO 2014/205401 | A1 | | 12/2014 | |
| WO | WO-2016044328 | A1 | * | 3/2016 | ............... C07K 1/13 |
| WO | WO 2016/069124 | A1 | | 5/2016 | |
| WO | WO 2016/160844 | A2 | | 10/2016 | |
| WO | WO 2016/164530 | A1 | | 10/2016 | |
| WO | WO 2016/193980 | A1 | | 12/2016 | |
| WO | WO 2017/024049 | A1 | | 2/2017 | |
| WO | WO 2017/192633 | A1 | | 11/2017 | |
| WO | WO-2017205251 | A1 | * | 11/2017 | ............... C12Q 1/68 |
| WO | WO 2018/045186 | A1 | | 3/2018 | |
| WO | WO 2019/040825 | A1 | | 2/2019 | |
| WO | WO 2019/063827 | A1 | | 4/2019 | |
| WO | WO 2019/089836 | A1 | | 5/2019 | |
| WO | WO 2019/089846 | A1 | | 5/2019 | |
| WO | WO 2019/167962 | A1 | | 9/2019 | |
| WO | WO-2019190954 | A1 | * | 10/2019 | ............. C07K 16/00 |
| WO | WO 2020/014586 | A1 | | 1/2020 | |
| WO | WO 2020/023488 | A1 | | 1/2020 | |
| WO | WO 2020/037205 | A1 | | 2/2020 | |
| WO | WO 2020/072907 | A1 | | 4/2020 | |
| WO | WO 2020/102741 | A1 | | 5/2020 | |
| WO | WO 2020/123309 | A1 | | 6/2020 | |
| WO | WO 2020/154307 | A1 | | 7/2020 | |
| WO | WO 2020/201350 | A1 | | 10/2020 | |
| WO | WO 2020/219365 | A1 | | 10/2020 | |
| WO | WO 2020/223000 | A1 | | 11/2020 | |
| WO | WO 2020/252345 | A1 | | 12/2020 | |
| WO | WO 2021/051011 | A1 | | 3/2021 | |
| WO | WO 2021/086913 | A1 | | 5/2021 | |
| WO | WO 2021/226290 | A1 | | 11/2021 | |
| WO | WO 2021/236983 | A2 | | 11/2021 | |
| WO | WO 2022/125973 | A1 | | 6/2022 | |
| WO | WO 2022/132188 | A1 | | 6/2022 | |
| WO | 2024/086832 | A1 | | 4/2023 | |
| WO | 2023/122769 | A2 | | 6/2023 | |
| WO | WO 2023/114732 | A2 | | 6/2023 | |
| WO | 2024/031031 | A2 | | 2/2024 | |
| WO | 2025/101639 | A3 | | 6/2025 | |
| WO | 2025/147658 | A1 | | 7/2025 | |
| WO | 2026/039788 | A1 | | 2/2026 | |

OTHER PUBLICATIONS

Addlagatta et al., Structural basis for the unusual specificity of *Escherichia coli* Aminopeptidase N. Biochemistry. May 13, 2008;47(19):5303-11. doi: 10.1021/bi7022333. Epub Apr. 17, 2008.

Astruc et al., Dendrimers designed for functions: from physical, photophysical, and supramolecular properties to applications in sensing, catalysis, molecular electronics, photonics, and nanomedicine. Chem Rev. Apr. 14, 2010;110(4):1857-959. doi: 10.1021/cr900327d.

Borgo et al., Computer-aided design of a catalyst for Edman degradation utilizing substrate- assisted catalysis. Protein Sci. Apr. 2015; 24(4): 571-579. https://doi.org/10.1002/pro.2633. Epub Dec. 16, 2014.

Chin et al., Addition of p-azido-L-phenylalanine to the genetic code of *Escherichia coli*. J Am Chem Soc. Aug. 7, 2002;124(31):9026-7. doi: 10.1021/ja027007w.

Cong et al., Site-specific PEGylation at histidine tags. Bioconjug Chem. Feb. 15, 2012;23(2):248-63. doi: 10.1021/bc200530x. Epub Feb. 6, 2012.

Corey et al., Generation of a hybrid sequence-specific single-stranded deoxyribonuclease. Science. Dec. 4, 1987;238(4832):1401-3. doi: 10.1126/science.3685986.

Debets et al., Aza-dibenzocyclooctynes for fast and efficient enzyme PEGylation via copper-free (3+2) cycloaddition. Chem Commun (Camb). Jan. 7, 2010;46(1):97-9. doi: 10.1039/b917797c. Epub Nov. 6, 2009.

Garcia-Guerrero et al. Crystal structure and mechanism of human carboxypeptidase O: Insights into its specific activity for acidic residues. PNAS. Apr. 24, 2018;115(17):E3932-E3939. doi: 10.1073/pnas.1803685115. Epub Apr. 10, 2018.

Giansanti et al., Six alternative proteases for mass spectrometry-based proteomics beyond trypsin. Nat Protoc. May 2016;11(5):993-1006. doi: 10.1038/nprot.2016.057. Epub Apr. 28, 2016.

Gurupriya et al., Proteases and Protease Inhibitors in Male Reproduction. In: Proteases in Physiology and Pathology. Chakraborti et al., Eds. 2017:195-216. https://doi.org/10.1007/978-981-10-2513-6_10.

Hamaguchi et al., Aptamer beacons for the direct detection of proteins. Anal Biochem. Jul. 15, 2001;294(2):126-31. doi: 10.1006/abio.2001.5169.

(56) References Cited

OTHER PUBLICATIONS

Koushik et al., Cerulean, Venus, and VenusY67C FRET reference standards. Biophys J. Dec. 15, 2006;91(12):L99-L101. doi: 10.1529/biophysj.106.096206. Epub Oct. 13, 2006. PMID: 17040988; PMCID: PMC1779932.

Kukolka et al., Synthesis of fluorescent oligonucleotide--EYFP conjugate: towards supramolecular construction of semisynthetic biomolecular antennae. Org Biomol Chem. Aug. 7, 2004;2(15):2203-6. doi: 10.1039/b406492e. Epub Jul. 8, 2004.

Malyshev et al., Efficient and sequence-independent replication of DNA containing a third base pair establishes a functional six-letter genetic alphabet. Proc Natl Acad Sci U S A. Jul. 24, 2012;109(30):12005-10. doi: 10.1073/pnas.1205176109. Epub Jul. 6, 2012.

Mattson et al., A practical approach to crosslinking. Mol Biol Rep. Apr. 1993;17(3):167-83. doi: 10.1007/BF00986726.

Needleman et al., A general method applicable to the search for similarities in the amino acid sequence of two proteins. J Mol Biol. Mar. 1970;48(3):443-53. doi: 10.1016/0022-2836(70)90057-4.

Pearson et al., Improved tools for biological sequence comparison. PNAS. Apr. 1, 1988;85(8):2444-8. https://doi.org/10.1073/pnas.85.8.2444.

Rosen et al., Template-directed covalent conjugation of DNA to native antibodies, transferrin and other metal-binding proteins. Nat Chem. Sep. 2014;6(9):804-9. doi: 10.1038/nchem.2003. Epub Jul. 20, 2014.

Saito et al., Dual-labeled oligonucleotide probe for sensing adenosine via FRET: a novel alternative to SNPs genotyping. Chem Commun (Camb). Jun. 7, 2007;(21):2133-5. doi: 10.1039/b618465k. Epub Feb. 28, 2007. PMID: 17520113.

Sato et al., Polyproline-rod approach to isolating protein targets of bioactive small molecules: isolation of a new target of indomethacin. J Am Chem Soc. Jan. 31, 2007;129(4):873-80. doi: 10.1021/ja0655643. PMID: 17243824.

Smith et al., Comparison of biosequences. Adv Appl Math. Dec. 1981;2(4):482-9. https://doi.org/10.1016/0196-8858(81)90046-4.

Smith et al., Proteoform: a single term describing protein complexity. Nat Methods. Mar. 2013;10(3):186-7. doi: 10.1038/nmeth.2369.

Smith et al., Proteoforms as the next proteomics currency. Science. Mar. 9, 2018;359(6380):1106-7. doi: 10.1126/science.aat1884. Epub Mar. 8, 2018.

Stryer et al., Energy transfer: a spectroscopic ruler. Proc Natl Acad Sci U S A. Aug. 1967;58(2):719-26. doi: 10.1073/pnas.58.2.719. PMID: 5233469; PMCID: PMC335693.

Swaminathan et al. A theoretical justification for single molecule peptide sequencing. PLoS Comput Biol. Feb. 25, 2015;11(2):e1004080. doi: 10.1371/journal.pcbi.1004080. eCollection Feb. 2015.

Takeda et al., Site-specific conjugation of oligonucleotides to the C-terminus of recombinant protein by expressed protein ligation. Bioorg Med Chem Lett. May 17, 2004;14(10):2407-10. doi: 10.1016/j.bmcl.2004.03.023.

Thakur et al., Real-time measurement of protein-protein interactions at single-molecule resolution using a biological nanopore. Nat. Biotechnol. Jan. 2019; 37(1):96-101.

Williams et al., An artificial processivity clamp made with streptavidin facilitates oriented attachment of polymerase-DNA complexes to surfaces. Nucleic Acids Res. Oct. 2008;36(18):e121. doi: 10.1093/nar/gkn531. Epub Aug. 22, 2008. PMID: 18723573; PMCID: PMC2566871.

Yang et al., DNA Nanostructures as Programmable Biomolecular Scaffolds. Bioconjug Chem. Aug. 19, 2015;26(8):1381-95. doi: 10.1021/acs.bioconjchem.5b00194. Epub May 22, 2015.

Yao et al. Single-molecule protein sequencing through fingerprinting: computational assessment. Phys Biol. Aug. 12, 2015;12(5):055003. doi: 10.1088/1478-3975/12/5/055003.

International Preliminary Report on Patentability for Application No. PCT/US2020/057647, mailed May 12, 2022.

Kim, Probing structures of membrane proteins and their inhibitors. 2005 (Doctoral dissertation, University of Oxford), 258 pages.

Invitation to Pay Additional Fees for Application No. PCT/US2020/057647, mailed Feb. 25, 2021.

International Search Report and Written Opinion for Application No. PCT/US2020/057647, mailed Apr. 20, 2021.

Bladergroen et al., Solid-phase extraction strategies to surmount body fluid sample complexity in high-throughput mass spectrometry-based proteomics. J Anal Methods Chem. 2015;2015:250131. doi: 10.1155/2015/250131. Epub Jan. 27, 2015.

Borgo, Strategies for Computational Protein Design with Application to the Development of a Biomolecular Tool-kit for Single Molecule Protein Sequencing. Dissertation presented at Washington University in St. Louis. May 2014; 203 pages.

Lee et al., Aptamer/ISET-MS: a new affinity-based MALDI technique for improved detection of biomarkers. Anal Chem. Aug. 5, 2014;86(15):7627-34. doi: 10.1021/ac501488b. Epub Jul. 11, 2014.

Radko et al., Evaluation of Aptamers as Affinity Reagents for an Enhancement of SRM-Based Detection of Low-Abundance Proteins in Blood Plasma. Biomedicines. May 24, 2020;8(5):133. doi: 10.3390/biomedicines8050133.

Reid et al., Application of aptamers as molecular recognition elements in lateral flow assays. Anal Biochem. Mar. 15, 2020;593:113574. doi: 10.1016/j.ab.2020.113574. Epub Jan. 3, 2020.

Richards et al., Aptamer based peptide enrichment for quantitative analysis of gonadotropin-releasing hormone by LC-MS/MS. Talanta. Apr. 1, 2016;150:671-80. doi: 10.1016/j.talanta.2016.01.006. Epub Jan. 7, 2016.

Shi et al., Advancing the sensitivity of selected reaction monitoring-based targeted quantitative proteomics. Proteomics. Apr. 2012;12(8):1074-92. doi: 10.1002/pmic.201100436.

Speicher et al., UNIT 11.10 N-terminal sequence analysis of proteins and peptides. Curr Protoc Protein Sci. May 2001;Chapter:Unit 11.10. doi: 10.1002/0471140864.ps1110s08. Author Manuscript, 41 pages.

Tanaka et al., Identification of low-abundance proteins in serum via the isolation of HSP72 complexes. J Proteomics. Mar. 16, 2016;136:214-21. doi: 10.1016/j.jprot.2016.01.008. Epub Jan. 15, 2016.

Zhao et al., Modification-specific proteomics: strategies for characterization of post-translational modifications using enrichment techniques. Proteomics. Oct. 2009;9(20):4632-41. doi: 10.1002/pmic.200900398.

Bostrom, High-throughput protein analysis using mass spectrometry-based methods (Doctoral dissertation, KTH Royal Institute of Technology). 2014. 135 pages.

Callahan et al. Strategies for Development of a Next-Generation Protein Sequencing Platform. Trends Biochem Sci. Jan. 2020;45(1):76-89. doi: 10.1016/j.tibs.2019.09.005. Epub Oct. 30, 2019.

Costa et al., Fusion tags for protein solubility, purification and immunogenicity in *Escherichia coli*: the novel Fh8 system. Front Microbiol. Feb. 19, 2014;5:63. doi: 10.3389/fmicb.2014.00063.

Jekel et al., Use of endoproteinase Lys-C from Lysobacter enzymogenes in protein sequence analysis. Anal Biochem. Oct. 15, 1983;134(2):347-54. doi: 10.1016/0003-2697(83)90308-1.

Samyn et al., A case study of de novo sequence analysis of N-sulfonated peptides by MALDI TOF/TOF mass spectrometry. J Am Soc Mass Spectrom. Dec. 2004;15(12):1838-52. doi: 10.1016/j.jasms.2004.08.010.

Shah, Programming DNA for molecular-scale temporal barcoding and enzymatic computation. Duke University Dissertation. Publicly available Jun. 10, 2020. 140 pages.

Steinhardt et al., Rational design of a trispecific antibody targeting the HIV-1 Env with elevated anti-viral activity. Nat Commun. Feb. 28, 2018;9(1):877. doi: 10.1038/s41467-018-03335-4.

Tullman et al., A ClpS-based N-terminal amino acid binding reagent with improved thermostability and selectivity. Biochemical Engineering Journal. Feb. 15, 2020;154:107438.

Uniprot Accession No. A0A0K1RWM1, ATP-dependent Clp protease adapter protein CLPS, XP55836295, Nov. 11, 2015. 4 pages.

Wagner et al., Specificity of Aeromonas aminopeptidase toward amino acid amides and dipeptides. J Biol Chem. Feb. 25, 1972;247(4):1208-10.

Witze et al., Mapping protein post-translational modifications with mass spectrometry. Nat Methods. Oct. 2007;4(10):798-806. doi: 10.1038/nmeth1100.

(56) References Cited

OTHER PUBLICATIONS

Altschul et al., Basic local alignment search tool. Journal of molecular biology. Oct. 5, 1990;215(3):403-10.

Choi et al., Structural basis for the recognition of N-end rule substrates by the UBR box of ubiquitin ligases. Nat Struct Mol Biol. Oct. 2010;17(10):1175-81. doi: 10.1038/nsmb.1907. Epub Sep. 12, 2010.

Higgins et al., Fast and sensitive multiple sequence alignments on a microcomputer. Bioinformatics. Apr. 1, 1989;5(2):151-3.

Stein et al., Structural Basis of an N-Degron Adaptor with More Stringent Specificity. Structure. Feb. 2, 2016;24(2):232-42. doi: 10.1016/j.str.2015.12.008. Epub Jan. 21, 2016.

Tullman et al., Engineering ClpS for selective and enhanced N-terminal amino acid binding. Appl Microbiol Biotechnol. Mar. 2019;103(6):2621-2633. doi: 10.1007/s00253-019-09624-2. Epub Jan. 24, 2019.

Boutureira et al., Advances in chemical protein modification. Chem Rev. Mar. 11, 2015;115(5):2174-95. doi: 10.1021/cr500399p. Epub Feb. 20, 2015.

Brownstein et al., Paired single residue-transposed Lys-N and Lys-C digestions for label-free identification of N-terminal and C-terminal MS/MS peptide product ions: ultrahigh resolution Fourier transform ion cyclotron resonance mass spectrometry and tandem mass spectrometry for peptide de novo sequencing. Rapid Communications in Mass Spectrometry. Apr. 15, 2015;29(7):659-66.

Cardozo et al., Multiplexed direct detection of barcoded protein reporters on a nanopore array. bioRxiv. Nov. 11, 2019:837542.

Kosobokova et al., Overview of Fusion Tags for Recombinant Proteins. Biochemistry (Mosc). Mar. 2016;81(3):187-200. doi: 10.1134/S0006297916030019.

Rodriques et al., A theoretical analysis of single molecule protein sequencing via weak binding spectra. PLoS One. Mar. 28, 2019;14(3):e0212868.

Van Vught et al., Site-specific functionalization of proteins and their applications to therapeutic antibodies. Comput Struct Biotechnol J. Feb. 14, 2014;9:e201402001. doi: 10.5936/csbj.201402001.

Wade et al., 124-Color super-resolution imaging by engineering DNA-PAINT blinking kinetics. Nano letters. Mar. 13, 2019;19(4):2641-6.

Yu et al., Synthetic fusion protein design and applications. Biotechnol Adv. Jan.-Feb. 2015;33(1):155-164. doi: 10.1016/j.biotechadv.2014.11.005. Epub Nov. 18, 2014.

International Search Report and Written Opinion for Application No. PCT/US2020/057638, mailed Feb. 16, 2021.

International Preliminary Report on Patentability for Application No. PCT/US2020/057638, mailed May 12, 2022.

Invitation to Pay Additional Fees for Application No. PCT/US2020/057656, mailed Feb. 23, 2021.

International Search Report and Written Opinion for Application No. PCT/US2020/057656, mailed Apr. 13, 2021.

International Preliminary Report on Patentability for Application No. PCT/US2020/057656, mailed May 12, 2022.

Invitation to Pay Additional Fees for Application No. PCT/US2020/057669, mailed Feb. 12, 2021.

International Search Report and Written Opinion for Application No. PCT/US2020/057669, mailed Apr. 7, 2021.

International Preliminary Report on Patentability for Application No. PCT/US2020/057669, mailed May 12, 2022.

Invitation to Pay Additional Fees for International Application No. PCT/US2021/010050 mailed Mar. 11, 2022.

International Search Report and Written Opinion for International Application No. PCT/US2021/010050 mailed May 4, 2022.

International Preliminary Report on Patentability for International Application No. PCT/US2021/010050 mailed Jun. 29, 2023.

Invitation to Pay Additional Fees, mailed Oct. 17, 2023, for Application No. PCT/US2023/068527.

International Search Report and Written Opinion, mailed Jan. 11, 2024, for Application No. PCT/US2023/068527.

International Preliminary Report on Patentability, mailed Dec. 26, 2024, for Application No. PCT/US2023/068527.

Invitation to Pay Additional Fees, mailed Oct. 21, 2024, for Application No. PCT/US2024/039374.

International Search Report and Written Opinion, mailed Dec. 17, 2024, for Application No. PCT/US2024/039374.

International Preliminary Report on Patentability, mailed Feb. 5, 2026, for Application No. PCT/US2024/039374.

International Search Report and Written Opinion, mailed Sep. 23, 2025, for Application No. PCT/US2025/039716.

International Search Report and Written Opinion, mailed Dec. 23, 2025, for Application No. PCT/US2025/051130.

Abrahmsén et al., Engineering subtilisin and its substrates for efficient ligation of peptide bonds in aqueous solution. Biochemistry. Apr. 30, 1991;30(17):4151-9. doi: 10.1021/bi00231a007.

Agasti et al., Photocleavable DNA barcode-antibody conjugates allow sensitive and multiplexed protein analysis in single cells. J Am Chem Soc. Nov. 14, 2012;134(45):18499-502. doi: 10.1021/ja307689w. Epub Nov. 2, 2012. Author Manuscript, 10 pages.

Aitken et al., An oxygen scavenging system for improvement of dye stability in single- molecule fluorescence experiments. Biophys J. Mar. 1, 2008;94(5):1826-35. doi: 10.1529/biophysj.107.117689. Epub Oct. 5, 2007.

Barbas et al., A search for peptide ligase: cosolvent-mediated conversion of proteases to esterases for irreversible synthesis of peptides. Journal of the American Chemical Society. Jul. 1988;110(15):5162-6.

Becer et al., Click chemistry beyond metal-catalyzed cycloaddition. Angew Chem Int Ed Engl. 2009;48(27):4900-8. doi: 10.1002/anie.200900755.

Bleeke et al., Catecholamine-induced vascular wall growth is dependent on generation of reactive oxygen species. Circ Res. Jan. 9, 2004;94(1):37-45. doi: 10.1161/01.RES.0000109412.80157.7D. Epub Dec. 1, 2003.

Chinnaraj et al., Protein barcoding and Next-generation protein sequencing for multiplexed protein selection, analysis, and tracking. Biorxiv. Jan. 2, 2025:2024-12.

Choi, Photocleavable linkers: Design and applications in nanotechnology. Photonanotechnology for Therapeutics and Imaging. Jan. 1, 2020 (pp. 243-275). doi:10.1016/b978-0-12-817840-9.00009-6.

Drummen et al., Attenuation of lipid peroxidation by antioxidants in rat-1 fibroblasts: comparison of the lipid peroxidation reporter molecules cis-parinaric acid and C11-BODIPY(581/591) in a biological setting. Biochim Biophys Acta. Mar. 22, 2004;1636(2-3):136-50. doi: 10.1016/j.bbalip.2003.10.013. Erratum in: Biochim Biophys Acta. Aug. 30, 2004;1684(1-3): 63.

Dumontet et al., Antibody-drug conjugates come of age in oncology. Nat Rev Drug Discov. Aug. 2023;22(8):641-661. doi: 10.1038/s41573-023-00709-2. Epub Jun. 12, 2023.

Egloff et al., Engineered peptide barcodes for in-depth analyses of binding protein libraries. Nat Methods. May 2019;16(5):421-428. doi: 10.1038/s41592-019-0389-8. Epub Apr. 22, 2019. Author Manuscript, 29 pges.

Franco et al., Glutathione depletion is necessary for apoptosis in lymphoid cells independent of reactive oxygen species formation. J Biol Chem. Oct. 19, 2007;282(42):30452-65. doi: 10.1074/jbc.M703091200. Epub Aug. 27, 2007.

Fu et al., Antibody drug conjugate: the “biological missile” for targeted cancer therapy. Signal Transduct Target Ther. Mar. 22, 2022;7(1):93. doi: 10.1038/s41392-022-00947-7.

Gauuan et al., Superoxide dismutase mimetics: synthesis and structure-activity relationship study of MnTBAP analogues. Bioorg Med Chem. Sep. 2002;10(9):3013-21. doi: 10.1016/s0968-0896(02)00153-0.

Goettig, Reversed proteolysis—proteases as peptide ligases. Catalysts. Dec. 30, 2020;11(1):33.

Gogia et al., Antibody-Drug Conjugates: A Review of Approved Drugs and Their Clinical Level of Evidence. Cancers (Basel). Jul. 30, 2023;15(15):3886. doi: 10.3390/cancers15153886.

Günther et al., Trypsin-specific acyl-4-guanidinophenyl esters for alpha-chymotrypsin-catalysed reactions computational predictions, hydrolyses, and peptide bond formation. Eur J Biochem. Jun. 2000;267(12):3496-501. doi: 10.1046/j.1432-1327.2000.01376.x.

Haensler et al., Reverse catalysis of elastase from porcine pancreas in frozen aqueous systems. Biol Chem. Jan. 1998;379(1):71-4.

(56) References Cited

OTHER PUBLICATIONS

Hale, Fibre Optic Sensors using Adiabatically Tapered Single Mode Fibres. Dissertation submitted to the University of Cambridge. Feb. 1994. 209 pages.
Halvorsen et al., Nanoengineering a single-molecule mechanical switch using DNA self- assembly. Nanotechnology. Dec. 9, 2011;22(49):494005. doi: 10.1088/0957-4484/22/49/494005. Epub Nov. 21, 2011.
Hänsler et al., Nonconventional protease catalysis in frozen aqueous solutions. J Pept Sci. Sep.-Oct. 1996;2(5):279-89. doi: 10.1002/psc.65.
Hawkins et al., Detection, identification, and quantification of oxidative protein modifications. J Biol Chem. Dec. 20, 2019;294(51):19683-19708. doi: 10.1074/jbc.REV119.006217. Epub Oct. 31, 2019.
Hoppenz et al., Peptide-Drug Conjugates and Their Targets in Advanced Cancer Therapies. Front Chem. Jul. 7, 2020;8:571. doi: 10.3389/fchem.2020.00571.
Hytönen et al., Dual-affinity avidin molecules. Proteins. Nov. 15, 2005;61(3):597-607. doi: 10.1002/prot.20604.
Khongorzul et al., Antibody-Drug Conjugates: A Comprehensive Review. Mol Cancer Res. Jan. 2020;18(1):3-19. doi: 10.1158/1541-7786.MCR-19-0582. Epub Oct. 28, 2019.
Kimple et al., Overview of affinity tags for protein purification. Curr Protoc Protein Sci. Sep. 24, 2013;73:9.9.1-9.9.23. doi: 10.1002/0471140864.ps0909s73. Author Manuscript, 26 pages.
Liebscher et al., Derivatization of antibody Fab fragments: a designer enzyme for native protein modification. Chembiochem. May 26, 2014;15(8):1096-100. doi: 10.1002/cbic.201400059. Epub Apr. 29, 2014.
Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.
Morihara et al., Peptide bond synthesis catalyzed by subtilisin, papain, and pepsin. J Biochem. Feb. 1981;89(2):385-95. doi: 10.1093/oxfordjournals.jbchem.a133213.
Munoz-Escobar et al., Bound Waters Mediate Binding of Diverse Substrates to a Ubiquitin Ligase. Structure. May 2, 2017;25(5):719-729.e3. doi: 10.1016/j.str.2017.03.004. Epub Apr. 6, 2017.
Nakatsuka et al., Peptide segment synthesis catalyzed by the semisynthetic enzyme thiolsubtilisin. Journal of the American Chemical Society. Jun. 1987;109(12):3808-10.
Nguyen et al., Butelase 1: A Versatile Ligase for Peptide and Protein Macrocyclization. J Am Chem Soc. Dec. 16, 2015;137(49):15398-401. doi: 10.1021/jacs.5b11014. Epub Dec. 7, 2015. Supporting Information, 23 pages.
Nicolescu et al., Nitroxidation, nitration, and oxidation of a BODIPY fluorophore by RNOS and ROS. Nitric Oxide. Sep. 2006;15(2):163-76. doi: 10.1016/j.niox.2006.01.010. Epub Mar. 23, 2006.
Nishino et al., Tryptic condensation combined with peptide segment synthesis-condensation strategy for the efficient synthesis of human growth hormone releasing factor (1-29) amide. Journal of the Chemical Society, Chemical Communications. 1992(8):648-50.
Ribeiro et al., Hydrogen peroxide, antioxidant compounds and biological targets: an in vitro approach for determination of scavenging capacity using fluorimetric multisyringe flow injection analysis. Talanta. Jun. 15, 2010;81(4-5):1840-6. doi: 10.1016/j.talanta.2010.03.049. Epub Mar. 31, 2010.
Riccardi et al., A comprehensive overview on antibody-drug conjugates: from the conceptualization to cancer therapy. Front Pharmacol. Sep. 18, 2023;14:1274088. doi: 10.3389/fphar.2023.1274088.
Schmidt et al., Design of a substrate-tailored peptiligase variant for the efficient synthesis of thymosin-a1. Org Biomol Chem. Jan. 24, 2018;16(4):609-618. doi: 10.1039/c7ob02812a.
Sealock et al., Enzymatic replacement of the arginyl by a lysyl residue in the reactive site of soybean trypsin inhibitor. Biochemistry. Sep. 1969;8(9):3703-10. doi: 10.1021/bi00837a032.
Shastry et al., Rise of Antibody-Drug Conjugates: The Present and Future. Am Soc Clin Oncol Educ Book. May 2023;43:e390094. doi: 10.1200/EDBK_390094.
Swoboda et al., Enzymatic oxygen scavenging for photostability without pH drop in single- molecule experiments. ACS Nano. Jul. 24, 2012;6(7):6364-9. doi: 10.1021/nn301895c. Epub Jun. 22, 2012.
Szczepaniak et al., Making ATRP More Practical: Oxygen Tolerance. Acc Chem Res. Apr. 6, 2021;54(7):1779-1790. doi: 10.1021/acs.accounts.1c00032. Epub Mar. 22, 2021.
Taitt et al., Evanescent wave fluorescence biosensors. Biosens Bioelectron. Jun. 2005;20(12):2470-87. Epub Dec. 8, 2004.
Third Party Observation for European Application No. 19817882.4 mailed Dec. 20, 2021.
Tsuchikama et al., Exploring the next generation of antibody-drug conjugates. Nat Rev Clin Oncol. Mar. 2024;21(3):203-223. doi: 10.1038/s41571-023-00850-2. Epub Jan. 8, 2024.
Van Der Velden et al., Peptidases: structure, function and modulation of peptide-mediated effects in the human lung. Clin Exp Allergy. Apr. 1999;29(4):445-56. doi: 10.1046/j.1365-2222.1999.00462.x.
Walford et al., Hypoxia potentiates nitric oxide-mediated apoptosis in endothelial cells via peroxynitrite-induced activation of mitochondria-dependent and -independent pathways. J Biol Chem. Feb. 6, 2004;279(6):4425-32. doi: 10.1074/jbc.M310582200. Epub Nov. 3, 2003.
Wayne et al., Thermolysin-catalyzed peptide bond synthesis. Proc Natl Acad Sci U S A. Jun. 1983;80(11):3241-4. doi: 10.1073/pnas.80.11.3241.
Wehofsky et al., Effect of freezing on the enzymatic coupling of specific amino acid-containing peptide fragments. Tetrahedron: Asymmetry. Jun. 16, 2000;11(11):2421-8.
Wu et al., Conversion of a protease into an acyl transferase: selenolsubtilisin. Journal of the American Chemical Society. Jun. 1989; 111(12):4513-4.
U.S. Appl. No. 16/686,028, filed Nov. 15, 2019, Reed et al.
U.S. Appl. No. 16/708,956, filed Dec. 10, 2019, Reed et al.
U.S. Appl. No. 16/708,989, filed Dec. 10, 2019, Reed et al.
U.S. Appl. No. 16/709,024, filed Dec. 10, 2019, Reed et al.
U.S. Appl. No. 16/709,052, filed Dec. 10, 2019, Reed et al.
U.S. Appl. No. 16/709,077, filed Dec. 10, 2019, Reed et al.
U.S. Appl. No. 16/709,103, filed Dec. 10, 2019, Reed et al.
U.S. Appl. No. 17/082,899, filed Oct. 28, 2020, Reed et al.
U.S. Appl. No. 17/082,918, filed Oct. 28, 2020, Dyer et al.
U.S. Appl. No. 17/082,940, filed Oct. 28, 2020, Dyer et al.
PCT/US2019/061831, Mar. 23, 2020, International Search Report and Written Opinion.
PCT/US2020/057647, Feb. 25, 2021, Invitation to Pay Additional Fees.
PCT/US2020/057647, Apr. 20, 2021, International Search Report and Written Opinion.

* cited by examiner

METHODS OF PREPARING SAMPLES FOR MULTIPLEX POLYPEPTIDE SEQUENCING

RELATED APPLICATIONS

This application claims the benefit under 35 U.S.C. § 119(e) of the filing date of U.S. Provisional Application Ser. No. 62/926,975, filed Oct. 28, 2019, the entire contents of which is incorporated herein by reference.

BACKGROUND OF INVENTION

Proteomics has emerged as an important and necessary complement to genomics and transcriptomics in the study of biological systems. However, approaches for multiplex proteomic analysis have been limited to date.

SUMMARY OF INVENTION

Provided herein are methods of preparing samples for polypeptide sequencing, which leverage polypeptide barcoding to facilitate multiplex proteomic analysis. Also provided herein are compositions, kits and devices useful for the same.

In some aspects, the disclosure relates to methods of preparing a multiplexed sample. In some embodiments, the method comprises: (i) contacting a population of polypeptides with a barcode component to produce a sample comprising one or more barcoded polypeptides; and (ii) combining the sample of (i) with one or more supplemental samples to generate a multiplexed sample for parallel polypeptide sequencing.

In some embodiments, (i) comprises: (a) providing a population of polypeptides; (b) contacting the population of polypeptides of (a) with a barcode component comprising a plurality of barcode molecules, wherein the contacting of the plurality of polypeptides with the barcode component produces a sample comprising one or more barcoded polypeptides.

In some embodiments, one or more of the supplemental samples in (ii) is produced by: (a) providing a population of polypeptides; (b) contacting the population of polypeptides of (a) with a barcode component comprising a plurality of barcode molecules, wherein the contacting of the population of polypeptides with the barcode component produces a sample comprising one or more barcoded polypeptides.

In some embodiments, the population of polypeptides in (a) consists of a single polypeptide. In some embodiments, the population of polypeptides in (a) comprises polypeptide fragments derived from a single polypeptide. In some embodiments, the population of polypeptides in (a) comprises a plurality of polypeptides.

In some embodiments, (a) comprises lysing a cell population to generate a lysis sample comprising a plurality of polypeptides expressed in the cell population. In some embodiments, the cell population: consists of a single cell; comprises a plurality of homogeneous cells; or comprises a plurality of heterogeneous cells. In some embodiments, the cell population is isolated from a subject. In some embodiments, the subject is a human, mouse, rat, or non-human primate.

In some embodiments, (a) further comprises contacting the lysis sample with a modifying agent, thereby generating a sample comprising modified polypeptides.

In some embodiments, (a) further comprises isolating a fraction of the polypeptides of the lysis sample, thereby generating an enriched sample comprising a subset of the polypeptides expressed in the cell population. In some embodiments, isolating a fraction of the polypeptides of the lysis sample comprises: i. contacting the lysis sample with a plurality of enrichment molecules, wherein at least a subset of the enrichment molecules in the plurality of enrichment molecules binds to a subset of the polypeptides in the lysis sample, thereby generating a bound subset of polypeptides and an unbound subset of polypeptides; and ii. isolating the bound subpopulation of polypeptides or the unbound subpopulation of polypeptides.

In some embodiments: each of the enrichment molecules in the plurality of enrichment molecules is an antibody, an aptamer, or an enzyme; or the enrichment molecules in a subset of the plurality of enrichment molecules comprise an antibody, an aptamer, or an enzyme.

In some embodiments: each of the enrichment molecules in the plurality of enrichment molecules is immobilized on a substrate; or the enrichment molecules in a subset of the plurality of enrichment molecules are immobilized on a substrate. In some embodiments, the contacting of the plurality of polypeptides with the plurality of enrichment molecules occurs when the lysis sample comprising the plurality of polypeptides contacts the substrate. In some embodiments, the substrate is selected from the group consisting of a surface, a bead, a particle, and a gel, optionally wherein: the surface is a solid surface; the bead is a magnetic bead; or the particle is a magnetic particle.

In some embodiments: each of the enrichment molecules in the plurality of enrichment molecules binds to two or more polypeptides comprising different amino acid sequences; or the enrichment molecules in a subset of the plurality of enrichment molecules bind to two or more polypeptides comprising different amino acid sequences.

In some embodiments: each of the enrichment molecules in the plurality of enrichment molecules binds to an amino acid post-translational modification; or the enrichment molecules in a subset of the plurality of enrichment molecules bind to an amino acid post-translational modification. In some embodiments, the post-translational modification is selected from the group consisting of acetylation, ADP-ribosylation, caspase cleavage, citrullination, formylation, hydroxylation, methylation, myristoylation, N-linked glycosylation, neddylation, nitration, O-linked glycosylation, oxidation, palmitoylation, phosphorylation, prenylation, S-nitrosylation, sulfation, sumoylation, ubiquitylation.

In some embodiments, the method further comprises contacting the polypeptides of the enriched sample with a modifying agent, thereby generating a sample comprising modified polypeptides. In some embodiments, the modifying agent comprises a denaturant and at least one polypeptide is modified by denaturation. In some embodiments, the modifying agent blocks free carboxylate groups and at least one polypeptide is modified by blocking free carboxylate groups of the polypeptide. In some embodiments, the modifying agent blocks free thiol groups and at least one polypeptide is modified by blocking free thiol groups of the polypeptide. In some embodiments, the modifying agent comprises a cleaving agent and at least one polypeptide is modified by cleavage.

In some embodiments, the barcode component of (i) comprises barcode molecules comprising a polynucleic acid portion. In some embodiments, the polynucleic acid portion is 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some embodiments, (ii) further comprises depositing the multiplexed sample on or within a solid substrate, wherein the solid substrate comprises immobilized detector molecules corresponding to the one or more of the polynucleic acid portions of the barcode molecules comprising polynucleic acid portions, optionally wherein the detector molecules comprise polynucleic acids that are complementary to one or more of the polynucleic acid portions of the barcode molecules comprising polynucleic acid portions. In some embodiments, the solid substrate is a chip array.

In some embodiments, the barcode component of (i) comprises barcode molecules comprising a polypeptide portion. In some embodiments, the polypeptide portion is 6, 7, 8, 9, 10, 11, 12, 13, 14, 15, 16, 17, 18, 19, or 20 amino acids in length. In some embodiments, the polypeptide portion is the amino acid sequence of an antibody. In some embodiments, (ii) further comprises depositing the multiplexed sample on or within a solid substrate, wherein the solid substrate comprises immobilized antigens corresponding to one or more of the polypeptide portions of barcode molecules comprising the amino acid sequence of an antibody. In some embodiments, the solid substrate is a chip array.

In some embodiments, the barcode component of (i) comprises barcode molecules comprising a small molecule portion, such as a fluorescent molecule portion. In some embodiments, the fluorescent molecule portion comprises an aromatic or heteroaromatic compound, such as a pyrene, anthracene, naphthalene, acridine, stilbene, indole, benzindole, oxazole, carbazole, thiazole, benzothiazole, phenanthridine, phenoxazine, porphyrin, quinoline, ethidium, benzamide, cyanine, carbocyanine, salicylate, anthranilate, coumarin, fluorescein, rhodamine, or the like. In some embodiments, the fluorescent molecule portion comprise a dye selected from the group consisting of a xanthene dye, a naphthalene dye, a coumarin dye, an acridine dye, a cyanine dye, a benzoxazole dye, a stilbene dye, a pyrene dye, a phthalocyanine dye, a phycobiliprotein dye, a squaraine dye, and a BODIPY dye.

In some embodiments, the sample generated in (i) comprises polypeptides each having a barcode molecule covalently attached to an amino acid within ten amino acids of its N-terminus or C-terminus. In some embodiments, the sample generated in (i) comprises polypeptides each having a barcode molecule covalently attached to its N-terminus or C-terminus.

In other embodiments, the method comprises: (i) providing two or more populations of polypeptides; (ii) depositing the two or more populations of polypeptides of (i) on or within a solid substrate, wherein each population of polypeptides remains physically separated from the other populations of polypeptides in (i); thereby preparing a multiplexed sample for parallel polypeptide sequencing. In some embodiments, the solid substrate is a chip array. In some embodiments, each population of polypeptides is deposited in a different injection port of the solid substrate.

In some embodiments, at least one of the populations of polypeptides in (a) consists of a single polypeptide. In some embodiments, at least one of the populations of polypeptides in (a) comprises polypeptide fragments derived from a single polypeptide. In some embodiments, at least one of the populations of polypeptides in (a) comprises a plurality of polypeptides.

In some embodiments, (i) comprises lysing a cell population to generate a lysis sample comprising a plurality of polypeptides expressed in the cell population. In some embodiments, the cell population: consists of a single cell; comprises a plurality of homogeneous cells; or comprises a plurality of heterogeneous cells. In some embodiments, the cell population is isolated from a subject. In some embodiments, the subject is a human, mouse, rat, or non-human primate. In some embodiments, (i) further comprises: (c) contacting each of the lysis samples generated in (b) with a modifying agent, thereby generating samples comprising modified polypeptides.

In some embodiments, (a) further comprises isolating a fraction of the polypeptides of the lysis sample, thereby generating an enriched sample comprising a subset of the polypeptides expressed in the cell population.

In some embodiments, (c) comprises: i. contacting each of the lysis samples generated in (b) with a plurality of enrichment molecules, wherein at least a subset of the enrichment molecules in the plurality of enrichment molecules binds to a subset of the polypeptides in each lysis sample, thereby generating a bound subset of polypeptides and an unbound subset of polypeptides; and ii. isolating the bound subpopulation of polypeptides or the unbound subpopulation of polypeptides.

In some embodiments: each of the enrichment molecules in the plurality of enrichment molecules is immobilized on a substrate; or the enrichment molecules in a subset of the plurality of enrichment molecules are immobilized on a substrate.

In some embodiments: each of the enrichment molecules in the plurality of enrichment molecules is immobilized on a substrate; or the enrichment molecules in a subset of the plurality of enrichment molecules are immobilized on a substrate. In some embodiments, the contacting of the plurality of polypeptides with the plurality of enrichment molecules occurs when the lysis sample comprising the plurality of polypeptides contacts the substrate. In some embodiments, the substrate is selected from the group consisting of a surface, a bead, a particle, and a gel, optionally wherein: the surface is a solid surface; the bead is a magnetic bead; or the particle is a magnetic particle.

In some embodiments: each of the enrichment molecules in the plurality of enrichment molecules binds to two or more polypeptides comprising different amino acid sequences; or the enrichment molecules in a subset of the plurality of enrichment molecules bind to two or more polypeptides comprising different amino acid sequences.

In some embodiments: each of the enrichment molecules in the plurality of enrichment molecules binds to an amino acid post-translational modification; or the enrichment molecules in a subset of the plurality of enrichment molecules bind to an amino acid post-translational modification. In some embodiments, the post-translational modification is selected from the group consisting of acetylation, ADP-ribosylation, caspase cleavage, citrullination, formylation, hydroxylation, methylation, myristoylation, N-linked glycosylation, neddylation, nitration, O-linked glycosylation, oxidation, palmitoylation, phosphorylation, prenylation, S-nitrosylation, sulfation, sumoylation, ubiquitylation.

In some embodiments, (i) further comprises: (d) contacting the polypeptides of each of the enriched samples generated in (c) with a modifying agent, thereby generating samples comprising modified polypeptides. In some embodiments, the modifying agent comprises a denaturant and at least one polypeptide is modified by denaturation. In some embodiments, the modifying agent blocks free carboxylate groups and at least one polypeptide is modified by blocking free carboxylate groups of the polypeptide. In some embodiments, the modifying agent blocks free thiol groups and at least one polypeptide is modified by blocking free thiol groups of the polypeptide. In some embodiments, the modifying agent comprises a cleaving agent and at least one polypeptide is modified by cleavage.

In some aspects, the disclosure relates to methods of determining at least partial amino acid sequences and origins of polypeptides in a multiplexed sample. In some embodiments, the method comprises: (i) preparing a multiplexed sample according to a method described herein; (ii) detecting the barcode identities of the barcoded polypeptides in the multiplexed sample, thereby determining the origins of the polypeptides of the multiplexed sample; and (iii) sequencing, in parallel, the polypeptides in the multiplexed sample, thereby determining at least the partial amino acid sequences of the polypeptides in the multiplexed sample; wherein (iii) occurs before, after, or concurrently with (ii).

In some embodiments, the barcode identities of the barcoded polypeptides is detected in (ii) by DNA sequencing, polypeptide sequencing, hybridization, luminescence, binding kinetics, and/or physical location on or within a solid substrate.

In some embodiments, (iii) comprises: (a) contacting a single polypeptide molecule of the multiplexed sample with one or more terminal amino acid recognition molecules; and (b) detecting a series of signal pulses indicative of association of the one or more terminal amino acid recognition molecules with successive amino acids exposed at a terminus of the single polypeptide while the single polypeptide is being degraded, thereby sequencing the single polypeptide molecule.

In some embodiments, (iii) comprises: (a) contacting a single polypeptide molecule of the multiplexed sample with a composition comprising one or more terminal amino acid recognition molecules and a cleaving reagent; and (b) detecting a series of signal pulses indicative of association of the one or more terminal amino acid recognition molecules with a terminus of the single polypeptide molecule in the presence of the cleaving reagent, wherein the series of signal pulses is indicative of a series of amino acids exposed at the terminus over time as a result of terminal amino acid cleavage by the cleaving reagent.

In some embodiments, (iii) comprises: (a) identifying a first amino acid at a terminus of a single polypeptide molecule of the multiplexed sample; (b) removing the first amino acid to expose a second amino acid at the terminus of the single polypeptide molecule, and (c) identifying the second amino acid at the terminus of the single polypeptide molecule, wherein (a)-(c) are performed in a single reaction mixture.

In some embodiments, (iii) comprises: (a) contacting a single polypeptide molecule of the multiplexed sample with one or more amino acid recognition molecules that bind to the single polypeptide molecule; (b) detecting a series of signal pulses indicative of association of the one or more amino acid recognition molecules with the single polypeptide molecule under polypeptide degradation conditions; and (c) identifying a first type of amino acid in the single polypeptide molecule based on a first characteristic pattern in the series of signal pulses.

In some embodiments, (iii) comprises: (a) obtaining data during a polypeptide degradation process; (b) analyzing the data to determine portions of the data corresponding to amino acids that are sequentially exposed at a terminus of the polypeptide during the degradation process; and (c) outputting an amino acid sequence representative of the polypeptide.

In some embodiments, (iii) comprises: (a) contacting a polypeptide of the multiplexed sample with one or more labeled affinity reagents that selectively bind one or more types of terminal amino acids at a terminus of the polypeptide; and (b) identifying a terminal amino acid at the terminus of the polypeptide by detecting an interaction of the polypeptide with the one or more labeled affinity reagents.

In some embodiments, (iii) comprises: (a) contacting a polypeptide in the multiplexed sample with one or more labeled affinity reagents that selectively bind one or more types of terminal amino acids at a terminus of the polypeptide; (b) identifying a terminal amino acid at the terminus of the polypeptide by detecting an interaction of the polypeptide with the one or more labeled affinity reagents; (c) removing the terminal amino acid; and (d) repeating (a)-(c) one or more times at the terminus of the polypeptide to determine an amino acid sequence of the polypeptide. In some embodiments, the method further comprises: after (a) and before (b), removing any of the one or more labeled affinity reagents that do not selectively bind the terminal amino acid; and/or after (b) and before (c), removing any of the one or more labeled affinity reagents that selectively bind the terminal amino acid. In some embodiments, (c) comprises modifying the terminal amino acid by contacting the terminal amino acid with an isothiocyanate, and: contacting the modified terminal amino acid with a protease that specifically binds and removes the modified terminal amino acid; or subjecting the modified terminal amino acid to acidic or basic conditions sufficient to remove the modified terminal amino acid.

In some embodiments, identifying the terminal amino acid comprises: identifying the terminal amino acid as being one type of the one or more types of terminal amino acids to which the one or more labeled affinity reagents bind; or identifying the terminal amino acid as being a type other than the one or more types of terminal amino acids to which the one or more labeled affinity reagents bind. In some embodiments, the one or more labeled affinity reagents comprise one or more labeled aptamers, one or more labeled peptidases, one or more labeled antibodies, one or more labeled degradation pathway protein, one or more aminotransferase, one or more tRNA synthetase, or a combination thereof. In some embodiments, the one or more labeled peptidases have been modified to inactivate cleavage activity; or wherein the one or more labeled peptidases retain cleavage activity for the removing of (c).

In some aspects, the disclosure relates to kits for performing the methods described herein.

In some embodiments, the kit comprises a barcode component comprising a plurality of barcode molecules. In some embodiments, the barcode component further comprises a reaction component comprising one or more reagent for covalently attaching a barcode molecule to polypeptide. In some embodiments, the barcode component comprises one or more barcode molecules comprising a polynucleic acid portion, a polypeptide portion, and/or a fluorescent molecule portion.

In some embodiments, the polynucleic acid portion is 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some embodiments, the polynucleic acid portion comprises an aptamer.

In some embodiments, the polypeptide portion is 6, 7, 8, 9, 10, 11, 12, 13, 14, 15, 16, 17, 18, 19, or 20 amino acids in length. In some embodiments, the polypeptide portion is an antibody or aptamer.

In some embodiments, the fluorescent molecule portion comprises an aromatic or heteroaromatic compound, such as a pyrene, anthracene, naphthalene, acridine, stilbene, indole, benzindole, oxazole, carbazole, thiazole, benzothiazole, phenanthridine, phenoxazine, porphyrin, quinoline, ethidium, benzamide, cyanine, carbocyanine, salicylate, anthranilate, coumarin, fluorescein, rhodamine, or the like. In some embodiments, the fluorescent molecule portion comprise a dye selected from the group consisting of a xanthene dye, a naphthalene dye, a coumarin dye, an acridine dye, a cyanine dye, a benzoxazole dye, a stilbene dye, a pyrene dye, a phthalocyanine dye, a phycobiliprotein dye, a squaraine dye, and a BODIPY dye.

In some embodiments, the kit further comprises a solid support. In some embodiments, the solid support comprises a immobilized detector molecule (or a plurality of immobilized detector molecules). In some embodiments, the detector molecule comprises a polynucleic acid portion corresponding to a barcode molecule of the barcode component. In some embodiments, the detector molecule comprises a polypeptide portion corresponding to a barcode molecule of the barcode component.

In some embodiments, the kit comprises a solid support that allows for the physical separation of populations of polypeptides of different origins.

In some aspects, the disclosure relates to devices for performing the methods described herein.

In some embodiments, a device comprises: at least one hardware processor; and at least one non-transitory computer-readable storage medium storing processor-executable instructions that, when executed by the at least one hardware processor, cause the at least one hardware processor to perform a method described herein.

In some embodiments, the device comprises at least one non-transitory computer-readable storage medium storing processor-executable instructions that, when executed by at least one hardware processor, cause the at least one hardware processor to perform a method described herein.

In some embodiments, the device comprises: (i) a sample preparation module configured to interface with one or more cartridge, each cartridge comprising: (a) one or more reservoirs or reaction vessels configured to receive a complex sample; (b) one or more sequence sample preparation reagents, wherein the sample preparation reagents comprise a plurality of barcode molecules; and (c) a matrix comprising one or more immobilized capture probes; (ii) a sequencing module comprising an array of pixels, wherein each pixel is configured to receive a sequencing sample from the sample preparation module and comprises: (a) a sample well; and (b) at least one photodetector.

In some embodiments, the sample preparation regents further comprise a plurality of enrichment molecules. In some embodiments, at least a subset of the enrichment molecules in the plurality of enrichment molecules are covalently attached to an immobilized capture probe. In some embodiments, at least a subset of the enrichment molecules are covalently attached to a bead or particle that is capable of being bound by an immobilized capture probe. In some embodiments, each of the enrichment molecules in the plurality of enrichment molecules comprises an antibody, an aptamer, or an enzyme. In some embodiments, the enrichment molecules in a subset of the plurality of enrichment molecules comprise an antibody, an aptamer, or an enzyme.

In some embodiments, the sample preparation reagents comprise a modifying agent. In some embodiments, the modifying agent mediates polypeptide fragmentation, polypeptide denaturation, addition of a post-translational modification, and/or the blocking of one or more functional groups.

In some embodiments, the sequencing module further comprises a reservoir or reaction vessel configured to deliver sequencing reagents to the sample well of each pixel.

In some embodiments, the sequencing reagents comprise a labeled affinity reagent. In some embodiments, the labeled affinity reagent comprises one or more labeled aptamers, one or more labeled peptidases, one or more labeled antibodies, one or more labeled degradation pathway protein, one or more aminotransferase, one or more tRNA synthetase, or a combination thereof.

BRIEF DESCRIPTION OF THE DRAWINGS

The skilled artisan will understand that the figures, described herein, are for illustration purposes only. It is to be understood that, in some instances, various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

When describing embodiments in reference to the drawings, direction references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of an embodied device. A device may be embodied in other orientations.

As is apparent from the detailed description, the examples depicted in the figures and further described for the purpose of illustration throughout the application describe non-limiting embodiments, and in some cases may simplify certain processes or omit features or steps for the purpose of clearer illustration.

Figure 1:
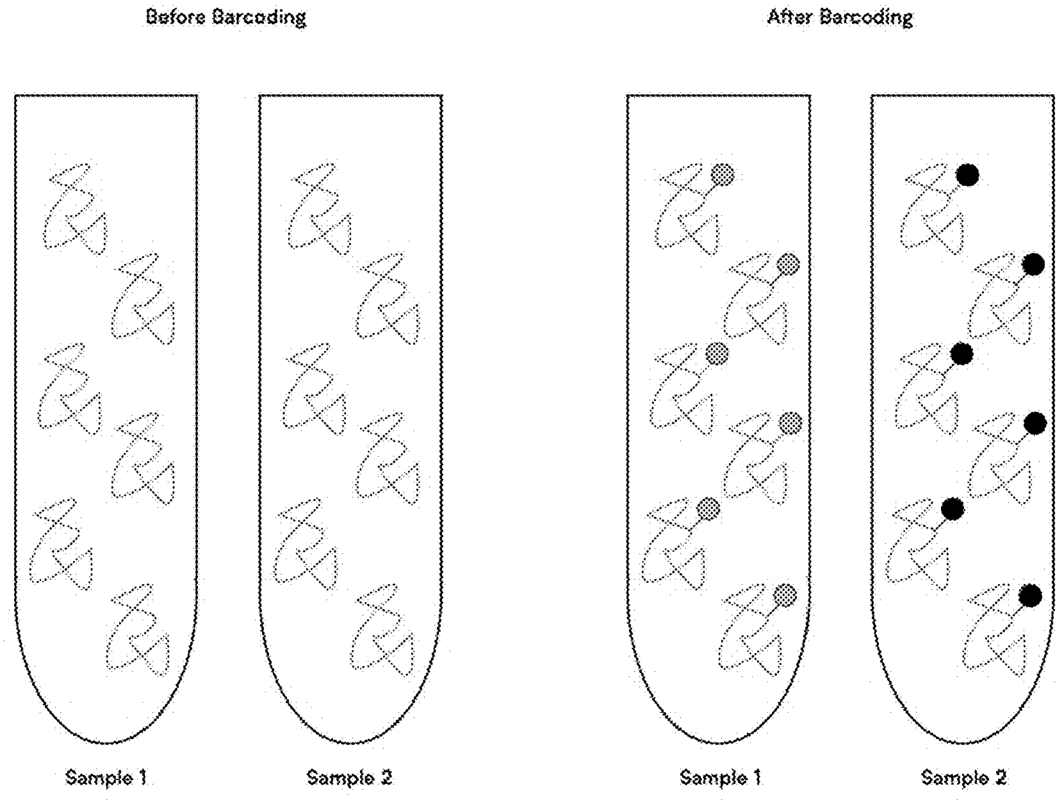

FIG. 1 provides an exemplary illustration of two samples before (left) and after (right) barcoding. The barcode molecules of the first sample are distinguishable from the barcoded molecules of the second sample.

Figure 2:
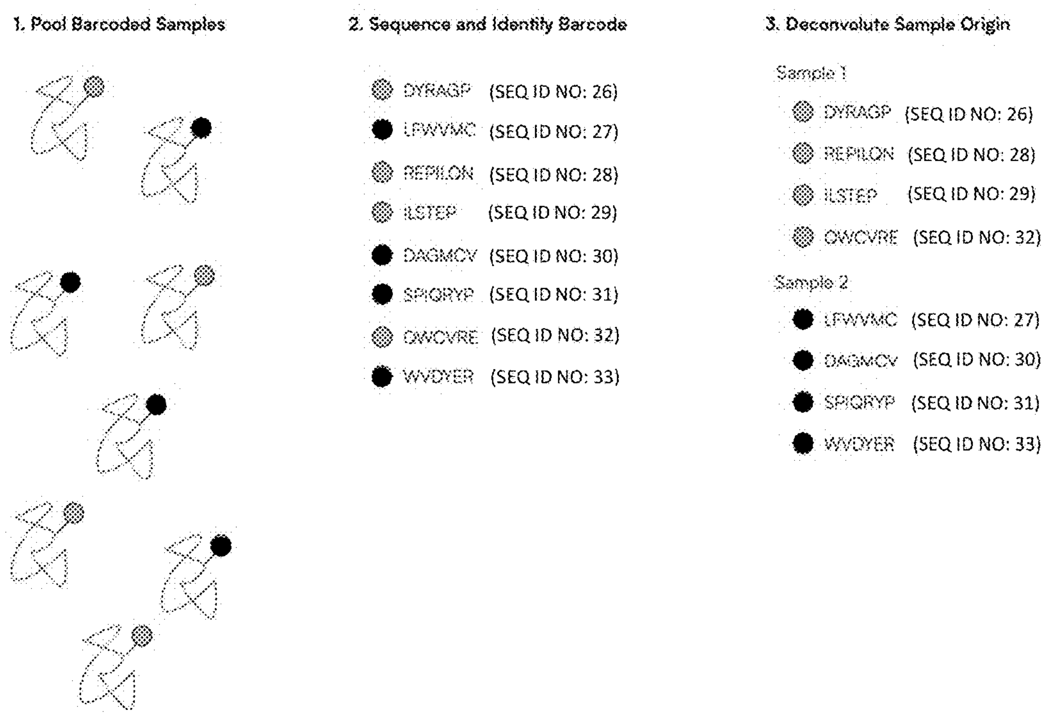

FIG. 2 provides an exemplary embodiment of a workflow following protein barcoding. Barcoded samples are pooled into a multiplex sample (1). The sequences and barcode identities (i.e., sample origins) of the polypeptides in the multiplex sample are then determined/identified (concurrently or sequentially) (2). Finally, the sequences are separated into groups based on their barcode identities (i.e., sample origins) (3).

Figure 3A:
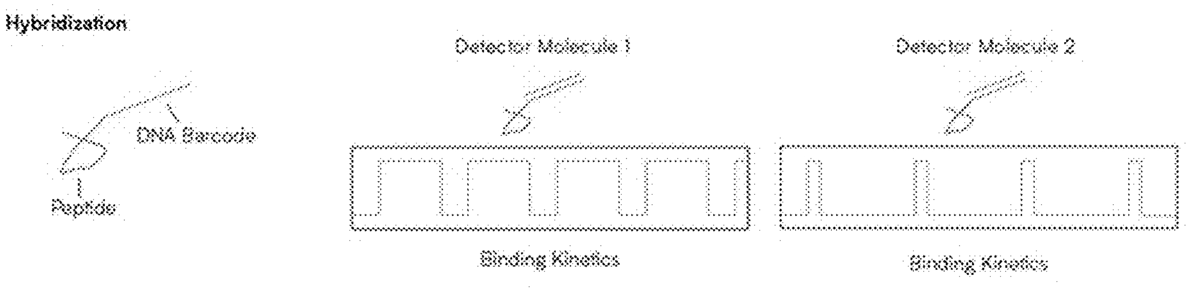
Figure 3B:
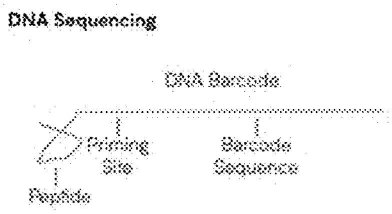
Figure 3C:
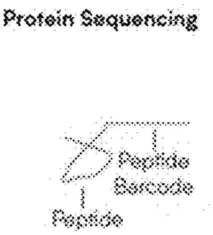
Figure 3D:
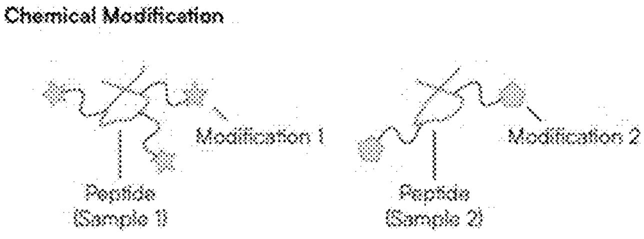
Figure 3E:
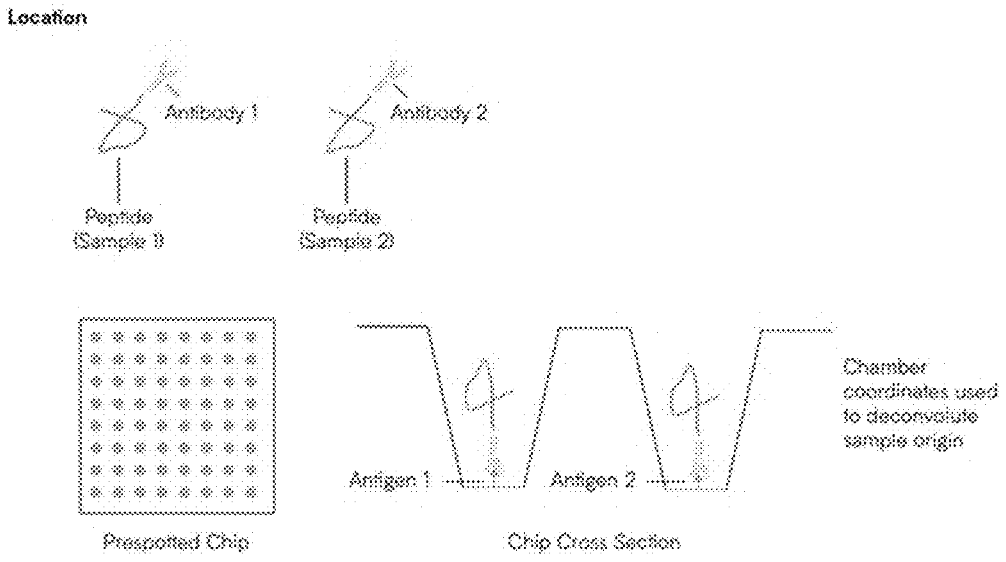

FIGS. 3A-3E provide exemplary barcode molecules and methods of detecting the exemplary barcodes. FIG. 3A. A barcode molecule may comprise a polynucleic acid portion ("DNA Barcode"), which is identified via hybridization using a detector molecule comprising a polynucleic acid portion (which may also comprise a luminescent molecule). FIG. 3B. A barcode molecule may comprise a polynucleic acid portion, which is identified by DNA sequencing. FIG. 3C. A barcode molecule may comprise a polypeptide portion (e.g., a short polypeptide tag), which is identified by polypeptide sequencing. FIG. 3D. A barcode molecule may comprise of a sample which has been chemically modified (e.g., tyrosine phosphorylation), which is identified by the chemical modification by polypeptide sequencing. FIG. 3E. A barcode molecule may comprise a polypeptide portion (e.g., an antibody; here "Antibody A" or "Antibody B"), which is identified by localization on a chip (e.g., via binding with a detector molecule; herein "Antigen A" or "Antigen B").

Figure 4:
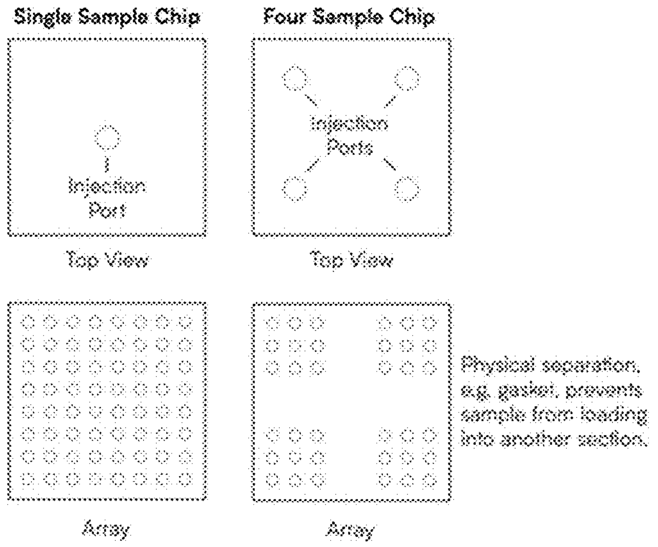

FIG. 4 provides an exemplary embodiment of barcoding by physical separation. A chip can by physically divided and optionally include other barcode molecules if desired.

Figure 5:
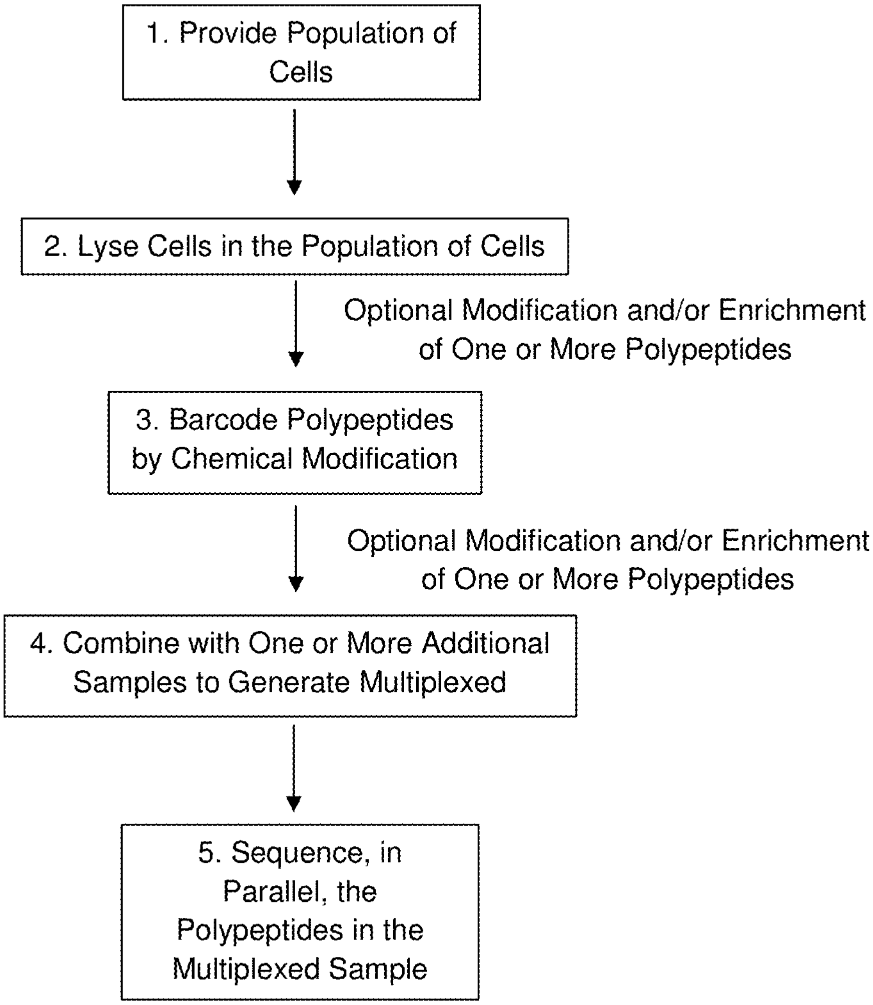

FIG. 5 provides an illustration depicting an exemplary workflow of preparing a multiplexed sample for polypeptide sequencing.

Figure 6:
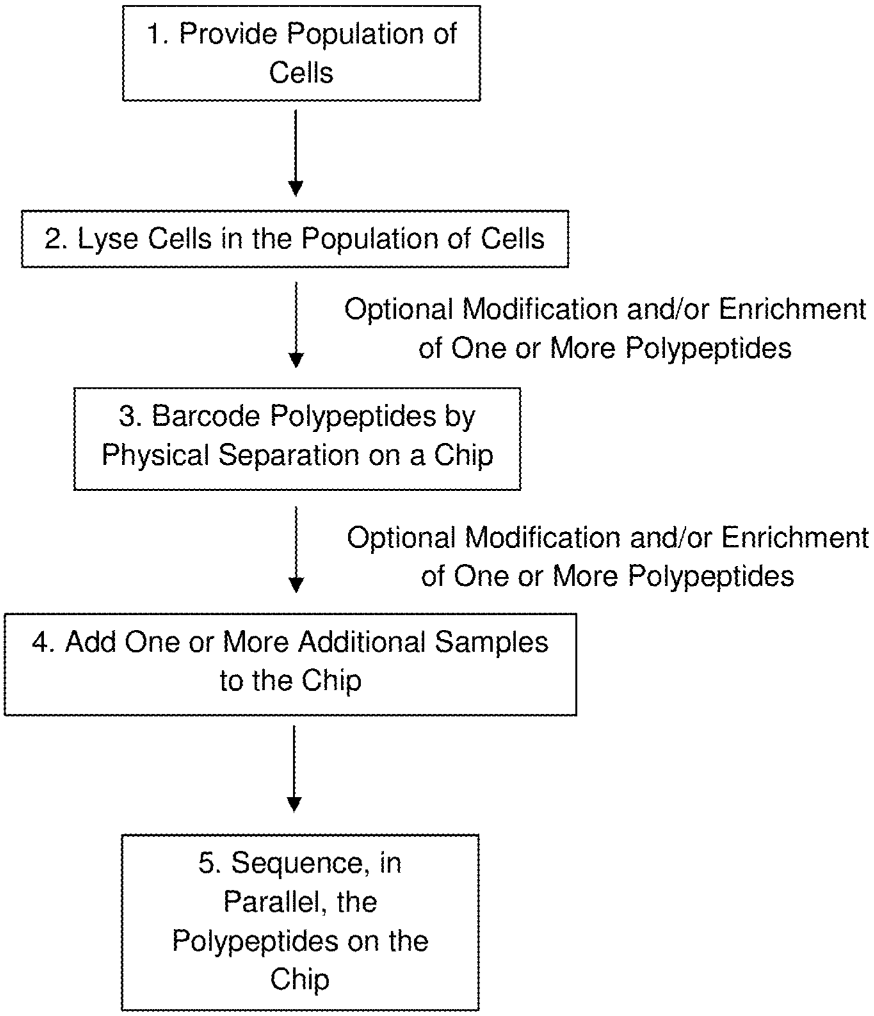

FIG. 6 provides an illustration depicting an exemplary workflow of preparing a multiplexed sample for polypeptide sequencing.

Figure 7:
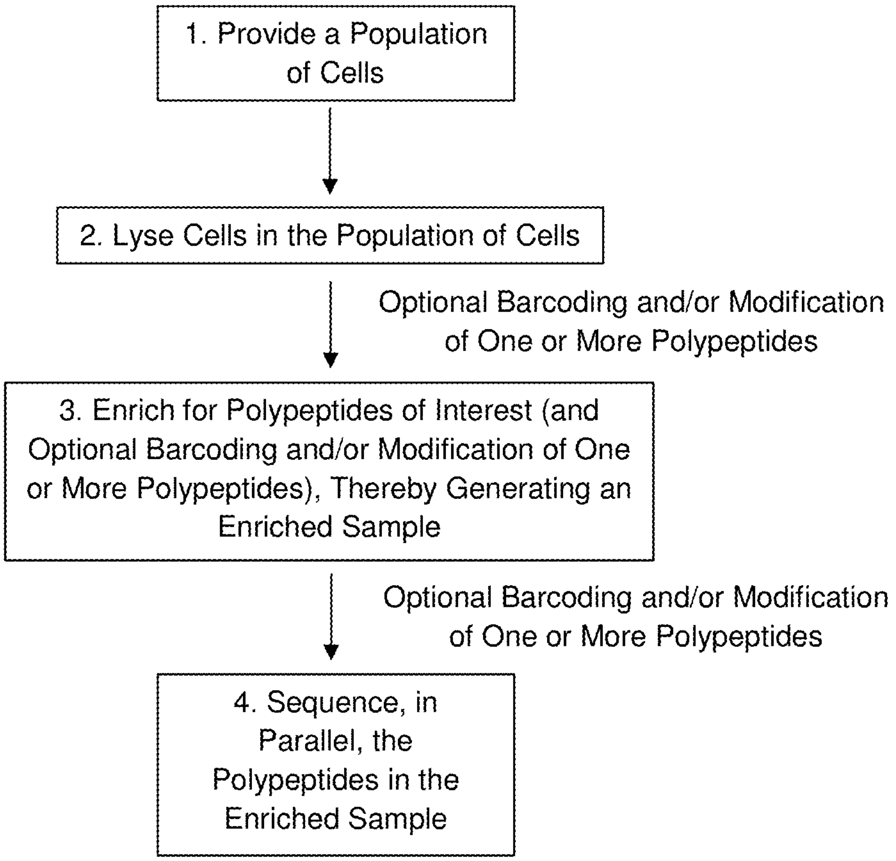

FIG. 7 provides an illustration depicting an exemplary workflow of preparing an enriched sample.

Figure 8:
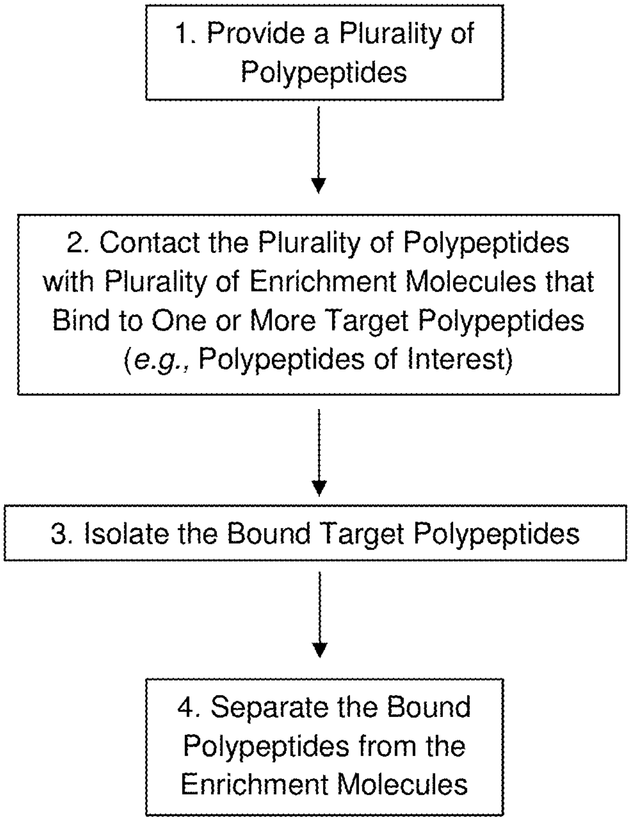

FIG. 8 provides an illustration depicting an exemplary workflow of preparing an enriched sample.

Figure 9:
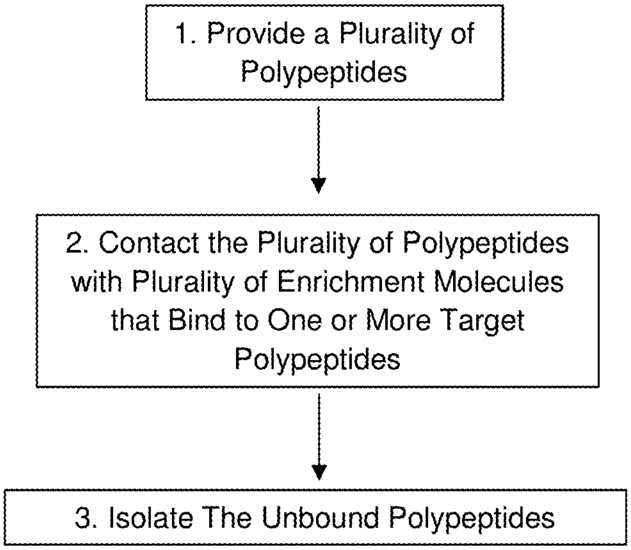

FIG. 9 provides an illustration depicting an exemplary workflow of preparing an enriched sample.

Figure 10:
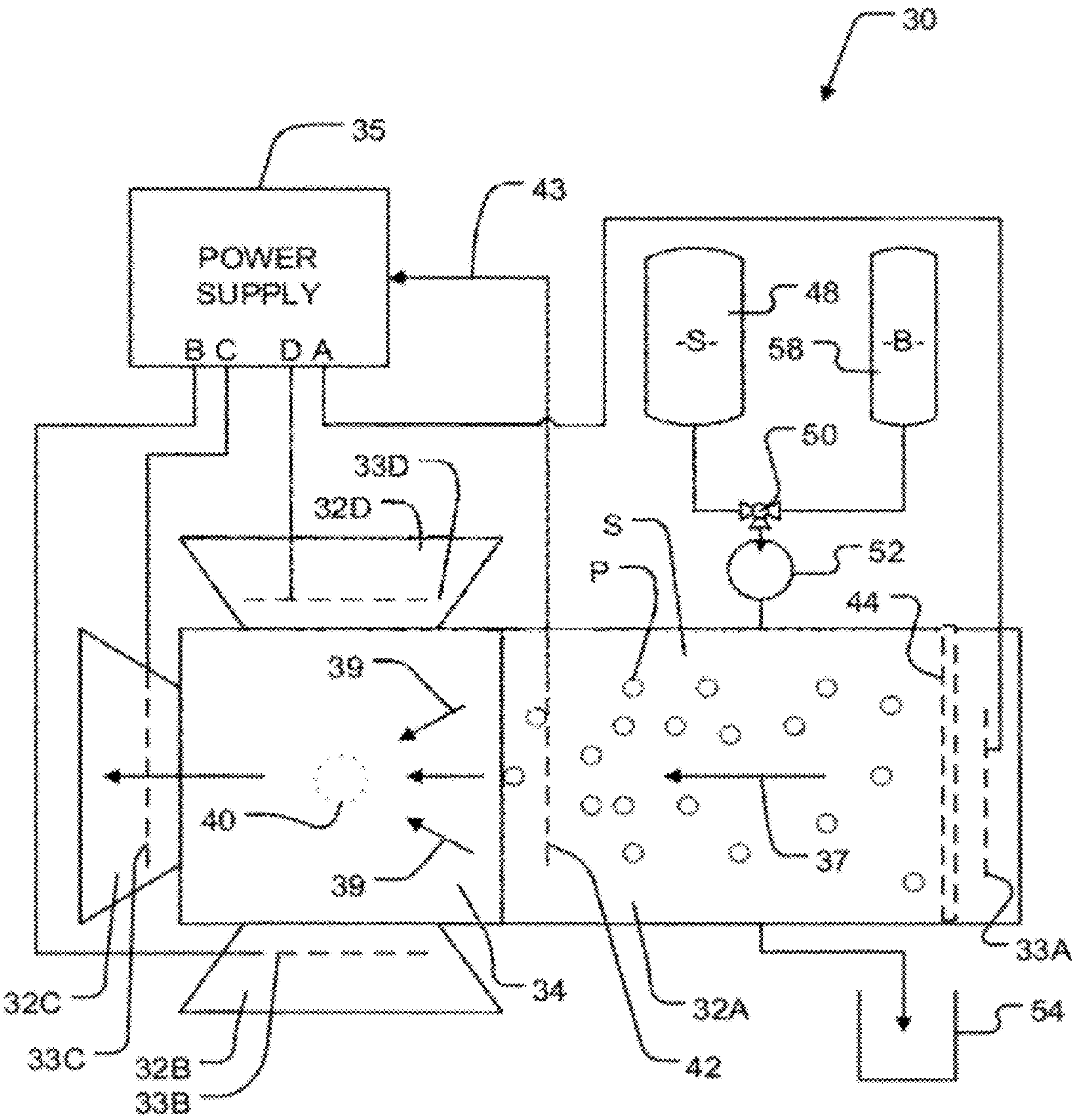

FIG. 10 provides an illustration depicting an exemplary apparatus for preparing an enriched and/or multiplexed sample.

DETAILED DESCRIPTION

As described herein, the inventors have recognized and appreciated that differential binding interactions can provide an additional or alternative approach to conventional labeling strategies in polypeptide sequencing. Conventional polypeptide sequencing can involve labeling each type of amino acid with a uniquely identifiable label. This process can be laborious and prone to error, as there are at least twenty different types of naturally occurring amino acids in addition to numerous post-translational variations thereof. In some aspects, the disclosure relates to the discovery of techniques involving the use of amino acid recognition molecules which differentially associate with different types of amino acids to produce detectable characteristic signatures indicative of an amino acid sequence of a polypeptide.

In some aspects, the disclosure relates to the discovery that a polypeptide sequencing reaction can be monitored in real-time using only a single reaction mixture (e.g., without requiring iterative reagent cycling through a reaction vessel). Conventional polypeptide sequencing reactions can involve exposing a polypeptide to different reagent mixtures to cycle between steps of amino acid detection and amino acid cleavage. Accordingly, in some aspects, the disclosure relates to an advancement in next generation sequencing that allows for the analysis of polypeptides by amino acid detection throughout an ongoing degradation reaction in real-time.

The proteomic analysis of an individual organism can provide insights into cellular processes and response patterns, which lead to improved diagnostic and therapeutic strategies. The ability to sequence multiple samples simultaneously (i.e., in multiplex) would increase the efficiency of, and decrease the costs associated with, proteomic analysis of individual samples. As such, in some aspects, the disclosure relates to methods of preparing multiplexed samples for polypeptide sequencing, which leverage polypeptide barcoding to facilitate multiplex proteomic analysis.

In some aspects, the disclosure relates to methods of preparing a multiplexed sample for polypeptide sequencing. In some embodiments, the method comprises: (i) providing a plurality of samples (e.g., from different subjects/patients); (ii) tagging polypeptides of each sample with a different barcode; and (iii) combining the tagged polypeptides to generate a single multiplexed sample for polypeptide sequencing.

In some aspects, the disclosure relates to methods of determining at least the partial amino acid sequences and origins of polypeptides in a multiplexed sample, the methods comprising: (i) preparing a multiplexed sample comprising barcoded polypeptides; (ii) detecting the barcode identities of the barcoded polypeptides in the multiplexed sample; (iii) and sequencing, in parallel, the polypeptides in the multiplexed sample; wherein (iii) occurs before, after, or concurrently with (ii). The barcodes detected in (ii) may be used to extract the sample-specific sequence information from the multiplexed data.

Also provide herein are compositions, kits and devices useful for the same.

I. Methods of Preparing a Complex Sample

In some aspects, the disclosure relates to methods of preparing a complex sample (e.g., a complex polypeptide sample). As used herein, the term "complex sample" refers to a sample comprising a plurality of molecules (e.g., polypeptides, polynucleic acids, metabolites, etc.), at least two of which are chemically unique. In some embodiments, a complex sample comprises a plurality of polypeptides, wherein the plurality comprises at least two polypeptides that comprise different amino acid sequences.

Typically, the complex sample is derived from a population of cells (e.g., produced by a population of cells). In some embodiments, the population of cells consists of a single cell. In other embodiments, the population of cells comprises two or more cells.

For example, in some embodiments the population of cells comprises at least 5, at least 10, at least 20, at least 30, at least 40, at least 50, at least 60, at least 70, at least 80, at least 90, at least 100, at least 150, at least 200, at least 250, at least 300, at least 350, at least 400, at least 450, a least 500, at least 600, at least 700, at least 800, at least 900, at least $1\times10^3$, at least $1\times10^4$, at least $1\times10^5$, at least $1\times10^6$, at least $1\times10^7$, at least $1\times10^8$, at least $1\times10^9$, or at least $1\times10^{10}$ cells.

In some embodiments, the population comprises 1-5, 1-10, 1-20, 1-30, 1-50, 1-60, 1-70, 1-80, 1-90, 1-100, 1-150, 1-200, 1-250, 1-300, 1-350, 1-400, 1-450, 1-500, 1-600, 1-700, 1-800, 1-900, $1\text{-}1\times10^3$, $1\text{-}1\times10^4$, $1\text{-}1\times10^5$, $1\text{-}1\times10^6$, $1\text{-}1\times10^7$, $1\text{-}1\times10^8$, $1\text{-}1\times10^9$, $1\text{-}1\times10^{10}$, 100-150, 100-200, 100-250, 100-300, 100-350, 100-400, 100-450, 100-500, 100-600, 100-700, 100-800, 100-900, $100\text{-}1\times10^3$, $100\text{-}1\times10^4$, $100\text{-}1\times10^5$, $100\text{-}1\times10^6$, $100\text{-}1\times10^7$, $100\text{-}1\times10^8$, $100\text{-}1\times10^9$, $100\text{-}1\times10^{10}$, $1\times10^3\text{-}1\times10^4$, $1\times10^3\text{-}1\times10^5$, $1\times10^3\text{-}1\times10^6$, $1\times10^3\text{-}1\times10^7$, $1\times10^3\text{-}1\times10^8$, $1\times10^3\text{-}1\times10^9$, $1\times10^3\text{-}1\times10^{10}$, $1\times10^4\text{-}1\times10^5$, $1\times10^4\text{-}1\times10^6$, $1\times10^4\text{-}1\times10^7$, $1\times10^4\text{-}1\times10^8$, $1\times10^4\text{-}1\times10^9$, $1\times10^4\text{-}1\times10^{10}$, $1\times10^5\text{-}1\times10^6$, $1\times10^5\text{-}1\times10^7$, $1\times10^5\text{-}1\times10^8$, $1\times10^5\text{-}1\times10^9$, or $1\times10^5\text{-}1\times10^{10}$ cells.

A population of cells may comprise prokaryotic cells and/or eukaryotic cells. A population of cells may comprise a plurality of homogeneous cells. Alternatively, a population of cells may comprise a plurality of heterogeneous cells.

A population of cells may be isolated from a subject (e.g., a multicellular or symbiotic organism). In some embodiments, the subject is a mouse, rat, rabbit, guinea pig, hamster, pig, sheep, dog, primate, cat, or human.

Methods of isolating populations of cells are known to those having skill in the art. For example, a method of preparing a complex sample may comprise biopsy, dissection (e.g., microdissection, such as laser capture), limited dilution, micromanipulation, immunomagnetic cell separation, fluorescence-activated cell sorting, density gradient centrifugation, immunodensity cell isolation, microfluidic cell sorting, sedimentation, adhesion, or a combination thereof.

In some embodiments, the method of preparing a complex sample comprises lysing a population of cells, thereby generating a lysis sample comprising a plurality of molecules (e.g., polypeptides, polynucleic acids, metabolites, etc.). Methods of lysing a population of cells are known to those having ordinary skill in the art. In some embodiments, a sample comprising cells is lysed using any one of known physical or chemical methodologies to release a target molecule from said cells. In some embodiments, a sample may be lysed using an electrolytic method, an enzymatic method, a detergent-based method, and/or mechanical homogenization. In some embodiments, if a sample does not comprise cells or tissue (e.g., a sample comprising purified polypeptides), a lysis step may be omitted.

Alternatively, or in addition, a method of preparing a complex sample may comprise subcellular fractionation (i.e., the isolation of one or more cellular compartment, such as endosomes, snyaptosomes, cytoplasm, nucleoplasm, chromatin, mitochondria, peroxisomes, lysosomes, melanosomes, exosomes, Golgi apparatus, endoplasmic reticulum, centrosomes, pseudopodia, or a combination thereof).

Molecules derived from the same cell population are described herein as having the same "origin."

II. Methods of Preparing a Multiplexed Sample

In some aspects, the disclosure relates to methods of preparing a multiplexed sample. As used herein, the term "multiplexed sample" refers to a sample comprising at least two subsamples having different origins (e.g., two or more samples, each prepared from a different population of cells or plurality of molecules).

In some embodiments, a multiplexed sample comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, at least 100, at least 200, at least 300, at least 400, at least 500, a least 600, at least 700, at least 800, at least 900, or at least 1000 subsamples each having different origins.

In some embodiments, a multiplexed sample comprises 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-25, 2-30, 2-35, 2-40, 2-45, 2-50, 2-60, 2-70, 2-80, 2-90, 2-100, 2-200, 2-300, 2-400, 2-500, 2-600, 2-700, 2-800, 2-900, 2-1000, 5-10, 5-15, 5-20, 5-25, 5-30, 5-35, 5-40, 5-45, 5-50, 5-60, 5-70, 5-80, 5-90, 5-100, 5-200, 5-300, 5-400, 5-500, 5-600, 5-700, 5-800, 5-900, 10-15, 10-20, 10-25, 10-30, 10-35, 10-40, 10-45, 10-50, 10-60, 10-70, 10-80, 10-90, 10-100, 10-200, 10-300, 10-400, 10-500, 10-600, 10-700, 10-800, 10-900, 10-1000, 20-30, 20-40, 20-50, 20-60, 20-70, 20-80, 20-90, 20-100, 20-200, 20-300, 20-400, 20-500, 20-600, 20-700, 20-800, 20-900, 20-1000, 50-60, 50-70, 50-80, 50-90, 50-100, 50-200, 50-300, 50-400, 50-500, 50-600, 50-700, 50-800, 50-900, 50-1000, 100-200, 100-300, 100-400, 100-500, 100-600, 100-700, 100-800, 100-900, 100-1000, 500-600, 500-700, 1500-800, 500-900, or 500-1000 subsamples each having different origins.

In some embodiments, a multiplexed sample comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 subsamples each having different origins.

Each subsample in a multiplexed sample may comprise a plurality of molecules. In some embodiments, one or more of the subsamples in a multiplexed sample comprises: the molecules (e.g., polypeptides) of a complex sample prepared from a cell population (which may be a single cell) (see "Methods of Preparing a Complex Sample"); or the molecules (e.g., polypeptides) of an enriched sample (see "Methods of Preparing an Enriched Sample"). In some embodiments, the plurality of molecules of a subsample are derived from a single molecule (e.g., through the fragmentation of a single polypeptide).

Each subsample in a multiplexed sample may comprises a single molecule (e.g., a single polypeptide). In some embodiments, one or more subsample in a multiplexed sample comprises a single molecule (e.g., a single polypeptide).

Typically, at least a subset of the molecules in each subsample in a multiplexed sample can be distinguished from the molecules of the other subsamples in the multiplexed sample. For example, in some embodiments, at least a subset of the polypeptides in each subsample in a multiplexed sample can be distinguished from the polypeptides of the other subsamples in the multiplexed sample. In this way, the origins of at least a subset of the molecules in a multiplexed sample can be identified.

As such, in some embodiments, at least one of the subsamples in a multiplexed sample comprises barcoded molecules, each barcoded molecule comprising a barcode unique to the subsample (i.e., a unique barcode). A barcode is considered unique to a subsample, if the barcode is not found on a molecule of any other subsample in the multiplexed sample.

In some embodiments, two or more of the subsamples in a multiplexed sample comprise barcoded molecules. In some embodiments, each of the subsamples in a multiplexed sample comprises barcoded molecules. In some embodiments, all but one of the subsamples in a multiplexed sample comprise barcoded molecules.

Within a multiplexed sample, the barcoded molecules of each subsample comprising barcoded molecules (i.e., each "labeled subsample") comprise unique barcodes. In some embodiments, each of the barcoded molecules in a labeled subsample comprise the same barcode. In some embodiments, the barcode molecules in a labeled subsample comprise a combination of unique barcodes. For example, in some embodiments, a labeled subsample comprises a unique combination of 2, 3, 4, 5, 6, 7, 8, 9, 10, 11, 12, 13, 14, 15, 16, 17, 18, 19, or 20 barcoded molecules.

In some embodiments, a labeled subsample comprises barcoded polypeptides and: barcoded DNA molecules, barcoded RNA molecules, barcoded cDNA molecules, barcoded metabolites, or a combination thereof, wherein: the barcoded polypeptides comprise a first barcode (or a first combination of barcodes); the barcoded DNA molecules comprise a second barcode (or a second combination of barcodes); the barcoded RNA molecules in the subsample comprise a third barcode (or a third combination of barcodes); the barcoded cDNA molecules comprise a fourth barcode (or a fourth combination of barcodes); the barcoded metabolites comprise a fifth barcode (or a fifth combination of barcodes); or a combination thereof.

In some embodiments, a method of preparing a multiplexed sample comprises: (i) contacting a population of cells with a barcode component to produce a sample (i.e., a first labeled subsample) comprising barcoded molecules (e.g., barcoded polypeptides); and (ii) combining the sample of (i) with one or more supplemental sample (i.e., one or more additional subsample) to generate a multiplexed sample for parallel molecule sequencing (e.g., polypeptide sequencing).

In some embodiments, a method of preparing a multiplexed sample comprises: (i) contacting a plurality of molecules with a barcode component to produce a sample (i.e., a first labeled subsample) comprising barcoded molecules (e.g., barcoded polypeptides); and (ii) combining the sample of (i) with one or more supplemental sample (i.e., one or more additional subsample) to generate a multiplexed sample for parallel molecule sequencing (e.g., polypeptide sequencing).

In some of the embodiments described in the preceding two paragraphs, step (ii) further comprises depositing the multiplexed sample on or within a solid substrate. In some embodiments, the solid substrate comprises a plurality of immobilized (e.g., covalently-attached) detector molecules, wherein one or more the detector molecules interacts with a barcode of a barcoded molecule of the multiplexed sample. In some embodiments, the solid substrate is a chip array.

In some embodiments, a method of preparing a multiplexed sample comprises: (i) providing at least two populations of molecules (e.g., polypeptides); (ii) depositing the at least two populations of molecules of (i) on or within a solid substrate, wherein each population of molecules remains physically separated from the other populations of molecules in (i); thereby preparing a multiplexed sample for parallel polypeptide sequencing.

A. Methods of Polypeptide Barcoding

In some aspects, the disclosure relates to methods of barcoding molecules (e.g., polypeptides, DNA, RNA, cDNA, metabolites, etc.) of a sample. In some embodiments, the sample comprises living cells. In some embodiments, the sample is a complex sample prepared from a cell population (which may be a single cell) (see "Methods of Preparing a Complex Sample"). In some embodiments, the sample is an enriched sample (see "Methods of Preparing an Enriched Sample"). In some embodiments, the sample comprises a single molecule (e.g., a polypeptide) or fragments derived from a single molecule (e.g., fragments of the polypeptide).

Of particular relevance here, the disclosure relates to methods of barcoding polypeptides. Polypeptides may be barcoded by chemical modification and/or physical separation.

(i) Chemical Modification

A polypeptide (or a plurality of polypeptides) may be barcoded by chemical modification. Chemical modification of a polypeptide changes the chemical composition of the polypeptide and can occur during synthesis of the polypeptide (in vivo or in vitro) or after synthesis of the polypeptide (i.e., post-translationally). A polypeptide may be modified at any position within its amino acid sequence. Methods of generating polypeptide conjugates (to arrive at a barcoded polypeptide) have been previously described, and are known to those having ordinary skill in the art. See e.g., Corey et al., Science, 1987; 238: 1401-1403; Kukolka et al., Org. Biomol. Chem., 2004; 2: 2203-2206; Debets et al., Chem. Commun., 2010; 46: 97-99; Takeda et al., Bioorg. Med. Chem. Lett., 2004; 14: 2407-2410; Yang et al., Bioconjug. Chem., 2015; 26: 1381-1395; Rosen et al., Nat. Chem., 2014; 6: 804-809; Cong et al., Bioconjug. Chem., 2012; 23: 248-263; Mattson, G., et al. Molecular Biology Reports, 1993; 17:167-183.

In some embodiments, a polypeptide (or a plurality of polypeptides) is barcoded through a method comprising contacting a population of cells with a barcode component to produce a sample comprising barcoded polypeptides. In such an instance, the polypeptide (or plurality of polypeptides) may be modified during synthesis or after synthesis (i.e., post-translationally).

In some embodiments, a polypeptide (or a plurality of polypeptides) is barcoded through a method comprising contacting the polypeptide (or the plurality of polypeptides) with a barcode component to produce a sample comprising barcoded polypeptides. In such an instance, the polypeptide (or plurality of polypeptides) would be modified after synthesis (i.e., post-translationally).

A barcode component may comprise a modifying agent. The modifying agent may comprise an endoprotease having a distinct cleavage pattern. Examples of endoproteases are known to those having ordinary skill in the art and include, but are not limited to, trypsin, chymotrypsin, elastase, thermolysin, pepsin, glutamyl endopeptidase, neprilysin, Lys-C, Arg-C, Asp-N, Lys-N, Glu-C, WaLP, and MaLP. See e.g., Giansanti et al., Nat. Protoc., 2016 Apr. 28; 11(5): 993-1006. The polypeptide modifying agent may comprise an enzyme capable of modifying polypeptides with a post-translational modification. Examples of post-translational modifications are known to those having skill in the art and include, but are not limited to, acetylation, adenylylation, ADP-ribosylation, alkylation (e.g., methylation), amidation, arginylation, biotinylation, butyrylation, carbamylation, carbonylation, carboxylation, citrullination, deamidation, eliminylation, formylation, glycosylation (e.g., N-linked glycosylation, O-linked glycosylation), glipyatyon, glycation, hydroxylation, iodination, ISGylation, isoprenylation, lipoylation, malonylation, myristoylation, neddylation, nitration, oxidation, palmitoylation pegylation, phosphorylation, phosphopantetheinylation, polyglcylation, polyglutamylation, prenylation, propionylation, pupylation, S-glutathionylation, S-nitrosylation, S-sulfenylation, S-sulfinylation, S-sulfonylation, succinylation, sulfation, SUMOylation, and ubiquitination. Enzymes responsible for modifying polypeptides in these ways are also known to those having skill in the art.

Alternatively or in addition, a barcode component may comprises a plurality of barcode molecules. In some embodiments, a barcode component consists of a plurality of barcode molecules. In some embodiments, a barcode component may further comprise one or more reagents (e.g., enzymes, compounds, small molecules, buffers, and the like) to facilitate the covalently attachment of a barcode molecule to a polypeptide. Barcode molecules may be covalently attached to a polypeptide at any position. In some embodiments, a barcode molecule is covalently attached to a polypeptide at an amino acid position within 10, 9, 8, 7, 6, 5, 4, 3, or 2 amino acids of its terminus (N-terminus or C-terminus). In some embodiments, a barcode molecule is covalently attached to a polypeptide at its N-terminus. In some embodiments, a barcode is covalently attached to a polypeptide at its C-terminus.

In some embodiments, each of the barcode molecules of a barcode component are chemically identical. In some embodiments, a barcode component comprises two or more chemically distinct barcode molecules. For example, a barcode component may comprise 2, 3, 4, 5, 6, 7, 8, 9, 10, 11, 12, 13, 14, 15, 16, 17, 18, 19, or 20 chemically distinct barcode molecules.

A barcode molecule of a barcode component may be an unnatural amino acid (i.e., non-canonical amino acid). Examples of unnatural amino acids are known to those having skill in the art and include, but are not limited to, homoallylglycine (Hag), homopropargylglycine (Hpg), azidohomoalanine (Aha), azidonorleucine (Anl), azidophenylalanine (Azf), acetylphenylalanine (Acf), and propargyloxyphenylalanine (Pxf). In some embodiments, wherein the barcode component comprises unnatural amino acid barcode molecules, the barcode component further comprises one or more non-natural tRNA (or a nucleic acid encoding an expressible form of a non-natural tRNA). Examples of non-natural tRNAs are known to those having skill in the art.

Alternatively, or in addition, a barcode molecule of a barcode component may comprise a polynucleic acid portion, a polypeptide portion, a small molecule portion, a linker (e.g., a peg-like linker), a dendrimer, a scaffold, or a combination thereof. In some embodiments, a barcode molecule of a barcode component comprises a polynucleic acid portion, a polypeptide portion, a small molecule portion, a linker (e.g., a peg-like linker), a dendrimer, a scaffold, or a combination thereof.

In some embodiments, a barcode molecule comprises a polynucleic acid portion. In some embodiments, a barcode molecule comprises two or more polynucleic acid portions. In embodiments wherein a barcode molecule comprises multiple polynucleic acid portions: each polynucleic acid portion may be identical; a subset of the polynucleic acid portions may be identical; or each polynucleic acid portion may be chemically distinct.

In some embodiment, the polynucleic acid portion is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length.

In some embodiment, the polynucleic acid portion is at least 5, at least 10, at least 15, at least 20, at least 25, at least 30, at least 40, at least 50, at least 60, at least 70, at least 80, at least 90, at least 100, at least 150, at least 200, at least 250, at least 300, at least 350, at least 400, at least 450, or at least 500 nucleotides in length.

In some embodiments, the polynucleic acid portion is 5-10, 5-15, 5-20, 5-25, 5-30, 5-40, 5-50, 5-60, 5-70, 5-80, 5-90, 5-100, 5-150, 5-200, 5-250, 5-300, 5-350, 5-400, 5-450, 5-500, 10-15, 10-20, 10-25, 10-30, 10-40, 10-50, 10-60, 10-70, 10-80, 10-90, 10-100, 10-150, 10-200, 10-250, 10-300, 10-350, 10-400, 10-450, 10-500, 20-30, 20-40, 20-50, 20-60, 20-70, 20-80, 20-90, 20-100, 20-150, 20-200, 20-250, 20-300, 20-350, 20-400, 20-450, 20-500, 50-75, 50-100, 50-150, 50-200, 50-250, 50-500, 50-350, 50-400, 50-450, 50-500, 100-200, 100-250, 100-500, 100-350, 100-400, 100-450, or 100-500 nucleotides in length.

In some embodiment, the polynucleic acid portion is an aptamer.

In some embodiments, a barcode molecule comprises a polypeptide portion. In some embodiments, a barcode molecule comprises two or more polypeptide portions. In embodiments wherein a barcode molecule comprises multiple polypeptide portions: each polypeptide portion may be identical; a subset of the polypeptide portions may be identical; or each polypeptide portion may be chemically distinct.

In some embodiment, the polypeptide portion is 2, 3, 4, 5, 6, 7, 8, 9, 10, 11, 12, 13, 14, 15, 16, 17, 18, 19, or 20 amino acids in length. In some embodiments, the polypeptide portion is at least 5, at least 10, at least 15, at least 20, at least 25, at least 30, at least 40, at least 50, at least 60, at least 70, at least 80, at least 90, at least 100, at least 150, at least 200, at least 250, at least 300, at least 350, at least 400, at least 450, or at least 500 amino acids in length. In some embodiments, the polypeptide portion is 5-10, 5-15, 5-20, 5-25, 5-30, 5-40, 5-50, 5-60, 5-70, 5-80, 5-90, 5-100, 5-150, 5-200, 5-250, 5-300, 5-350, 5-400, 5-450, 5-500, 10-15, 10-20, 10-25, 10-30, 10-40, 10-50, 10-60, 10-70, 10-80, 10-90, 10-100, 10-150, 10-200, 10-250, 10-300, 10-350, 10-400, 10-450, 10-500, 20-30, 20-40, 20-50, 20-60, 20-70, 20-80, 20-90, 20-100, 20-150, 20-200, 20-250, 20-300, 20-350, 20-400, 20-450, 20-500, 50-75, 50-100, 50-150, 50-200, 50-250, 50-500, 50-350, 50-400, 50-450, 50-500, 100-200, 100-250, 100-500, 100-350, 100-400, 100-450, or 100-500 amino acids in length.

In some embodiments, the polypeptide portion is an aptamer. In some embodiment, the polypeptide portion is an antibody. In some embodiments, the polypeptide portion is an antigen.

In some embodiments, a barcode molecule comprises a small molecule portion. In some embodiments, a barcode molecule comprises two or more small molecule portions. In embodiments wherein a barcode molecule comprises multiple small molecule portions: each small molecule portion may be identical; a subset of the small molecule portions may be identical; or each small molecule portion may be chemically distinct.

In some embodiments, the small molecule portion comprises biotin.

In some embodiments, the small molecule portion comprises a drug or a luminescent molecule (or a fluorescent molecule). Examples of drugs and luminescent molecules suitable for the methods described herein are known to those having skill in the art. As used herein, a luminescent molecule is a molecule that absorbs one or more photons and may subsequently emit one or more photons after one or more time durations.

In some embodiments, a luminescent molecule may comprise a first and second chromophore. In some embodiments, an excited state of the first chromophore is capable of relaxation via an energy transfer to the second chromophore. In some embodiments, the energy transfer is a Förster resonance energy transfer (FRET). Such a FRET pair may be useful for providing a luminescent label with properties that make the label easier to differentiate from amongst a plurality of luminescent labels in a mixture. In yet other embodiments, a FRET pair comprises a first chromophore of a first luminescent label and a second chromophore of a second luminescent label. In certain embodiments, the FRET pair may absorb excitation energy in a first spectral range and emit luminescence in a second spectral range.

In some embodiments, a luminescent molecule refers to a fluorophore or a dye. Typically, a luminescent molecule comprises an aromatic or heteroaromatic compound and can be a pyrene, anthracene, naphthalene, naphthylamine, acridine, stilbene, indole, benzindole, oxazole, carbazole, thiazole, benzothiazole, benzoxazole, phenanthridine, phenoxazine, porphyrin, quinoline, ethidium, benzamide, cyanine, carbocyanine, salicylate, anthranilate, coumarin, fluorescein, rhodamine, xanthene, or other like compound.

In some embodiments, a luminescent molecule comprises a dye selected from one or more of the following: 5/6-Carboxyrhodamine 6G, 5-Carboxyrhodamine 6G, 6-Carboxyrhodamine 6G, 6-TAMRA, Abberior® STAR 440SXP, Abberior® STAR 470SXP, Abberior® STAR 488, Abberior® STAR 512, Abberior® STAR 520SXP, Abberior® STAR 580, Abberior® STAR 600, Abberior® STAR 635, Abberior® STAR 635P, Abberior® STAR RED, Alexa Fluor® 350, Alexa Fluor® 405, Alexa Fluor® 430, Alexa Fluor® 480, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610-X, Alexa Fluor® 633, Alexa Fluor® 647, Alexa Fluor® 660, Alexa Fluor® 680, Alexa Fluor® 700, Alexa Fluor® 750, Alexa Fluor® 790, AMCA, ATTO 390, ATTO 425, ATTO 465, ATTO 488, ATTO 495, ATTO 514, ATTO 520, ATTO 532, ATTO 542, ATTO 550, ATTO 565, ATTO 590, ATTO 610, ATTO 620, ATTO 633, ATTO 647, ATTO 647N, ATTO 655, ATTO 665, ATTO 680, ATTO 700, ATTO 725, ATTO 740, ATTO Oxa12, ATTO Rho101, ATTO Rho11, ATTO Rho12, ATTO Rho13, ATTO Rho14, ATTO Rho3B, ATTO Rho6G, ATTO Thio12, BD Horizon™ V450, BODIPY® 493/501, BODIPY® 530/550, BODIPY® 558/568, BODIPY® 564/570, BODIPY® 576/589, BODIPY® 581/591, BODIPY® 630/650, BODIPY® 650/665, BODIPY® FL, BODIPY® FL-X, BODIPY® R6G, BODIPY® TMR, BODIPY® TR, CAL Fluor® Gold 540, CAL Fluor® Green 510, CAL Fluor® Orange 560, CAL Fluor® Red 590, CAL Fluor® Red 610, CAL Fluor® Red 615, CAL Fluor® Red 635, Cascade® Blue, CF™350, CF™405M, CF™405S, CF™488A, CF™514, CF™532, CF™543, CF™546, CF™555, CF™568, CF™594, CF™620R, CF™633, CF™633-V1, CF™640R, CF™640R-V1, CF™640R-V2, CF™660C, CF™660R, CF™680, CF™680R, CF™680R-V1, CF™750, CF™770, CF™790, Chromeo™ 642, Chromis 425N, Chromis 500N, Chromis 515N, Chromis 530N, Chromis 550A, Chromis 550C, Chromis 550Z, Chromis 560N, Chromis 570N, Chromis 577N, Chromis 600N, Chromis 630N, Chromis 645A, Chromis 645C, Chromis 645Z, Chromis 678A, Chromis 678C, Chromis 678Z, Chromis 770A, Chromis 770C, Chromis 800A, Chromis 800C, Chromis 830A, Chromis 830C, Cy®3, Cy®3.5, Cy®3B, Cy®5, Cy®5.5, Cy®7, DyLight® 350, DyLight® 405, DyLight® 415-Co1, DyLight® 425Q, DyLight® 485-LS, DyLight® 488, DyLight® 504Q, DyLight® 510-LS, DyLight® 515-LS, DyLight® 521-LS, DyLight® 530-R2, DyLight® 543Q, DyLight® 550, DyLight® 554-R0, DyLight® 554-R1, DyLight® 590-R2, DyLight® 594, DyLight® 610-B1, DyLight® 615-B2, DyLight® 633, DyLight® 633-B1, DyLight® 633-B2, DyLight® 650, DyLight® 655-B1, DyLight® 655-B2, DyLight® 655-B3, DyLight® 655-B4, DyLight® 662Q, DyLight® 675-B1, DyLight® 675-B2, DyLight® 675-B3, DyLight® 675-B4, DyLight® 679-05, DyLight® 680, DyLight® 683Q, DyLight® 690-B1, DyLight® 690-B2, DyLight® 696Q, DyLight® 700-B1, DyLight® 700-B1, DyLight® 730-B1, DyLight® 730-B2, DyLight® 730-B3, DyLight® 730-B4, DyLight® 747, DyLight® 747-B1, DyLight® 747-B2, DyLight® 747-B3, DyLight® 747-B4, DyLight® 755, DyLight® 766Q, DyLight® 775-B2, DyLight® 775-B3, DyLight® 775-B4, DyLight® 780-B1, DyLight® 780-B2, DyLight® 780-B3, DyLight® 800, DyLight® 830-B2, Dyomics-350, Dyomics-350XL, Dyomics-360XL, Dyomics-370XL, Dyomics-375XL, Dyomics-380XL, Dyomics-390XL, Dyomics-405, Dyomics-415, Dyomics-430, Dyomics-431, Dyomics-478, Dyomics-480XL, Dyomics-481XL, Dyomics-485XL, Dyomics-490, Dyomics-495, Dyomics-505, Dyomics-510XL, Dyomics-511XL, Dyomics-520XL, Dyomics-521XL, Dyomics-530, Dyomics-547, Dyomics-547P1, Dyomics-548, Dyomics-549, Dyomics-549P1, Dyomics-550, Dyomics-554, Dyomics-555, Dyomics-556, Dyomics-560, Dyomics-590, Dyomics-591, Dyomics-594, Dyomics-601XL, Dyomics-605, Dyomics-610, Dyomics-615, Dyomics-630, Dyomics-631, Dyomics-632, Dyomics-633, Dyomics-634, Dyomics-635, Dyomics-636, Dyomics-647, Dyomics-647P1, Dyomics-648, Dyomics-648P1, Dyomics-649, Dyomics-649P1, Dyomics-650, Dyomics-651, Dyomics-652, Dyomics-654, Dyomics-675, Dyomics-676, Dyomics-677, Dyomics-678, Dyomics-679P1, Dyomics-680, Dyomics-681, Dyomics-682, Dyomics-700, Dyomics-701, Dyomics-703, Dyomics-704, Dyomics-730, Dyomics-731, Dyomics-732, Dyomics-734, Dyomics-749, Dyomics-749P1, Dyomics-750, Dyomics-751, Dyomics-752, Dyomics-754, Dyomics-776, Dyomics-777, Dyomics-778, Dyomics-780, Dyomics-781, Dyomics-782, Dyomics-800, Dyomics-831, eFluor® 450, Eosin, FITC, Fluorescein, HiLyte™ Fluor 405, HiLyte™ Fluor 488, HiLyte™ Fluor 532, HiLyte™ Fluor 555, HiLyte™ Fluor 594, HiLyte™ Fluor 647, HiLyte™ Fluor 680, HiLyte™ Fluor 750, IRDye® 680LT, IRDye® 750, IRDye® 800CW, JOE, LightCycler® 640R, LightCycler® Red 610, LightCycler® Red 640, LightCycler® Red 670, LightCycler® Red 705, Lissamine Rhodamine B, Napthofluorescein, Oregon Green® 488, Oregon Green® 514, Pacific Blue™, Pacific Green™, Pacific Orange™, PET, PF350, PF405, PF415, PF488, PF505, PF532, PF546, PF555P, PF568, PF594, PF610, PF633P, PF647P, Quasar® 570, Quasar® 670, Quasar® 705, Rhodamine 123, Rhodamine 6G, Rhodamine B, Rhodamine Green, Rhodamine Green-X, Rhodamine Red, ROX, Seta™ 375, Seta™ 470, Seta™ 555, Seta™ 632, Seta™ 633, Seta™ 650, Seta™ 660, Seta™ 670, Seta™ 680, Seta™ 700, Seta™ 750, Seta™ 780, Seta™ APC-780, Seta™ PerCP-680, Seta™ R-PE-670, Seta™ 646, SeTau 380, SeTau 425, SeTau 647, SeTau 405, Square 635, Square 650, Square 660, Square 672, Square 680, Sulforhodamine 101, TAMRA, TET, Texas Red®, TMR, TRITC, Yakima Yellow™, Zenon®, Zy3, Zy5, Zy5.5, and Zy7.

(ii) Physical Separation

A polypeptide (or plurality of polypeptides) may be barcoded by physical separation. In some embodiments, a polypeptide (or plurality of polypeptides) is deposited on or within a solid substrate such that the polypeptide (or plurality of polypeptides) remains physically separated from additional polypeptides (or additional pluralities of polypeptides).

In some embodiments, the solid substrate is a chip array.

In some embodiments, the chip array comprises a plurality of compartments (e.g., wells) and/or injection ports. For example, in some embodiments, the chip array comprises 1, 2, 3, 4, 5, 6, 7, 8, 9, 10, 11, 12, 13, 14, 15, 16, 17, 18, 19, or 20 compartments. In some embodiments, the chip array comprises 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 5-6, 5-7, 5-8, 5-9, 5-10, 5-11, 5-12, 5-13, 5-14, 5-15, 5-16, 5-17, 5-18, 5-19, 5-20, 10-15, or 15-20 compartments. In some embodiments, the chip array comprises 1, 2, 3, 4, 5, 6, 7, 8, 9, 10, 11, 12, 13, 14, 15, 16, 17, 18, 19, or 20 injection ports. In some embodiments, the chip array comprises 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 5-6, 5-7, 5-8, 5-9, 5-10, 5-11, 5-12, 5-13, 5-14, 5-15, 5-16, 5-17, 5-18, 5-19, 5-20, 10-15, or 15-20 injection ports.

In some embodiments, the chip array comprises a plurality of physically separated spots (or regions) comprising immobilized detector molecules, as described herein. For example, in some embodiments, the chip array comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, at least 75, at least 80, at least 85, at least 90, at least 95, at least 100, at least 150, at least 200, at least 250, at least 300, at least 400, at least 450, at least 500, at least 550, at least 600, at least 700, at least 800, at least 900, at least 1000, at least 5000, or at least 10,000 physically separated spots. In some embodiments, a chip array comprises 2-10, 2-20, 2-30, 2-40, 2-50, 2-60, 2-70, 2-80, 2-90, 2-100, 10-20, 10-30, 10-40, 10-50, 10-60, 10-70, 10-80, 10-90, 10-100, 50-100, 50-150, 50-200, 50-250, 50-300, 50-350, 50-400, 50-450, 50-500, 50-550, 50-600, 50-650, 50-700, 50-750, 50-800, 50-850, 50-900, 50-950, 50-1000, 500-1000, 500-2000, 500-3000, 500-4000, 500-5000, 500-6000, 500-7000, 500-8000, 500-9000, or 500-10,000 physically separated spots. In some embodiments, the immobilized detector molecules are covalently attached to the chip array.

B. Methods of Determining the Origin of a Barcoded Molecule in a Multiplexed Sample In some aspects, the disclosure relates to methods of determining the origin(s) of a barcoded molecule(s) (e.g., polypeptides, DNA, RNA, cDNA, metabolites) in a multiplexed sample. The origin of a barcoded molecule (or origins of a plurality of barcoded molecules) is determined through the identification of the barcode(s) of the molecule(s). Barcode identities may be detected by sequencing (e.g., polypeptide and/or polynucleic acid sequencing), luminescence, hybridization, binding kinetics, physical location on or within a solid substrate, or a combination thereof.

In some embodiments, a barcoded polypeptide (or plurality of barcoded polypeptides) of a multiplexed sample may be sequenced (e.g., sequenced in parallel) to determine the amino acid sequence(s) of the polypeptide(s). In such embodiments, the origin(s) of the barcoded polypeptide(s) may be determined before, after, or concurrently with the sequencing of the polypeptide(s) of the multiplexed sample. In some embodiments, the origin(s) of the barcoded polypeptide(s) is determined before the sequencing of the polypeptide(s). In some embodiments, the origin(s) of the barcoded polypeptide(s) is determined after the sequencing of the polypeptide(s). In some embodiments, the origin(s) of the barcoded polypeptide(s) is determined concurrently with the sequencing of the polypeptide(s). In some embodiments, the amino acid sequences of barcoded polypeptides of a multiplexed sample are grouped according to their origins (as determined by their barcode identities).

(i) Polynucleic Acid Sequencing Methodologies

In some embodiment, a method of determining the origin of a barcoded molecule (or the origins of a plurality of barcoded molecules) comprises detecting the barcode identity of the molecule (or the barcode identities of the barcoded molecules) by sequencing the barcode(s) of the molecule(s). As such, is some aspects, the disclosure relates to methods of sequencing polypeptides and/or polynucleic acids (e.g., deoxyribonucleic acids or ribonucleic acid). Methods of sequencing polypeptides are discussed below (see "Polypeptide Sequencing Methodologies"). Also described herein are polynucleic acid sequencing methodologies.

In some embodiments, a method of polynucleic acid sequencing comprises the steps of: (i) exposing a complex in a target volume to one or more labeled nucleotides, the complex comprising a target polynucleic acid or a plurality of polynucleic acids present in a sample, at least one primer, and a polymerizing enzyme; (ii) directing one or more excitation energies, or a series of pulses of one or more excitation energies, towards a vicinity of the target volume; (iii) detecting a plurality of emitted photons from the one or more labeled nucleotides during sequential incorporation into a polynucleic acid comprising one of the at least one primers; and (iv) identifying the sequence of incorporated nucleotides by determining one or more characteristics of the emitted photons.

In some embodiments, a primer is a sequencing primer. In some embodiments, a sequencing primer can be annealed to a polynucleic acid (e.g., a target polynucleic acid) that may or may not be immobilized to a solid support. A solid support can comprise, for example, a sample well (e.g., a nanoaperture, a reaction chamber) on a chip or cartridge used for polynucleic acid sequencing. In some embodiments, a sequencing primer may be immobilized to a solid support and hybridization of the polynucleic acid (e.g., the target nucleic acid) further immobilizes the nucleic acid molecule to the solid support. In some embodiments, a polymerase (e.g., RNA Polymerase) is immobilized to a solid support and soluble sequencing primer and polynucleic acid are contacted to the polymerase. In some embodiments a complex comprising a polymerase, a polynucleic acid (e.g., a target nucleic acid) and a primer is formed in solution and the complex is immobilized to a solid support (e.g., via immobilization of the polymerase, primer, and/or target polynucleic acid). In some embodiments, none of the components are immobilized to a solid support. For example, in some embodiments, a complex comprising a polymerase, a target polynucleic acid, and a sequencing primer is formed in situ and the complex is not immobilized to a solid support.

In some embodiments, a plurality of single molecule sequencing reactions are performed in parallel (e.g., on a single chip or cartridge) according to aspects of the instant disclosure. For example, in some embodiments, a plurality of single molecule sequencing reactions are each performed in separate sample wells (e.g., nanoapertures, reaction chambers) on a single chip or cartridge.

Additional polynucleic acid sequencing methodologies are known to those having skill in the art.

(ii) Detector Molecules

In some embodiment, a method of determining the origin of a barcoded molecule (or the origins of a plurality of barcoded molecules) comprises detecting the barcode identity of the molecule (or barcode identities of the barcoded molecules) indirectly using detector molecules. For example, in some embodiments, barcode identity is detected in a method comprising: (i) contacting a barcoded molecule (or plurality of barcoded molecules) with a plurality of detector molecules, wherein one or more of the detector molecules in the plurality interacts with the barcode of the barcoded molecule (or interacts with one or more barcode of the barcoded molecules); and (ii) detecting any interaction between a barcoded molecule and a detector molecule. An interaction between a barcoded molecule and a detector molecule may be identified through luminescence, hybridization, binding kinetics, or physical location.

In some embodiments, each of the detector molecules of the plurality of detector molecules are chemically identical. In some embodiments, a plurality of detector molecules comprises two or more chemically distinct detector molecules.

For example, in some embodiments, a plurality of detector molecules comprises 2, 3, 4, 5, 6, 7, 8, 9, 10, 11, 12, 13, 14, 15, 16, 17, 18, 19, or 20 chemically distinct detector molecules.

In some embodiments, a plurality of detector molecules comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, at least 100, at least 200, at least 300, at least 400, at least 500, a least 600, at least 700, at least 800, at least 900, or at least 1000 chemically distinct detector molecules.

In some embodiments, a plurality of detector molecules comprises 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-25, 2-30, 2-35, 2-40, 2-45, 2-50, 2-60, 2-70, 2-80, 2-90, 2-100, 2-200, 2-300, 2-400, 2-500, 2-600, 2-700, 2-800, 2-900, 2-1000, 5-10, 5-15, 5-20, 5-25, 5-30, 5-35, 5-40, 5-45, 5-50, 5-60, 5-70, 5-80, 5-90, 5-100, 5-200, 5-300, 5-400, 5-500, 5-600, 5-700, 5-800, 5-900, 10-15, 10-20, 10-25, 10-30, 10-35, 10-40, 10-45, 10-50, 10-60, 10-70, 10-80, 10-90, 10-100, 10-200, 10-300, 10-400, 10-500, 10-600, 10-700, 10-800, 10-900, 10-1000, 20-30, 20-40, 20-50, 20-60, 20-70, 20-80, 20-90, 20-100, 20-200, 20-300, 20-400, 20-500, 20-600, 20-700, 20-800, 20-900, 20-1000, 50-60, 50-70, 50-80, 50-90, 50-100, 50-200, 50-300, 50-400, 50-500, 50-600, 50-700, 50-800, 50-900, 50-1000, 100-200, 100-300, 100-400, 100-500, 100-600, 100-700, 100-800, 100-900, 100-1000, 500-600, 500-700, 1500-800, 500-900, or 500-1000 chemically distinct detector molecules.

A detector molecule may comprise a polynucleic acid portion, a polypeptide portion, a small molecule portion, or a combination thereof.

In some embodiments, a detector molecule comprises a polynucleic acid portion. In some embodiments, a detector molecule comprises two or more polynucleic acid portions. In embodiments wherein a detector molecule comprises multiple polynucleic acid portions: each polynucleic acid portion may be identical; a subset of the polynucleic acid portions may be identical; or each polynucleic acid portion may be chemically distinct.

In some embodiment, the polynucleic acid portion is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length.

In some embodiment, the polynucleic acid portion is at least 5, at least 10, at least 15, at least 20, at least 25, at least 30, at least 40, at least 50, at least 60, at least 70, at least 80, at least 90, at least 100, at least 150, at least 200, at least 250, at least 300, at least 350, at least 400, at least 450, or at least 500 nucleotides in length.

In some embodiments, the polynucleic acid portion is 5-10, 5-15, 5-20, 5-25, 5-30, 5-40, 5-50, 5-60, 5-70, 5-80, 5-90, 5-100, 5-150, 5-200, 5-250, 5-300, 5-350, 5-400, 5-450, 5-500, 10-15, 10-20, 10-25, 10-30, 10-40, 10-50, 10-60, 10-70, 10-80, 10-90, 10-100, 10-150, 10-200, 10-250, 10-300, 10-350, 10-400, 10-450, 10-500, 20-30, 20-40, 20-50, 20-60, 20-70, 20-80, 20-90, 20-100, 20-150, 20-200, 20-250, 20-300, 20-350, 20-400, 20-450, 20-500, 50-75, 50-100, 50-150, 50-200, 50-250, 50-500, 50-350, 50-400, 50-450, 50-500, 100-200, 100-250, 100-500, 100-350, 100-400, 100-450, or 100-500 nucleotides in length.

In some embodiment, the polynucleic acid portion is an aptamer.

In some embodiments, a detector molecule comprises a polypeptide portion. In some embodiments, a detector molecule comprises two or more polypeptide portions. In embodiments wherein a detector molecule comprises multiple polypeptide portions: each polypeptide portion may be identical; a subset of the polypeptide portions may be identical; or each polypeptide portion may be chemically distinct.

In some embodiment, the polypeptide portion is 2, 3, 4, 5, 6, 7, 8, 9, 10, 11, 12, 13, 14, 15, 16, 17, 18, 19, or 20 amino acids in length.

In some embodiments, the polypeptide portion is at least 5, at least 10, at least 15, at least 20, at least 25, at least 30, at least 40, at least 50, at least 60, at least 70, at least 80, at least 90, at least 100, at least 150, at least 200, at least 250, at least 300, at least 350, at least 400, at least 450, or at least 500 amino acids in length.

In some embodiments, the polypeptide portion is 5-10, 5-15, 5-20, 5-25, 5-30, 5-40, 5-50, 5-60, 5-70, 5-80, 5-90, 5-100, 5-150, 5-200, 5-250, 5-300, 5-350, 5-400, 5-450, 5-500, 10-15, 10-20, 10-25, 10-30, 10-40, 10-50, 10-60, 10-70, 10-80, 10-90, 10-100, 10-150, 10-200, 10-250, 10-300, 10-350, 10-400, 10-450, 10-500, 20-30, 20-40, 20-50, 20-60, 20-70, 20-80, 20-90, 20-100, 20-150, 20-200, 20-250, 20-300, 20-350, 20-400, 20-450, 20-500, 50-75, 50-100, 50-150, 50-200, 50-250, 50-500, 50-350, 50-400, 50-450, 50-500, 100-200, 100-250, 100-500, 100-350, 100-400, 100-450, or 100-500 amino acids in length.

In some embodiments, the polypeptide portion is an aptamer. In some embodiment, the polypeptide portion is an antibody. In some embodiment, the polypeptide portion is an antigen.

In some embodiments, the polypeptide portion is avidin, streptavidin, or other avidin-like polypeptide, for example, traptavidin, tamavidin, bradavidin, xenavidin, and homologues and variants thereof.

In some embodiments, a detector molecule comprises a small molecule portion, such as a drug portion or a luminescent molecule portion (of fluorescent molecule portion). In some embodiments, a detector molecule comprises two or more small molecule portions. In embodiments wherein a detector molecule comprises multiple small molecule portions: each small molecule portion may be identical; a subset of the small molecule portions may be identical; or each small molecule portion may be chemically distinct.

Examples of drugs and luminescent molecules suitable for the methods described herein are known to those having skill in the art. As used herein, a luminescent molecule is a molecule that absorbs one or more photons and may subsequently emit one or more photons after one or more time durations.

In some embodiments, a luminescent molecule may comprise a first and second chromophore. In some embodiments, an excited state of the first chromophore is capable of relaxation via an energy transfer to the second chromophore. In some embodiments, the energy transfer is a Förster resonance energy transfer (FRET). Such a FRET pair may be useful for providing a luminescent label with properties that make the label easier to differentiate from amongst a plurality of luminescent labels in a mixture. In yet other embodiments, a FRET pair comprises a first chromophore of a first luminescent label and a second chromophore of a second luminescent label. In certain embodiments, the FRET pair may absorb excitation energy in a first spectral range and emit luminescence in a second spectral range.

In some embodiments, a luminescent molecule refers to a fluorophore or a dye. Typically, a luminescent molecule comprises an aromatic or heteroaromatic compound and can be a pyrene, anthracene, naphthalene, naphthylamine, acridine, stilbene, indole, benzindole, oxazole, carbazole, thiazole, benzothiazole, benzoxazole, phenanthridine, phenoxazine, porphyrin, quinoline, ethidium, benzamide, cyanine, carbocyanine, salicylate, anthranilate, coumarin, fluorescein, rhodamine, xanthene, or other like compound.

In some embodiments, a luminescent molecule comprises a dye selected from one or more of the following: 5/6-Carboxyrhodamine 6G, 5-Carboxyrhodamine 6G, 6-Carboxyrhodamine 6G, 6-TAMRA, Abberior® STAR 440SXP, Abberior® STAR 470SXP, Abberior® STAR 488, Abberior® STAR 512, Abberior® STAR 520SXP, Abberior® STAR 580, Abberior® STAR 600, Abberior® STAR 635, Abberior® STAR 635P, Abberior® STAR RED, Alexa Fluor® 350, Alexa Fluor® 405, Alexa Fluor® 430, Alexa Fluor® 480, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610-X, Alexa Fluor® 633, Alexa Fluor® 647, Alexa Fluor® 660, Alexa Fluor® 680, Alexa Fluor® 700, Alexa Fluor® 750, Alexa Fluor® 790, AMCA, ATTO 390, ATTO 425, ATTO 465, ATTO 488, ATTO 495, ATTO 514, ATTO 520, ATTO 532, ATTO 542, ATTO 550, ATTO 565, ATTO 590, ATTO 610, ATTO 620, ATTO 633, ATTO 647, ATTO 647N, ATTO 655, ATTO 665, ATTO 680, ATTO 700, ATTO 725, ATTO 740, ATTO Oxa12, ATTO Rho101, ATTO Rho11, ATTO Rho12, ATTO Rho13, ATTO Rho14, ATTO Rho3B, ATTO Rho6G, ATTO Thio12, BD Horizon™ V450, BODIPY® 493/501, BODIPY® 530/550, BODIPY® 558/568, BODIPY® 564/570, BODIPY® 576/589, BODIPY® 581/591, BODIPY® 630/650, BODIPY® 650/665, BODIPY® FL, BODIPY® FL-X, BODIPY® R6G, BODIPY® TMR, BODIPY® TR, CAL Fluor® Gold 540, CAL Fluor® Green 510, CAL Fluor® Orange 560, CAL Fluor® Red 590, CAL Fluor® Red 610, CAL Fluor® Red 615, CAL Fluor® Red 635, Cascade® Blue, CF™350, CF™405M, CF™405S, CF™488A, CF™514, CF™532, CF™543, CF™546, CF™555, CF™568, CF™594, CF™620R, CF™633, CF™633-V1, CF™640R, CF™640R-V1, CF™640R-V2, CF™660C, CF™660R, CF™680, CF™680R, CF™680R-V1, CF™750, CF™770, CF™790, Chromeo™ 642, Chromis 425N, Chromis 500N, Chromis 515N, Chromis 530N, Chromis 550A, Chromis 550C, Chromis 550Z, Chromis 560N, Chromis 570N, Chromis 577N, Chromis 600N, Chromis 630N, Chromis 645A, Chromis 645C, Chromis 645Z, Chromis 678A, Chromis 678C, Chromis 678Z, Chromis 770A, Chromis 770C, Chromis 800A, Chromis 800C, Chromis 830A, Chromis 830C, Cy®3, Cy®3.5, Cy®3B, Cy®5, Cy®5.5, Cy®7, DyLight® 350, DyLight® 405, DyLight® 415-Col, DyLight® 425Q, DyLight® 485-LS, DyLight® 488, DyLight® 504Q, DyLight® 510-LS, DyLight® 515-LS, DyLight® 521-LS, DyLight® 530-R2, DyLight® 543Q, DyLight® 550, DyLight® 554-R0, DyLight® 554-R1, DyLight® 590-R2, DyLight® 594, DyLight® 610-B1, DyLight® 615-B2, DyLight® 633, DyLight® 633-B1, DyLight® 633-B2, DyLight® 650, DyLight® 655-B1, DyLight® 655-B2, DyLight® 655-B3, DyLight® 655-B4, DyLight® 662Q, DyLight® 675-B1, DyLight® 675-B2, DyLight® 675-B3, DyLight® 675-B4, DyLight® 679-05, DyLight® 680, DyLight® 683Q, DyLight® 690-B1, DyLight® 690-B2, DyLight® 696Q, DyLight® 700-B1, DyLight® 700-B1, DyLight® 730-B1, DyLight® 730-B2, DyLight® 730-B3, DyLight® 730-B4, DyLight® 747, DyLight® 747-B1, DyLight® 747-B2, DyLight® 747-B3, DyLight® 747-B4, DyLight® 755, DyLight® 766Q, DyLight® 775-B2, DyLight® 775-B3, DyLight® 775-B4, DyLight® 780-B1, DyLight® 780-B2, DyLight® 780-B3, DyLight® 800, DyLight® 830-B2, Dyomics-350, Dyomics-350XL, Dyomics-360XL, Dyomics-370XL, Dyomics-375XL, Dyomics-380XL, Dyomics-390XL, Dyomics-405, Dyomics-415, Dyomics-430, Dyomics-431, Dyomics-478, Dyomics-480XL, Dyomics-481XL, Dyomics-485XL, Dyomics-490, Dyomics-495, Dyomics-505, Dyomics-510XL, Dyomics-511XL, Dyomics-520XL, Dyomics-521XL, Dyomics-530, Dyomics-547, Dyomics-547P1, Dyomics-548, Dyomics-549, Dyomics-549P1, Dyomics-550, Dyomics-554, Dyomics-555, Dyomics-556, Dyomics-560, Dyomics-590, Dyomics-591, Dyomics-594, Dyomics-601XL, Dyomics-605, Dyomics-610, Dyomics-615, Dyomics-630, Dyomics-631, Dyomics-632, Dyomics-633, Dyomics-634, Dyomics-635, Dyomics-636, Dyomics-647, Dyomics-647P1, Dyomics-648, Dyomics-648P1, Dyomics-649, Dyomics-649P1, Dyomics-650, Dyomics-651, Dyomics-652, Dyomics-654, Dyomics-675, Dyomics-676, Dyomics-677, Dyomics-678, Dyomics-679P1, Dyomics-680, Dyomics-681, Dyomics-682, Dyomics-700, Dyomics-701, Dyomics-703, Dyomics-704, Dyomics-730, Dyomics-731, Dyomics-732, Dyomics-734, Dyomics-749, Dyomics-749P1, Dyomics-750, Dyomics-751, Dyomics-752, Dyomics-754, Dyomics-776, Dyomics-777, Dyomics-778, Dyomics-780, Dyomics-781, Dyomics-782, Dyomics-800, Dyomics-831, eFluor® 450, Eosin, FITC, Fluorescein, HiLyte™ Fluor 405, HiLyte™ Fluor 488, HiLyte™ Fluor 532, HiLyte™ Fluor 555, HiLyte™ Fluor 594, HiLyte™ Fluor 647, HiLyte™ Fluor 680, HiLyte™ Fluor 750, IRDye® 680LT, IRDye® 750, IRDye® 800CW, JOE, LightCycler® 640R, LightCycler® Red 610, LightCycler® Red 640, LightCycler® Red 670, LightCycler® Red 705, Lissamine Rhodamine B, Napthofluorescein, Oregon Green® 488, Oregon Green® 514, Pacific Blue™, Pacific Green™, Pacific Orange™, PET, PF350, PF405, PF415, PF488, PF505, PF532, PF546, PF555P, PF568, PF594, PF610, PF633P, PF647P, Quasar® 570, Quasar® 670, Quasar® 705, Rhodamine 123, Rhodamine 6G, Rhodamine B, Rhodamine Green, Rhodamine Green-X, Rhodamine Red, ROX, Seta™ 375, Seta™ 470, Seta™ 555, Seta™ 632, Seta™ 633, Seta™ 650, Seta™ 660, Seta™ 670, Seta™ 680, Seta™ 700, Seta™ 750, Seta™ 780, Seta™ APC-780, Seta™ PerCP-680, Seta™ R-PE-670, Seta™ 646, SeTau 380, SeTau 425, SeTau 647, SeTau 405, Square 635, Square 650, Square 660, Square 672, Square 680, Sulforhodamine 101, TAMRA, TET, Texas Red®, TMR, TRITC, Yakima Yellow™, Zenon®, Zy3, Zy5, Zy5.5, and Zy7.

In some embodiments, a detector molecule is immobilized on (e.g., covalently attached to) a substrate. The substrate may be a surface (e.g., a solid surface), a bead (e.g., a magnetic bead), a particle (e.g., a magnetic particle), or a gel.

(iii) Luminescence

In some embodiment, a method of determining the origin of a barcoded molecule (or the origins of a plurality of barcoded molecules) comprises detecting the barcode identity of the molecule (or plurality of barcoded molecules) by luminescence. Detection of barcode identity may be direct or indirect (e.g., by detecting luminescence of a detector molecule). In some embodiments, barcode identity is identified based on luminescence lifetime, luminescence intensity, brightness, absorption spectra, emission spectra, luminescence quantum yield, or a combination of two or more thereof. In some embodiments, a plurality of barcode identities can be distinguished from each other based on different luminescence lifetimes, luminescence intensities, brightnesses, absorption spectra, emission spectra, luminescence quantum yields, or combinations of two or more thereof.

In some embodiments, luminescence is detected by exposing a luminescent molecule to a series of separate light pulses and evaluating the timing or other properties of each photon that is emitted from the molecule. In some embodiments, a luminescence lifetime of a molecule is determined from a plurality of photons that are emitted sequentially from the molecule, and the luminescence lifetime can be used to identify the molecule. In some embodiments, a luminescence intensity of a molecule is determined from a plurality of photons that are emitted sequentially from the molecule, and the luminescence intensity can be used to identify the molecule. In some embodiments, a luminescence lifetime and luminescence intensity of a molecule is determined from a plurality of photons that are emitted sequentially from the molecule, and the luminescence lifetime and luminescence intensity can be used to identify the molecule.

In certain embodiments, a luminescent molecule absorbs one photon and emits one photon after a time duration. In some embodiments, the luminescence lifetime of a molecule can be determined or estimated by measuring the time duration. In some embodiments, the luminescence lifetime of a molecule can be determined or estimated by measuring a plurality of time durations for multiple pulse events and emission events. In some embodiments, the luminescence lifetime of a molecule can be differentiated amongst the luminescence lifetimes of a plurality of types of molecules by measuring the time duration. In some embodiments, the luminescence lifetime of a molecule can be differentiated amongst the luminescence lifetimes of a plurality of types of molecules by measuring a plurality of time durations for multiple pulse events and emission events. In certain embodiments, a molecule is identified or differentiated amongst a plurality of types of labels by determining or estimating the luminescence lifetime of the label. In certain embodiments, a molecule is identified or differentiated amongst a plurality of types of molecules by differentiating the luminescence lifetime of the molecule amongst a plurality of the luminescence lifetimes of a plurality of types of molecules.

Determination of a luminescence lifetime of a luminescent molecule can be performed using any suitable method (e.g., by measuring the lifetime using a suitable technique or by determining time-dependent characteristics of emission). In some embodiments, determining the luminescence lifetime of a molecule comprises determining the lifetime relative to another label. In some embodiments, determining the luminescence lifetime of a molecule comprises determining the lifetime relative to a reference. In some embodiments, determining the luminescence lifetime of a molecule comprises measuring the lifetime (e.g., fluorescence lifetime). In some embodiments, determining the luminescence lifetime of a molecule comprises determining one or more temporal characteristics that are indicative of lifetime. In some embodiments, the luminescence lifetime of a molecule can be determined based on a distribution of a plurality of emission events (e.g., 1, 2, 3, 4, 5, 6, 7, 8, 9, 10, 11, 12, 13, 14, 15, 16, 17, 18, 19, 20, 30, 40, 50, 60, 70, 80, 90, 100, or more emission events) occurring across one or more time-gated windows relative to an excitation pulse. For example, a luminescence lifetime of a molecule can be distinguished from a plurality of molecules having different luminescence lifetimes based on the distribution of photon arrival times measured with respect to an excitation pulse.

It should be appreciated that a luminescence lifetime of a luminescent molecule is indicative of the timing of photons emitted after the label reaches an excited state and the label can be distinguished by information indicative of the timing of the photons. Some embodiments may include distinguishing a molecule from a plurality of molecules based on the luminescence lifetime of the label by measuring times associated with photons emitted by the molecule. The distribution of times may provide an indication of the luminescence lifetime which may be determined from the distribution. In some embodiments, the molecule is distinguishable from the plurality of molecules based on the distribution of times, such as by comparing the distribution of times to a reference distribution corresponding to a known molecule. In some embodiments, a value for the luminescence lifetime is determined from the distribution of times.

As used herein, in some embodiments, luminescence intensity refers to the number of emitted photons per unit time that are emitted by a luminescent molecule which is being excited by delivery of a pulsed excitation energy. In some embodiments, the luminescence intensity refers to the detected number of emitted photons per unit time that are emitted by a molecule which is being excited by delivery of a pulsed excitation energy, and are detected by a particular sensor or set of sensors.

As used herein, in some embodiments, brightness refers to a parameter that reports on the average emission intensity per luminescent molecule. Thus, in some embodiments, "emission intensity" may be used to generally refer to brightness of a composition comprising one or more molecules. In some embodiments, brightness of a molecule is equal to the product of its quantum yield and extinction coefficient.

As used herein, in some embodiments, luminescence quantum yield refers to the fraction of excitation events at a given wavelength or within a given spectral range that lead to an emission event, and is typically less than 1. In some embodiments, the luminescence quantum yield of a luminescent label described herein is between 0 and about 0.001, between about 0.001 and about 0.01, between about 0.01 and about 0.1, between about 0.1 and about 0.5, between about 0.5 and 0.9, or between about 0.9 and 1. In some embodiments, a molecule is identified by determining or estimating the luminescence quantum yield.

As used herein, in some embodiments, an excitation energy is a pulse of light from a light source. In some embodiments, an excitation energy is in the visible spectrum. In some embodiments, an excitation energy is in the ultraviolet spectrum. In some embodiments, an excitation energy is in the infrared spectrum. In some embodiments, an excitation energy is at or near the absorption maximum of a luminescent label from which a plurality of emitted photons are to be detected. In certain embodiments, the excitation energy is between about 500 nm and about 700 nm (e.g., between about 500 nm and about 600 nm, between about 600 nm and about 700 nm, between about 500 nm and about 550 nm, between about 550 nm and about 600 nm, between about 600 nm and about 650 nm, or between about 650 nm and about 700 nm). In certain embodiments, an excitation energy may be monochromatic or confined to a spectral range. In some embodiments, a spectral range has a range of between about 0.1 nm and about 1 nm, between about 1 nm and about 2 nm, or between about 2 nm and about 5 nm. In some embodiments, a spectral range has a range of between about 5 nm and about 10 nm, between about 10 nm and about 50 nm, or between about 50 nm and about 100 nm.

(iv) Physical Separation

In some embodiment, a method of determining the origin of a barcoded molecule (or the origins of a plurality of barcoded molecules) comprises detecting the barcode identity of the molecule (or plurality of barcoded molecules) by physical separation. Detection of barcode identity by physical separation may comprise determining the location of a barcoded molecule on a substrate (e.g., a microarray chip).

For example, a substrate may comprise a plurality of detector molecules (as described herein) that are organized at discrete locations on the substrate. In such instances, barcoded molecules comprising a barcode that hybridizes to, binds to, or is bound by a detector molecule on the substrate can be positioned at the location of the detector molecule. As such, in some embodiments, a method of determining the origin of a barcoded molecule (or the origins of a plurality of barcoded molecules) comprises contacting the polypeptide (or plurality of polypeptides) with a substrate comprising a plurality of detector molecules.

As described above, in some embodiments, a polypeptide (or plurality of polypeptides) is barcoded by depositing the polypeptide (or plurality of polypeptides) on or within a solid substrate such that the polypeptide (or plurality of polypeptides remains physically separated from additional polypeptides (or additional pluralities of polypeptides). In such embodiments, a method of determining the origin of a barcoded molecule (or the origins of a plurality of barcoded molecules) comprises detecting the location of the barcoded molecule (or the plurality of barcoded molecules) on the solid substrate.

C. Exemplary Embodiments

In some embodiments, a barcode molecule comprises a polynucleic acid portion, which is identified by DNA sequencing (FIG. 3B).

In some embodiments, a barcode molecule comprises a polynucleic acid portion, which is identified via hybridization using a detector molecule comprising a polynucleic acid portion (FIG. 3A). In some embodiments, the detector molecule further comprises a luminescent molecule portion. In some embodiments, the detector molecule is immobilized on (e.g., covalently attached to) a substrate.

In some embodiments, a barcode molecule comprises a polynucleic acid portion, which is identified via hybridization using a detector molecule comprising a polypeptide portion (e.g., a DNA binding protein, an aptamer, etc.). In some embodiments, the detector molecule further comprises a luminescent molecule portion. In some embodiments, the detector molecule is covalently attached to a substrate.

In some embodiments, a barcode molecule comprises a polypeptide portion (e.g., a short polypeptide tag), which is identified by polypeptide sequencing (FIG. 3C).

In some embodiments, a barcode molecule comprises a polypeptide portion (e.g., a DNA binding protein, or portion thereof), which is identified using a detector molecule comprising a polynucleic acid portion (e.g., a polynucleic acid sequence bound by the DNA binding protein, or portion thereof). In some embodiments, the detector molecule further comprises a luminescent molecule portion. In some embodiments, the detector molecule is covalently attached to a substrate.

In some embodiments, a barcode molecule comprises a polypeptide portion, which is identified using a detector molecule comprising a polynucleic acid portion (e.g., an aptamer). In some embodiments, the detector molecule further comprises a luminescent molecule portion. In some embodiments, the detector molecule is covalently attached to a substrate.

In some embodiments, a barcode molecule comprises an amino acid modification that is made to a polypeptide after it has been translated (FIG. 3D).

In some embodiments, a barcode molecule comprises a polypeptide portion (e.g., an antibody, antigen, aptamer, etc.), which is identified using a detector molecule comprising a polypeptide portion (e.g., an antigen, antibody, or substrate, etc.). In some embodiments, the detector molecule further comprises a luminescent molecule portion. In some embodiments, the detector molecule is covalently attached to a substrate (FIG. 3E).

In some embodiments, a barcode component comprise an endoprotease with distinct cutting profiles, which can be detected by polypeptide sequencing.

III. Methods of Preparing an Enriched Sample

In some embodiments, a sample is enriched prior to, concurrently with, or subsequent to barcoding (e.g., polypeptide barcoding). Accordingly, in some aspects, the disclosure relates to methods of polypeptide enrichment. As used herein, the term "polypeptide enrichment" refers to a process wherein the abundance of one or more polypeptides of interest is increased relative to the abundance of one or more reference polypeptides (e.g., a polypeptide in a complex sample that is not of interest). The term "polypeptide of interest" as used herein, refers to a polypeptide that one seeks to enrich. A polypeptide of interest may comprise a specific amino acid sequence. Alternatively, or in addition, a polypeptide of interest may comprise a specific polypeptide modification (e.g., a post-translational modification). These methods facilitate proteomic analysis of complex samples, which are made up of many different polypeptides, only some of which may be of interest.

In some embodiments, a method for polypeptide enrichment comprises using a plurality of enrichment molecules to select a subset of polypeptides from a plurality of polypeptides, thereby generating an enriched sample comprising the subset of polypeptides. In some embodiments, the method comprises contacting a plurality of polypeptides with a plurality of enrichment molecules to produce an enriched sample comprising a subset of the polypeptides in the plurality of polypeptides.

In some embodiments, a method for polypeptide enrichment comprises: (a) contacting a plurality of polypeptides with a plurality of enrichment molecules, wherein at least a subset of the enrichment molecules in the plurality of enrichment molecules binds to a subset of the polypeptides in the plurality of polypeptides, thereby generating a bound subset of polypeptides and an unbound subset of polypeptides; and (b) isolating the bound subset of polypeptides to produce an enriched sample comprising a subset of the polypeptides in the plurality of polypeptides.

In some embodiments, a method for polypeptide enrichment comprises: (a) contacting a plurality of polypeptides with a plurality of enrichment molecules, wherein at least a subset of the enrichment molecules in the plurality of enrichment molecules binds to a subset of the polypeptides in the plurality of polypeptides, thereby generating a bound subset of polypeptides and an unbound subset of polypeptides; and (b) isolating the unbound subset of polypeptides to produce an enriched sample comprising a subset of the polypeptides in the plurality of polypeptides.

In the embodiments described in the preceding paragraphs, it is understood that the binding of an enrichment molecule to a polypeptide is equivalent to the binding of the polypeptide to the enrichment molecule. Accordingly, step (a) in the embodiments described above can be equivalently describe as: (a) contacting a plurality of polypeptides with a plurality of enrichment molecules, wherein at least a subset of the enrichment molecules in the plurality of enrichment molecules is bound by a subset of the polypeptides in the plurality of polypeptides, thereby generating a bound subset of polypeptides and an unbound subset of polypeptides.

It is also understood that steps (a) and (b) of the embodiments described above may be repeated one or more times using additional pluralities of enrichment molecules to produce a further enriched sample. For example, in some embodiments, the method comprises: (a) contacting a plurality of polypeptides with a first plurality of enrichment molecules, wherein at least a subset of the enrichment molecules in the first plurality of enrichment molecules binds to a subset of the polypeptides in the plurality of polypeptides, thereby generating a first bound subset of polypeptides and a first unbound subset of polypeptides; (b) isolating the first bound subset of polypeptides or the first unbound subset of polypeptides of (a); and (c) iteratively repeating steps (a) and (b) with one or more additional plurality of enrichment molecules to produce an enriched sample comprising a subset of the polypeptides in the plurality of polypeptides. In some embodiments, steps (a) and (b) are repeated using a second, third, fourth, fifth, sixth, seventh, eighth, ninth, tenth, or any number of additional plurality of enrichment molecules.

For example, in some embodiments the method comprises: (a) contacting a plurality of polypeptides with a first plurality of enrichment molecules, wherein at least a subset of the enrichment molecules in the first plurality of enrichment molecules binds to a subset of the polypeptides in the plurality of polypeptides, thereby generating a first bound subset of polypeptides and a first unbound subset of polypeptides; (b) isolating the first bound subset of polypeptides or the first unbound subset of polypeptides of (a); (c) contacting the isolated polypeptides of (b) with a second plurality of enrichment molecules, wherein at least a subset of the enrichment molecules in the second plurality of enrichment molecules binds to a subset of the polypeptides isolated in (b), thereby generating a second bound subset of polypeptides and a second unbound subset of polypeptides; (d) isolating the second bound subset of polypeptides or the second unbound subset of polypeptides of (c) to produce an enriched sample comprising a subset of the polypeptides in the plurality of polypeptides.

Alternatively, or in addition, a method of enrichment may comprise chromatography (e.g., size exclusion, ion exchange, etc.), isoelectric focusing, membrane filtration, molecular sieve filtration, concentration, precipitation (e.g., cryoprecipitation), dry down, dialysis, or a combination thereof.

In some embodiments, the method comprises contacting a complex sample with a kit or device described herein. See "Kits for Sample Preparation" and "Devices for Sample Preparation and Sample Sequencing".

In some embodiments, the polypeptides in an enriched sample are identical (i.e., contain the same amino acid sequence). In some embodiments, an enriched sample comprises at least two unique polypeptides (i.e., having differing amino acid sequences). For example, in some embodiments, an enriched sample comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, or at least 100 unique polypeptides. In some embodiments, an enriched sample comprises 1-2, 1-5, 1-10, 1-15, 1-20, 1-30, 1-40, 1-50, 1-60, 1-70, 1-80, 1-90, 1-100, 2-5, 2-10, 2-15, 2-20, 2-30, 2-40, 2-50, 2-60, 2-70, 2-80, 2-90, 2-100, 5-10, 5-15, 5-20, 5-30, 5-40, 5-50, 5-60, 5-70, 5-80, 5-90, 5-100, 10-15, 10-20, 10-30, 10-40, 10-50, 10-60, 10-70, 10-80, 10-90, 10-100, 15-20, 20-30, 20-40, 20-50, 20-60, 20-70, 20-80, 20-90, 20-100, 20-30, 20-40, 20-50, 20-60, 20-70, 20-80, 20-90, 20-100, 30-40, 30-50, 30-60, 30-70, 30-80, 30-90, 30-100, 40-50, 40-60, 40-70, 40-80, 40-90, 40-100, 50-60, 50-70, 50-80, 50-90, or 50-100 unique polypeptides.

In some embodiments, the enriched sample comprises polypeptides that share at least 50%, 60%, 70%, 80%, 90% 95%, or 99% sequence identity. In some embodiments, the enriched sample comprises polypeptides that share one or more polypeptide modification (e.g., post-translational modification). Examples of post-translational modifications are known to those having skill in the art and include, but are not limited to, acetylation, adenylylation, ADP-ribosylation, alkylation (e.g., methylation), amidation, arginylation, biotinylation, butyrylation, carbamylation, carbonylation, carboxylation, citrullination, deamidation, eliminylation, formylation, glycosylation (e.g., N-linked glycosylation, O-linked glycosylation), glipyatyon, glycation, hydroxylation, iodination, ISGylation, isoprenylation, lipoylation, malonylation, myristoylation, neddylation, nitration, oxidation, palmitoylation pegylation, phosphorylation, phosphopantetheinylation, polyglcylation, polyglutamylation, prenylation, propionylation, pupylation, S-glutathionylation, S-nitrosylation, S-sulfenylation, S-sulfinylation, S-sulfonylation, succinylation, sulfation, SUMOylation, and ubiquitination.

A. Enrichment Molecules

As used herein, the term "enrichment molecule" refers to a molecule that exhibits preferentially binding to (or by) one or more target polypeptides. An enrichment molecule may bind to (or be bound by) a target polypeptide through a direct interaction with the amino acid sequence of the target polypeptide. Alternatively, or in addition, an enrichment molecule may bind to (or be bound by) a target polypeptide through an interaction with a modification of the target polypeptide (e.g., a post-translational modification). The binding of an enrichment molecule to (or by) a target polypeptide may be mediated through electrostatic interactions, hydrophobic interactions, complementary shape, or a combination thereof.

In some embodiments, a target polypeptide is a polypeptide of interest. In other embodiments, a target polypeptide is not a polypeptide of interest.

Exemplary enrichment molecules that preferentially bind to one or more target polypeptides (or target polypeptide variants) include immunoglobulins, anticalins, lipocalins, DARPins, aptamers, enzymes, lectins, and peptide interaction domains.

As used herein, the term "immunoglobulin" refers to polypeptides characterized as having an immunoglobulin fold and which function as antibodies and bind to one or more substrates (e.g., target polypeptides). As such, the term "immunoglobulin" encompasses conventional immunoglobulins (i.e., IgA, IgD, IgE, IgG, and IgM), single-chain variable fragments (scFv), antigen-binding fragments (Fab), affibodies, and single domain antibodies (sdAb), such as Nanobodies, VHHs and VNARs.

The term "aptamer" as used herein refers to a polynucleic acid (e.g., DNA or RNA) or polypeptide that preferentially binds to one or more target molecules (e.g., target polypeptides). Although there are examples found in nature, aptamers are usually engineered through repeated rounds of in vitro selection.

As used herein, the term "enzyme" refers to a macromolecular biological catalyst that accelerates a chemical reaction upon binding one or more substrates (e.g., target polypeptides). Typically, an enzyme will release its substrate after completion of a chemical reaction. As such, in some embodiments, wherein an enrichment molecule comprises an enzyme, the enzyme is catalytically inactivated so as to increase the likelihood that the enzyme remains bound to the substrate. Catalytic inactivation may be performed via mutagenesis and/or depletion of one or more enzymatic cofactor (i.e., a non-protein chemical compound or metallic ion that is required for an enzyme's activity as a catalyst).

The term "peptide interaction domain" as used herein, refers to a polypeptide (or a portion of a polypeptide) that interacts with one or more polypeptides (e.g., target polypeptides). For example, a peptide interaction domain may be a scaffold protein, a polypeptide of a multiprotein complex, or a portion thereof.

In some embodiments, an enrichment molecule comprises an immunoglobulin, an aptamer, an enzyme, and/or a peptide interaction domain.

Exemplary enrichment molecules that are preferentially bound by one or more target polypeptides include oligonucleotides (e.g., double-stranded DNA, single-stranded DNA, double-stranded RNA, single-stranded RNA, or the like), oligosaccharides (or polysaccharides), lipids, glycoproteins, receptor ligands, receptor agonists, receptor antagonists, enzyme substrates, and enzyme cofactors.

In some embodiments, an enrichment molecule comprises an oligonucleotide (e.g., double-stranded DNA, single-stranded DNA, double-stranded RNA, single-stranded RNA, or the like), an oligosaccharide, a lipid, a receptor ligand, a receptor agonist, a receptor antagonist, an enzyme substrate, and/or an enzyme cofactor.

Preferential binding is used herein to characterize enrichment molecules to emphasize: (i) that an enrichment molecule need not exhibit high specificity (i.e., only bind to (or be bound by) a single target polypeptide to an appreciable level); (ii) that an enrichment molecule may exhibit some degree of off-target binding (i.e., bind to (or be bound by) an off-target molecule to a detectable level); and (iii) that an enrichment molecule need not bind to a target polypeptide with 100% efficiency (i.e., not all target polypeptides in a complex sample need necessarily be bound, even in the presence of excess enrichment molecules).

In some embodiments, an enrichment molecule preferentially binds to (or is preferentially bound by) a single target polypeptide. However, in other embodiments, an enrichment molecule preferential binds to (or is preferentially bound by) two or more target polypeptides.

In some embodiments, an enrichment molecule exhibits preferential binding to (or is preferentially bound by) at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, or at least 100, at least 200, at least 300, at least 400, at least 500, at least 600, at least 700, at least 800, at least 900, at least 1000, at least 2000, at least 3000, at least 4000, at least 5000, or at least 10,000 target polypeptides.

In some embodiments, an enrichment molecule exhibits preferential binding to (or is preferentially bound by) two, three, four, five, six, seven, eight, nine, ten, eleven, twelve, thirteen, fourteen, or fifteen target polypeptides.

In some embodiments, an enrichment molecule exhibits preferential binding to (or is preferentially bound by) 1-2, 1-5, 1-10, 1-15, 1-20, 1-30, 1-40, 1-50, 1-60, 1-70, 1-80, 1-90, 1-100, 2-5, 2-10, 2-15, 2-20, 2-30, 2-40, 2-50, 2-60, 2-70, 2-80, 2-90, 2-100, 5-10, 5-15, 5-20, 5-30, 5-40, 5-50, 5-60, 5-70, 5-80, 5-90, 5-100, 10-15, 10-20, 10-30, 10-40, 10-50, 10-60, 10-70, 10-80, 10-90, 10-100, 15-20, 20-30, 20-40, 20-50, 20-60, 20-70, 20-80, 20-90, 20-100, 20-30, 20-40, 20-50, 20-60, 20-70, 20-80, 20-90, 20-100, 30-40, 30-50, 30-60, 30-70, 30-80, 30-90, 30-100, 40-50, 40-60, 40-70, 40-80, 40-90, 40-100, 50-60, 50-70, 50-80, 50-90, or 50-100, 100-200, 100-300, 100-400, 100-500, 100-600, 100-700, 100-800, 100-900, 100-1000, 100-5000, 100-10,000, 500-600, 500-700, 500-800, 500-900, 500-1000, 500-5000, 500-10,000, 1000-5000, or 1000-10,000 target polypeptides.

In some embodiments, an enrichment molecule exhibits preferential binding to (or is preferentially bound by) a plurality of related target polypeptides (e.g., 2, 3, 4, 5, 6, 7, 8, 9, 10, 20, 30, 40, 50, or more related polypeptides) that share at least 50%, 60%, 70%, 80%, 90% 95%, or 99% sequence homology.

In some embodiments, an enrichment molecule exhibits preferential binding to (or is preferentially bound by) a post-translational modification, such as acetylation, adenylylation, ADP-ribosylation, alkylation (e.g., methylation), amidation, arginylation, biotinylation, butyrylation, carbamylation, carbonylation, carboxylation, citrullination, deamidation, eliminylation, formylation, glycosylation (e.g., N-linked glycosylation, O-linked glycosylation), glipyatyon, glycation, hydroxylation, iodination, ISGylation, isoprenylation, lipoylation, malonylation, myristoylation, neddylation, nitration, oxidation, palmitoylation pegylation, phosphorylation, phosphopantetheinylation, polyglcylation, polyglutamylation, prenylation, propionylation, pupylation, S-glutathionylation, S-nitrosylation, S-sulfenylation, S-sulfinylation, S-sulfonylation, succinylation, sulfation, SUMOylation, and ubiquitination An enrichment molecule may be immobilized on (e.g., covalently attached to) a substrate (e.g., a capture probe as described in "Devices for Sample Preparation and Sample Sequencing"). The substrate may be a surface (e.g., a solid surface), a bead (e.g., a magnetic bead), a particle (e.g., a magnetic particle), or a gel.

(i) Pluralities of Enrichment Molecules

Typically, the enrichment methods described herein utilize a plurality of enrichment molecules. The enrichment molecules in a plurality may be chemically identical (i.e., a plurality having one enrichment molecule "type"). Alternatively, pluralities of enrichment molecules may contain a combination of different enrichment molecules (i.e., have two or more enrichment molecule "types").

In some embodiments, a plurality of enrichment molecules contains a single enrichment molecule type. In other embodiments, a plurality of enrichment molecules comprises a combination of two or more, three or more, four or more, five or more, six or more, seven or more, eight or more, nine or more, ten or more, eleven or more, twelve or more, thirteen or more, fourteen or more, or fifteen or more enrichment molecule types. In some embodiments, a plurality of enrichment molecules comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, or at least 100, at least 200, at least 300, at least 400, at least 500 enrichment molecule types.

In some embodiments, a plurality of enrichment molecules comprises a combination of two, three, four, five, six, seven, eight, nine, ten, eleven, twelve, thirteen, fourteen, or fifteen enrichment molecule types.

In some embodiments, a plurality of enrichment molecules contains a combination of 1-2, 1-5, 1-10, 1-15, 1-20, 1-30, 1-40, 1-50, 1-60, 1-70, 1-80, 1-90, 1-100, 2-5, 2-10, 2-15, 2-20, 2-30, 2-40, 2-50, 2-60, 2-70, 2-80, 2-90, 2-100, 5-10, 5-15, 5-20, 5-30, 5-40, 5-50, 5-60, 5-70, 5-80, 5-90, 5-100, 10-15, 10-20, 10-30, 10-40, 10-50, 10-60, 10-70, 10-80, 10-90, 10-100, 15-20, 20-30, 20-40, 20-50, 20-60, 20-70, 20-80, 20-90, 20-100, 20-30, 20-40, 20-50, 20-60, 20-70, 20-80, 20-90, 20-100, 30-40, 30-50, 30-60, 30-70, 30-80, 30-90, 30-100, 40-50, 40-60, 40-70, 40-80, 40-90, 40-100, 50-60, 50-70, 50-80, 50-90, or 50-100, 100-200, 100-300, 100-400, or 100-500 enrichment molecule types.

In some embodiments, each of the enrichment molecules in the plurality of enrichment molecules preferentially binds to (or is preferentially bound by) a single target polypeptide. In other embodiments, one or more (e.g., a subset) of the enrichment molecules in a plurality of enrichment molecules exhibits preferential binding to (or is preferentially bound by) two or more target polypeptides. In yet other embodiments, each of the enrichment molecules in the plurality of enrichment molecules exhibits preferential binding to (or is preferentially bound by) two or more target polypeptides.

In some embodiments, one or more (e.g., a subset) of the enrichment molecules in the plurality of enrichment molecules binds to a post-translational polypeptide modification. In other embodiments, each of the enrichment molecules in a plurality of enrichment molecules exhibits preferential binding to two or more post-translational polypeptide modifications.

In some embodiments, each of the enrichment molecules in the plurality of enrichment molecules is immobilized on (e.g., covalently attached to) a substrate (e.g., a capture probe as described in "Devices for Sample Preparation and Sample Sequencing"), such as a surface (e.g., a solid surface), a bead (e.g., a magnetic bead), a particle (e.g., a magnetic particle, or a gel). In some embodiments, one or more (e.g., a subset) of the plurality of enrichment molecules is immobilized on (e.g., covalently attached to) a substrate. As such, in some embodiments, the contacting of the plurality of polypeptides with the plurality of enrichment molecules occurs when a sample comprising the plurality of polypeptides contacts the substrate.

For example, in some embodiments, the enrichment molecules are covalently attached (e.g., crosslinked) in a gel and the sample is pulled through the gel. In some embodiments, the enrichment molecules are covalently attached to a bead (e.g., a magnetic bead), which are then pulled down.

(ii) Multiple Enrichment Molecule Pluralities

As described above, in some embodiments, the method comprises: (a) contacting a plurality of polypeptides with a first plurality of enrichment molecules, wherein at least a subset of the enrichment molecules in the first plurality of enrichment molecules binds to a subset of the polypeptides in the plurality of polypeptides, thereby generating a first bound subset of polypeptides and a first unbound subset of polypeptides; (b) isolating the first bound subset of polypeptides or the first unbound subset of polypeptides of (a); and (c) iteratively repeating steps (a) and (b) with one or more additional plurality of enrichment molecules to produce an enriched sample comprising a subset of the polypeptides in the plurality of polypeptides. In some embodiments, steps (a) and (b) are repeated using a second, third, fourth, fifth, sixth, seventh, eighth, ninth, tenth, or any number of additional plurality of enrichment molecules.

In some embodiments, each plurality of enrichment molecules utilized in the method of polypeptide enrichment is unique (i.e., each comprises a different plurality of enrichment molecules). In other embodiments, two or more of the pluralities are identical. In some embodiments, at least one of the pluralities of enrichment molecules targets a post-translational polypeptide modification and at least one of the pluralities of enrichment molecules does not target a post-translational modification.

For example, the first enrichment step (utilizing a first plurality of enrichment molecules) may enrich of a particular post-translational polypeptide modification, and a second enrichment step (utilizing a second plurality of enrichment molecules) may enrich for a particular polypeptide (and variants of that polypeptide). Alternatively, the first enrichment step (utilizing a first plurality of enrichment molecules) may enrich of a particular polypeptide (and variants of that polypeptide), and a second enrichment step (utilizing a second plurality of enrichment molecules) may enrich for a particular post-translational modification.

B. Polypeptide Modifications

One or more of the polypeptides of a complex sample may be modified in vitro prior to, concurrently with, and/or subsequent to the polypeptide enrichment described above. For example, in some embodiments, a complex sample is contacted with a modifying agent prior to, concurrently with, and/or subsequent to performance of polypeptide enrichment. Among other things, a modifying agent may mediate polypeptide fragmentation, polypeptide denaturation, addition of a post-translational modification, and/or the blocking of one or more functional groups.

In some embodiments, one or more polypeptides of a complex sample are modified by fragmentation. In some embodiments, fragmentation comprises enzymatic digestion. In some embodiments, digestion is carried out by contacting a polypeptide with an endopeptidase (e.g., trypsin) under digestion conditions. In some embodiments, fragmentation comprises chemical digestion. Examples of suitable reagents for chemical and enzymatic digestion are known in the art and include, without limitation, trypsin, chemotrypsin, Lys-C, Arg-C, Asp-N, Lys-N, BNPS-Skatole, CNBr, caspase, formic acid, glutamyl endopeptidase, hydroxylamine, iodosobenzoic acid, neutrophil elastase, pepsin, proline-endopeptidase, proteinase K, staphylococcal peptidase I, thermolysin, and thrombin.

In some embodiments, one or more polypeptides of a complex sample are modified by denaturation (e.g., by heat and/or chemical means).

In some embodiments, one or more polypeptides of a complex sample are modified by in vitro post-translational modification, such as by acetylation, adenylylation, ADP-ribosylation, alkylation (e.g., methylation), amidation, arginylation, biotinylation, butyrylation, carbamylation, carbonylation, carboxylation, citrullination, deamidation, eliminylation, formylation, glycosylation (e.g., N-linked glycosylation, O-linked glycosylation), glipyatyon, glycation, hydroxylation, iodination, ISGylation, isoprenylation, lipoylation, malonylation, myristoylation, neddylation, nitration, oxidation, palmitoylation pegylation, phosphorylation, phosphopantetheinylation, polyglcylation, polyglutamylation, prenylation, propionylation, pupylation, S-glutathionylation, S-nitrosylation, S-sulfenylation, S-sulfinylation, S-sulfonylation, succinylation, sulfation, SUMOylation, or ubiquitination.

In some embodiments, one or more polypeptides of a complex sample are modified by the blocking of one or more functional groups (e.g., free carboxylate groups and/or thiol groups).

In some embodiments, blocking free carboxylate groups refers to a chemical modification of these groups which alters chemical reactivity relative to an unmodified carboxylate. Suitable carboxylate blocking methods are known in the art and should modify side-chain carboxylate groups to be chemically different from a carboxy-terminal carboxylate group of a polypeptide to be functionalized. In some embodiments, blocking free carboxylate groups comprises esterification or amidation of free carboxylate groups of a polypeptide. In some embodiments, blocking free carboxylate groups comprises methyl esterification of free carboxylate groups of a polypeptide, e.g., by reacting the polypeptide with methanolic HCl. Additional examples of reagents and techniques useful for blocking free carboxylate groups include, without limitation, 4-sulfo-2,3,5,6-tetrafluorophenol (STP) and/or a carbodiimide such as N-(3-Dimethylaminopropyl)-N'-ethylcarbodiimide hydrochloride (EDAC), uronium reagents, diazomethane, alcohols and acid for Fischer esterification, the use of N-hydroxylsuccinimide (NHS) to form NHS esters (potentially as an intermediate to subsequent ester or amine formation), or reaction with carbonyldiimidazole (CDI) or the formation of mixed anhydrides, or any other method of modifying or blocking carboxylic acids, potentially through the formation of either esters or amides.

In some embodiments, blocking free thiol groups refers to a chemical modification of these groups which alters chemical reactivity relative to an unmodified thiol. In some embodiments, blocking free thiol groups comprises reducing and alkylating free thiol groups of a polypeptide. In some embodiments, reduction and alkylation is carried out by contacting a polypeptide with dithiothreitol (DTT) and one or both of iodoacetamide and iodoacetic acid. Examples of additional and alternative cysteine-reducing reagents which may be used are well known and include, without limitation, 2-mercaptoethanol, Tris (2-carboxyehtyl) phosphine hydrochloride (TCEP), tributylphosphine, dithiobutylamine (DTBA), or any reagent capable of reducing a thiol group. Examples of additional and alternative cysteine-blocking (e.g., cysteine-alkylating) reagents which may be used are well known and include, without limitation, acrylamide, 4-vinylpyridine, N-Ethylmalemide (NEM), N-ε-maleimidocaproic acid (EMCA), or any reagent that modifies cysteines so as to prevent disulfide bond formation.

In some embodiments, the N-terminal amino acid or the C-terminal amino acid of a polypeptide is modified.

In some embodiments, a carboxy-terminus of a polypeptide is modified in a method comprising: (i) blocking free carboxylate groups of the polypeptide; (ii) denaturing the polypeptide (e.g., by heat and/or chemical means); (iii) blocking free thiol groups of the polypeptide; (iv) digesting the polypeptide to produce at least one polypeptide fragment comprising a free C-terminal carboxylate group; and (v) conjugating (e.g., chemically) a functional moiety to the free C-terminal carboxylate group. In some embodiments, the method further comprises, after (i) and before (ii), dialyzing a sample comprising the polypeptide.

In some embodiments, a carboxy-terminus of a polypeptide is modified in a method comprising: (i) denaturing the polypeptide (e.g., by heat and/or chemical means); (ii) blocking free thiol groups of the polypeptide; (iii) digesting the polypeptide to produce at least one polypeptide fragment comprising a free C-terminal carboxylate group; (iv) blocking the free C-terminal carboxylate group to produce at least one polypeptide fragment comprising a blocked C-terminal carboxylate group; and (v) conjugating (e.g., enzymatically) a functional moiety to the blocked C-terminal carboxylate group. In some embodiments, the method further comprises, after (iv) and before (v), dialyzing a sample comprising the polypeptide.

In some embodiments, a complex sample is contacted with a modifying agent prior to enrichment to mediate polypeptide fragmentation, polypeptide denaturation, addition of a post-translational modification, and/or the blocking of one or more functional groups. Alternatively, or in addition, in some embodiments, a complex sample with a modifying agent concurrently with enrichment to mediate polypeptide fragmentation, polypeptide denaturation, addition of a post-translational modification, and/or the blocking of one or more functional groups. Alternatively, or in addition, in some embodiments, a complex sample (or a sample derived therefrom, comprising the one or more polypeptides of interest) with a modifying agent after enrichment to mediate polypeptide fragmentation, polypeptide denaturation, addition of a post-translational modification, and/or the blocking of one or more functional groups.

IV. Polypeptide Sequencing Methodologies

In some embodiments, molecules (e.g., polypeptides) of a multiplexed sample are sequenced. As such, in some aspects, the disclosure relates to methods of polypeptide sequencing and identification. Various methods of sequencing polypeptide molecules are known to those having ordinary skill in the art and include mass spectrometry (e.g., peptide mass fingerprinting and tandem mass spectrometry) and Edman degradation. Additional, previously undescribed methods of sequencing polypeptides are described herein.

As used herein, "sequencing," "sequence determination," "determining a sequence," and like terms, in reference to a polypeptide include determination of partial amino acid sequence information as well as full amino acid sequence information of the polypeptide. That is, the terminology includes sequence comparisons, fingerprinting, and like levels of information about a target molecule, as well as the express identification and ordering of each amino acid of the target molecule within a region of interest. The terminology includes identifying a single amino acid (or the probability of a single amino acid) of a polypeptide. In some embodiments, more than one amino acid (or the probability of more than one amino acid) of a polypeptide is identified. Accordingly, in some embodiments, the terms "amino acid sequence" and "polypeptide sequence" as used herein may refer to the polypeptide material itself and is not restricted to the specific sequence information (e.g., the succession of letters representing the order of amino acids from one terminus to another terminus) that biochemically characterizes a specific polypeptide.

In some embodiments, the probability of an amino acid at a specific position within a polypeptide is determined and illustrated in a probability array. For example, for a polypeptide consisting of two amino acids, the terms "sequencing," "sequence determination," "determining a sequence," and like terms may involve determining the probability of an amino at position 1 and/or position 2, such as [[0.80, 0.12. 0.05, 0.01, 0.01, 0.01, 0.00, 0.00, 0.00, 0.00, 0.00, 0.00, 0.00, 0.00, 0.00, 0.00, 0.00, 0.00, 0.00, 0.00], [0.00, 0.10, 0.90, 0.00, 0.00, 0.00, 0.00, 0.00, 0.00, 0.00, 0.00, 0.00, 0.00, 0.00, 0.00, 0.00, 0.00, 0.00, 0.00, 0.00]] where the probabilities in the array correspond to A, R, N, D, C, Q, E, G, H, I, L, K, M, F, P, S, T, W, Y, and V, respectively. One having ordinary skill in the art will understand that this example (and exemplary probability array) can be expanded to accommodate the analysis of additional amino acid identities (e.g., modified amino acids), such as those described herein.

In some embodiments, sequencing of a polypeptide molecule comprises identifying at least two (e.g., at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, at least 100, or more) amino acids (or amino acid probabilities) in the polypeptide molecule. In some embodiments, the at least two amino acids are contiguous amino acids. In some embodiments, the at least two amino acids are non-contiguous amino acids.

In some embodiments, sequencing of a polypeptide molecule comprises identification of less than 100% (e.g., less than 99%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 1% or less) of all amino acids in the polypeptide molecule. For example, in some embodiments, sequencing of a polypeptide molecule comprises identification of less than 100% of one type of amino acid in the polypeptide molecule (e.g., identification of a portion of all amino acids of one type in the polypeptide molecule). In some embodiments, sequencing of a polypeptide molecule comprises identification of less than 100% of each type of amino acid in the polypeptide molecule.

In some embodiments, sequencing of a polypeptide molecule comprises identification of at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100 or more types of amino acids in the polypeptide.

In some embodiments, the application provides compositions and methods for sequencing a polypeptide by identifying a series of amino acids that are present at a terminus of a polypeptide over time (e.g., by iterative detection and cleavage of amino acids at the terminus). In yet other embodiments, the application provides compositions and methods for sequencing a polypeptide by identifying labeled amino content of the polypeptide and comparing to a reference sequence database.

In some embodiments, the application provides compositions and methods for sequencing a polypeptide by sequencing a plurality of fragments of the polypeptide. In some embodiments, sequencing a polypeptide comprises combining sequence information for a plurality of polypeptide fragments to identify and/or determine a sequence for the polypeptide. In some embodiments, combining sequence information may be performed by computer hardware and software. See "Devices for Sample Preparation and Sample Sequencing." The methods described herein may allow for a set of related polypeptides, such as an entire proteome of an organism, to be sequenced. In some embodiments, a plurality of single molecule sequencing reactions are performed in parallel (e.g., on a single chip) according to aspects of the present application. For example, in some embodiments, a plurality of single molecule sequencing reactions are each performed in separate sample wells on a single chip or array.

In some embodiments, methods provided herein may be used for the sequencing and identification of an individual polypeptide in a sample comprising a complex mixture or an enriched mixture of polypeptides. In some embodiments, the application provides methods of uniquely identifying an individual polypeptide in a complex mixture or an enriched mixture of polypeptides. In some embodiments, an individual polypeptide is detected in a mixed sample by determining a partial amino acid sequence of the polypeptide. In some embodiments, the partial amino acid sequence of the polypeptide is within a contiguous stretch of approximately 5 to 50 amino acids.

Without wishing to be bound by any particular theory, it is believed that most human proteins can be identified using incomplete sequence information with reference to proteomic databases. For example, simple modeling of the human proteome has shown that approximately 98% of proteins can be uniquely identified by detecting just four types of amino acids within a stretch of 6 to 40 amino acids (see, e.g., Swaminathan, et al. PLoS Comput Biol. 2015, 11(2):e1004080; and Yao, et al. Phys. Biol. 2015, 12(5): 055003). Therefore, a complex mixture or enriched mixture of polypeptides can be degraded (e.g., chemically degraded, enzymatically degraded) into short polypeptide fragments of approximately 6 to 40 amino acids, and sequencing of this polypeptide library would reveal the identity and abundance of each of the polypeptides present in the original complex mixture or enriched mixture. Compositions and methods for selective amino acid labeling and identifying polypeptides by determining partial sequence information are described in in detail in U.S. patent application Ser. No. 15/510,962, filed Sep. 15, 2015, titled "SINGLE MOLECULE PEPTIDE SEQUENCING," which is incorporated by reference in its entirety.

Embodiments are capable of sequencing single polypeptide molecules with high accuracy, such as an accuracy of at least about 50%, 60%, 70%, 75%, 80%, 85%, 90%, 95%, 96%, 97%, 98%, 99%, 99.9%, 99.99%, 99.999%, or 99.9999%. In some embodiments, the target molecule used in single molecule sequencing is a polypeptide that is immobilized on a surface of a solid support such as a bottom surface or a sidewall surface of a sample well. The sample well also can contain other reagents needed for a sequencing reaction in accordance with the application, such as one or more suitable buffers, co-factors, labeled affinity reagents, and enzymes (e.g., catalytically active or inactive exopeptidase enzymes, which may be luminescently labeled or unlabeled).

Sequencing in accordance with the application, in some aspects, may involve immobilizing a polypeptide on a surface of a substrate (e.g., of a solid support, for example a chip, for example an integrated device as described herein). In some embodiments, a polypeptide may be immobilized on a surface of a sample well (e.g., on a bottom surface of a sample well) on a substrate. In some embodiments, the N-terminal amino acid of the polypeptide is immobilized (e.g., attached to the surface). In some embodiments, the C-terminal amino acid of the polypeptide is immobilized (e.g., attached to the surface). In some embodiments, one or more non-terminal amino acids are immobilized (e.g., attached to the surface). The immobilized amino acid(s) can be attached using any suitable covalent or non-covalent linkage, for example as described in this application. In some embodiments, a plurality of polypeptides are attached to a plurality of sample wells (e.g., with one polypeptide attached to a surface, for example a bottom surface, of each sample well), for example in an array of sample wells on a substrate.

Sequencing in accordance with the application, in some aspects, may be performed using a system that permits single molecule analysis. The system may include a sequencing device and an instrument configured to interface with the sequencing device. See "Devices for Sample Preparation and Sample Sequencing".

A. Labeled Affinity Reagents and Methods of Use

In some embodiments, methods provided herein comprise contacting a polypeptide with a labeled affinity reagent (also referred to herein as an amino acid recognition molecule, which may or may not comprise a label) that selectively binds one type of terminal amino acid. As used herein, in some embodiments, a terminal amino acid may refer to an amino-terminal amino acid of a polypeptide or a carboxy-terminal amino acid of a polypeptide. In some embodiments, a labeled affinity reagent selectively binds one type of terminal amino acid over other types of terminal amino acids. In some embodiments, a labeled affinity reagent selectively binds one type of terminal amino acid over an internal amino acid of the same type. In yet other embodiments, a labeled affinity reagent selectively binds one type of amino acid at any position of a polypeptide, e.g., the same type of amino acid as a terminal amino acid and an internal amino acid.

As used herein, in some embodiments, a type of amino acid refers to one of the twenty naturally occurring amino acids or a subset of types thereof. In some embodiments, a type of amino acid refers to a modified variant of one of the twenty naturally occurring amino acids or a subset of unmodified and/or modified variants thereof. Examples of modified amino acid variants include, without limitation, post-translationally-modified variants (e.g., acetylation, ADP-ribosylation, caspase cleavage, citrullination, formylation, N-linked glycosylation, O-linked glycosylation, hydroxylation, methylation, myristoylation, neddylation, nitration, oxidation, palmitoylation, phosphorylation, prenylation, S-nitrosylation, sulfation, sumoylation, and ubiquitination), chemically modified variants, unnatural amino acids, and proteinogenic amino acids such as selenocysteine and pyrrolysine. In some embodiments, a subset of types of amino acids includes more than one and fewer than twenty amino acids having one or more similar biochemical properties. For example, in some embodiments, a type of amino acid refers to one type selected from amino acids with charged side chains (e.g., positively and/or negatively charged side chains), amino acids with polar side chains (e.g., polar uncharged side chains), amino acids with non-polar side chains (e.g., nonpolar aliphatic and/or aromatic side chains), and amino acids with hydrophobic side chains.

In some embodiments, methods provided herein comprise contacting a polypeptide with one or more labeled affinity reagents that selectively bind one or more types of terminal amino acids. As an illustrative and non-limiting example, where four labeled affinity reagents are used in a method of the application, any one reagent selectively binds one type of terminal amino acid that is different from another type of amino acid to which any of the other three selectively binds (e.g., a first reagent binds a first type, a second reagent binds a second type, a third reagent binds a third type, and a fourth reagent binds a fourth type of terminal amino acid). For the purposes of this discussion, one or more labeled affinity reagents in the context of a method described herein may be alternatively referred to as a set of labeled affinity reagents.

In some embodiments, a set of labeled affinity reagents comprises at least one and up to six labeled affinity reagents. For example, in some embodiments, a set of labeled affinity reagents comprises one, two, three, four, five, or six labeled affinity reagents. In some embodiments, a set of labeled affinity reagents comprises ten or fewer labeled affinity reagents. In some embodiments, a set of labeled affinity reagents comprises eight or fewer labeled affinity reagents. In some embodiments, a set of labeled affinity reagents comprises six or fewer labeled affinity reagents. In some embodiments, a set of labeled affinity reagents comprises four or fewer labeled affinity reagents. In some embodiments, a set of labeled affinity reagents comprises three or fewer labeled affinity reagents. In some embodiments, a set of labeled affinity reagents comprises two or fewer labeled affinity reagents. In some embodiments, a set of labeled affinity reagents comprises four labeled affinity reagents. In some embodiments, a set of labeled affinity reagents comprises at least two and up to twenty (e.g., at least two and up to ten, at least two and up to eight, at least four and up to twenty, at least four and up to ten) labeled affinity reagents. In some embodiments, a set of labeled affinity reagents comprises more than twenty (e.g., 20 to 25, 20 to 30) affinity reagents. It should be appreciated, however, that any number of affinity reagents may be used in accordance with a method of the application to accommodate a desired use.

In accordance with the application, in some embodiments, one or more types of amino acids are identified by detecting luminescence of a labeled affinity reagent (e.g., an amino acid recognition molecule comprising a luminescent label). In some embodiments, a labeled affinity reagent comprises an affinity reagent that selectively binds one type of amino acid and a luminescent label having a luminescence that is associated with the affinity reagent. In this way, the luminescence (e.g., luminescence lifetime, luminescence intensity, and other luminescence properties described elsewhere herein) may be associated with the selective binding of the affinity reagent to identify an amino acid of a polypeptide. In some embodiments, a plurality of types of labeled affinity reagents may be used in a method according to the application, wherein each type comprises a luminescent label having a luminescence that is uniquely identifiable from among the plurality. Suitable luminescent labels may include luminescent molecules, such as fluorophore dyes, and are described elsewhere herein.

In some embodiments, one or more types of amino acids are identified by detecting one or more electrical characteristics of a labeled affinity reagent. In some embodiments, a labeled affinity reagent comprises an affinity reagent that selectively binds one type of amino acid and a conductivity label that is associated with the affinity reagent. In this way, the one or more electrical characteristics (e.g., charge, current oscillation color, and other electrical characteristics) may be associated with the selective binding of the affinity reagent to identify an amino acid of a polypeptide. In some embodiments, a plurality of types of labeled affinity reagents may be used in a method according to the application, wherein each type comprises a conductivity label that produces a change in an electrical signal (e.g., a change in conductance, such as a change in amplitude of conductivity and conductivity transitions of a characteristic pattern) that is uniquely identifiable from among the plurality. In some embodiments, the plurality of types of labeled affinity reagents each comprises a conductivity label having a different number of charged groups (e.g., a different number of negatively and/or positively charged groups). Accordingly, in some embodiments, a conductivity label is a charge label. Examples of charge labels include dendrimers, nanoparticles, nucleic acids and other polymers having multiple charged groups. In some embodiments, a conductivity label is uniquely identifiable by its net charge (e.g., a net positive charge or a net negative charge), by its charge density, and/or by its number of charged groups.

In some embodiments, an affinity reagent (e.g., an amino acid recognition molecule) may be engineered by one skilled in the art using conventionally known techniques. In some embodiments, desirable properties may include an ability to bind selectively and with high affinity to one type of amino acid only when it is located at a terminus (e.g., an N-terminus or a C-terminus) of a polypeptide. In yet other embodiments, desirable properties may include an ability to bind selectively and with high affinity to one type of amino acid when it is located at a terminus (e.g., an N-terminus or a C-terminus) of a polypeptide and when it is located at an internal position of the polypeptide.

As used herein, in some embodiments, the terms "selective" and "specific" (and variations thereof, e.g., selectively, specifically, selectivity, specificity) refer to a preferential binding interaction. For example, in some embodiments, a labeled affinity reagent that selectively binds one type of amino acid preferentially binds the one type over another type of amino acid. A selective binding interaction will discriminate between one type of amino acid (e.g., one type of terminal amino acid) and other types of amino acids (e.g., other types of terminal amino acids), typically more than about 10- to 100-fold or more (e.g., more than about 1,000- or 10,000-fold). Accordingly, it should be appreciated that a selective binding interaction can refer to any binding interaction that is uniquely identifiable to one type of amino acid over other types of amino acids. For example, in some aspects, the application provides methods of polypeptide sequencing by obtaining data indicative of association of one or more amino acid recognition molecules with a polypeptide molecule. In some embodiments, the data comprises a series of signal pulses corresponding to a series of reversible amino acid recognition molecule binding interactions with an amino acid of the polypeptide molecule, and the data may be used to determine the identity of the amino acid. As such, in some embodiments, a "selective" or "specific" binding interaction refers to a detected binding interaction that discriminates between one type of amino acid and other types of amino acids. In some embodiments, a labeled affinity reagent (e.g., an amino acid recognition molecule) selectively binds one type of amino acid with a dissociation constant ($K_D$) of less than about $10^{-6}$ M (e.g., less than about $10^{-7}$ M, less than about $10^{-8}$ M, less than about $10^{-9}$ M, less than about $10^{-10}$ M, less than about $10^{-11}$ M, less than about $10^{-12}$ M, to as low as $10^{-16}$ M) without significantly binding to other types of amino acids. In some embodiments, a labeled affinity reagent selectively binds one type of amino acid (e.g., one type of terminal amino acid) with a $K_D$ of less than about 100 nM, less than about 50 nM, less than about 25 nM, less than about 10 nM, or less than about 1 nM. In some embodiments, a labeled affinity reagent selectively binds one type of amino acid with a $K_D$ between about 50 nM and about 50 μM (e.g., between about 50 nM and about 500 nM, between about 50 nM and about 5 μM, between about 500 nM and about 50 μM, between about 5 μM and about 50 μM, or between about 10 μM and about 50 μM). In some embodiments, an amino acid recognition molecule binds one type of amino acid with a KD of about 50 nM.

In some embodiments, a labeled affinity reagent (e.g., an amino acid recognition molecule) binds two or more types of amino acids with a KD of less than about $10^{-6}$ M (e.g., less than about $10^{-7}$ M, less than about $10^{-8}$ M, less than about $10^{-9}$ M, less than about $10^{-10}$ M, less than about $10^{-11}$ M, less than about $10^{-12}$ M, to as low as $10^{-16}$ M). In some embodiments, an amino acid recognition molecule binds two or more types of amino acids with a KD of less than about 100 nM, less than about 50 nM, less than about 25 nM, less than about 10 nM, or less than about 1 nM. In some embodiments, an amino acid recognition molecule binds two or more types of amino acids with a KD of between about 50 nM and about 50 μM (e.g., between about 50 nM and about 500 nM, between about 50 nM and about 5 μM, between about 500 nM and about 50 μM, between about 5 μM and about 50 μM, or between about 10 μM and about 50 μM). In some embodiments, an amino acid recognition molecule binds two or more types of amino acids with a KD of about 50 nM.

In some embodiments, a labeled affinity reagent (e.g., an amino acid recognition molecule) binds at least one type of amino acid with a dissociation rate (koff) of at least 0.1 $s^{-1}$. In some embodiments, the dissociation rate is between about 0.1 $s^{-1}$ and about 1,000 $s^{-1}$ (e.g., between about 0.5 $s^{-1}$ and about 500 $s^{-1}$, between about 0.1 $s^{-1}$ and about 100 $s^{-1}$, between about 1 $s^{-1}$ and about 100 $s^{-1}$, or between about 0.5 $s^{-1}$ and about 50 $s^{-1}$). In some embodiments, the dissociation rate is between about 0.5 $s^{-1}$ and about 20 $s^{-1}$. In some embodiments, the dissociation rate is between about 2 $s^{-1}$ and about 20 $s^{-1}$. In some embodiments, the dissociation rate is between about 0.5 s-1 and about 2 $s^{-1}$.

In some embodiments, the value for KD or koff can be a known literature value, or the value can be determined empirically. For example, the value for KD or koff can be measured in a single-molecule assay or an ensemble assay. In some embodiments, the value for koff can be determined empirically based on signal pulse information obtained in a single-molecule assay as described elsewhere herein. For example, the value for koff can be approximated by the reciprocal of the mean pulse duration. In some embodiments, an amino acid recognition molecule binds two or more types of amino acids with a different KD or koff for each of the two or more types. In some embodiments, a first KD or koff for a first type of amino acid differs from a second KD or koff for a second type of amino acid by at least 10% (e.g., at least 25%, at least 50%, at least 100%, or more). In some embodiments, the first and second values for KD or koff differ by about 10-25%, 25-50%, 50-75%, 75-100%, or more than 100%, for example by about 2-fold, 3-fold, 4-fold, 5-fold, or more.

In some embodiments, a labeled affinity reagent comprises a luminescent label (e.g., a label) and an affinity reagent that selectively binds one or more types of terminal amino acids of a polypeptide. In some embodiments, an affinity reagent is selective for one type of amino acid or a subset (e.g., fewer than the twenty common types of amino acids) of types of amino acids at a terminal position or at both terminal and internal positions.

As described herein, an affinity reagent (also known as a "recognition molecule") may be any biomolecule capable of selectively or specifically binding one molecule over another molecule (e.g., one type of amino acid over another type of amino acid, as with an "amino acid recognition molecule" referred to herein). Affinity reagents (e.g., recognition molecules) include, for example, proteins and nucleic acids, which may be synthetic or recombinant. In some embodiments, an affinity reagent or recognition molecule may be an antibody or an antigen-binding portion of an antibody, or an enzymatic biomolecule, such as a peptidase, an aminotransferase, a ribozyme, an aptazyme, or a tRNA synthetase, including aminoacyl-tRNA synthetases and related molecules described in U.S. patent application Ser. No. 15/255,433, filed Sep. 2, 2016, titled "MOLECULES AND METHODS FOR ITERATIVE POLYPEPTIDE ANALYSIS AND PROCESSING".

In some embodiments, an affinity reagent or recognition molecule of the application is a degradation pathway protein. Examples of degradation pathway proteins suitable for use as recognition molecules include, without limitation, N-end rule pathway proteins, such as Arg/N-end rule pathway proteins, Ac/N-end rule pathway proteins, and Pro/N-end rule pathway proteins. In some embodiments, a recognition molecule is an N-end rule pathway protein selected from a Gid4 protein, a Ubr1 UBR box protein, and a ClpS protein (e.g., ClpS2).

A peptidase, also referred to as a protease or proteinase, is an enzyme that catalyzes the hydrolysis of a peptide bond. Peptidases digest polypeptides into shorter fragments and may be generally classified into endopeptidases and exopeptidases, which cleave a polypeptide chain internally and terminally, respectively. In some embodiments, labeled affinity reagent comprises a peptidase that has been modified to inactivate exopeptidase or endopeptidase activity. In this way, labeled affinity reagent selectively binds without also cleaving the amino acid from a polypeptide. In yet other embodiments, a peptidase that has not been modified to inactivate exopeptidase or endopeptidase activity may be used. For example, in some embodiments, a labeled affinity reagent comprises a labeled exopeptidase.

In accordance with certain embodiments of the application, polypeptide sequencing methods may comprise iterative detection and cleavage at a terminal end of a polypeptide. In some embodiments, labeled exopeptidase may be used as a single reagent that performs both steps of detection and cleavage of an amino acid. As generically depicted, in some embodiments, labeled exopeptidase has aminopeptidase or carboxypeptidase activity such that it selectively binds and cleaves an N-terminal or C-terminal amino acid, respectively, from a polypeptide. It should be appreciated that, in certain embodiments, labeled exopeptidase may be catalytically inactivated by one skilled in the art such that labeled exopeptidase retains selective binding properties for use as a non-cleaving labeled affinity reagent, as described herein.

An exopeptidase generally requires a polypeptide substrate to comprise at least one of a free amino group at its amino-terminus or a free carboxyl group at its carboxy-terminus. In some embodiments, an exopeptidase in accordance with the application hydrolyses a bond at or near a terminus of a polypeptide. In some embodiments, an exopeptidase hydrolyses a bond not more than three residues from a polypeptide terminus. For example, in some embodiments, a single hydrolysis reaction catalyzed by an exopeptidase cleaves a single amino acid, a dipeptide, or a tripeptide from a polypeptide terminal end.

In some embodiments, an exopeptidase in accordance with the application is an aminopeptidase or a carboxypeptidase, which cleaves a single amino acid from an amino- or a carboxy-terminus, respectively. In some embodiments, an exopeptidase in accordance with the application is a dipeptidyl-peptidase or a peptidyl-dipeptidase, which cleave a dipeptide from an amino- or a carboxy-terminus, respectively. In yet other embodiments, an exopeptidase in accordance with the application is a tripeptidyl-peptidase, which cleaves a tripeptide from an amino-terminus. Peptidase classification and activities of each class or subclass thereof is well known and described in the literature (see, e.g., Gurupriya, V. S. & Roy, S. C. Proteases and Protease Inhibitors in Male Reproduction. Proteases in Physiology and Pathology 195-216 (2017); and Brix, K. & Stocker, W. Proteases: Structure and Function. Chapter 1).

An exopeptidase in accordance with the application may be selected or engineered based on the directionality of a sequencing reaction. For example, in embodiments of sequencing from an amino-terminus to a carboxy-terminus of a polypeptide, an exopeptidase comprises aminopeptidase activity. Conversely, in embodiments of sequencing from a carboxy-terminus to an amino-terminus of a polypeptide, an exopeptidase comprises carboxypeptidase activity. Examples of carboxypeptidases that recognize specific carboxy-terminal amino acids, which may be used as labeled exopeptidases or inactivated to be used as non-cleaving labeled affinity reagents described herein, have been described in the literature (see, e.g., Garcia-Guerrero, M. C., et al. (2018) *PNAS* 115(17)).

Suitable peptidases for use as cleaving reagents and/or affinity reagents (e.g., recognition molecules) include aminopeptidases that selectively bind one or more types of amino acids. In some embodiments, an aminopeptidase recognition molecule is modified to inactivate aminopeptidase activity. In some embodiments, an aminopeptidase cleaving reagent is non-specific such that it cleaves most or all types of amino acids from a terminal end of a polypeptide. In some embodiments, an aminopeptidase cleaving reagent is more efficient at cleaving one or more types of amino acids from a terminal end of a polypeptide as compared to other types of amino acids at the terminal end of the polypeptide. For example, an aminopeptidase in accordance with the application specifically cleaves alanine, arginine, asparagine, aspartic acid, cysteine, glutamine, glutamic acid, glycine, histidine, isoleucine, leucine, lysine, methionine, phenylalanine, proline, selenocysteine, serine, threonine, tryptophan, tyrosine, and/or valine. In some embodiments, an aminopeptidase is a proline aminopeptidase. In some embodiments, an aminopeptidase is a proline iminopeptidase. In some embodiments, an aminopeptidase is a glutamate/aspartate-specific aminopeptidase. In some embodiments, an aminopeptidase is a methionine-specific aminopeptidase. In some embodiments, an aminopeptidase is an aminopeptidase set forth in TABLE 1. In some embodiments, an aminopeptidase cleaving reagent cleaves a peptide substrate set forth in TABLE 1.

In some embodiments, an aminopeptidase is a non-specific aminopeptidase. In some embodiments, a non-specific aminopeptidase is a zinc metalloprotease. In some embodiments, a non-specific aminopeptidase is an aminopeptidase set forth in TABLE 2. In some embodiments, a non-specific aminopeptidase cleaves a peptide substrate set forth in TABLE 2.

Accordingly, in some embodiments, the application provides an aminopeptidase (e.g., an aminopeptidase recognition molecule, an aminopeptidase cleaving reagent) having an amino acid sequence selected from TABLE 1 or TABLE 2 (or having an amino acid sequence that has at least 50%, at least 60%, at least 70%, at least 80%, 80-90%, 90-95%, 95-99%, or higher, amino acid sequence identity to an amino acid sequence selected from TABLE 1 or TABLE 2). In some embodiments, an aminopeptidase has 25-50%, 50-60%, 60-70%, 70-80%, 80-90%, 90-95%, or 95-99%, or higher, amino acid sequence identity to an aminopeptidase listed in TABLE 1 or TABLE 2. In some embodiments, an aminopeptidase is a modified aminopeptidase and includes one or more amino acid mutations relative to a sequence set forth in TABLE 1 or TABLE 2.

TABLE 1

| Non-limiting examples of aminopeptidases | | |
|---|---|---|
| Name | SEQ ID NO: | Sequence |
| *L. pneumophila* M1 Aminopeptidase (Glu/Asp Specific) | 1 | MGSSHHHHHHSSGLVPRGSHMMVKQGVFMKTDQSKVKKLSDYKSLDYF VIHVDLQIDLSKKPVESKARLTVVPNLNVDSHSNDLVLDGENMTLVSLQ MNDNLLKENEYELTKDSLIIKNIPQNTPFTIEMTSLLGENTDLFGLYETEGV ALVKAESEGLRRVFYLPDRPDNLATYKTTIIANQEDYPVLLSNGVLIEKKE LPLGLHSVTWLDDVPKPSYLFALVAGNLQRSVTYYQTKSGRELPIEFYVP PSATSKCDFAKEVLKEAMAWDERTFNLECALRQHMVAGVDKYASGASE PTGLNLFNTENLFASPETKTDLGILRVLEVVAHEFFHYWSGDRVTIRDWF NLPLKEGLTTFRAAMFREELFGTDLIRLLDGKNLDERAPRQSAYTAVRSL YTAAAYEKSADIFRMMMLFIGKEPFIEAVAKFFKDNDGGAVTLEDFIESIS NSSGKDLRSFLSWFTESGIPELIVTDELNPDTKQYFLKIKTVNGRNRPIPIL MGLLDSSGAEIVADKLLIVDQEEIEFQFENIQTRPIPSLLRSFSAPVHMKYE YSYQDLLLLMQFDTNLYNRCEAAKQLISALINDFCIGKKIELSPQFFAVYK ALLSDNSLNEWMLAELITLPSLEELIENQDKPDFEKLNEGRQLIQNALANE LKTDFYNLLFRIQISGDDDKQKLKGFDLKQAGLRRLKSVCFSYLLNVDFE KTKEKLILQFEDALGKNMTETALALSMLCEINCEEADVALEDYYHYWKN DPGAVNNWFSIQALAHSPDVIERVKKLMRHGDFDLSNPNKVYALLGSFIK NPFGFHSVTGEGYQLVADAIFDLDKINPTLAANLTEKFTYWDKYDVNRQ AMMISTLKIIYSNATSSDVRTMAKKGLDKVKEDLPLPIHLTFHGGSTMQD RTAQLIADGNKENAYQLH |
| *E. coli* methionine aminopeptidase (Met specific) | 2 | MAHHHHHHMGTAISIKTPEDIEKMRVAGRLAAEVLEMIEPYVKPGVSTGE LDRICNDYIVNEQHAVSACLGYHGYPKSVCISINEVVCHGIPDDAKLLKD GDIVNIDVTVIKDGFHGDTSKMFIVGKPTIMGERLCRITQESLYLALRMVK PGINLREIGAAIQKFVEAEGFSVVREYCGHGIGRGFHEEPQVLHYDSRETN VVLKPGMTFTIEPMVNAGKKEIRTMKDGWTVKTKDRSLSAQYEHTIVVT DNGCEILTLRKDDTIPAIISHD |
| *M. smegmatis* Proline iminopeptidase (Pro specific) | 3 | MAHHHHHHMGTLEANTNGPGSMLSRMPVSSRTVPFGDHETWVQVTTPE NAQPHALPLIVLHGGPGMAHNYVANIAALADETGRTVIHYDQVGCGNST HLPDAPADFWTPQLFVDEFHAVCTALGIERYHVLGQSWGGMLGAEIAVR QPSGLVSLAICNSPASMRLWSEAAGDLRAQLPAETRAALDRHEAAGTITH PDYLQAAAEFYRRHVCRVVPTPQDFADSVAQMEAEPTVYHTMNGPNEF HVVGTLGDWSVIDRLPDVTAPVLVIAGEHDEATPKTWQPFVDHIPDVRSH VFPGTSHCTHLEKPEEFRAVVAQFLHQHDLAADARV |
| *Y. pestis* Proline iminopeptidase (Pro Specific) | 4 | MTQQEYQNRRQALLAKMAPGSAAIIFAAPEATRSADSEYPYRQNSDFSYL TGFNEPEAVLILVKSDETHNHSVLFNRIRDLTAEIWFGRRLGQEAAPTKLA VDRALPFDEINEQLYLLLNRLDVIYHAQGQYAYADNIVFAALEKLRHGFR KNLRAPATLTDWRPWLHEMRLFKSAEEIAVLRRAGEISALAHTRAMEKC RPGMFEYQLEGEILHEFTRHGARYPAYNTIVGGGENGCILHYTENECELR DGDLVLIDAGCEYRGYAGDITRTFPVNGKFTPAQRAVYDIVLAAINKSLT LFRPGTSIREVTEEVVRIMVVGLVELGILKGDIEQLIAEQAHRPFFMHGLSH WLGMDVHDVGDYGSSDRGRILEPGMVLTVEPGLYIAPDADVPPQYRGIGI RIEDDIVITATGNENLTASVVKDPDDIEALMALNHAGENLYFQEHHHHHH |
| *P. furiosus* Methionine aminopeptidase | 5 | MDTEKLMKAGEIAKKVREKAIKLARPGMLLLELAESIEKMIMELGGKPAF PVNLSINEIAAHYTPYKGDTTVLKEGDYLKIDVGVHIDGFIADTAVTVRVG MEEDELMEAAKEALNAAISVARAGVEIKELGKAIENEIRKRGFKPIVNLSG HKIERYKLHAGISIPNIYRPHDNYVLKEGDVFAIEPFATIGAGQVIEVPPTLI YMYVRDVPVRVAQARFLLAKIKREYGTLPFAYRWLQNDMPEGQLKLAL KTLEKAGAIYGYPVLKEIRNGIVAQFEHTIIVEKDSVIVTQDMINKSTLE |
| *Aeromonas sobria* Proline aminopeptidase | 6 | HMSSPLHYVLDGIHCEPHFFTVPLDHQQPDDEETITLFGRTLCRKDRLDDE LPWLLYLQGGPGFGAPRPSANGGWIKRALQEFRVLLLDQRGTGHSTPIHA ELLAHLNPRQQADYLSHFRADSIVRDAELIREQLSPDHPWSLLGQSFGGFC SLTYLSLFPDSLHEVYLTGGVAPIGRSADEVYRATYQRVADKNRAFFARF PHAQAIANRLATHLQRHDVRLPNGQRLTVEQLQQQGLDLGASGAFEELY YLLEDAFIGEKLNPAFLYQVQAMQPFNTNPVFAILHELIYCEGAASHWAA ERVRGEFPALAWAQGKDFAFTGEMIFPWMFEQFRELIPLKEAAHLLAEKA DWGPLYDPVQLARNKVPVACAVYAEDMYVEFDYSRETLKGLSNSRAWI TNEYEHNGLRVDGEQILDRLIRLNRDCLE |
| *Pyrococcus furiosus* Proline Aminopeptidase (X-/-Pro) | 7 | MKERLEKLVKFMDENSIDRVFIAKPVNVYYFSGTSPLGGGYIIVDGDEATL YVPELEYEMAKEESKLPVVKFKKFDEIYEILKNTETLGIEGTLSYSMVENF KEKSNVKEFKKIDDVIKDLRIIKTKEEIEIIEKACEIADKAVMAAIEEITEGK REREVAAKVEYLMKMNGAEKPAFDTIIASGHRSALPHGVASDKRIERGDL VVIDLGALYNHYNSDITRTIVVGSPNEKQREIYEIVLEAQKRAVEAAKPG MTAKELDSIAREIIKEYGYGDYFIHSLGHGVGLEIHEWPRISQYDETVLKE GMVITIEPGIYIPKLGGVRIEDTVLITENGAKRLTKTERELL |
| *Elizabethkingia meningoseptica* Proline aminopeptidase | 8 | MIPITTPVGNFKVWTKRFGTNPKIKVLLLHGGPAMTHEYMECFETFFQRE GFEFYEYDQLGSYYSDQPTDEKLWNIDRFVDEVEQVRKAIHADKENFYV LGNSWGGILAMEYALKYQQNLKGLIVANMMASAPEYVKYAEVLSKQM KPEVLAEVRAIEAKKDYANPRYTELLFPNYYAQHICRLKEWPDALNRSLK |

TABLE 1-continued

Non-limiting examples of aminopeptidases

| Name | SEQ ID NO: | Sequence |
|---|---|---|
| | | HVNSTVYTLMQGPSELGMSSDARLAKWDIKNRLHEIATPTLMIGARYDT MDPKAMEEQSKLVQKGRYLYCPNGSHLAMWDDQKVFMDGVIKFIKDV DTKSFN |
| *Aeromonas sobria* Proline aminopeptidase | 9 | HMSSPLHYVLDGIHCEPHFFTVPLDHQQPDDEETITLFGRTLCRKDRLDDE LPWLLYLQGGPGFGAPRPSANGGWIKRALQEFRVLLLDQRGTGHSTPIHA ELLAHLNPRQQADYLSHFRADSIVRDAELIREQLSPDHPWSLLGQSFGGFC SLTYLSLFPDSLHEVYLTGGVAPIGRSADEVYRATYQRVADKNRAFFARF PHAQAIANRLATHLQRHDVRLPNGQRLTVEQLQQQGLDLGASGAFEELY YLLEDAFIGEKLNPAFLYQVQAMQPFNTNPVFAILHELIYCEGAASHWAA ERVRGEFPALAWAQGKDFAFTGEMIFPWMFEQFRELIPLKEAAHLLAEKA DWGPLYDPVQLARNKVPVACAVYAEDMYVEFDYSRETLKGLSNSRAWI TNEYEHNGLRVDGEQILDRLIRLNRDCLE |
| *N. gonorrhoeae* Proline Iminopeptidase | 10 | MYEIKQPFHSGYLQVSEIHQIYWEESGNPDGVPVIFLHGGPGAGASPECRG FFNPDVFRIVIIDQRGCGRSHPYACAEDNTTWDLVADIEKVREMLGIGKW LVFGGSWGSTLSLAYAQTHPERVKGLVLRGIFLCRPSETAWLNEAGGVSR IYPEQWQKFVAPIAENRRNRLIEAYHGLLFHQDEEVCLSAAKAWADWES YLIRFEPEGVDEDAYASLAIARLENHYFVNGGWLQGDKAILNNIGKIRHIP TVIVQGRYDLCTPMQSAWELSKAFPEAELRVVQAGHCAFDPPLADALVQ AVEDILPRLL |

TABLE 2

Non-limiting example of non-specific aminopeptidases

| Name | SEQ ID NO: | Sequence |
|---|---|---|
| *E. coli* Aminopeptidase N (Zinc Metalloprotease)* | 11 | MGSSHHHHHHSSGENLYFQGHMTQQPQAKYRHDYRAPDYQITDIDLTFD LDAQKTVVTAVSQAVRHGASDAPLRLNGEDLKLVSVHINDEPWTAWKE EEGALVISNLPERFTLKIINEISPAANTALEGLYQSGDALCTQCEAEGFRHIT YYLDRPDVLARFTTKIIADKIKYPFLLSNGNRVAQGELENGRHWVQWQD PFPKPCYLFALVAGDFDVLRDTFTTRSGREVALELYVDRGNLDRAPWAM TSLKNSMKWDEERFGLEYDLDIYMIVAVDFFNMGAMENKGLNIFNSKYV LARTDTATDKDYLDIERVIGHEYFHNWTGNRVTCRDWFQLSLKEGLTVF RDQEFSSDLGSRAVNRINNVRTMRGLQFAEDASPMAHPIRPDMVIEMNNF YTLTVYEKGAEVIRMIHTLLGEENFQKGMQLYFERHDGSAATCDDFVQA MEDASNVDLSHFRRWYSQSGTPIVTVKDDYNPETEQYTLTISQRTPATPD QAEKQPLHIPFAIELYDNEGKVIPLQKGGHPVNSVLNVTQAEQTFVFDNV YFQPVPALLCEFSAPVKLEYKWSDQQLTFLMRHARNDFSRWDAAQSLLA TYIKLNVARHQQGQPLSLPVHVADAFRAVLLDEKIDPALAAEILTLPSVNE MAELFDIIDPIAIAEVREALTRTLATELADELLAIYNANYQSEYRVEHEDIA KRTLRNACLRFLAFGETHLADVLVSKQFHEANNMTDALAALSAAVAAQL PCRDALMQEYDDKWHQNGLVMDKWFILQATSPAANVLETVRGLLQHRS FTMSNPNRIRSLIGAFAGSNPAAFHAEDGSGYLFLVEMLTDLNSRNPQVAS RLIEPLIRLKRYDAKRQEKMRAALEQLKGLENLSGDLYEKITKALA |
| *P. falciparum* M1 aminopeptidase** | 12 | PKIHYRKDYKPSGFIINQVTLNINIHDQETIVRSVLDMDISKHNVGEDLVFD GVGLKINEISINNKKLVEGEEYTYDNEFLTIFSKFVPKSKFAFSSEVIIHPET NYALTGLYKSKNIIVSQCEATGFRRITFFIDRPDMMAKYDVTVTADKEKY PVLLSNGDKVNEFEIPGGRHGARFNDPPLKPCYLFAVVAGDLKHLSATYI TKYTKKKVELYVFSEEKYVSKLQWALECLKKSMAFDEDYFGLEYDLSRL NLVAVSDFNVGAMENKGLNIFNANSLLASKKNSIDFSYARILTVVGHEYF HQYTGNRVTLRDWFQLTLKEGLTVHRENLFSEEMTKTVTTRLSHVDLLR SVQFLEDSSPLSHPIRPESYVSMENFYTTTVYDKGSEVMRMYLTILGEEYY KKGFDIYIKKNDGNTATCEDFNYAMEQAYKMKKADNSANLNQYLLWFS QSGTPHVSFKYNYDAEKKQYSIHVNQYTKPDENQKEKKPLFIPISVGLINP ENGKEMISQTTLELTKESDTFVFNNIAVKPIPSLFRGFSAPVYIEDQLTDEE RILLLKYDSDAFVRYNSCTNIYMKQILMNYNEFLKAKNEKLESFQLTPVN AQFIDAIKYLLEDPHADAGFKSYIVSLPQDRYIINFVSNLDTDVLADTKEYI YKQIGDKLNDVYYKMFKSLEAKADDLTYFNDESHVDFDQMNMRTLRNT LLSLLSKAQYPNILNEIIEHSKSPYPSNWLTSLSVSAYFDKYFELYDKTYKL SKDDELLLQEWLKTVSRSDRKDIYEILKKLENEVLKDSKNPNDIRAVYLPF TNNLRRFHDISGKGYKLIAEVITKTDKFNPMVATQLCEPFKLWNKLDTKR QELMLNEMNTMLQEPQISNNLKEYLLRLTNK |
| NPEPPS | 13 | MGSSHHHHHHSSGMWLAAAAPSLARRLLFLGPPPPPLLLLVFSRSSRRRL HSLGLAAMPEKRPFERLPADVSPINYSLCLKPDLLDFTFEGKLEAAAQVR QATNQIVMNCADIDIITASYAPEGDEEIHATGFNYQNEDEKVTLSFPSTLQ |

TABLE 2-continued

| Name | SEQ ID NO: | Sequence |
|---|---|---|
| | | TGTGTLKIDFVGELNDKMKGFYRSKYTTPSGEVRYAAVTQFEATDARRA FPCWDEPAIKATFDISLVVPKDRVALSNMNVIDRKPYPDDENLVEVKFAR TPVMSTYLVAFVVGEYDFVETRSKDGVCVRVYTPVGKAEQGKFALEVA AKTLPFYKDYFNVPYPLPKIDLIAIADFAAGAMENWGLVTYRETALLIDPK NSCSSSRQWVALVVGHELAHQWFGNLVTMEWWTHLWLNEGFASWIEY LCVDHCFPEYDIWTQFVSADYTRAQELDALDNSHPIEVSVGHPSEVDEIFD AISYSKGASVIRMLHDYIGDKDFKKGMNMYLTKFQQKNAATEDLWESLE NASGKPIAAVMNTWTKQMGFPLIYVEAEQVEDDRLLRLSQKKFCAGGSY VGEDCPQWMVPITISTSEDPNQAKLKILMDKPEMNVVLKNVKPDQWVKL NLGTVGFYRTQYSSAMLESLLPGIRDLSLPPVDRLGLQNDLFSLARAGIIST VEVLKVMEAFVNEPNYTVWSDLSCNLGILSTLLSHTDFYEEIQEFVKDVFS PIGERLGWDPKPGEGHLDALLRGLVLGKLGKAGHKATLEEARRRFKDHV EGKQILSADLRSPVYLTVLKHGDGTTLDIMLKLHKQADMQEEKNRIERVL GATLLPDLIQKVLTFALSEEVRPQDTVSVIGGVAGGSKHGRKAAWKFIKD NWEELYNRYQGGFLISRLIKLSVEGFAVDKMAGEVKAFFESHPAPSAERTI QQCCENILLNAAWLKRDAESIHQYLLQRKASPPTV |
| NPEPPS E366V | 14 | MGSSHHHHHHSSGMWLAAAAPSLARRLLFLGPPPPPLLLLVFSRSSRRRL HSLGLAAMPEKRPFERLPADVSPINYSLCLKPDLLDFTFEGKLEAAAQVR QATNQIVMNCADIDIITASYAPEGDEEIHATGFNYQNEDEKVTLSFPSTLQ TGTGTLKIDFVGELNDKMKGFYRSKYTTPSGEVRYAAVTQFEATDARRA FPCWDEPAIKATFDISLVVPKDRVALSNMNVIDRKPYPDDENLVEVKFAR TPVMSTYLVAFVVGEYDFVETRSKDGVCVRVYTPVGKAEQGKFALEVA AKTLPFYKDYFNVPYPLPKIDLIAIADFAAGAMENWGLVTYRETALLIDPK NSCSSSRQWVALVVGHVLAHQWFGNLVTMEWWTHLWLNEGFASWIEY LCVDHCFPEYDIWTQFVSADYTRAQELDALDNSHPIEVSVGHPSEVDEIFD AISYSKGASVIRMLHDYIGDKDFKKGMNMYLTKFQQKNAATEDLWESLE NASGKPIAAVMNTWTKQMGFPLIYVEAEQVEDDRLLRLSQKKFCAGGSY VGEDCPQWMVPITISTSEDPNQAKLKILMDKPEMNVVLKNVKPDQWVKL NLGTVGFYRTQYSSAMLESLLPGIRDLSLPPVDRLGLQNDLFSLARAGIIST VEVLKVMEAFVNEPNYTVWSDLSCNLGILSTLLSHTDFYEEIQEFVKDVFS PIGERLGWDPKPGEGHLDALLRGLVLGKLGKAGHKATLEEARRRFKDHV EGKQILSADLRSPVYLTVLKHGDGTTLDIMLKLHKQADMQEEKNRIERVL GATLLPDLIQKVLTFALSEEVRPQDTVSVIGGVAGGSKHGRKAAWKFIKD NWEELYNRYQGGFLISRLIKLSVEGFAVDKMAGEVKAFFESHPAPSAERTI QQCCENILLNAAWLKRDAESIHQYLLQRKASPPTV |
| *Francisella tularensis* Aminopeptidase N | 15 | MIYEFVMTDPKIKYLKDYKPSNYLIDETHLIFELDESKTRVTANLYIVANR ENRENNTLVLDGVELKLLSIKLNNKHLSPAEFAVNENQLIINNVPEKFVLQ TVVEINPSANTSLEGLYKSGDVFSTQCEATGFRKITYYLDRPDVMAAFTV KIIADKKKYPIILSNGDKIDSGDISDNQHFAVWKDPFKKPCYLFALVAGDL ASIKDTYITKSQRKVSLEIYAFKQDIDKCHYAMQAVKDSMKWDEDRFGL EYDLDTFMIVAVPDFNAGAMENKGLNIFNTKYIMASNKTATDKDFELVQ SVVGHEYFHNWTGDRVTCRDWFQLSLKEGLTVFRDQEFTSDLNSRDVKR IDDVRIIRSAQFAEDASPMSHPIRPESYIEMNNFYTVTVYNKGAEIIRMIHTL LGEEGFQKGMKLYFERHDGQAVTCDDFVNAMADANNRDFSLFKRWYA QSGTPNIKVSENYDASSQTYSLTLEQTTLPTADQKEKQALHIPVKMGLINP EGKNIAEQVIELKEQKQTYTFENIAAKPVASLFRDFSAPVKVEHKRSEKDL LHIVKYDNNAFNRWDSLQQIATNIILNNADLNDEFLNAFKSILHDKDLDK ALISNALLIPIESTIAEAMRVIMVDDIVLSRKNVVNQLADKLKDDWLAVY QQCNDNKPYSLSAEQIAKRKLKGVCLSYLMNASDQKVGTDLAQQLFDN ADNMTDQQTAFTELLKSNDKQVRDNAINEFYNRWRHEDLVVNKWLLSQ AQISHESALDIVKGLVNHPAYNPKNPNKVYSLIGGFGANFLQYHCKDGLG YAFMADTVLALDKFNHQVAARMARNLMSWKRYDSDRQAMMKNALEKI KASNPSKNVFEIVSKSLES |
| *Pyrococcus horikoshii* TET Aminopeptidase | 16 | MGSSHHHHHHSSGMEVRNMVDYELLKKVVEAPGVSGYEFLGIRDVVIEE IKDYVDEVKVDKLGNVIAHKKGEGPKVMIAAHMDQIGLMVTHIEKNGFL RVAPIGGVDPKTLIAQRFKVWIDKGKFIYGVGASVPPHIQKPEDRKKAPD WDQIFIDIGAESKEEAEDMGVKIGTVITWDGRLERLGKHRFVSIAFDDRIA VYTILEVAKQLKDAKADVYFVATVQEEVGLRGARTSAFGIEPDYGFAIDV TIAADIPGTPEHKQVTHLGKGTAIKIMDRSVICHPTIVRWLEELAKKHEIPY QLEILLGGGTDAGAIHLTKAGVPTGALSVPARYIHSNTEVVDERDVDATV ELMTKALENIHELKI |
| *T. aquaticus* Aminopeptidase T | 17 | MDAFTENLNKLAELAIRVGLNLEEGQEIVATAPIEAVDFVRLLAEKAYEN GASLFTVLYGDNLIARKRLALVPEAHLDRAPAWLYEGMAKAFHEGAARL AVSGNDPKALEGLPPERVGRAQQAQSRAYRPTLSAITEFVTNWTIVPFAH PGWAKAVFPGLPEEEAVQRLWQAIFQATRVDQEDPVAAWEAHNRVLHA KVAFLNEKRFHALHFQGPGTDLTVGLAEGHLWQGGATPTKKGRLCNPNL PTEEVFTAPHRERVEGVVRASRPLALSGQLVEGLWARFEGGVAVEVGAE KGEEVLKKLLDTDEGARRLGEVALVPADNPIAKTGLVFFDTLFDENAASH IAFGQAYAENLEGRPSGEEFRRRGGNESMVHVDWMIGSEEVDVDGLLED GTRVPLMRRGRWVI |

Non-limiting example of non-specific aminopeptidases

TABLE 2-continued

| Non-limiting example of non-specific aminopeptidases | | |
|---|---|---|
| Name | SEQ ID NO: | Sequence |
| *Bacillus stearothermophilus* Peptidase M28 | 18 | MAKLDETLTMLKALTDAKGVPGNEREARDVMKTYIAPYADEVTTDGLG SLIAKKEGKSGGPKVMIAGHLDEVGFMVTQIDDKGFIRFQTLGGWWSQV MLAQRVTIVTKKGDITGVIGSKPPHILPSEARKKPVEIKDMFIDIGATSREE AMEWGVRPGDMIVPYFEFTVLNNEKMLLAKAWDNRIGCAVAIDVLKQL KGVDHPNTVYGVGTVQEEVGLRGARTAAQFIQPDIAFAVDVGIAGDTPG VSEKEAMGKLGAGPHIVLYDATMVSHRGLREFVIEVAEELNIPHHFDAMP GVGTDAGAIHLTGIGVPSLTIAIPTRYIHSHAAILHRDDYENTVKLLVEVIK RLDADKVKQLTFDE |
| *Vibrio cholera* Aminopeptidase | 19 | MEDKVWISMGADAVGSLNPALSESLLPHSFASGSQVWIGEVAIDELAELS HTMHEQHNRCGGYMVHTSAQGAMAALMMPESIANFTIPAPSQQDLVNA WLPQVSADQITNTIRALSSFNNRFYTTTSGAQASDWLANEWRSLISSLPGS RIEQIKHSGYNQKSVVLTIQGSEKPDEWVIVGGHLDSTLGSHTNEQSIAPG ADDDASGIASLSEIIRVLRDNNFRPKRSVALMAYAAEEVGLRGSQDLANQ YKAQGKKVVSVLQLDMTNYRGSAEDIVFITDYTDSNLTQFLTTLIDEYLP ELTYGYDRCGYACSDHASWHKAGFSAAMPFESKFKDYNPKIHTSQDTLA NSDPTGNHAVKFTKLGLAYVIEMANAGSSQVPDDSVLQDGTAKINLSGA RGTQKRFTFELSQSKPLTIQTYGGSGDVDLYVKYGSAPSKSNWDCRPYQN GNRETCSFNNAQPGIYHVMLDGYTNYNDVALKASTQHHHHHH |
| *Photobacterium halotolerans* Aminopeptidasej | 20 | MEDKVWISIGSDASQTVKSVMQSNARSLLPESLASNGPVWVGQVDYSQL AELSHHMHEDHQRCGGYMVHSSPESAIAASNMPQSLVAFSIPEISQQDTV NAWLPQVNSQAITGTITSLTSFINRFYTTTSGAQASDWLANEWRSLSASLP NASVRQVSHFGYNQKSVVLTITGSEKPDEWIVLGGHLDSTIGSHTNEQSV APGADDDASGIASVTEIIRVLSENNFQPKRSIAFMAYAAEEVGLRGSQDLA NQYKAEGKQVISALQLDMTNYKGSVEDIVFITDYTDSNLTTFLSQLVDEY LPSLTYGFDTCGYACSDHASWHKAGFSAAMPFEAKFNDYNPMIHTPNDT LQNSDPTASHAVKFTKLGLAYAIEMASTTGGTPPPTGNVLKDGVPVNGLS GATGSQVHYSFELPAQKNLQISTAGGSGDVDLYVSFGSEATKQNWDCRP YRNGNNEVCTFAGATPGTYSIMLDGYRQFSGVTLKASTQHHHHHH |
| *Yersinia pestis* AminopeptidaseN | 21 | MTQQPQAKYRHDYRAPDYTITDIDLDFALDAQKTTVTAVSKVKRQGTDV TPLILNGEDLTLISVSVDGQAWPHYRQQDNTLVIEQLPADFTLTIVNDIHPA TNSALEGLYLSGEALCTQCEAEGFRHITYYLDRPDVLARFTTRIVADKSRY PYLLSNGNRVGQGELDDGRHWVKWEDPFPKPSYLFALVAGDFDVLQDK FITRSGREVALEIFVDRGNLDRADWAMTSLKNSMKWDETRFGLEYDLDI YMIVAVDFFNMGAMENKGLNVFNSKYVLAKAETATDKDYLNIEAVIGHE YFHNWTGNRVTCRDWFQLSLKEGLTVFRDQEFSSDLGSRSVNRIENVRV MRAAQFAEDASPMAHAIRPDKVIEMNNFYTLTVYEKGSEVIRMMHTLLG EQQFQAGMRLYFERHDGSAATCDDFVQAMEDVSNVDLSLFRRWYSQSG TPLLTVHDDYDVEKQQYHLFVSQKTLPTADQPEKLPLHIPLDIELYDSKGN VIPLQHNGLPVHHVLNVTEAEQTFTFDNVAQKPIPSLLREFSAPVKLDYPY SDQQLTFLMQHARNEFSRWDAAQSLLATYIKLNVAKYQQQQPLSLPAHV ADAFRAILLDEHLDPALAAQILTLPSENEMAELFTTIDPQAISTVHEAITRC LAQELSDELLAVYVANMTPVYRIEHGDIAKRALRNTCLNYLAFGDEEFAN KLVSLQYHQADNMTDSLAALAAAVAAQLPCRDELLAAFDVRWNHDGL VMDKWFALQATSPAANVLVQVRTLLKHPAFSLSNPNRTRSLIGSFASGNP AAFHAADGSGYQFLVEILSDLNTRNPQVAARLIEPLIRLKRYDAGRQALM RKALEQLKTLDNLSGDLYEKITKALAAHHHHHH |
| *Vibrio anguillarum* Aminopeptidase | 22 | MEEKVWISIGGDATQTALRSGAQSLLPENLINQTSVWVGQVPVSELATLS HEMHENHQRCGGYMVHPSAQSAMSVSAMPLNLNAFSAPEITQQTTVNA WLPSVSAQQITSTITTLTQFKNRFYTTSTGAQASNWIADHWRSLSASLPAS KVEQITHSGYNQKSVMLTITGSEKPDEWVVIGGHLDSTLGSRTNESSIAPG ADDDASGIAGVTEIIRLLSEQNFRPKRSIAFMAYAAEEVGLRGSQDLANRF KAEGKKVMSVMQLDMTNYQGSREDIVFITDYTDSNFTQYLTQLLDEYLP SLTYGFDTCGYACSDHASWHAVGYPAAMPFESKFNDYNPNIHSPQDTLQ NSDPTGFHAVKFTKLGLAYVVEMGNASTPPTPSNQLKNGVPVNGLSASR NSKTWYQFELQEAGNLSIVLSGGSGDADLYVKYQTDADLQQYDCRPYRS GNNETCQFSNAQPGRYSILLHGYNNYSNASLVANAQHHHHHH |
| Salinivibrio spYCSC6 Aminopeptidase | 23 | MEDKKVWISIGADAQQTALSSGAQPLLAQSVAHNGQAWIGEVSESELAA LSHEMHENHHRCGGYIVHSSAQSAMAASNMPLSRASFIAPAISQQALVTP WISQIDSALIVNTIDRLTDFPNRFYTTTSGAQASDWIKQRWQSLSAGLAGA SVTQISHSGYNQASVMLTIEGSESPDEWVVVGGHLDSTIGSRTNEQSIAPG ADDDASGIAAVTEVIRVLAQNNFQPKRSIAFVAYAAEEVGLRGSQDVAN QFKQAGKDVRGVLQLDMTNYQGSAEDIVFITDYTDNQLTQYLTQLLDEY LPTLNYGFDTCGYACSDHASWHQVGYPAAMPFEAKFNDYNPNIHTPQDT LANSDSEGAHAAKFTKLGLAYTVELANADSSPNPGNELKLGEPINGLSGA RGNEKYFNYRLDQSGELVIRTYGGSGDVDLYVKANGDVSTGNWDCRPY RSGNDEVCRFDNATPGNYAVMLRGYRTYDNVSLIVEHHHHHH |

TABLE 2-continued

Non-limiting example of non-specific aminopeptidases

| Name | SEQ ID NO: | Sequence |
|---|---|---|
| *Vibrio proteolyticus* Aminopeptidase I | 24 | **G**MPPITQQATVTAWLPQVDASQITGTISSLESFTNRFYTTTSGAQASDWIA SEWQ***F***LSASLPNASVKQVSHSGYNQKSVVMTITGSEAPDEWIVIGGHLDS TIGSHTNEQSVAPGADDDASGIAAVTEVIRVLSENNFQPKRSIAFMAYAAE EVGLRGSQDLANQYKSEGKNVVSALQLDMTNYKGSAQDVVFITDYTDS NFTQYLTQLMDEYLPSLTYGFDTCGYACSDHASWHNAGYPAAMPFESKF NDYNPRIHTTQDTLANSDPTGSHAKKFTQLGLAYAIEMGSATGDTPTPGN QLEHHHHHH |
| *P. furiosus* Aminopeptidase I | 25 | MVDWELMKKIIESPGVSGYEHLGIRDLVVDILKDVADEVKIDKLGNVIAH FKGSAPKVMVAAHMDKIGLMVNHIDKDGYLRVVPIGGVLPETLIAQKIRF FTEKGERYGVVGVLPPHLRREAKDQGGKIDWDSIIVDVGASSREEAEEMG FRIGTIGEFAPNFTRLSEHRFATPYLDDRICLYAMIEAARQLGEHEADIYIV ASVQEEIGLRGARVASFAIDPEVGIAMDVTFAKQPNDKGKIVPELGKGPV MDVGPNINPKLRQFADEVAKKYEIPLQVEPSPRPTGTDANVMQINREGVA TAVLSIPIRYMHSQVELADARDVDNTIKLAKALLEELKPMDFTPLEHHHH HH |

*Cleavage efficiency (from most to least): arginine > lysine > hydrophobic residues (including alanine, leucine, methionine, and phenylalanine) > proline (see, e.g., Matthews Biochemistry 47, 2008, 5303-5311).

**Cleavage efficiency (from most to least): leucine > alanine > arginine > phenylalanine > proline; does not cleave after glutamate and aspartate.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100], in which each deletion, insertion, substitution or addition of an amino acid residue in the second amino acid sequence compared to the first amino acid sequence is considered as a difference at a single amino acid residue (position). Alternatively, the degree of sequence identity between two amino acid sequences may be calculated using a known computer algorithm (e.g., by the local homology algorithm of Smith and Waterman (1970) Adv. Appl. Math. 2:482c, by the homology alignment algorithm of Needleman and Wunsch, J. Mol. Biol. (1970) 48:443, by the search for similarity method of Pearson and Lipman. Proc. Natl. Acad. Sci. USA (1998) 85:2444, or by computerized implementations of algorithms available as Blast, Clustal Omega, or other sequence alignment algorithms) and, for example, using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Additionally, or alternatively, two or more sequences may be assessed for the identity between the sequences. The terms "identical" or percent "identity" in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8%, or 99.9% identical) over a specified region or over the entire sequence, when compared and aligned for maximum correspondence over a comparison window, or designated region as measured using one of the above sequence comparison algorithms or by manual alignment and visual inspection. Optionally, the identity exists over a region that is at least about 25, 50, 75, or 100 amino acids in length, or over a region that is 100 to 150, 150 to 200, 100 to 200, or 200 or more, amino acids in length.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the above sequence comparison algorithms or by manual alignment and visual inspection. Optionally, the alignment exists over a region that is at least about 25, 50, 75, or 100 amino acids in length, or over a region that is 100 to 150, 150 to 200, 100 to 200, or 200 or more amino acids in length.

In addition to polypeptide molecules, nucleic acid molecules possess a variety of advantageous properties for use as affinity reagents (e.g., amino acid recognition molecules) in accordance with the application.

Nucleic acid aptamers are nucleic acid molecules that have been engineered to bind desired targets with high affinity and selectivity. Accordingly, nucleic acid aptamers may be engineered to selectively bind a desired type of amino acid using selection and/or enrichment techniques known in the art. Thus, in some embodiments, an affinity reagent comprises a nucleic acid aptamer (e.g., a DNA aptamer, an RNA aptamer). In some embodiments, a labeled affinity reagent is a labeled aptamer that selectively binds one type of terminal amino acid. For example, in some embodiments, labeled aptamer selectively binds one type of amino acid (e.g., a single type of amino acid or a subset of types of amino acids) at a terminus of a polypeptide, as described herein. Although not shown, it should be appreciated that labeled aptamer may be engineered to selectively bind one type of amino acid at any position of a polypeptide (e.g., at a terminal position or at terminal and internal positions of a polypeptide) in accordance with a method of the application.

In some embodiments, a labeled affinity reagent comprises a label having binding-induced luminescence. For example, in some embodiments, a labeled aptamer comprises a donor label and an acceptor label and functions. In yet other embodiments, labeled aptamer comprises a quenching moiety and functions analogously to a molecular beacon, wherein luminescence of labeled aptamer is internally quenched as a free molecule and restored as a selectively bound molecule (see, e.g., Hamaguchi, et al. (2001) Analytical Biochemistry 294, 126-131). Without wishing to be bound by theory, it is thought that these and other types of mechanisms for binding-induced luminescence may advantageously reduce or eliminate background luminescence to increase overall sensitivity and accuracy of the methods described herein.

In addition to methods of identifying a terminal amino acid of a polypeptide, the application provides methods of sequencing polypeptides using labeled affinity reagents. In some embodiments, methods of sequencing may involve subjecting a polypeptide terminus to repeated cycles of terminal amino acid detection and terminal amino acid cleavage. For example, in some embodiments, the application provides a method of determining an amino acid sequence of a polypeptide comprising contacting a polypeptide with one or more labeled affinity reagents described herein and subjecting the polypeptide to Edman degradation.

Conventional Edman degradation involves repeated cycles of modifying and cleaving the terminal amino acid of a polypeptide, wherein each successively cleaved amino acid is identified to determine an amino acid sequence of the polypeptide. As an illustrative example of a conventional Edman degradation, the N-terminal amino acid of a polypeptide is modified using phenyl isothiocyanate (PITC) to form a PITC-derivatized N-terminal amino acid. The PITC-derivatized N-terminal amino acid is then cleaved using acidic conditions, basic conditions, and/or elevated temperatures. It has also been shown that the step of cleaving the PITC-derivatized N-terminal amino acid may be accomplished enzymatically using a modified cysteine protease from the protozoa *Trypanosoma cruzi*, which involves relatively milder cleavage conditions at a neutral or near-neutral pH. Non-limiting examples of useful enzymes are described in U.S. patent application Ser. No. 15/255,433, filed Sep. 2, 2016, titled "MOLECULES AND METHODS FOR ITERATIVE POLYPEPTIDE ANALYSIS AND PROCESSING".

In some embodiments, sequencing by Edman degradation comprises providing a polypeptide that is immobilized on a surface of a solid support (e.g., immobilized to a bottom or sidewall surface of a sample well) through a linker. In some embodiments, as described herein, polypeptide is immobilized at one terminus (e.g., an amino-terminal amino acid or a carboxy-terminal amino acid) such that the other terminus is free for detecting and cleaving of a terminal amino acid. Accordingly, in some embodiments, the reagents used in Edman degradation methods described herein preferentially interact with terminal amino acids at the non-immobilized (e.g., free) terminus of polypeptide. In this way, polypeptide remains immobilized over repeated cycles of detecting and cleaving. To this end, in some embodiments, linker may be designed according to a desired set of conditions used for detecting and cleaving, e.g., to limit detachment of polypeptide from surface under chemical cleavage conditions. Suitable linker compositions and techniques for immobilizing a polypeptide to a surface are described in detail elsewhere herein.

In accordance with the application, in some embodiments, a method of sequencing by Edman degradation comprises a step (i) of contacting a polypeptide with one or more labeled affinity reagents that selectively bind one or more types of terminal amino acids. In some embodiments, a labeled affinity reagent interacts with the polypeptide by selectively binding the terminal amino acid. In some embodiments, step (i) further comprises removing any of the one or more labeled affinity reagents that do not selectively bind the terminal amino acid (e.g., the free terminal amino acid) of polypeptide.

In some embodiments, the method further comprises identifying the terminal amino acid of the polypeptide by detecting labeled affinity reagent. In some embodiments, detecting comprises detecting a luminescence from labeled affinity reagent. As described herein, in some embodiments, the luminescence is uniquely associated with labeled affinity reagent, and the luminescence is thereby associated with the type of amino acid to which labeled affinity reagent selectively binds. As such, in some embodiments, the type of amino acid is identified by determining one or more luminescence properties of labeled affinity reagent.

In some embodiments, a method of sequencing by Edman degradation comprises a step (ii) of removing the terminal amino acid of the polypeptide. In some embodiments, step (ii) comprises removing labeled affinity reagent (e.g., any of the one or more labeled affinity reagents that selectively bind the terminal amino acid) from the polypeptide. In some embodiments, step (ii) comprises modifying the terminal amino acid (e.g., the free terminal amino acid) of the polypeptide by contacting the terminal amino acid with an isothiocyanate (e.g., PITC) to form an isothiocyanate-modified terminal amino acid. In some embodiments, an isothiocyanate-modified terminal amino acid is more susceptible to removal by a cleaving reagent (e.g., a chemical or enzymatic cleaving reagent) than an unmodified terminal amino acid.

In some embodiments, step (ii) comprises removing the terminal amino acid by contacting the polypeptide with a protease that specifically binds and cleaves the isothiocyanate-modified terminal amino acid. In some embodiments, the protease comprises a modified cysteine protease. In some embodiments, the protease comprises a modified cysteine protease, such as a cysteine protease from *Trypanosoma cruzi* (see, e.g., Borgo, et al. (2015) Protein Science 24:571-579). In yet other embodiments, step (ii) comprises removing the terminal amino acid by subjecting the polypeptide to chemical (e.g., acidic, basic) conditions sufficient to cleave the isothiocyanate-modified terminal amino acid.

In some embodiments, a method of sequencing by Edman degradation comprises a step (iii) of washing the polypeptide following terminal amino acid cleavage. In some embodiments, washing comprises removing the protease. In some embodiments, washing comprises restoring the polypeptide to neutral pH conditions (e.g., following chemical cleavage by acidic or basic conditions). In some embodiments, a method of sequencing by Edman degradation comprises repeating steps (i) through (iii) for a plurality of cycles.

In some embodiments, a sample containing a complex mixture or enriched mixture of polypeptides (e.g., a mixture of polypeptides) can be degraded using common enzymes into short polypeptide fragments of approximately 6 to 40 amino acids. In some embodiments, sequencing of this polypeptide library in accordance with methods of the application would reveal the identity and abundance of each of the polypeptides present in the original complex mixture or enriched mixture. As described herein and in the literature, most polypeptides in the size range of 6 to 40 amino acids can be uniquely identified by determining the number and location of just four amino acids within a polypeptide chain.

Accordingly, in some embodiments, a method of sequencing by Edman degradation may be performed using a set of labeled aptamers comprising four DNA aptamer types, each type recognizing a different N-terminal amino acid. Each aptamer type may be labeled with a different luminescent label, such that the different aptamer types can be distinguished based on one or more luminescence properties. For illustrative purposes, the example set of labeled aptamers includes: a cysteine-specific aptamer labeled with a first luminescent label ("dye 1"); a lysine-specific aptamer labeled with a second luminescent label ("dye 2"); a tryptophan-specific aptamer labeled with a third luminescent label ("dye 3"); and a glutamate-specific aptamer labeled with a fourth luminescent label ("dye 4").

In some embodiments, prior to step (i), single polypeptide molecules from a polypeptide library are immobilized on a surface of a solid support, e.g., at a bottom or sidewall surface of a sample well of an array of sample wells. In some embodiments, as described elsewhere herein, moieties that enable surface immobilization (e.g., biotin) or improve solubility (e.g., oligonucleotides) may be chemically or enzymatically attached to the C-terminus of the polypeptides. To determine the sequence of each polypeptide, in some embodiments, immobilized polypeptides are subjected to repeated cycles of N-terminal amino acid detection and N-terminal amino acid cleavage. In some embodiments, the process comprises reagent addition and wash steps which are performed by injection into a flowcell above the detection surface using an automated fluidic system. In some embodiments, steps (i) through (iv) illustrate one cycle of detection and cleavage using labeled aptamers.

In some embodiments, a method of sequencing by Edman degradation comprises a step (i) of flowing in a mixture of four orthogonally labeled DNA aptamers and incubating to allow the aptamers to bind to any immobilized polypeptides (e.g., polypeptides immobilized within a sample well of an array) that contain one of the four correct amino acids at the N-terminus. In some embodiments, the method further comprises washing the immobilized polypeptides to remove unbound aptamers. In some embodiments, the method further comprises imaging the immobilized polypeptides ("Imaging step (i)"). In some embodiments, the acquired images contain enough information to determine the location of aptamer-bound polypeptides (e.g., location within an array of sample wells) and which of the four aptamers is bound at each location. In some embodiments, the method further comprises washing the immobilized polypeptides using an appropriate buffer to remove the aptamers from the immobilized polypeptides.

In some embodiments, a method of sequencing comprises a step (ii) of flowing in a solution containing a reactive molecule (e.g., PITC, as shown) that specifically modifies the N-terminal amine group. An isothiocyanate molecule such as PITC, in some embodiments, modifies the N-terminal amino acid into a substrate for cleavage by a modified protease such as the cysteine protease cruzain from *Trypanosoma cruzi.*

In some embodiments, a method of sequencing according comprises a step (iii) of washing the immobilized polypeptides before flowing in a suitable modified protease that recognizes and cleaves the modified N-terminal amino acid from the immobilized polypeptide.

In some embodiments, the method comprises a step (iv) of washing the immobilized polypeptides after enzymatic cleavage. In some embodiments, steps (i) through (iv) depict one cycle of Edman degradation. Accordingly, step (i') as shown is the start of the next reaction cycle which proceeds as steps (i') through (iv') performed as described above for steps (i) through (iv). In some embodiments, steps (i) through (iv) are repeated for approximately 20-40 cycles.

In some embodiments, a labeled isothiocyanate (e.g., a dye-labeled PITC) may be used to monitor sample loading. For example, in some embodiments, prior to subjecting a polypeptide sample to a method of sequencing, the polypeptide sample is pre-conjugated with a luminescent label at a terminal end by modification of the terminal end using a dye-labeled PITC. In this way, loading of the polypeptide sample into an array of sample wells may be monitored by detecting luminescence from the labels prior to step (i) described above. In some embodiments, the luminescence is used to determine single occupancy of sample wells in the array (e.g., a fraction of sample wells containing a single polypeptide molecule), which may advantageously increase the amount of information reliably obtained for a given sample. Once a desired sample loading status is determined by luminescence, chemical or enzymatic cleavage may be performed, as described, before proceeding with step (i).

In some embodiments, a labeled isothiocyanate (e.g., a dye-labeled PITC) may be used to monitor reaction progress for a polypeptide sample in an array. For example, in some embodiments, step (ii) comprises flowing in a solution containing a dye-labeled PITC that specifically modifies and labels N-terminal amine groups of polypeptides in the sample. In some embodiments, luminescence from the labels may be detected during or after step (ii) to evaluate N-terminal PITC modification of polypeptides in the sample. Accordingly, in some embodiments, luminescence is used to determine whether or when to proceed from step (ii) to step (iii). In some embodiments, luminescence from the labels may be detected during or after step (iii) to evaluate N-terminal amino acid cleavage of polypeptides in the sample—e.g., to determine whether or when to proceed from step (iii) to step (iv).

A method of sequencing may utilize separate reagents for detecting and cleaving a terminal amino acid of a polypeptide. Nonetheless, in some aspects, the application provides a method of sequencing in which a single reagent comprising a peptidase (such as a labeled exopeptidase that selectively binds and cleaves a different type of terminal amino acid) may be used for detecting and cleaving a terminal amino acid of a polypeptide.

Labeled exopeptidases may comprise a lysine-specific exopeptidase comprising a first luminescent label, a glycine-specific exopeptidase comprising a second luminescent label, an aspartate-specific exopeptidase comprising a third luminescent label, and a leucine-specific exopeptidase comprising a fourth luminescent label. In accordance with certain embodiments described herein, each of labeled exopeptidases selectively binds and cleaves its respective amino acid only when that amino acid is at an amino- or carboxy-terminus of a polypeptide. Accordingly, as sequencing by this approach proceeds from one terminus of a peptide toward the other, labeled exopeptidases are engineered or selected such that all reagents of the set will possess either aminopeptidase or carboxypeptidase activity.

In some aspects, the application provides methods of polypeptide sequencing in real-time by evaluating binding interactions of terminal amino acids with labeled amino acid recognition molecules (e.g., labeled affinity reagents) and a labeled cleaving reagent (e.g., a labeled non-specific exopeptidase). Without wishing to be bound by theory, a labeled affinity reagent selectively binds according to a binding affinity ($K_D$) defined by an association rate, or an "on" rate, of binding ($k_{on}$) and a dissociation rate, or an "off" rate, of binding ($k_{off}$). The rate constants koff and $k_{on}$ are the critical determinants of pulse duration (e.g., the time corresponding to a detectable binding event) and interpulse duration (e.g., the time between detectable binding events), respectively. In some embodiments, these rates can be engineered to achieve pulse durations and pulse rates (e.g., the frequency of signal pulses) that give the best sequencing accuracy.

A sequencing reaction mixture may further comprise a labeled non-specific exopeptidase comprising a luminescent label that is different than that of labeled affinity reagent. In some embodiments, a labeled non-specific exopeptidase is present in the mixture at a concentration that is less than that of the labeled affinity reagent. In some embodiments, the labeled non-specific exopeptidase displays broad specificity such that it cleaves most or all types of terminal amino acids.

In some embodiments, terminal amino acid cleavage by a labeled non-specific exopeptidase gives rise to a signal pulse, and these events occur with lower frequency than the binding pulses of a labeled affinity reagent. In this way, amino acids of a polypeptide may be counted and/or identified in a real-time sequencing process. In some embodiments, a plurality of labeled affinity reagents may be used, each with a diagnostic pulsing pattern (e.g., characteristic pattern) which may be used to identify a corresponding terminal amino acid. For example, in some embodiments, different characteristic patterns correspond to the association of more than one labeled affinity reagent with different types of terminal amino acids. As described herein, it should be appreciated that a single affinity reagent that associates with more than one type of amino acid may be used in accordance with the application. Accordingly, in some embodiments, different characteristic patterns correspond to the association of one labeled affinity reagent with different types of terminal amino acids.

As detailed above, a real-time sequencing process can generally involve cycles of terminal amino acid recognition and terminal amino acid cleavage, where the relative occurrence of recognition and cleavage can be controlled by a concentration differential between a labeled affinity reagent and a labeled non-specific exopeptidase. In some embodiments, the concentration differential can be optimized such that the number of signal pulses detected during recognition of an individual amino acid provides a desired confidence interval for identification. For example, if an initial sequencing reaction provides signal data with too few signal pulses between cleavage events to permit determination of characteristic patterns with a desired confidence interval, the sequencing reaction can be repeated using a decreased concentration of non-specific exopeptidase relative to affinity reagent. The inventors have recognized further techniques for controlling real-time sequencing reactions, which may be used in combination with, or alternatively to, the concentration differential approach as described.

In some embodiments, a sequencing reaction involves cycles of temperature-dependent terminal amino acid recognition and terminal amino acid cleavage. Each cycle of the sequencing reaction may be carried out over two temperature ranges: a first temperature range ("$T_1$") that is optimal for affinity reagent activity over exopeptidase activity (e.g., to promote terminal amino acid recognition), and a second temperature range ("$T_2$") that is optimal for exopeptidase activity over affinity reagent activity (e.g., to promote terminal amino acid cleavage). The sequencing reaction may progress by alternating the reaction mixture temperature between the first temperature range $T_1$ (to initiate amino acid recognition) and the second temperature range $T_2$ (to initiate amino acid cleavage). Accordingly, progression of a temperature-dependent sequencing process is controllable by temperature, and alternating between different temperature ranges (e.g., between $T_1$ and $T_2$) which may be carried through manual or automated processes. In some embodiments, affinity reagent activity (e.g., binding affinity ($K_D$) for an amino acid) within the first temperature range $T_1$ as compared to the second temperature range $T_2$ is increased by at least 10-fold, at least 100-fold, at least 1,000-fold, at least 10,000-fold, at least 100,000-fold, or more. In some embodiments, exopeptidase activity (e.g., rate of substrate conversion to cleavage product) within the second temperature range $T_2$ as compared to the first temperature range $T_1$ is increased by at least 2-fold, 10-fold, at least 25-fold, at least 50-fold, at least 100-fold, at least 1,000-fold, or more.

In some embodiments, the first temperature range $T_1$ is lower than the second temperature range $T_2$. In some embodiments, the first temperature range $T_1$ is between about 15° C. and about 40° C. (e.g., between about 25° C. and about 35° C., between about 15° C. and about 30° C., between about 20° C. and about 30° C.). In some embodiments, the second temperature range $T_2$ is between about 40° C. and about 100° C. (e.g., between about 50° C. and about 90° C., between about 60° C. and about 90° C., between about 70° C. and about 90° C.). In some embodiments, the first temperature range $T_1$ is between about 20° C. and about 40° C. (e.g., approximately 30° C.), and the second temperature range $T_2$ is between about 60° C. and about 100° C. (e.g., approximately 80° C.).

In some embodiments, the first temperature range $T_1$ is higher than the second temperature range $T_2$. In some embodiments, the first temperature range $T_1$ is between about 40° C. and about 100° C. (e.g., between about 50° C. and about 90° C., between about 60° C. and about 90° C., between about 70° C. and about 90° C.). In some embodiments, the second temperature range $T_2$ is between about 15° C. and about 40° C. (e.g., between about 25° C. and about 35° C., between about 15° C. and about 30° C., between about 20° C. and about 30° C.). In some embodiments, the first temperature range $T_1$ is between about 60° C. and about 100° C. (e.g., approximately 80° C.), and the second temperature range $T_2$ is between about 20° C. and about 40° C. (e.g., approximately 30° C.).

In some embodiments, the application provides a luminescence-dependent sequencing process using luminescence-activated reagents. In some embodiments, a luminescence-dependent sequencing process involves cycles of luminescence-dependent amino acid recognition and cleavage. Each cycle of the sequencing reaction may be carried out by exposing a sequencing reaction mixture to two different luminescent conditions: a first luminescent condition that is optimal for affinity reagent activity over exopeptidase activity (e.g., to promote amino acid recognition), and a second luminescent condition that is optimal for exopeptidase activity over affinity reagent activity (e.g., to promote amino acid cleavage). The sequencing reaction progresses by alternating between exposing the reaction mixture to the first luminescent condition (to initiate amino acid recognition) and exposing the reaction mixture to the second luminescent condition (to initiate amino acid cleavage). By way of example and not limitation, in some embodiments, the two different luminescent conditions comprise a first wavelength and a second wavelength.

In some aspects, the application provides methods of polypeptide sequencing in real-time by evaluating binding interactions of one or more labeled affinity reagents with terminal and internal amino acids and binding interactions of a labeled non-specific exopeptidase with terminal amino acids. In some embodiments, a labeled affinity reagent is used that selectively binds to and dissociates from one type of amino acid at both terminal and internal positions. The selective binding gives rise to a series of pulses in signal output. In this approach, however, the series of pulses occur at a rate that is determined by the number of the type of amino acid throughout the polypeptide. Accordingly, in some embodiments, the rate of pulsing corresponding to binding events would be diagnostic of the number of cognate amino acids currently present in the polypeptide.

A labeled non-specific peptidase may be present at a relatively lower concentration than the labeled affinity reagent, e.g., to give optimal time windows in between cleavage events. Additionally, in certain embodiments, uniquely identifiable luminescent label of labeled non-specific peptidase would indicate when cleavage events have occurred. As the polypeptide undergoes iterative cleavage, the rate of pulsing corresponding to binding by the labeled affinity reagent would drop in a step-wise manner whenever a terminal amino acid is cleaved by the labeled non-specific peptidase. Thus, in some embodiments, amino acids may be identified—and polypeptides thereby sequenced—in this approach based on a pulsing pattern and/or on the rate of pulsing that occurs within a pattern detected between cleavage events.

B. Sequencing by Degradation of Labeled Polypeptides

In some aspects, the application provides methods of sequencing a polypeptide by identifying a unique combination of amino acids corresponding to a known polypeptide sequence. In some embodiments, the method comprises detecting selectively labeled amino acids of a labeled polypeptide. In some embodiments, the labeled polypeptide comprises selectively modified amino acids such that different amino acid types comprise different luminescent labels. As used herein, unless otherwise indicated, a labeled polypeptide refers to a polypeptide comprising one or more selectively labeled amino acid sidechains. Methods of selective labeling and details relating to the preparation and analysis of labeled polypeptides are known in the art (see, e.g., Swaminathan, et al. PLoS Comput Biol. 2015, 11(2): e1004080).

As described herein, in some aspects, the application provides methods of sequencing a polypeptide by obtaining data during a polypeptide degradation process, and analyzing the data to determine portions of the data corresponding to amino acids that are sequentially exposed at a terminus of the polypeptide during the degradation process. In some embodiments, the portions of the data comprise a series of signal pulses indicative of association of one or more amino acid recognition molecules with successive amino acids exposed at the terminus of the polypeptide (e.g., during a degradation). In some embodiments, the series of signal pulses corresponds to a series of reversible single molecule binding interactions at the terminus of the polypeptide during the degradation process.

In some aspects, the polypeptide sequencing techniques described herein generate data indicating how a polypeptide interacts with a binding means (e.g., one or more amino acid recognition molecules) while the polypeptide is being degraded by a cleaving means (e.g., one or more cleaving reagents). As discussed above, the data can include a series of characteristic patterns corresponding to association events at a terminus of a polypeptide in between cleavage events at the terminus. In some embodiments, methods of sequencing described herein comprise contacting a single polypeptide molecule with a binding means and a cleaving means, where the binding means and the cleaving means are configured to achieve at least 10 association events prior to a cleavage event. In some embodiments, the means are configured to achieve the at least 10 association events between two cleavage events.

As described herein, in some embodiments, a plurality of single-molecule sequencing reactions are performed in parallel in an array of sample wells. In some embodiments, an array comprises between about 10,000 and about 1,000,000 sample wells. The volume of a sample well may be between about $10^{-21}$ liters and about $10^{-15}$ liters, in some implementations. Because the sample well has a small volume, detection of single-molecule events may be possible as only about one polypeptide may be within a sample well at any given time. Statistically, some sample wells may not contain a single-molecule sequencing reaction and some may contain more than one single polypeptide molecule. However, an appreciable number of sample wells may each contain a single-molecule reaction (e.g., at least 30% in some embodiments), so that single-molecule analysis can be carried out in parallel for a large number of sample wells. In some embodiments, the binding means and the cleaving means are configured to achieve at least 10 association events prior to a cleavage event in at least 10% (e.g., 10-50%, more than 50%, 25-75%, at least 80%, or more) of the sample wells in which a single-molecule reaction is occurring. In some embodiments, the binding means and the cleaving means are configured to achieve at least 10 association events prior to a cleavage event for at least 50% (e.g., more than 50%, 50-75%, at least 80%, or more) of the amino acids of a polypeptide in a single-molecule reaction.

In some embodiments, a labeled polypeptide is immobilized and exposed to an excitation source. An aggregate luminescence from the labeled polypeptide may be detected and, in some embodiments, exposure to luminescence over time may result in a loss in detected signal due to luminescent label degradation (e.g., degradation due to photobleaching). In some embodiments, the labeled polypeptide comprises a unique combination of selectively labeled amino acids that give rise to an initial detected signal. Degradation of luminescent labels over time results in a corresponding decrease in a detected signal for the photobleached labeled polypeptide. In some embodiments, the signal can be deconvoluted by analysis of one or more luminescence properties (e.g., signal deconvolution by luminescence lifetime analysis). In some embodiments, the unique combination of selectively labeled amino acids of the labeled polypeptide have been computationally precomputed and empirically verified—e.g., based on known polypeptide sequences of a proteome. In some embodiments, the combination of detected amino acid labels are compared against a database of known sequences of a proteome of an organism to identify a particular polypeptide of the database corresponding to the labeled polypeptide.

In some embodiments, an optimal sample concentration is determined for performing a sequencing reaction that maximizes sampling in massively parallel analysis. In some embodiments, the concentration is selected so that a desired fraction of the sample wells of an array (e.g., 30%) are occupied at any given time. Without wishing to be bound by theory, it is thought that while a polypeptide is bleached over a period of time, the same well continues to be available for further analysis. Through diffusion, approximately 30% of the sample wells of an array can be used for analysis every 3 minutes. As an illustrative example, in a million sample well chip, 6,000,000 polypeptides per hour may be sampled, or 24,000,000 over a 4 hour period.

In some aspects, the application provides a method of sequencing a polypeptide by detecting luminescence of a labeled polypeptide which is subjected to repeated cycles of terminal amino acid modification and cleavage. In some embodiments, the method generally proceeds as described herein for other methods of sequencing by Edman degradation.

In some embodiments, the method comprises a step of (i) modifying the terminal amino acid of a labeled polypeptide. As described elsewhere herein, in some embodiments, modifying comprises contacting the terminal amino acid with an isothiocyanate (e.g., PITC) to form an isothiocyanate-modified terminal amino acid. In some embodiments, an isothiocyanate modification converts the terminal amino acid to a form that is more susceptible to removal by a cleaving reagent (e.g., a chemical or enzymatic cleaving reagent, as described herein). Accordingly, in some embodiments, the method comprises a step of (ii) removing the modified terminal amino acid using chemical or enzymatic means detailed elsewhere herein for Edman degradation.

In some embodiments, the method comprises repeating steps (i) through (ii) for a plurality of cycles, during which luminescence of the labeled polypeptide is detected, and cleavage events corresponding to the removal of a labeled amino acid from the terminus may be detected as a decrease in detected signal. In some embodiments, no change in signal following step (ii) identifies an amino acid of unknown type. Accordingly, in some embodiments, partial sequence information may be determined by evaluating a signal detected following step (ii) during each sequential round by assigning an amino acid type by a determined identity based on a change in detected signal or identifying an amino acid type as unknown based on no change in a detected signal.

In some aspects, a method of sequencing a polypeptide in accordance with the application comprises sequencing by processive enzymatic cleavage of a labeled polypeptide. In some embodiments, a labeled polypeptide is subjected to degradation using a modified processive exopeptidase that continuously cleaves a terminal amino acid from one terminus to another terminus. Exopeptidases are described in detail elsewhere herein. In some embodiments, a labeled polypeptide is subjected to degradation by an immobilized processive exopeptidase. In some embodiments, an immobilized labeled polypeptide is subjected to degradation by a processive exopeptidase.

In some embodiments, the rate of processivity of processive exopeptidase is known, such that the timing between a detected decrease in signal may be used to calculate the number of unlabeled amino acids between each detection event. For example, if a polypeptide of 40 amino acids was cleaved in such a way that an amino acid was removed every second, a labeled polypeptide having 3 signals would show all 3 initially, then 2, then 1, and finally no signal. In this way, the order of the labeled amino acids can be determined. Accordingly, these methods may be used to determine partial sequence information, e.g., for proteomic analysis based on polypeptide fragment sequencing.

In some embodiments, single molecule polypeptide sequencing can be achieved using an ATP-based Förster resonance energy transfer (FRET) scheme (e.g., with one or more labeled cofactors). In some embodiments, sequencing by cofactor-based FRET can be performed using an immobilized ATP-dependent protease, donor-labeled ATP, and acceptor-labeled amino acids of a polypeptide substrate. In some embodiments, amino acids can be labeled with acceptors, and the one or more cofactors can be labeled with donors.

For example, in some embodiments, extracted polypeptides are denatured, and cysteines and lysines are labeled with fluorescent dyes. In some embodiments, an engineered version of a protein translocase (e.g., bacterial ClpX) is used to bind to individual substrate polypeptides, unfold them, and translocate them through its nano-channel. In some embodiments, the translocase is labeled with a donor dye, and FRET occurs between the donor on the translocase and two or more distinct acceptor dyes on a substrate when the substrate passes through the nano-channel. The order of the labeled amino acids can then be determined from the FRET signal. In some embodiments, one or more of the following non-limiting labeled ATP analogues shown in Table 3 can be used.

TABLE 3

| Non-limiting examples of labeled ATP analogues |
| --- |
| Phosphate-labeled ATP: |
| 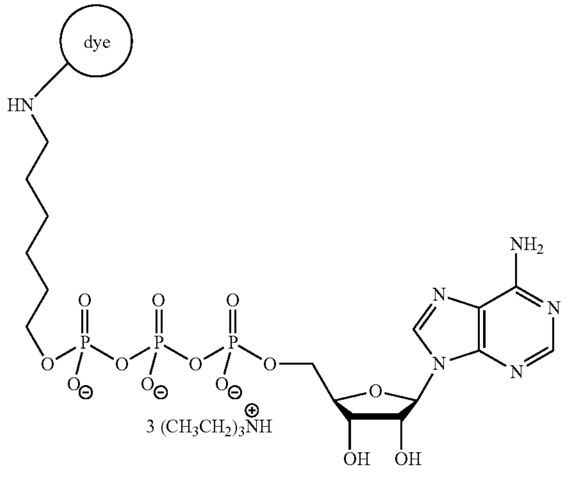 |

TABLE 3-continued
| Non-limiting examples of labeled ATP analogues |
|---|
| (γ-[(6-Amino)hexyl]-ATP) |
| 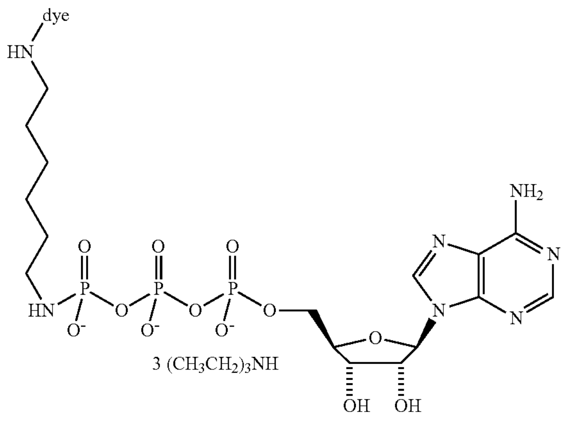 |
| (γ-[(6-Aminohexyl)imido]-ATP) |
| 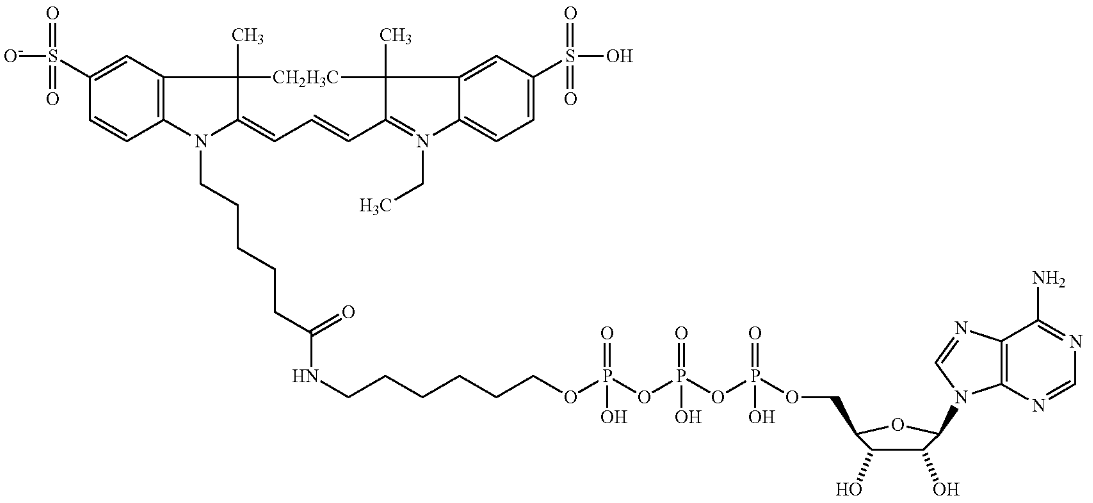 |

TABLE 3-continued
| Non-limiting examples of labeled ATP analogues |
| --- |
| (γ-(6-Aminohexyl)-ATP—Cy3) |
| 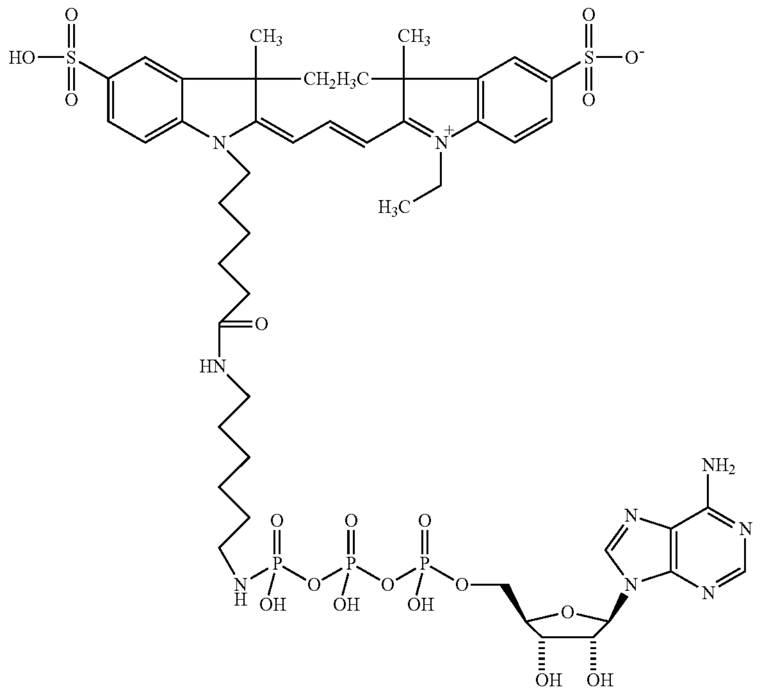 |
| (γ-[(6-Aminohexyl)imido]-ATP—Cy3) |
| 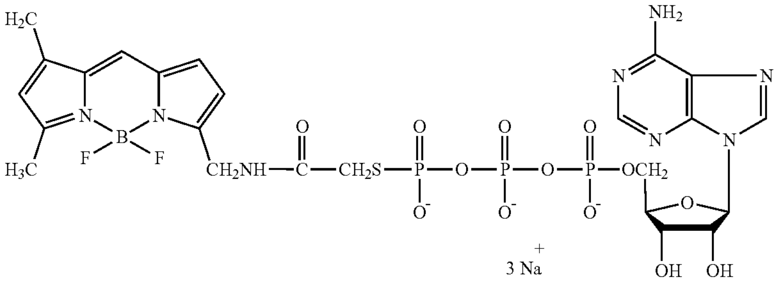 |

TABLE 3-continued
| Non-limiting examples of labeled ATP analogues |
| --- |
| (BODIPY FL ATPγS) |
| Ribose-labeled ATP: |
| 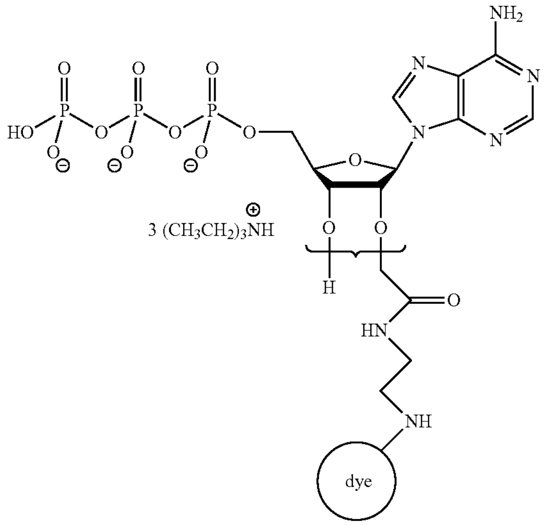 |
| (EDA-ATP) |
| 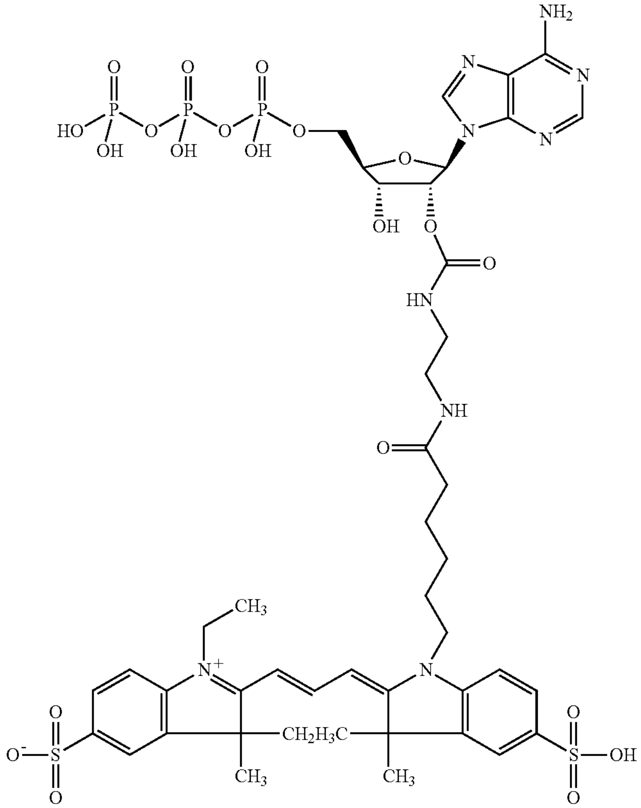 |

TABLE 3-continued
| Non-limiting examples of labeled ATP analogues |
|---|
| (EDA-ATP—Cy3) |
| 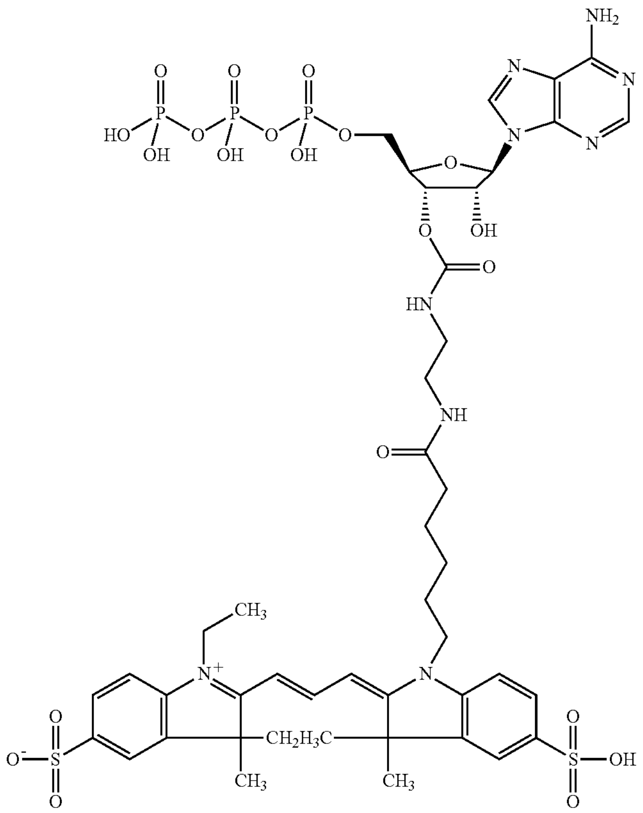 |
| (EDA-ATP—Cy3)<br>Base-labeled ATP: |
| 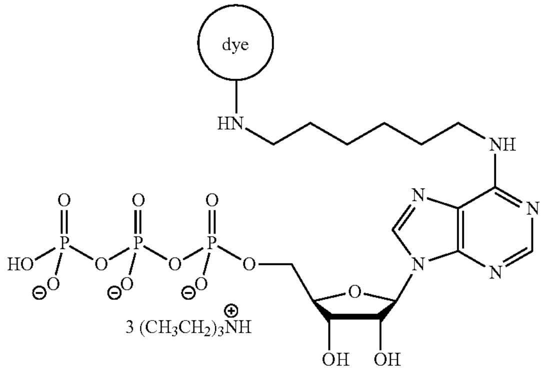 |

TABLE 3-continued

Non-limiting examples of labeled ATP analogues ($N^6$-(6-Amino)hexyl-ATP)

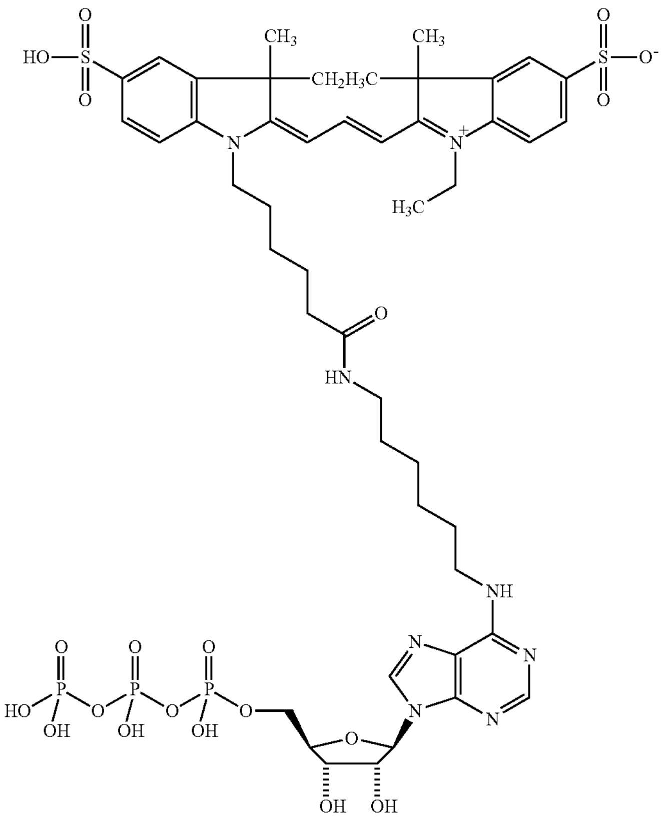

($N^6$-(6-Aminohexyl)-ATP—Cy3)

C. Preparation of Samples for Sequencing

A polypeptide sample (e.g., an enriched polypeptide sample) can be modified prior to sequencing.

In some embodiments, the N-terminal amino acid or the C-terminal amino acid of a polypeptide is modified. In some embodiments, a terminal end of a polypeptides is modified with moieties that enable immobilization to a surface (e.g., a surface of a sample well on a chip used for polypeptide analysis). In some embodiments, such methods comprise modifying a terminal end of a labeled polypeptide to be analyzed in accordance with the application. In yet other embodiments, such methods comprise modifying a terminal end of a protein or enzyme that degrades or translocates a polypeptide substrate in accordance with the application.

In some embodiments, a carboxy-terminus of a polypeptide is modified in a method comprising: (i) blocking free carboxylate groups of the polypeptide; (ii) denaturing the polypeptide (e.g., by heat and/or chemical means); (iii) blocking free thiol groups of the polypeptide; (iv) digesting the polypeptide to produce at least one polypeptide fragment comprising a free C-terminal carboxylate group; and (v) conjugating (e.g., chemically) a functional moiety to the free C-terminal carboxylate group. In some embodiments, the method further comprises, after (i) and before (ii), dialyzing a sample comprising the polypeptide.

In some embodiments, a carboxy-terminus of a polypeptide is modified in a method comprising: (i) denaturing the polypeptide (e.g., by heat and/or chemical means); (ii) blocking free thiol groups of the polypeptide; (iii) digesting the polypeptide to produce at least one polypeptide fragment comprising a free C-terminal carboxylate group; (iv) blocking the free C-terminal carboxylate group to produce at least one polypeptide fragment comprising a blocked C-terminal carboxylate group; and (v) conjugating (e.g., enzymatically) a functional moiety to the blocked C-terminal carboxylate group. In some embodiments, the method further comprises, after (iv) and before (v), dialyzing a sample comprising the polypeptide.

In some embodiments, blocking free carboxylate groups refers to a chemical modification of these groups which alters chemical reactivity relative to an unmodified carboxylate. Suitable carboxylate blocking methods are known in the art and should modify side-chain carboxylate groups to be chemically different from a carboxy-terminal carboxylate group of a polypeptide to be functionalized. In some embodiments, blocking free carboxylate groups comprises esterification or amidation of free carboxylate groups of a polypeptide. In some embodiments, blocking free carboxylate groups comprises methyl esterification of free carboxylate groups of a polypeptide, e.g., by reacting the polypeptide with methanolic HCl. Additional examples of reagents and techniques useful for blocking free carboxylate groups include, without limitation, 4-sulfo-2,3,5,6-tetrafluorophenol (STP) and/or a carbodiimide such as N-(3-Dimethylaminopropyl)-N'-ethylcarbodiimide hydrochloride (EDAC), uronium reagents, diazomethane, alcohols and acid for Fischer esterification, the use of N-hydroxylsuccinimide (NHS) to form NHS esters (potentially as an intermediate to subsequent ester or amine formation), or reaction with carbonyldiimidazole (CDI) or the formation of mixed anhydrides, or any other method of modifying or blocking carboxylic acids, potentially through the formation of either esters or amides.

In some embodiments, blocking free thiol groups refers to a chemical modification of these groups which alters chemical reactivity relative to an unmodified thiol. In some embodiments, blocking free thiol groups comprises reducing and alkylating free thiol groups of a polypeptide. In some embodiments, reduction and alkylation is carried out by contacting a polypeptide with dithiothreitol (DTT) and one or both of iodoacetamide and iodoacetic acid. Examples of additional and alternative cysteine-reducing reagents which may be used are well known and include, without limitation, 2-mercaptoethanol, Tris (2-carboxyehtyl) phosphine hydrochloride (TCEP), tributylphosphine, dithiobutylamine (DTBA), or any reagent capable of reducing a thiol group. Examples of additional and alternative cysteine-blocking (e.g., cysteine-alkylating) reagents which may be used are well known and include, without limitation, acrylamide, 4-vinylpyridine, N-Ethylmalemide (NEM), N-ε-maleimidocaproic acid (EMCA), or any reagent that modifies cysteines so as to prevent disulfide bond formation.

In some embodiments, digestion comprises enzymatic digestion. In some embodiments, digestion is carried out by contacting a polypeptide with an endopeptidase (e.g., trypsin) under digestion conditions. In some embodiments, digestion comprises chemical digestion. Examples of suitable reagents for chemical and enzymatic digestion are known in the art and include, without limitation, trypsin, chemotrypsin, Lys-C, Arg-C, Asp-N, Lys-N, BNPS-Skatole, CNBr, caspase, formic acid, glutamyl endopeptidase, hydroxylamine, iodosobenzoic acid, neutrophil elastase, pepsin, proline-endopeptidase, proteinase K, staphylococcal peptidase I, thermolysin, and thrombin.

In some embodiments, the functional moiety comprises a biotin molecule. In some embodiments, the functional moiety comprises a reactive chemical moiety, such as an alkynyl. In some embodiments, conjugating a functional moiety comprises biotinylation of carboxy-terminal carboxymethyl ester groups by carboxypeptidase Y, as known in the art.

In some embodiments, a solubilizing moiety is added to a polypeptide. Accordingly, in some embodiments methods and compositions provided herein are useful for modifying terminal ends of polypeptides with moieties that increase their solubility. In some embodiments, a solubilizing moiety is useful for small polypeptides that result from fragmentation (e.g., enzymatic fragmentation, for example using trypsin) and that are relatively insoluble. For example, in some embodiments, short polypeptides in a polypeptide pool can be solubilized by conjugating a polymer (e.g., a short oligo, a sugar, or other charged polymer) to the polypeptides.

D. Luminescent Labels

As used herein, a luminescent label is a molecule that absorbs one or more photons and may subsequently emit one or more photons after one or more time durations. In some embodiments, the term is used interchangeably with "label" or "luminescent molecule" depending on context. A luminescent label in accordance with certain embodiments described herein may refer to a luminescent label of a labeled affinity reagent, a luminescent label of a labeled peptidase (e.g., a labeled exopeptidase, a labeled non-specific exopeptidase), a luminescent label of a labeled peptide, a luminescent label of a labeled cofactor, or another labeled composition described herein. In some embodiments, a luminescent label in accordance with the application refers to a labeled amino acid of a labeled polypeptide comprising one or more labeled amino acids.

In some embodiments, a luminescent label may comprise a first and second chromophore. In some embodiments, an excited state of the first chromophore is capable of relaxation via an energy transfer to the second chromophore. In some embodiments, the energy transfer is a Förster resonance energy transfer (FRET). Such a FRET pair may be useful for providing a luminescent label with properties that make the label easier to differentiate from amongst a plurality of luminescent labels in a mixture. In yet other embodiments, a FRET pair comprises a first chromophore of a first luminescent label and a second chromophore of a second luminescent label. In certain embodiments, the FRET pair may absorb excitation energy in a first spectral range and emit luminescence in a second spectral range.

In some embodiments, a luminescent label refers to a fluorophore or a dye. Typically, a luminescent label comprises an aromatic or heteroaromatic compound and can be a pyrene, anthracene, naphthalene, naphthylamine, acridine, stilbene, indole, benzindole, oxazole, carbazole, thiazole, benzothiazole, benzoxazole, phenanthridine, phenoxazine, porphyrin, quinoline, ethidium, benzamide, cyanine, carbocyanine, salicylate, anthranilate, coumarin, fluorescein, rhodamine, xanthene, or other like compound.

In some embodiments, a luminescent label comprises a dye selected from one or more of the following: 5/6-Carboxyrhodamine 6G, 5-Carboxyrhodamine 6G, 6-Carboxyrhodamine 6G, 6-TAMRA, Abberior® STAR 440SXP, Abberior® STAR 470SXP, Abberior® STAR 488, Abberior® STAR 512, Abberior® STAR 520SXP, Abberior® STAR 580, Abberior® STAR 600, Abberior® STAR 635, Abberior® STAR 635P, Abberior® STAR RED, Alexa Fluor® 350, Alexa Fluor® 405, Alexa Fluor® 430, Alexa Fluor® 480, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610-X, Alexa Fluor® 633, Alexa Fluor® 647, Alexa Fluor® 660, Alexa Fluor® 680, Alexa Fluor® 700, Alexa Fluor® 750, Alexa Fluor® 790, AMCA, ATTO 390, ATTO 425, ATTO 465, ATTO 488, ATTO 495, ATTO 514, ATTO 520, ATTO 532, ATTO 542, ATTO 550, ATTO 565, ATTO 590, ATTO 610, ATTO 620, ATTO 633, ATTO 647, ATTO 647N, ATTO 655, ATTO 665, ATTO 680, ATTO 700, ATTO 725, ATTO 740, ATTO Oxa12, ATTO Rho101, ATTO Rho11, ATTO Rho12, ATTO Rho13, ATTO Rho14, ATTO Rho3B, ATTO Rho6G, ATTO Thio12, BD Horizon™ V450, BODIPY® 493/501, BODIPY® 530/550, BODIPY® 558/568, BODIPY® 564/570, BODIPY® 576/589, BODIPY® 581/591, BODIPY® 630/650, BODIPY® 650/665, BODIPY® FL, BODIPY® FL-X, BODIPY® R6G, BODIPY® TMR, BODIPY® TR, CAL Fluor® Gold 540, CAL Fluor® Green 510, CAL Fluor® Orange 560, CAL Fluor® Red 590, CAL Fluor® Red 610, CAL Fluor® Red 615, CAL Fluor® Red 635, Cascade® Blue, CF™350, CF™405M, CF™405S, CF™488A, CF™514, CF™532, CF™543, CF™546, CF™555, CF™568, CF™594, CF™620R, CF™633, CF™633-V1, CF™640R, CF™640R-V1, CF™640R-V2, CF™660C, CF™660R, CF™680, CF™680R, CF™680R-V1, CF™750, CF™770, CF™790, Chromeo™ 642, Chromis 425N, Chromis 500N, Chromis 515N, Chromis 530N, Chromis 550A, Chromis 550C, Chromis 550Z, Chromis 560N, Chromis 570N, Chromis 577N, Chromis 600N, Chromis 630N, Chromis 645A, Chromis 645C, Chromis 645Z, Chromis 678A, Chromis 678C, Chromis 678Z, Chromis 770A, Chromis 770C, Chromis 800A, Chromis 800C, Chromis 830A, Chromis 830C, Cy®3, Cy®3.5, Cy®3B, Cy®5, Cy®5.5, Cy®7, DyLight® 350, DyLight® 405, DyLight® 415-Co1, DyLight® 425Q, DyLight® 485-LS, DyLight® 488, DyLight® 504Q, DyLight® 510-LS, DyLight® 515-LS, DyLight® 521-LS, DyLight® 530-R2, DyLight® 543Q, DyLight® 550, DyLight® 554-R0, DyLight® 554-R1, DyLight® 590-R2, DyLight® 594, DyLight® 610-B1, DyLight® 615-B2, DyLight® 633, DyLight® 633-B1, DyLight® 633-B2, DyLight® 650, DyLight® 655-B1, DyLight® 655-B2, DyLight® 655-B3, DyLight® 655-B4, DyLight® 662Q, DyLight® 675-B1, DyLight® 675-B2, DyLight® 675-B3, DyLight® 675-B4, DyLight® 679-05, DyLight® 680, DyLight® 683Q, DyLight® 690-B1, DyLight® 690-B2, DyLight® 696Q, DyLight® 700-B1, DyLight® 700-B1, DyLight® 730-B1, DyLight® 730-B2, DyLight® 730-B3, DyLight® 730-B4, DyLight® 747, DyLight® 747-B1, DyLight® 747-B2, DyLight® 747-B3, DyLight® 747-B4, DyLight® 755, DyLight® 766Q, DyLight® 775-B2, DyLight® 775-B3, DyLight® 775-B4, DyLight® 780-B1, DyLight® 780-B2, DyLight® 780-B3, DyLight® 800, DyLight® 830-B2, Dyomics-350, Dyomics-350XL, Dyomics-360XL, Dyomics-370XL, Dyomics-375XL, Dyomics-380XL, Dyomics-390XL, Dyomics-405, Dyomics-415, Dyomics-430, Dyomics-431, Dyomics-478, Dyomics-480XL, Dyomics-481XL, Dyomics-485XL, Dyomics-490, Dyomics-495, Dyomics-505, Dyomics-510XL, Dyomics-511XL, Dyomics-520XL, Dyomics-521XL, Dyomics-530, Dyomics-547, Dyomics-547P1, Dyomics-548, Dyomics-549, Dyomics-549P1, Dyomics-550, Dyomics-554, Dyomics-555, Dyomics-556, Dyomics-560, Dyomics-590, Dyomics-591, Dyomics-594, Dyomics-601XL, Dyomics-605, Dyomics-610, Dyomics-615, Dyomics-630, Dyomics-631, Dyomics-632, Dyomics-633, Dyomics-634, Dyomics-635, Dyomics-636, Dyomics-647, Dyomics-647P1, Dyomics-648, Dyomics-648P1, Dyomics-649, Dyomics-649P1, Dyomics-650, Dyomics-651, Dyomics-652, Dyomics-654, Dyomics-675, Dyomics-676, Dyomics-677, Dyomics-678, Dyomics-679P1, Dyomics-680, Dyomics-681, Dyomics-682, Dyomics-700, Dyomics-701, Dyomics-703, Dyomics-704, Dyomics-730, Dyomics-731, Dyomics-732, Dyomics-734, Dyomics-749, Dyomics-749P1, Dyomics-750, Dyomics-751, Dyomics-752, Dyomics-754, Dyomics-776, Dyomics-777, Dyomics-778, Dyomics-780, Dyomics-781, Dyomics-782, Dyomics-800, Dyomics-831, eFluor® 450, Eosin, FITC, Fluorescein, HiLyte™ Fluor 405, HiLyte™ Fluor 488, HiLyte™ Fluor 532, HiLyte™ Fluor 555, HiLyte™ Fluor 594, HiLyte™ Fluor 647, HiLyte™ Fluor 680, HiLyte™ Fluor 750, IRDye® 680LT, IRDye® 750, IRDye® 800CW, JOE, LightCycler® 640R, LightCycler® Red 610, LightCycler® Red 640, LightCycler® Red 670, LightCycler® Red 705, Lissamine Rhodamine B, Napthofluorescein, Oregon Green® 488, Oregon Green® 514, Pacific Blue™, Pacific Green™, Pacific Orange™, PET, PF350, PF405, PF415, PF488, PF505, PF532, PF546, PF555P, PF568, PF594, PF610, PF633P, PF647P, Quasar® 570, Quasar® 670, Quasar® 705, Rhodamine 123, Rhodamine 6G, Rhodamine B, Rhodamine Green, Rhodamine Green-X, Rhodamine Red, ROX, Seta™ 375, Seta™ 470, Seta™ 555, Seta™ 632, Seta™ 633, Seta™ 650, Seta™ 660, Seta™ 670, Seta™ 680, Seta™ 700, Seta™ 750, Seta™ 780, Seta™ APC-780, Seta™ PerCP-680, Seta™ R-PE-670, Seta™ 646, SeTau 380, SeTau 425, SeTau 647, SeTau 405, Square 635, Square 650, Square 660, Square 672, Square 680, Sulforhodamine 101, TAMRA, TET, Texas Red®, TMR, TRITC, Yakima Yellow™, Zenon®, Zy3, Zy5, Zy5.5, and Zy7.

E. Luminescence

In some aspects, the application relates to polypeptide sequencing and/or identification based on one or more luminescence properties of a luminescent label. In some embodiments, a luminescent label is identified based on luminescence lifetime, luminescence intensity, brightness, absorption spectra, emission spectra, luminescence quantum yield, or a combination of two or more thereof. In some embodiments, a plurality of types of luminescent labels can be distinguished from each other based on different luminescence lifetimes, luminescence intensities, brightnesses, absorption spectra, emission spectra, luminescence quantum yields, or combinations of two or more thereof. Identifying may mean assigning the exact identity and/or quantity of one type of amino acid (e.g., a single type or a subset of types) associated with a luminescent label, and may also mean assigning an amino acid location in a polypeptide relative to other types of amino acids.

In some embodiments, luminescence is detected by exposing a luminescent label to a series of separate light pulses and evaluating the timing or other properties of each photon that is emitted from the label. In some embodiments, information for a plurality of photons emitted sequentially from a label is aggregated and evaluated to identify the label and thereby identify an associated type of amino acid. In some embodiments, a luminescence lifetime of a label is determined from a plurality of photons that are emitted sequentially from the label, and the luminescence lifetime can be used to identify the label. In some embodiments, a luminescence intensity of a label is determined from a plurality of photons that are emitted sequentially from the label, and the luminescence intensity can be used to identify the label. In some embodiments, a luminescence lifetime and luminescence intensity of a label is determined from a plurality of photons that are emitted sequentially from the label, and the luminescence lifetime and luminescence intensity can be used to identify the label.

In some aspects of the application, a single polypeptide molecule is exposed to a plurality of separate light pulses and a series of emitted photons are detected and analyzed. In some embodiments, the series of emitted photons provides information about the single polypeptide molecule that is present and that does not change in the reaction sample over the time of the experiment. However, in some embodiments, the series of emitted photons provides information about a series of different molecules that are present at different times in the reaction sample (e.g., as a reaction or process progresses). By way of example and not limitation, such information may be used to sequence and/or identify a polypeptide subjected to chemical or enzymatic degradation in accordance with the application.

In certain embodiments, a luminescent label absorbs one photon and emits one photon after a time duration. In some embodiments, the luminescence lifetime of a label can be determined or estimated by measuring the time duration. In some embodiments, the luminescence lifetime of a label can be determined or estimated by measuring a plurality of time durations for multiple pulse events and emission events. In some embodiments, the luminescence lifetime of a label can be differentiated amongst the luminescence lifetimes of a plurality of types of labels by measuring the time duration. In some embodiments, the luminescence lifetime of a label can be differentiated amongst the luminescence lifetimes of a plurality of types of labels by measuring a plurality of time durations for multiple pulse events and emission events. In certain embodiments, a label is identified or differentiated amongst a plurality of types of labels by determining or estimating the luminescence lifetime of the label. In certain embodiments, a label is identified or differentiated amongst a plurality of types of labels by differentiating the luminescence lifetime of the label amongst a plurality of the luminescence lifetimes of a plurality of types of labels.

Determination of a luminescence lifetime of a luminescent label can be performed using any suitable method (e.g., by measuring the lifetime using a suitable technique or by determining time-dependent characteristics of emission). In some embodiments, determining the luminescence lifetime of one label comprises determining the lifetime relative to another label. In some embodiments, determining the luminescence lifetime of a label comprises determining the lifetime relative to a reference. In some embodiments, determining the luminescence lifetime of a label comprises measuring the lifetime (e.g., fluorescence lifetime). In some embodiments, determining the luminescence lifetime of a label comprises determining one or more temporal characteristics that are indicative of lifetime. In some embodiments, the luminescence lifetime of a label can be determined based on a distribution of a plurality of emission events (e.g., 1, 2, 3, 4, 5, 6, 7, 8, 9, 10, 11, 12, 13, 14, 15, 16, 17, 18, 19, 20, 30, 40, 50, 60, 70, 80, 90, 100, or more emission events) occurring across one or more time-gated windows relative to an excitation pulse. For example, a luminescence lifetime of a label can be distinguished from a plurality of labels having different luminescence lifetimes based on the distribution of photon arrival times measured with respect to an excitation pulse.

It should be appreciated that a luminescence lifetime of a luminescent label is indicative of the timing of photons emitted after the label reaches an excited state and the label can be distinguished by information indicative of the timing of the photons. Some embodiments may include distinguishing a label from a plurality of labels based on the luminescence lifetime of the label by measuring times associated with photons emitted by the label. The distribution of times may provide an indication of the luminescence lifetime which may be determined from the distribution. In some embodiments, the label is distinguishable from the plurality of labels based on the distribution of times, such as by comparing the distribution of times to a reference distribution corresponding to a known label. In some embodiments, a value for the luminescence lifetime is determined from the distribution of times.

As used herein, in some embodiments, luminescence intensity refers to the number of emitted photons per unit time that are emitted by a luminescent label which is being excited by delivery of a pulsed excitation energy. In some embodiments, the luminescence intensity refers to the detected number of emitted photons per unit time that are emitted by a label which is being excited by delivery of a pulsed excitation energy, and are detected by a particular sensor or set of sensors.

As used herein, in some embodiments, brightness refers to a parameter that reports on the average emission intensity per luminescent label. Thus, in some embodiments, "emission intensity" may be used to generally refer to brightness of a composition comprising one or more labels. In some embodiments, brightness of a label is equal to the product of its quantum yield and extinction coefficient.

As used herein, in some embodiments, luminescence quantum yield refers to the fraction of excitation events at a given wavelength or within a given spectral range that lead to an emission event, and is typically less than 1. In some embodiments, the luminescence quantum yield of a luminescent label described herein is between 0 and about 0.001, between about 0.001 and about 0.01, between about 0.01 and about 0.1, between about 0.1 and about 0.5, between about 0.5 and 0.9, or between about 0.9 and 1. In some embodiments, a label is identified by determining or estimating the luminescence quantum yield.

As used herein, in some embodiments, an excitation energy is a pulse of light from a light source. In some embodiments, an excitation energy is in the visible spectrum. In some embodiments, an excitation energy is in the ultraviolet spectrum. In some embodiments, an excitation energy is in the infrared spectrum. In some embodiments, an excitation energy is at or near the absorption maximum of a luminescent label from which a plurality of emitted photons are to be detected. In certain embodiments, the excitation energy is between about 500 nm and about 700 nm (e.g., between about 500 nm and about 600 nm, between about 600 nm and about 700 nm, between about 500 nm and about 550 nm, between about 550 nm and about 600 nm, between about 600 nm and about 650 nm, or between about 650 nm and about 700 nm). In certain embodiments, an excitation energy may be monochromatic or confined to a spectral range. In some embodiments, a spectral range has a range of between about 0.1 nm and about 1 nm, between about 1 nm and about 2 nm, or between about 2 nm and about 5 nm. In some embodiments, a spectral range has a range of between about 5 nm and about 10 nm, between about 10 nm and about 50 nm, or between about 50 nm and about 100 nm.

V. Kits for Sample Preparation

In some aspects, the disclosure relates to kits for preparing a polypeptide sample (e.g., a multiplexed sample) for sequencing. A kit may be sufficient to prepare one or more polypeptide samples (e.g., multiplexed samples) for sequencing. In some embodiments, a kit is sufficient to prepare a single polypeptide sample. In other embodiments, a kit is sufficient to prepare, at least 2, at least 3, at least 4, at least 5, at least 6, at least 7, at least 8, at least 9, at least 10, at least 11, at least 12, at least 13, at least 14, at least 15, at least 20, at least 25, at least 30, at least 40, at least 50, at least 60, at least 70, at least 80, at least 90, or at least 100 polypeptide samples.

In some embodiments, a kit comprises a barcode component comprising a plurality of barcode molecules, as described herein. See "Methods of Preparing a Multiplexed Sample." In some embodiments, a kit comprises one or more detector molecules, as described herein. See "Methods of Preparing a Multiplexed Sample." In some embodiments, a kit comprises a solid support that allows for the physical separation of population of polypeptides of different origins, as described herein. See "Methods of Preparing a Multiplexed Sample." In some embodiments, a kit comprises an enrichment component comprising a plurality of enrichment molecules, as described herein. See "Methods of Polypeptide Enrichment." In some embodiments, a kit comprises a modifying agent, as described herein. See "Methods of Polypeptide Enrichment." In some embodiments, a kit comprises an affinity reagent, as described herein. See "Polypeptide Sequencing Methodologies." In some embodiments, a kit comprises a labeled peptidase, as described herein. See "Polypeptide Sequencing Methodologies".

A kit may be specific for one or more organisms (e.g., one or more single-cellular and/or multicellular organisms). In some embodiments, a kit comprises components (e.g., barcode molecules, detector molecules, enrichment molecules, or a combination thereof) that modify, bind to, are bound by, etc., polypeptides of one or more organisms. For example, in some embodiments, a kit comprises components that modify, bind to, are bound by, etc., one or more known polypeptides in the human proteome.

In some embodiments, a kit is specific for one or more disease or condition. For example, a kit may be an oncology kit, a cardiology kit, an inherited disease kit, or a combination thereof. An oncology kit may comprise enrichment molecules that bind to (or are bound by) ABL1, ABL2, ACSL3, ACVR2A, ADAMTS20, ADGRA2, ADGRB3, ADGRL3, AFF1, AFF3, AKAP9, AKT1, AKT2, AKT3, ALK, AMER1, APC, AR, ARID1A, ARID2, ARNT, ASXL1, ATF1, ATM, ATR, ATRX, AURKA, AURKB, AURKC, AXL, BAP1, BCL10, BCL11A, BCL11B, BCL2, BCL2L1, BCL2L2, BCL3, BCL6, BCL7A, BCL9, BCR, BIRC2, BIRC3, BIRC5, BLM, BLNK, BMPR1A, BRAF, BRCA1, BRCA2, BRD3, BRIP1, BTK, BUB1B, CACNA1D, CARD11, CASC5, CASP8, CBFA2T3, CBFB, CBL, CCND1, CCND2, CCNE1, CD79A, CD79B, CDCl73, CDH1, CDH11, CDH2, CDH20, CDH5, CDK12, CDK4, CDK6, CDK8, CDKN2A, CDKN2B, CDKN2C, CEBPA, CHEK1, CHEK2, CIC, CKS1B, CMPK1, COL1A1, CRBN, CREB1, CREBBP, CRKL, CRLF2, CRTC1, CSF1R, CSMD3, CTNNA1, CTNNB1, CYLD, CYP2C19, CYP2D6, DAXX, DCC, DDB2, DDIT3, DDR2, DEK, DICER1, DNMT3A, DPYD, DST, EGFR, EML4, EP300, EP400, EPHA3, EPHA7, EPHB1, EPHB4, EPHB6, ERBB2, ERBB3, ERBB4, ERCC1, ERCC2, ERCC3, ERCC4, ERCC5, ERG, ESR1, ETS1, ETV1, ETV4, EXT1, EXT2, EZH2, FANCA, FANCC, FANCD2, FANCF, FANCG, FAS, FBXW7, FCGR2B, FGFR1, FGFR2, FGFR3, FGFR4, FH, FLCN, FLI1, FLT1, FLT3, FLT4, FN1, FOXA1, FOXL2, FOXO1, FOXO3, FOXP1, FOXP4, FZR1, G6PD, GATA1, GATA2, GATA3, GDNF, GNA11, GNAQ, GNAS, GPC3, GRM8, GUCY1A2, HCAR1, HEY1, HIF1A, HIST1H3B, HLF, HMGA1, HNF1A, HOOK3, HOXA13, HOXD11, HRAS, HSP90AA1, HSP90AB1, ICK, IDH1, IDH2, IGF1R, IGF2, IGF2R, IKBKB, IKBKE, IKZF1, IL2, IL21R, IL6ST, IL7R, ING4, IRF4, IRS2, ITGA10, ITGA9, ITGB2, ITGB3, JAK1, JAK2, JAK3, JUN, KAT6A, KAT6B, KDM5C, KDM6A, KDR, KEAP1, KIAA1549, KIT, KLF6, KMT2A, KMT2C, KMT2D, KRAS, LAMP1, LCK, LIFR, LPP, LRP1B, LTF, LTK, MAF, MAFB, MAGEA1, MAGI1, MALT1, MAML2, MAP2K1, MAP2K2, MAP2K4, MAP3K7, MAPK1, MAPK8, MARK1, MARK4, MBD1, MCL1, MDM2, MDM4, MEN1, MET, MITF, MLH1, MLLT10, MLLT4, MLLT6, MMP2, MN1, MPL, MRE11A, MSH2, MSH6, MTCP1, MTOR, MTR, MTRR, MUC1, MUTYH, MYB, MYC, MYCL, MYCN, MYD88, MYH11, MYH9, NBN, NCOA1, NCOA2, NCOA4, NF1, NF2, NFE2L2, NFKB1, NFKB2, NIN, NKX2-1, NLRP1, NOTCH1, NOTCH2, NOTCH4, NPM1, NR4A3, NRAS, NSD1, NTRK1, NTRK3, NUMA1, NUP214, NUP98, NUTM2A, NUTM2B, OMD, P2RY8, PAK3, PALB2, PARP1, PAX3, PAX5, PAX7, PAX8, PBRM1, PBX1, PDE4DIP, PDGFB, PDGFRA, PDGFRB, PER1, PGAP3, PHOX2B, PIK3C2B, PIK3CA, PIK3CB, PIK3CD, PIK3CG, PIK3R1, PIK3R2, PIM1, PKHD1, PLAG1, PLCG1, PLEKHG5, PML, PMS1, PMS2, POT1, POU5F1, PPARG, PPP2R1A, PRDM1, PRKAR1A, PRKDC, PSIP1, PTCH1, PTEN, PTGS2, PTPN11, PTPRD, PTPRT, RAD50, RAF1, RALGDS, RAP1GDS1, RARA, RB1, RECQL4, REL, RET, RHOH, RNASEL, RNF2, RNF213, ROS1, RPS6KA2, RRM1, RUNX1, RUNX1T1, SAMD9, SBDS, SDHA, SDHB, SDHC, SDHD, SET, SETBP1, SETD2, SF3B1, SGK1, SH2D1A, SH3GL1, SMAD2, SMAD4, SMARCA4, SMARCB1, SMO, SMUG1, SOCS1, SOX11, SOX2, SRC, SSX1, SSX2, SSX4, STAT5B, STK11, STK36, SUFU, SYK, SYNE1, TAF1, TAF1L, TAL1, TBL1XR1, TBX22, TCF12, TCF3, TCF7L1, TCF7L2, TCL1A, TERT, TET1, TET2, TFE3, TGFBR2, TGM7, THBS1, TIMP3, TLR4, TLX1, TMPRSS2, TNFAIP3, TNFRSF14, TNK2, TOP1, TP53, TPR, TRIM24, TRIM33, TRIP11, TRRAP, TSC1, TSC2, TSHR, TTL, UBR5, UGT1A1, USP9X, VHL, WAS, WHSC1, WRN, WT1, XPA, XPC, XPO1, XRCC2, ZNF384, ZNF521, or any combination thereof.

A cardiology kit may comprise enrichment molecules that bind to (or are bound by) ABCC9, ABCG5, ABCG8, ACTA1, ACTA2, ACTC1, ACTN2, AKAP9, ALMS1, ANK2, ANKRD1, APOA4, APOA5, APOB, APOC2, APOE, BAGS, BRAF, CACNA1C, CACNA2D1, CACNB2, CALM1, CALR3, CASQ2, CAV3, CBL, CBS, CETP, COL3A1, COL5A1, COL5A2, COX15, CREB3L3, CRELD1, CRYAB, CSRP3, CTF1, DES, DMD, DNAJC19, DOLK, DPP6, DSC2, DSG2, DSP, DTNA, EFEMP2, ELN, EMD, EYA4, FBN1, FBN2, FHL1, FHL2, FKRP, FKTN, FXN, GAA, GATAD1, GCKR, GJA5, GLA, GPD1L, GPIHBP1, HADHA, HCN4, HFE, HRAS, HSPB8, ILK, JAG1, JPH2, JUP, KCNA5, KCND3, KCNE1, KCNE2, KCNE3, KCNH2, KCNJ2, KCNJ5, KCNJ8, KCNQ1, KLF10, KRAS, LAMA2, LAMA4, LAMP2, LDB3, LDLR, LDLRAP1, LMF1, LMNA, LPL, LTBP2, MAP2K1, MAP2K2, MIB1, MURC, MYBPC3, MYH11, MYH6, MYH7, MYL2, MYL3, MYLK, MYLK2, MYO6, MYOZ2, MYPN, NEXN, NKX2-5, NODAL, NOTCH1, NPPA, NRAS, PCSK9, PDLIM3, PKP2, PLN, PRDM16, PRKAG2, PRKAR1A, PTPN11, RAF1, RANGRF, RBM20, RYR1, RYR2, SALL4, SCN1B, SCN2B, SCN3B, SCN4B, SCN5A, SCO2, SDHA, SEPN1, SGCB, SGCD, SGCG, SHOC2, SLC25A4, SLC2A10, SMAD3, SMAD4, SNTA1, SOS1, SREBF2, TAZ, TBX20, TBX3, TBX5, TCAP, TGFB2, TGFB3, TGFBR1, TGFBR2, TMEM43, TMPO, TNNC1, TNNI3, TNNT2, TPM1, TRDN, TRIM63, TRPM4, TTN, TTR, TXNRD2, VCL, ZBTB17, ZHX3, and/or ZIC3.

An inherited disease kit may comprise enrichment molecules that bind to (or are bound by) ABCA4, ABCC9, ABCD1, ACADVL, ACTA2, ACTC1, ACTN2, ADA, AIPL1, AIRE, AKAP9, ALPL, AMT, ANK2, APC, APP, APTX, ARL6, ARSA, ASL, ASPA, ATL1, ATM, ATP2A2, ATP7A, ATP7B, ATXN1, ATXN2, ATXN7, BAGS, BCKDHA, BCKDHB, BEST1, BMPR1A, BTD, BTK, CA4, CACNA1C, CACNB2, CALR3, CAPN3, CASQ2, CAV3, CCDCl39, CCDCl40, CDH23, CEP290, CERKL, CFTR, CHAT, CHD7, CHEK2, CHM, CHRNA1, CHRNB1, CHRND, CHRNE, CLCN1, CNGB1, COL11A1, COL11A2, COL1A1, COL1A2, COL2A1, COL3A1, COL4A1, COL4A5, COL5A1, COL5A2, COL7A1, COL9A1, CRB1, CRX, CTDP1, CTNS, CYP27A1, DBT, DCX, DES, DHCR7, DKC1, DLD, DMD, DNAH11, DNAH5, DNAH9, DNAI1, DNAI2, DNM2, DOK7, DSC2, DSG2, DSP, DYSF, ELN, EMD, ENG, EXT1, EYA1, EYS, F8, F9, FANCA, FANCC, FANCF, FANCG, FBN1, FBXO7, FGFR1, FGFR3, FMO3, FOXL2, FRG1, FRMD7, FSCN2, FXN, GAA, GALT, GATA4, GBA, GBE1, GCSH, GDF5, GJB2, GJB3, GJB6, GLA, GLDC, GNE, GNPTAB, GPC3, GPD1L, GPR143, GUCY2D, HBA2, HBB, HCN4, HEXA, HFE, HIBCH, HMBS, HR, IDS, IDUA, IKBKAP, IL2RG, IMPDH1, ITGB4, JAG1, JUP, KCNE1, KCNE2, KCNE3, KCNH2, KCNJ2, KCNQ1, KCNQ4, KIAA0196, KLHL7, KRAS, KRT14, KRT5, L1CAM, LAMB3, LAMP2, LDB3, LMNA, LRAT, LRRK2, MAPT, MC1R, MECP2, MED12, MEN1, MERTK, MFN2, MLH1, MMAA, MMAB, MMACHC, MPZ, MSH2, MTM1, MUT, MYBPC3, MYH11, MYH6, MYH7, MYL2, MYL3, MYLK, MYO7A, MYOZ2, NF1, NF2, NIPBL, NKX2-5, NME8, NPC1, NPC2, NR2E3, NRAS, NSD1, OCA2, OCRL, OTC, PABPN1, PAFAH1B1, PAH, PAX3, PAX6, PCDH15, PEX1, PEX10, PEX13, PEX14, PEX19, PEX26, PEX3, PEX5, PINK1, PKD1, PKD2, PKHD1, PKP2, PLEC, PLN, PLOD1, PMM2, PMP22, POLG, PPT1, PRCD, PRKAG2, PROM1, PRPF31, PRPF8, PRPH2, PSEN1, PSEN2, PTCH1, PTPN11, RAF1, RAG1, RAG2, RAIl, RAPSN, RB1, RDH12, RET, RHO, ROR2, RP9, RPE65, RPGR, RPGRIP1, RPL11, RPL35A, RPS10, RPS19, RPS24, RPS26, RPS6KA3, RPS7, RS1, RSPH4A, RSPH9, RYR1, RYR2, SALL4, SCN1B, SCN3B, SCN4B, SCN5A, SCN9A, SEMA4A, SERPINA1, SERPING1, SGCD, SH3BP2, SIX1, SIX5, SLC25A13, SLC25A4, SLC26A4, SMAD3, SMAD4, SNCA, SNRNP200, SNTA1, SOD1, SOS1, SOX9, SPATA7, SPG7, STARD3, TAF1, TAZ, TBX5, TCOF1, TGFBR1, TGFBR2, TMEM43, TNNC1, TNNI3, TNNT1, TNNT2, TNXB, TOPORS, TP53, TPM1, TSC1, TSC2, TTPA, TTR, TULP1, TWIST1, TYR, USH1C, USH2A, VCL, VHL, WAS, WRN, WT1, or any combination thereof.

In some embodiments, at least one component in the kit is provided in a desiccated or lyophilized form. In other embodiments, at least one component of the kit is provided in a solubilized form.

The kits provided herein are in suitable packaging. Suitable packaging includes, but is not limited to, vials, bottles, jars, flexible packaging, and the like. Also contemplated are packages for use in combination with a specific device. See "Devices for Sample Preparation and Sample Sequencing." A kit may have a sterile access port (for example, the container may be an intravenous solution bag or a vial having a stopper pierceable by a hypodermic injection needle). The container may also have a sterile access port.

Kits optionally may provide additional components such as buffers and interpretive information. In some embodiments, the kit further comprises at least one buffer. Buffers suitable for the methods described herein have been described previously. In some embodiments, the kit can additionally comprise instructions for use in any of the methods described herein.

In some embodiment, the disclosure provides articles of manufacture comprising contents of the kits described above.

VI. Devices for Sample Preparation and Sample Sequencing

In some aspects, the disclosure relates to devices for sample preparation and/or sample sequencing. In some embodiments, the device comprises a sample preparation module. In some embodiments, the device comprises a sample sequencing module. In some embodiments, the device comprises a sample preparation module and a sample sequencing module.

A. Device for Sample Preparation

Devices including apparatuses, cartridges (e.g., comprising channels (e.g., microfluidic channels)), and/or pumps (e.g., peristaltic pumps) for use in a process of preparing a sample for analysis are generally provided. Devices can be used in accordance with the instant disclosure to enable enrichment, concentration, manipulation, and/or detection of a target molecule from a biological sample. In some embodiments, devices and related methods are provided for automated processing of a sample to produce material for next generation sequencing and/or other downstream analytical techniques. Devices and related methods may be used for performing chemical and/or biological reactions, including reactions for nucleic acid and/or polypeptide processing in accordance with sample preparation or sample analysis processes described elsewhere herein.

In some embodiments, a sample preparation device is positioned to deliver or transfer to a sequencing module or device a target molecule or sample comprising a plurality of molecules (e.g., a target nucleic acid or a target polypeptide). In some embodiments, a sample preparation device is connected directly to (e.g., physically attached to) or indirectly to a sequencing device.

In some embodiments, a device comprise a sequence preparation module that is configured to receive one or more cartridges. In some embodiments, a cartridge comprises one or more reservoirs or reaction vessels configured to receive a fluid and/or contain one or more reagents used in a sample preparation process. In some embodiments, a cartridge comprises one or more channels (e.g., microfluidic channels) configured to contain and/or transport a fluid (e.g., a fluid comprising one or more reagents) used in a sample preparation process. Reagents include buffers, enzymatic reagents, polymer matrices, barcode components (e.g., barcode molecules), detector molecules, enrichment molecules, capture reagents, size-specific selection reagents, sequence-specific selection reagents, and/or purification reagents. Additional reagents for use in a sample preparation process are described elsewhere herein.

In some embodiments, a cartridge includes one or more stored reagents (e.g., of a liquid or lyophilized form suitable for reconstitution to a liquid form). The stored reagents of a cartridge include reagents suitable for carrying out a desired process and/or reagents suitable for processing a desired sample type. In some embodiments, a cartridge is a single-use cartridge (e.g., a disposable cartridge) or a multiple-use cartridge (e.g., a reusable cartridge). In some embodiments, a cartridge is configured to receive a user-supplied sample. The user-supplied sample may be added to the cartridge before or after the cartridge is received by the device, e.g., manually by the user or in an automated process.

In some embodiments, the device may facilitate the preparation of a multiplexed sample in a process in accordance with the instant disclosure. See "Methods of Preparing a Multiplexed Sample".

In some embodiments, the device may facilitate enrichment of a target molecule in a process in accordance with the instant disclosure. See "Methods of Polypeptide Enrichment." In this way, the device enables the leveraging of molecules to enrich for polypeptides of interest in a highly multiplexed fashion.

In some embodiments, a sample is enriched for a target molecule using an electropheretic method. In some embodiments, a sample is enriched for a target molecule using affinity SCODA. In some embodiments, a sample is enriched for a target molecule using field inversion gel electrophoresis (FIGE). In some embodiments, a sample is enriched for a target molecule using pulsed field gel electrophoresis (PFGE).

In some embodiments, a device comprises sample preparation module comprising a matrix used during enrichment (e.g., a porous media, electrophoretic polymer gel) comprising immobilized capture probes that bind (directly or indirectly) to target molecules present in the sample. In some embodiments, a matrix used during enrichment comprises 1, 2, 3, 4, 5, or more unique immobilized capture probes, each of which binds to a unique target molecule and/or bind to the same target molecule with different binding affinities.

In some embodiments, an immobilized capture probe is a polypeptide capture probe that binds to a target polypeptide or polypeptide fragment. For example, in some embodiments, an immobilized capture probe is an enrichment molecule as described herein.

In some embodiments, a polypeptide capture probe binds to a target polypeptide (or polypeptide fragment) with a binding affinity of $10^{-9}$ to $10^{-8}$ M, $10^{-8}$ to $10^{-7}$ M, $10^{-7}$ to $10^{-6}$ M, $10^{-6}$ to $10^{-5}$ M, $10^{-5}$ to $10^{-4}$ M, $10^{-4}$ to $10^{-3}$ M, or $10^{-3}$ to $10^{-2}$ M. In some embodiments, the binding affinity is in the picomolar to nanomolar range (e.g., between about $10^{-12}$ and about $10^{-9}$ M). In some embodiments, the binding affinity is in the nanomolar to micromolar range (e.g., between about $10^{-9}$ and about $10^{-6}$ M). In some embodiments, the binding affinity is in the micromolar to millimolar range (e.g., between about $10^{-6}$ and about $10^{-3}$ M). In some embodiments, the binding affinity is in the picomolar to micromolar range (e.g., between about $10^{-12}$ and about $10^{-6}$ M). In some embodiments, the binding affinity is in the nanomolar to millimolar range (e.g., between about $10^{-9}$ and about $10^{-3}$ M).

In some embodiments, an immobilized capture probe is an oligonucleotide capture probe that hybridizes to a target nucleic acid. In some embodiments, an oligonucleotide capture probe is at least 50%, 60%, 70%, 80%, 90% 95%, or 100% complementary to a target nucleic acid. In some embodiments, a single oligonucleotide capture probe may be used to enrich a plurality of related target nucleic acids (e.g., 2, 3, 4, 5, 6, 7, 8, 9, 10, 20, 30, 40, 50, or more related target nucleic acids) that share at least 50%, 60%, 70%, 80%, 90% 95%, or 99% sequence identity. Enrichment of a plurality of related target nucleic acids may allow for the generation of a metagenomic library. In some embodiments, an oligonucleotide capture probe may enable differential enrichment of related target nucleic acids. In some embodiments, an oligonucleotide capture probe may enable enrichment of a target nucleic acid relative to a nucleic acid of identical sequence that differs in its modification state (e.g., methylation state, acetylation state).

In some embodiments, for the purposes of enriching nucleic acid target molecules with a length of 0.5-2 kilobases, oligonucleotide capture probes may be covalently immobilized in an acrylamide matrix using a 5' Acrydite moiety. In some embodiments, for the purposes of enriching larger nucleic acid target molecules (e.g., with a length of >2 kilobases), oligonucleotide capture probes may be immobilized in an agarose matrix. In some embodiments, oligonucleotide capture probes may be immobilized in an agarose matrix using thiol-epoxide chemistries (e.g., by covalently attached thiol-modified oligonucleotides to crosslinked agarose beads). Oligonucleotide capture probes linked to agarose beads can be combined and solidified within standard agarose matrices (e.g., at the same agarose percentage).

In some embodiments, multiple capture probes (e.g., populations of multiple capture probe types, e.g., that bind to deterministic target molecules of infectious agents such as adenovirus, *Staphylococcus*, pneumonia, or tuberculosis) may be immobilized in an enrichment matrix. Application of a sample to an enrichment matrix with multiple deterministic capture probes may result in diagnosis of a disease or condition (e.g., presence of an infectious agent).

In some embodiments, a device may facilitate release of a target molecule from the enrichment matrix after removal of non-target molecules, in a process in accordance with the instant disclosure. In some embodiments, a target molecule may be released from the enrichment matrix by increasing the temperature of the enrichment matrix. Adjusting the temperature of the matrix further influences migration rate as increased temperatures provide a higher capture probe stringency, requiring greater binding affinities between the target molecule and the capture probe. In some embodiments, when enriching related target molecules, the matrix temperature may be gradually increased in a step-wise manner in order to release and isolate target molecules in steps of ever-increasing homology. This may allow for the sequencing of target polypeptides or target nucleic acids that are increasingly distant in their relation to an initial reference target molecule, enabling discovery of novel proteins (e.g., enzymes) or functions (e.g., enzymatic function or gene function). In some embodiments, when using multiple capture probes (e.g., multiple deterministic capture probes), the matrix temperature may be increased in a step-wise or gradient fashion, permitting temperature-dependent release of different target molecules and resulting in generation of a series of barcoded release bands that represent the presence or absence of control and target molecules.

Devices in accordance with the instant disclosure generally contain mechanical and electronic and/or optical components which can be used to operate a cartridge as described herein. In some embodiments, the device components operate to achieve and maintain specific temperatures on a cartridge or on specific regions of the cartridge. In some embodiments, the device components operate to apply specific voltages for specific time durations to electrodes of a cartridge. In some embodiments, the device components operate to move liquids to, from, or between reservoirs and/or reaction vessels of a cartridge. In some embodiments, the device components operate to move liquids through channel(s) of a cartridge, e.g., to, from, or between reservoirs and/or reaction vessels of a cartridge. In some embodiments, the device components move liquids via a peristaltic pumping mechanism (e.g., apparatus) that interacts with an elastomeric, reagent-specific reservoir or reaction vessel of a cartridge. In some embodiments, the device components move liquids via a peristaltic pumping mechanism (e.g., apparatus) that is configured to interact with an elastomeric component (e.g., surface layer comprising an elastomer) associated with a channel of a cartridge to pump fluid through the channel. Device components can include computer resources, for example, to drive a user interface where sample information can be entered, specific processes can be selected, and run results can be reported.

The following non-limiting example is meant to illustrate aspects of the devices, methods, and compositions described herein. The use of a sample preparation device in accordance with the instant disclosure may proceed with one or more of the following described steps. A user may open the lid of the device and insert a cartridge that supports the desired process. The user may then add a sample, which may be combined with a specific lysis solution, to a sample port on the cartridge. The user may then close the device lid, enter any sample specific information via a touch screen interface on the device, select any process specific parameters (e.g., range of desired size selection, desired degree of homology for target molecule capture, etc.), and initiate the sample preparation process run.

Following the run, the user may receive relevant run data (e.g., confirmation of successful completion of the run, run specific metrics, etc.), as well as process specific information (e.g., amount of sample generated, presence or absence of specific target sequence, etc.). Data generated by the run may be subjected to subsequent bioinformatics analysis, which can be either local or cloud based. Depending on the process, a finished sample may be extracted from the cartridge for subsequent use (e.g., genomic sequencing, qPCR quantification, cloning, etc.). The device may then be opened, and the cartridge may then be removed.

FIG. 10 provides an illustration depicting an exemplary apparatus for preparing a sample (e.g., an enriched or multiplexed sample). See e.g., U.S. Pat. No. 8,608,929, the entirety of which is incorporated herein by reference.

B. Device for Sequencing

Devices including apparatuses, cartridges (e.g., comprising channels (e.g., microfluidic channels)), and/or pumps (e.g., peristaltic pumps) for use in a process of sequencing a sample (e.g., a multiplexed sample) comprising polypeptides are also generally provided. Sequencing of nucleic acids or polypeptides in accordance with the instant disclosure, in some aspects, may be performed using a system that permits single molecule analysis and/or the sequencing of single molecules in parallel. The system may include a sequencing device and an instrument configured to interface with the sequencing device.

The sequencing device may include a sequencing module comprising an array of pixels, where individual pixels include a sample well and at least one photodetector. The sample wells of the sequencing device may be formed on or through a surface of the sequencing device and be configured to receive a sample placed on the surface of the sequencing device. In some embodiments, the sample wells are a component of a cartridge (e.g., a disposable or single-use cartridge) that can be inserted into the device. Collectively, the sample wells may be considered as an array of sample wells. The plurality of sample wells may have a suitable size and shape such that at least a portion of the sample wells receive a single target molecule or sample comprising a plurality of molecules (e.g., a target nucleic acid or a target polypeptide). In some embodiments, the number of molecules within a sample well may be distributed among the sample wells of the sequencing device such that some sample wells contain one molecule (e.g., a target nucleic acid or a target polypeptide) while others contain zero, two, or a plurality of molecules.

In some embodiments, a sequencing device is positioned to receive a sample comprising a plurality of molecules (e.g., one or more polypeptides of interest) from a sample preparation device. In some embodiments, a sequencing device is connected directly (e.g., physically attached to) or indirectly to a sample preparation device.

The sequencing device may include an array of pixels, where individual pixels include a sample well and at least one photodetector. The sample wells of the sequencing device may be formed on or through a surface of the sequencing device and be configured to receive a sample placed on the surface of the sequencing device. Collectively, the sample wells may be considered as an array of sample wells. The plurality of sample wells may have a suitable size and shape such that at least a portion of the sample wells receive a single sample (e.g., a single molecule, such as a polypeptide). In some embodiments, the number of samples within a sample well may be distributed among the sample wells of the sequencing device such that some sample wells contain one sample while others contain zero, two or more samples.

Excitation light is provided to the sequencing device from one or more light source, which may be external or internal to the sequencing device. Optical components of the sequencing device may receive the excitation light from the light source and direct the light towards the array of sample wells of the sequencing device and illuminate an illumination region within the sample well. In some embodiments, a sample well may have a configuration that allows for the sample to be retained in proximity to a surface of the sample well, which may ease delivery of excitation light to the sample and detection of emission light from the sample. A sample positioned within the illumination region may emit emission light in response to being illuminated by the excitation light. For example, the sample may be labeled with a fluorescent marker, which emits light in response to achieving an excited state through the illumination of excitation light. Emission light emitted by a sample may then be detected by one or more photodetectors within a pixel corresponding to the sample well with the sample being analyzed. When performed across the array of sample wells, which may range in number between approximately 10,000 pixels to 1,000,000 pixels according to some embodiments, multiple samples can be analyzed in parallel.

The sequencing device may include an optical system for receiving excitation light and directing the excitation light among the sample well array. The optical system may include one or more grating couplers configured to couple excitation light to the sequencing device and direct the excitation light to other optical components. The optical system may include optical components that direct the excitation light from a grating coupler towards the sample well array. Such optical components may include optical splitters, optical combiners, and waveguides. In some embodiments, one or more optical splitters may couple excitation light from a grating coupler and deliver excitation light to at least one of the waveguides. According to some embodiments, the optical splitter may have a configuration that allows for delivery of excitation light to be substantially uniform across all the waveguides such that each of the waveguides receives a substantially similar amount of excitation light. Such embodiments may improve performance of the sequencing device by improving the uniformity of excitation light received by sample wells of the sequencing device. Examples of suitable components, e.g., for coupling excitation light to a sample well and/or directing emission light to a photodetector, to include in a sequencing device are described in U.S. patent application Ser. No. 14/821,688, filed Aug. 7, 2015, titled “INTEGRATED DEVICE FOR PROBING, DETECTING AND ANALYZING MOLECULES,” and U.S. patent application Ser. No. 14/543,865, filed Nov. 17, 2014, titled “INTEGRATED DEVICE WITH EXTERNAL LIGHT SOURCE FOR PROBING, DETECTING, AND ANALYZING MOLECULES,” both of which are incorporated by reference in their entirety. Examples of suitable grating couplers and waveguides that may be implemented in the sequencing device are described in U.S. patent application Ser. No. 15/844,403, filed Dec. 15, 2017, titled “OPTICAL COUPLER AND WAVEGUIDE SYSTEM,” which is incorporated by reference in its entirety.

Additional photonic structures may be positioned between the sample wells and the photodetectors and configured to reduce or prevent excitation light from reaching the photodetectors, which may otherwise contribute to signal noise in detecting emission light. In some embodiments, metal layers which may act as a circuitry for the sequencing device, may also act as a spatial filter. Examples of suitable photonic structures may include spectral filters, a polarization filters, and spatial filters and are described in U.S. patent application Ser. No. 16/042,968, filed Jul. 23, 2018, titled “OPTICAL REJECTION PHOTONIC STRUCTURES,” which is incorporated by reference in its entirety.

Components located off of the sequencing device may be used to position and align an excitation source to the sequencing device. Such components may include optical components including lenses, mirrors, prisms, windows, apertures, attenuators, and/or optical fibers. Additional mechanical components may be included in the instrument to allow for control of one or more alignment components. Such mechanical components may include actuators, stepper motors, and/or knobs. Examples of suitable excitation sources and alignment mechanisms are described in U.S. patent application Ser. No. 15/161,088, filed May 20, 2016, titled "PULSED LASER AND SYSTEM," which is incorporated by reference in its entirety. Another example of a beam-steering module is described in U.S. patent application Ser. No. 15/842,720, filed Dec. 14, 2017, titled "COMPACT BEAM SHAPING AND STEERING ASSEMBLY," which is incorporated herein by reference. Additional examples of suitable excitation sources are described in U.S. patent application Ser. No. 14/821,688, filed Aug. 7, 2015, titled "INTEGRATED DEVICE FOR PROBING, DETECTING AND ANALYZING MOLECULES," which is incorporated by reference in its entirety.

The photodetector(s) positioned with individual pixels of the sequencing device may be configured and positioned to detect emission light from the pixel's corresponding sample well. Examples of suitable photodetectors are described in U.S. patent application Ser. No. 14/821,656, filed Aug. 7, 2015, titled "INTEGRATED DEVICE FOR TEMPORAL BINNING OF RECEIVED PHOTONS," which is incorporated by reference in its entirety. In some embodiments, a sample well and its respective photodetector(s) may be aligned along a common axis. In this manner, the photodetector(s) may overlap with the sample well within the pixel.

Characteristics of the detected emission light may provide an indication for identifying the marker associated with the emission light. Such characteristics may include any suitable type of characteristic, including an arrival time of photons detected by a photodetector, an amount of photons accumulated over time by a photodetector, and/or a distribution of photons across two or more photodetectors. In some embodiments, a photodetector may have a configuration that allows for the detection of one or more timing characteristics associated with a sample's emission light (e.g., luminescence lifetime). The photodetector may detect a distribution of photon arrival times after a pulse of excitation light propagates through the sequencing device, and the distribution of arrival times may provide an indication of a timing characteristic of the sample's emission light (e.g., a proxy for luminescence lifetime). In some embodiments, the one or more photodetectors provide an indication of the probability of emission light emitted by the marker (e.g., luminescence intensity). In some embodiments, a plurality of photodetectors may be sized and arranged to capture a spatial distribution of the emission light. Output signals from the one or more photodetectors may then be used to distinguish a marker from among a plurality of markers, where the plurality of markers may be used to identify a sample within the sample. In some embodiments, a sample may be excited by multiple excitation energies, and emission light and/or timing characteristics of the emission light emitted by the sample in response to the multiple excitation energies may distinguish a marker from a plurality of markers.

In operation, parallel analyses of samples within the sample wells are carried out by exciting some or all of the samples within the wells using excitation light and detecting signals from sample emission with the photodetectors. Emission light from a sample may be detected by a corresponding photodetector and converted to at least one electrical signal. The electrical signals may be transmitted along conducting lines in the circuitry of the sequencing device, which may be connected to an instrument interfaced with the sequencing device. The electrical signals may be subsequently processed and/or analyzed. Processing or analyzing of electrical signals may occur on a suitable computing device either located on or off the instrument.

The instrument may include a user interface for controlling operation of the instrument and/or the sequencing device. The user interface may be configured to allow a user to input information into the instrument, such as commands and/or settings used to control the functioning of the instrument. In some embodiments, the user interface may include buttons, switches, dials, and a microphone for voice commands. The user interface may allow a user to receive feedback on the performance of the instrument and/or sequencing device, such as proper alignment and/or information obtained by readout signals from the photodetectors on the sequencing device. In some embodiments, the user interface may provide feedback using a speaker to provide audible feedback. In some embodiments, the user interface may include indicator lights and/or a display screen for providing visual feedback to a user.

In some embodiments, the instrument may include a computer interface configured to connect with a computing device. The computer interface may be a USB interface, a FireWire interface, or any other suitable computer interface. A computing device may be any general purpose computer, such as a laptop or desktop computer. In some embodiments, a computing device may be a server (e.g., cloud-based server) accessible over a wireless network via a suitable computer interface. The computer interface may facilitate communication of information between the instrument and the computing device. Input information for controlling and/or configuring the instrument may be provided to the computing device and transmitted to the instrument via the computer interface. Output information generated by the instrument may be received by the computing device via the computer interface. Output information may include feedback about performance of the instrument, performance of the sequencing device, and/or data generated from the readout signals of the photodetector.

In some embodiments, the instrument may include a processing device configured to analyze data received from one or more photodetectors of the sequencing device and/or transmit control signals to the excitation source(s). In some embodiments, the processing device may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof). In some embodiments, the processing of data from one or more photodetectors may be performed by both a processing device of the instrument and an external computing device. In other embodiments, an external computing device may be omitted and processing of data from one or more photodetectors may be performed solely by a processing device of the sequencing device.

According to some embodiments, the instrument that is configured to analyze samples based on luminescence emission characteristics may detect differences in luminescence lifetimes and/or intensities between different luminescent molecules, and/or differences between lifetimes and/or intensities of the same luminescent molecules in different environments. The inventors have recognized and appreciated that differences in luminescence emission lifetimes can be used to discern between the presence or absence of different luminescent molecules and/or to discern between different environments or conditions to which a luminescent molecule is subjected. In some cases, discerning luminescent molecules based on lifetime (rather than emission wavelength, for example) can simplify aspects of the system. As an example, wavelength-discriminating optics (such as wavelength filters, dedicated detectors for each wavelength, dedicated pulsed optical sources at different wavelengths, and/or diffractive optics) may be reduced in number or eliminated when discerning luminescent molecules based on lifetime. In some cases, a single pulsed optical source operating at a single characteristic wavelength may be used to excite different luminescent molecules that emit within a same wavelength region of the optical spectrum but have measurably different lifetimes. An analytic system that uses a single pulsed optical source, rather than multiple sources operating at different wavelengths, to excite and discern different luminescent molecules emitting in a same wavelength region can be less complex to operate and maintain, more compact, and may be manufactured at lower cost.

Although analytic systems based on luminescence lifetime analysis may have certain benefits, the amount of information obtained by an analytic system and/or detection accuracy may be increased by allowing for additional detection techniques. For example, some embodiments of the systems may additionally be configured to discern one or more properties of a sample based on luminescence wavelength and/or luminescence intensity. In some implementations, luminescence intensity may be used additionally or alternatively to distinguish between different luminescent labels. For example, some luminescent labels may emit at significantly different intensities or have a significant difference in their probabilities of excitation (e.g., at least a difference of about 35%) even though their decay rates may be similar. By referencing binned signals to measured excitation light, it may be possible to distinguish different luminescent labels based on intensity levels.

According to some embodiments, different luminescence lifetimes may be distinguished with a photodetector that is configured to time-bin luminescence emission events following excitation of a luminescent label. The time binning may occur during a single charge-accumulation cycle for the photodetector. A charge-accumulation cycle is an interval between read-out events during which photo-generated carriers are accumulated in bins of the time-binning photodetector. Examples of a time-binning photodetector are described in U.S. patent application Ser. No. 14/821,656, filed Aug. 7, 2015, titled "INTEGRATED DEVICE FOR TEMPORAL BINNING OF RECEIVED PHOTONS," which is incorporated herein by reference. In some embodiments, a time-binning photodetector may generate charge carriers in a photon absorption/carrier generation region and directly transfer charge carriers to a charge carrier storage bin in a charge carrier storage region. In such embodiments, the time-binning photodetector may not include a carrier travel/capture region. Such a time-binning photodetector may be referred to as a "direct binning pixel." Examples of time-binning photodetectors, including direct binning pixels, are described in U.S. patent application Ser. No. 15/852,571, filed Dec. 22, 2017, titled "INTEGRATED PHOTODETECTOR WITH DIRECT BINNING PIXEL," which is incorporated herein by reference.

In some embodiments, different numbers of fluorophores of the same type may be linked to different reagents in a sample, so that each reagent may be identified based on luminescence intensity. For example, two fluorophores may be linked to a first labeled affinity reagent and four or more fluorophores may be linked to a second labeled affinity reagent. Because of the different numbers of fluorophores, there may be different excitation and fluorophore emission probabilities associated with the different affinity reagents. For example, there may be more emission events for the second labeled affinity reagent during a signal accumulation interval, so that the apparent intensity of the bins is significantly higher than for the first labeled affinity reagent.

The inventors have recognized and appreciated that distinguishing nucleotides or any other biological or chemical samples based on fluorophore decay rates and/or fluorophore intensities may enable a simplification of the optical excitation and detection systems. For example, optical excitation may be performed with a single-wavelength source (e.g., a source producing one characteristic wavelength rather than multiple sources or a source operating at multiple different characteristic wavelengths). Additionally, wavelength discriminating optics and filters may not be needed in the detection system. Also, a single photodetector may be used for each sample well to detect emission from different fluorophores. The phrase "characteristic wavelength" or "wavelength" is used to refer to a central or predominant wavelength within a limited bandwidth of radiation (e.g., a central or peak wavelength within a 20 nm bandwidth output by a pulsed optical source). In some cases, "characteristic wavelength" or "wavelength" may be used to refer to a peak wavelength within a total bandwidth of radiation output by a source.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more"

of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the application describes "a composition comprising A and B," the application also contemplates the alternative embodiments "a composition consisting of A and B" and "a composition consisting essentially of A and B."

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

The invention claimed is:

1. A method comprising:

(a) producing a first sample comprising one or more barcoded polypeptides;

(b) combining the first sample with one or more additional samples to generate a multiplexed sample comprising barcoded polypeptides originating from different samples, wherein each barcoded polypeptide comprises a barcode indicative of sample origin;

(c) contacting the multiplexed sample with one or more detector molecules; and (d) determining the sample origin of a first barcoded polypeptide based on kinetics of binding between at least one detector molecule and the barcode of the first barcoded polypeptide, wherein (d) comprises detecting a series of signal pulses indicative of association of the at least one detector molecule with the barcode of the first barcoded polypeptide.

2. The method of claim 1, wherein (d) comprises determining the sample origin for each of a plurality of different barcoded polypeptides in the multiplexed sample.

3. The method of claim 2, wherein (d) comprises detecting binding interactions between the one or more detector molecules and barcodes of the plurality of different barcoded polypeptides.

4. The method of claim 1, wherein the barcode comprises a peptide barcode.

5. The method of claim 4, wherein (a) comprises synthesizing the one or more barcoded polypeptides in vitro or in vivo.

6. The method of claim 4, wherein (a) comprises contacting a population of polypeptides with (i) a barcode molecule comprising the peptide barcode and (ii) one or more reagents that facilitate covalent attachment of the peptide barcode to one or more polypeptides of the population.

7. The method of claim 4, wherein each of the one or more barcoded polypeptides in the first sample comprises a peptide barcode covalently attached to an N-terminus or C-terminus of a polypeptide.

8. The method of claim 4, wherein the one or more detector molecules comprise one or more amino acid recognition molecules.

9. The method of claim 8, wherein the series of signal pulses is indicative of association of the one or more amino acid recognition molecules with successive amino acids exposed at the terminus of the peptide barcode while the peptide barcode is degraded.

10. The method of claim 1, wherein the barcode comprises a nucleic acid barcode.

11. The method of claim 10, wherein (a) comprises contacting a population of polypeptides with (i) a barcode molecule comprising the nucleic acid barcode and (ii) one or more reagents that facilitate covalent attachment of the nucleic acid barcode to one or more polypeptides of the population.

12. The method of claim 10, wherein the one or more detector molecules comprise one or more nucleic acids.

13. The method of claim 1, wherein the barcode comprises a luminescent molecule.

14. The method of claim 13, wherein the series of signal pulses is indicative of emission from the luminescent molecule.

15. The method of claim 1, wherein each of the one or more detector molecules comprises a luminescent label.

16. The method of claim 2, wherein the barcode comprises a peptide barcode.

17. A method comprising:

(a) producing a first sample comprising one or more barcoded polypeptides;

(b) combining the first sample with one or more additional samples to generate a multiplexed sample comprising barcoded polypeptides originating from different samples, wherein each barcoded polypeptide comprises a barcode indicative of sample origin, wherein the barcode comprises a peptide barcode;

(c) contacting the multiplexed sample with one or more detector molecules, wherein the one or more detector molecules comprise one or more amino acid recognition molecules; and (d) determining the sample origin of a first barcoded polypeptide based on kinetics of binding between at least one detector molecule and the barcode of the first barcoded polypeptide, wherein (d) comprises detecting a series of signal pulses indicative of association of the one or more amino acid recognition molecules with successive amino acids exposed at the terminus of the peptide barcode while the peptide barcode is degraded.

18. The method of claim 17, wherein (a) comprises contacting a population of polypeptides with (i) a barcode molecule comprising the peptide barcode and (ii) one or more reagents that facilitate covalent attachment of the peptide barcode to one or more polypeptides of the population.

19. The method of claim 17, wherein each of the one or more barcoded polypeptides in the first sample comprises a peptide barcode covalently attached to an N-terminus or C-terminus of a polypeptide.

20. A method comprising:

(a) producing a first sample comprising one or more barcoded polypeptides;

(b) combining the first sample with one or more additional samples to generate a multiplexed sample comprising barcoded polypeptides originating from different samples, wherein each barcoded polypeptide comprises a barcode indicative of sample origin, wherein the barcode comprises a luminescent molecule;

(c) contacting the multiplexed sample with one or more detector molecules; and (d) determining the sample origin of a first barcoded polypeptide based on kinetics of binding between at least one detector molecule and the barcode of the first barcoded polypeptide, wherein (d) comprises detecting a series of signal pulses indicative of emission from the luminescent molecule.

* * * * *

SEQUENCE LISTING

```
<160> NUMBER OF SEQ ID NOS: 33

<210> SEQ ID NO 1
<211> LENGTH: 921
<212> TYPE: PRT
<213> ORGANISM: Artificial Sequence
```

<220> FEATURE:
<223> OTHER INFORMATION: Synthetic

<400> SEQUENCE: 1

Met Gly Ser Ser His His His His His His Ser Ser Gly Leu Val Pro
1               5                   10                  15

Arg Gly Ser His Met Met Val Lys Gln Gly Val Phe Met Lys Thr Asp
            20                  25                  30

Gln Ser Lys Val Lys Lys Leu Ser Asp Tyr Lys Ser Leu Asp Tyr Phe
        35                  40                  45

Val Ile His Val Asp Leu Gln Ile Asp Leu Ser Lys Lys Pro Val Glu
    50                  55                  60

Ser Lys Ala Arg Leu Thr Val Val Pro Asn Leu Asn Val Asp Ser His
65                  70                  75                  80

Ser Asn Asp Leu Val Leu Asp Gly Glu Asn Met Thr Leu Val Ser Leu
                85                  90                  95

Gln Met Asn Asp Asn Leu Leu Lys Glu Asn Glu Tyr Glu Leu Thr Lys
            100                 105                 110

Asp Ser Leu Ile Ile Lys Asn Ile Pro Gln Asn Thr Pro Phe Thr Ile
        115                 120                 125

Glu Met Thr Ser Leu Leu Gly Glu Asn Thr Asp Leu Phe Gly Leu Tyr
    130                 135                 140

Glu Thr Glu Gly Val Ala Leu Val Lys Ala Glu Ser Glu Gly Leu Arg
145                 150                 155                 160

Arg Val Phe Tyr Leu Pro Asp Arg Pro Asp Asn Leu Ala Thr Tyr Lys
                165                 170                 175

Thr Thr Ile Ile Ala Asn Gln Glu Asp Tyr Pro Val Leu Leu Ser Asn
            180                 185                 190

Gly Val Leu Ile Glu Lys Lys Glu Leu Pro Leu Gly Leu His Ser Val
        195                 200                 205

Thr Trp Leu Asp Asp Val Pro Lys Pro Ser Tyr Leu Phe Ala Leu Val
    210                 215                 220

Ala Gly Asn Leu Gln Arg Ser Val Thr Tyr Tyr Gln Thr Lys Ser Gly
225                 230                 235                 240

Arg Glu Leu Pro Ile Glu Phe Tyr Val Pro Pro Ser Ala Thr Ser Lys
                245                 250                 255

Cys Asp Phe Ala Lys Glu Val Leu Lys Glu Ala Met Ala Trp Asp Glu
            260                 265                 270

Arg Thr Phe Asn Leu Glu Cys Ala Leu Arg Gln His Met Val Ala Gly
        275                 280                 285

Val Asp Lys Tyr Ala Ser Gly Ala Ser Glu Pro Thr Gly Leu Asn Leu
    290                 295                 300

Phe Asn Thr Glu Asn Leu Phe Ala Ser Pro Glu Thr Lys Thr Asp Leu
305                 310                 315                 320

Gly Ile Leu Arg Val Leu Glu Val Val Ala His Glu Phe Phe His Tyr
                325                 330                 335

Trp Ser Gly Asp Arg Val Thr Ile Arg Asp Trp Phe Asn Leu Pro Leu
            340                 345                 350

Lys Glu Gly Leu Thr Thr Phe Arg Ala Ala Met Phe Arg Glu Glu Leu
        355                 360                 365

Phe Gly Thr Asp Leu Ile Arg Leu Leu Asp Gly Lys Asn Leu Asp Glu
    370                 375                 380

Arg Ala Pro Arg Gln Ser Ala Tyr Thr Ala Val Arg Ser Leu Tyr Thr
385                 390                 395                 400

-continued

```
Ala Ala Ala Tyr Glu Lys Ser Ala Asp Ile Phe Arg Met Met Met Leu
                405                 410                 415

Phe Ile Gly Lys Glu Pro Phe Ile Glu Ala Val Ala Lys Phe Phe Lys
            420                 425                 430

Asp Asn Asp Gly Gly Ala Val Thr Leu Glu Asp Phe Ile Glu Ser Ile
        435                 440                 445

Ser Asn Ser Ser Gly Lys Asp Leu Arg Ser Phe Leu Ser Trp Phe Thr
    450                 455                 460

Glu Ser Gly Ile Pro Glu Leu Ile Val Thr Asp Glu Leu Asn Pro Asp
465                 470                 475                 480

Thr Lys Gln Tyr Phe Leu Lys Ile Lys Thr Val Asn Gly Arg Asn Arg
                485                 490                 495

Pro Ile Pro Ile Leu Met Gly Leu Leu Asp Ser Ser Gly Ala Glu Ile
            500                 505                 510

Val Ala Asp Lys Leu Leu Ile Val Asp Gln Glu Glu Ile Glu Phe Gln
        515                 520                 525

Phe Glu Asn Ile Gln Thr Arg Pro Ile Pro Ser Leu Leu Arg Ser Phe
    530                 535                 540

Ser Ala Pro Val His Met Lys Tyr Glu Tyr Ser Tyr Gln Asp Leu Leu
545                 550                 555                 560

Leu Leu Met Gln Phe Asp Thr Asn Leu Tyr Asn Arg Cys Glu Ala Ala
                565                 570                 575

Lys Gln Leu Ile Ser Ala Leu Ile Asn Asp Phe Cys Ile Gly Lys Lys
            580                 585                 590

Ile Glu Leu Ser Pro Gln Phe Phe Ala Val Tyr Lys Ala Leu Leu Ser
        595                 600                 605

Asp Asn Ser Leu Asn Glu Trp Met Leu Ala Glu Leu Ile Thr Leu Pro
    610                 615                 620

Ser Leu Glu Glu Leu Ile Glu Asn Gln Asp Lys Pro Asp Phe Glu Lys
625                 630                 635                 640

Leu Asn Glu Gly Arg Gln Leu Ile Gln Asn Ala Leu Ala Asn Glu Leu
                645                 650                 655

Lys Thr Asp Phe Tyr Asn Leu Leu Phe Arg Ile Gln Ile Ser Gly Asp
            660                 665                 670

Asp Asp Lys Gln Lys Leu Lys Gly Phe Asp Leu Lys Gln Ala Gly Leu
        675                 680                 685

Arg Arg Leu Lys Ser Val Cys Phe Ser Tyr Leu Leu Asn Val Asp Phe
    690                 695                 700

Glu Lys Thr Lys Glu Lys Leu Ile Leu Gln Phe Glu Asp Ala Leu Gly
705                 710                 715                 720

Lys Asn Met Thr Glu Thr Ala Leu Ala Leu Ser Met Leu Cys Glu Ile
                725                 730                 735

Asn Cys Glu Glu Ala Asp Val Ala Leu Glu Asp Tyr Tyr His Tyr Trp
            740                 745                 750

Lys Asn Asp Pro Gly Ala Val Asn Asn Trp Phe Ser Ile Gln Ala Leu
        755                 760                 765

Ala His Ser Pro Asp Val Ile Glu Arg Val Lys Lys Leu Met Arg His
    770                 775                 780

Gly Asp Phe Asp Leu Ser Asn Pro Asn Lys Val Tyr Ala Leu Leu Gly
785                 790                 795                 800

Ser Phe Ile Lys Asn Pro Phe Gly Phe His Ser Val Thr Gly Glu Gly
                805                 810                 815
```

-continued

```
Tyr Gln Leu Val Ala Asp Ala Ile Phe Asp Leu Asp Lys Ile Asn Pro
            820                 825                 830

Thr Leu Ala Ala Asn Leu Thr Glu Lys Phe Thr Tyr Trp Asp Lys Tyr
        835                 840                 845

Asp Val Asn Arg Gln Ala Met Met Ile Ser Thr Leu Lys Ile Ile Tyr
    850                 855                 860

Ser Asn Ala Thr Ser Ser Asp Val Arg Thr Met Ala Lys Lys Gly Leu
865                 870                 875                 880

Asp Lys Val Lys Glu Asp Leu Pro Leu Pro Ile His Leu Thr Phe His
                885                 890                 895

Gly Gly Ser Thr Met Gln Asp Arg Thr Ala Gln Leu Ile Ala Asp Gly
            900                 905                 910

Asn Lys Glu Asn Ala Tyr Gln Leu His
        915                 920


<210> SEQ ID NO 2
<211> LENGTH: 273
<212> TYPE: PRT
<213> ORGANISM: Artificial Sequence
<220> FEATURE:
<223> OTHER INFORMATION: Synthetic

<400> SEQUENCE: 2

Met Ala His His His His His His Met Gly Thr Ala Ile Ser Ile Lys
1               5                   10                  15

Thr Pro Glu Asp Ile Glu Lys Met Arg Val Ala Gly Arg Leu Ala Ala
            20                  25                  30

Glu Val Leu Glu Met Ile Glu Pro Tyr Val Lys Pro Gly Val Ser Thr
        35                  40                  45

Gly Glu Leu Asp Arg Ile Cys Asn Asp Tyr Ile Val Asn Glu Gln His
    50                  55                  60

Ala Val Ser Ala Cys Leu Gly Tyr His Gly Tyr Pro Lys Ser Val Cys
65                  70                  75                  80

Ile Ser Ile Asn Glu Val Val Cys His Gly Ile Pro Asp Asp Ala Lys
                85                  90                  95

Leu Leu Lys Asp Gly Asp Ile Val Asn Ile Asp Val Thr Val Ile Lys
            100                 105                 110

Asp Gly Phe His Gly Asp Thr Ser Lys Met Phe Ile Val Gly Lys Pro
        115                 120                 125

Thr Ile Met Gly Glu Arg Leu Cys Arg Ile Thr Gln Glu Ser Leu Tyr
    130                 135                 140

Leu Ala Leu Arg Met Val Lys Pro Gly Ile Asn Leu Arg Glu Ile Gly
145                 150                 155                 160

Ala Ala Ile Gln Lys Phe Val Glu Ala Glu Gly Phe Ser Val Val Arg
                165                 170                 175

Glu Tyr Cys Gly His Gly Ile Gly Arg Gly Phe His Glu Glu Pro Gln
            180                 185                 190

Val Leu His Tyr Asp Ser Arg Glu Thr Asn Val Val Leu Lys Pro Gly
        195                 200                 205

Met Thr Phe Thr Ile Glu Pro Met Val Asn Ala Gly Lys Lys Glu Ile
    210                 215                 220

Arg Thr Met Lys Asp Gly Trp Thr Val Lys Thr Lys Asp Arg Ser Leu
225                 230                 235                 240

Ser Ala Gln Tyr Glu His Thr Ile Val Val Thr Asp Asn Gly Cys Glu
                245                 250                 255
```

```
Ile Leu Thr Leu Arg Lys Asp Asp Thr Ile Pro Ala Ile Ile Ser His
            260                 265                 270

Asp


<210> SEQ ID NO 3
<211> LENGTH: 330
<212> TYPE: PRT
<213> ORGANISM: Artificial Sequence
<220> FEATURE:
<223> OTHER INFORMATION: Synthetic

<400> SEQUENCE: 3

Met Ala His His His His His His Met Gly Thr Leu Glu Ala Asn Thr
1               5                   10                  15

Asn Gly Pro Gly Ser Met Leu Ser Arg Met Pro Val Ser Ser Arg Thr
            20                  25                  30

Val Pro Phe Gly Asp His Glu Thr Trp Val Gln Val Thr Thr Pro Glu
        35                  40                  45

Asn Ala Gln Pro His Ala Leu Pro Leu Ile Val Leu His Gly Gly Pro
    50                  55                  60

Gly Met Ala His Asn Tyr Val Ala Asn Ile Ala Ala Leu Ala Asp Glu
65                  70                  75                  80

Thr Gly Arg Thr Val Ile His Tyr Asp Gln Val Gly Cys Gly Asn Ser
                85                  90                  95

Thr His Leu Pro Asp Ala Pro Ala Asp Phe Trp Thr Pro Gln Leu Phe
            100                 105                 110

Val Asp Glu Phe His Ala Val Cys Thr Ala Leu Gly Ile Glu Arg Tyr
        115                 120                 125

His Val Leu Gly Gln Ser Trp Gly Gly Met Leu Gly Ala Glu Ile Ala
    130                 135                 140

Val Arg Gln Pro Ser Gly Leu Val Ser Leu Ala Ile Cys Asn Ser Pro
145                 150                 155                 160

Ala Ser Met Arg Leu Trp Ser Glu Ala Ala Gly Asp Leu Arg Ala Gln
                165                 170                 175

Leu Pro Ala Glu Thr Arg Ala Ala Leu Asp Arg His Glu Ala Ala Gly
            180                 185                 190

Thr Ile Thr His Pro Asp Tyr Leu Gln Ala Ala Ala Glu Phe Tyr Arg
        195                 200                 205

Arg His Val Cys Arg Val Val Pro Thr Pro Gln Asp Phe Ala Asp Ser
    210                 215                 220

Val Ala Gln Met Glu Ala Glu Pro Thr Val Tyr His Thr Met Asn Gly
225                 230                 235                 240

Pro Asn Glu Phe His Val Val Gly Thr Leu Gly Asp Trp Ser Val Ile
                245                 250                 255

Asp Arg Leu Pro Asp Val Thr Ala Pro Val Leu Val Ile Ala Gly Glu
            260                 265                 270

His Asp Glu Ala Thr Pro Lys Thr Trp Gln Pro Phe Val Asp His Ile
        275                 280                 285

Pro Asp Val Arg Ser His Val Phe Pro Gly Thr Ser His Cys Thr His
    290                 295                 300

Leu Glu Lys Pro Glu Glu Phe Arg Ala Val Val Ala Gln Phe Leu His
305                 310                 315                 320

Gln His Asp Leu Ala Ala Asp Ala Arg Val
                325                 330
```

<210> SEQ ID NO 4
<211> LENGTH: 452
<212> TYPE: PRT
<213> ORGANISM: Artificial Sequence
<220> FEATURE:
<223> OTHER INFORMATION: Synthetic

<400> SEQUENCE: 4

```
Met Thr Gln Gln Glu Tyr Gln Asn Arg Arg Gln Ala Leu Leu Ala Lys
1               5                   10                  15

Met Ala Pro Gly Ser Ala Ala Ile Ile Phe Ala Ala Pro Glu Ala Thr
            20                  25                  30

Arg Ser Ala Asp Ser Glu Tyr Pro Tyr Arg Gln Asn Ser Asp Phe Ser
        35                  40                  45

Tyr Leu Thr Gly Phe Asn Glu Pro Glu Ala Val Leu Ile Leu Val Lys
    50                  55                  60

Ser Asp Glu Thr His Asn His Ser Val Leu Phe Asn Arg Ile Arg Asp
65                  70                  75                  80

Leu Thr Ala Glu Ile Trp Phe Gly Arg Arg Leu Gly Gln Glu Ala Ala
                85                  90                  95

Pro Thr Lys Leu Ala Val Asp Arg Ala Leu Pro Phe Asp Glu Ile Asn
            100                 105                 110

Glu Gln Leu Tyr Leu Leu Leu Asn Arg Leu Asp Val Ile Tyr His Ala
        115                 120                 125

Gln Gly Gln Tyr Ala Tyr Ala Asp Asn Ile Val Phe Ala Ala Leu Glu
    130                 135                 140

Lys Leu Arg His Gly Phe Arg Lys Asn Leu Arg Ala Pro Ala Thr Leu
145                 150                 155                 160

Thr Asp Trp Arg Pro Trp Leu His Glu Met Arg Leu Phe Lys Ser Ala
                165                 170                 175

Glu Glu Ile Ala Val Leu Arg Arg Ala Gly Glu Ile Ser Ala Leu Ala
            180                 185                 190

His Thr Arg Ala Met Glu Lys Cys Arg Pro Gly Met Phe Glu Tyr Gln
        195                 200                 205

Leu Glu Gly Glu Ile Leu His Glu Phe Thr Arg His Gly Ala Arg Tyr
    210                 215                 220

Pro Ala Tyr Asn Thr Ile Val Gly Gly Gly Glu Asn Gly Cys Ile Leu
225                 230                 235                 240

His Tyr Thr Glu Asn Glu Cys Glu Leu Arg Asp Gly Asp Leu Val Leu
                245                 250                 255

Ile Asp Ala Gly Cys Glu Tyr Arg Gly Tyr Ala Gly Asp Ile Thr Arg
            260                 265                 270

Thr Phe Pro Val Asn Gly Lys Phe Thr Pro Ala Gln Arg Ala Val Tyr
        275                 280                 285

Asp Ile Val Leu Ala Ala Ile Asn Lys Ser Leu Thr Leu Phe Arg Pro
    290                 295                 300

Gly Thr Ser Ile Arg Glu Val Thr Glu Glu Val Val Arg Ile Met Val
305                 310                 315                 320

Val Gly Leu Val Glu Leu Gly Ile Leu Lys Gly Asp Ile Glu Gln Leu
                325                 330                 335

Ile Ala Glu Gln Ala His Arg Pro Phe Phe Met His Gly Leu Ser His
            340                 345                 350

Trp Leu Gly Met Asp Val His Asp Val Gly Asp Tyr Gly Ser Ser Asp
        355                 360                 365
```

```
Arg Gly Arg Ile Leu Glu Pro Gly Met Val Leu Thr Val Glu Pro Gly
    370                 375                 380

Leu Tyr Ile Ala Pro Asp Ala Asp Val Pro Pro Gln Tyr Arg Gly Ile
385                 390                 395                 400

Gly Ile Arg Ile Glu Asp Asp Ile Val Ile Thr Ala Thr Gly Asn Glu
                405                 410                 415

Asn Leu Thr Ala Ser Val Val Lys Asp Pro Asp Asp Ile Glu Ala Leu
            420                 425                 430

Met Ala Leu Asn His Ala Gly Glu Asn Leu Tyr Phe Gln Glu His His
        435                 440                 445

His His His His
    450


<210> SEQ ID NO 5
<211> LENGTH: 303
<212> TYPE: PRT
<213> ORGANISM: Artificial Sequence
<220> FEATURE:
<223> OTHER INFORMATION: Synthetic

<400> SEQUENCE: 5

Met Asp Thr Glu Lys Leu Met Lys Ala Gly Glu Ile Ala Lys Lys Val
1               5                   10                  15

Arg Glu Lys Ala Ile Lys Leu Ala Arg Pro Gly Met Leu Leu Leu Glu
            20                  25                  30

Leu Ala Glu Ser Ile Glu Lys Met Ile Met Glu Leu Gly Gly Lys Pro
        35                  40                  45

Ala Phe Pro Val Asn Leu Ser Ile Asn Glu Ile Ala Ala His Tyr Thr
    50                  55                  60

Pro Tyr Lys Gly Asp Thr Thr Val Leu Lys Glu Gly Asp Tyr Leu Lys
65                  70                  75                  80

Ile Asp Val Gly Val His Ile Asp Gly Phe Ile Ala Asp Thr Ala Val
                85                  90                  95

Thr Val Arg Val Gly Met Glu Glu Asp Glu Leu Met Glu Ala Ala Lys
            100                 105                 110

Glu Ala Leu Asn Ala Ala Ile Ser Val Ala Arg Ala Gly Val Glu Ile
        115                 120                 125

Lys Glu Leu Gly Lys Ala Ile Glu Asn Glu Ile Arg Lys Arg Gly Phe
    130                 135                 140

Lys Pro Ile Val Asn Leu Ser Gly His Lys Ile Glu Arg Tyr Lys Leu
145                 150                 155                 160

His Ala Gly Ile Ser Ile Pro Asn Ile Tyr Arg Pro His Asp Asn Tyr
                165                 170                 175

Val Leu Lys Glu Gly Asp Val Phe Ala Ile Glu Pro Phe Ala Thr Ile
            180                 185                 190

Gly Ala Gly Gln Val Ile Glu Val Pro Pro Thr Leu Ile Tyr Met Tyr
        195                 200                 205

Val Arg Asp Val Pro Val Arg Val Ala Gln Ala Arg Phe Leu Leu Ala
    210                 215                 220

Lys Ile Lys Arg Glu Tyr Gly Thr Leu Pro Phe Ala Tyr Arg Trp Leu
225                 230                 235                 240

Gln Asn Asp Met Pro Glu Gly Gln Leu Lys Leu Ala Leu Lys Thr Leu
                245                 250                 255

Glu Lys Ala Gly Ala Ile Tyr Gly Tyr Pro Val Leu Lys Glu Ile Arg
            260                 265                 270
```

```
Asn Gly Ile Val Ala Gln Phe Glu His Thr Ile Ile Val Glu Lys Asp
        275                 280                 285

Ser Val Ile Val Thr Gln Asp Met Ile Asn Lys Ser Thr Leu Glu
    290                 295                 300


<210> SEQ ID NO 6
<211> LENGTH: 428
<212> TYPE: PRT
<213> ORGANISM: Artificial Sequence
<220> FEATURE:
<223> OTHER INFORMATION: Synthetic

<400> SEQUENCE: 6

His Met Ser Ser Pro Leu His Tyr Val Leu Asp Gly Ile His Cys Glu
1               5                   10                  15

Pro His Phe Phe Thr Val Pro Leu Asp His Gln Gln Pro Asp Asp Glu
            20                  25                  30

Glu Thr Ile Thr Leu Phe Gly Arg Thr Leu Cys Arg Lys Asp Arg Leu
        35                  40                  45

Asp Asp Glu Leu Pro Trp Leu Leu Tyr Leu Gln Gly Gly Pro Gly Phe
    50                  55                  60

Gly Ala Pro Arg Pro Ser Ala Asn Gly Gly Trp Ile Lys Arg Ala Leu
65                  70                  75                  80

Gln Glu Phe Arg Val Leu Leu Leu Asp Gln Arg Gly Thr Gly His Ser
                85                  90                  95

Thr Pro Ile His Ala Glu Leu Leu Ala His Leu Asn Pro Arg Gln Gln
            100                 105                 110

Ala Asp Tyr Leu Ser His Phe Arg Ala Asp Ser Ile Val Arg Asp Ala
        115                 120                 125

Glu Leu Ile Arg Glu Gln Leu Ser Pro Asp His Pro Trp Ser Leu Leu
    130                 135                 140

Gly Gln Ser Phe Gly Gly Phe Cys Ser Leu Thr Tyr Leu Ser Leu Phe
145                 150                 155                 160

Pro Asp Ser Leu His Glu Val Tyr Leu Thr Gly Gly Val Ala Pro Ile
                165                 170                 175

Gly Arg Ser Ala Asp Glu Val Tyr Arg Ala Thr Tyr Gln Arg Val Ala
            180                 185                 190

Asp Lys Asn Arg Ala Phe Phe Ala Arg Phe Pro His Ala Gln Ala Ile
        195                 200                 205

Ala Asn Arg Leu Ala Thr His Leu Gln Arg His Asp Val Arg Leu Pro
    210                 215                 220

Asn Gly Gln Arg Leu Thr Val Glu Gln Leu Gln Gln Gln Gly Leu Asp
225                 230                 235                 240

Leu Gly Ala Ser Gly Ala Phe Glu Glu Leu Tyr Tyr Leu Leu Glu Asp
                245                 250                 255

Ala Phe Ile Gly Glu Lys Leu Asn Pro Ala Phe Leu Tyr Gln Val Gln
            260                 265                 270

Ala Met Gln Pro Phe Asn Thr Asn Pro Val Phe Ala Ile Leu His Glu
        275                 280                 285

Leu Ile Tyr Cys Glu Gly Ala Ala Ser His Trp Ala Ala Glu Arg Val
    290                 295                 300

Arg Gly Glu Phe Pro Ala Leu Ala Trp Ala Gln Gly Lys Asp Phe Ala
305                 310                 315                 320

Phe Thr Gly Glu Met Ile Phe Pro Trp Met Phe Glu Gln Phe Arg Glu
                325                 330                 335
```

```
Leu Ile Pro Leu Lys Glu Ala Ala His Leu Leu Ala Glu Lys Ala Asp
            340                 345                 350

Trp Gly Pro Leu Tyr Asp Pro Val Gln Leu Ala Arg Asn Lys Val Pro
        355                 360                 365

Val Ala Cys Ala Val Tyr Ala Glu Asp Met Tyr Val Glu Phe Asp Tyr
    370                 375                 380

Ser Arg Glu Thr Leu Lys Gly Leu Ser Asn Ser Arg Ala Trp Ile Thr
385                 390                 395                 400

Asn Glu Tyr Glu His Asn Gly Leu Arg Val Asp Gly Glu Gln Ile Leu
                405                 410                 415

Asp Arg Leu Ile Arg Leu Asn Arg Asp Cys Leu Glu
            420                 425


<210> SEQ ID NO 7
<211> LENGTH: 348
<212> TYPE: PRT
<213> ORGANISM: Artificial Sequence
<220> FEATURE:
<223> OTHER INFORMATION: Synthetic

<400> SEQUENCE: 7

Met Lys Glu Arg Leu Glu Lys Leu Val Lys Phe Met Asp Glu Asn Ser
1               5                   10                  15

Ile Asp Arg Val Phe Ile Ala Lys Pro Val Asn Val Tyr Tyr Phe Ser
            20                  25                  30

Gly Thr Ser Pro Leu Gly Gly Gly Tyr Ile Ile Val Asp Gly Asp Glu
        35                  40                  45

Ala Thr Leu Tyr Val Pro Glu Leu Glu Tyr Glu Met Ala Lys Glu Glu
    50                  55                  60

Ser Lys Leu Pro Val Val Lys Phe Lys Lys Phe Asp Glu Ile Tyr Glu
65                  70                  75                  80

Ile Leu Lys Asn Thr Glu Thr Leu Gly Ile Glu Gly Thr Leu Ser Tyr
                85                  90                  95

Ser Met Val Glu Asn Phe Lys Glu Lys Ser Asn Val Lys Glu Phe Lys
            100                 105                 110

Lys Ile Asp Asp Val Ile Lys Asp Leu Arg Ile Ile Lys Thr Lys Glu
        115                 120                 125

Glu Ile Glu Ile Ile Glu Lys Ala Cys Glu Ile Ala Asp Lys Ala Val
    130                 135                 140

Met Ala Ala Ile Glu Glu Ile Thr Glu Gly Lys Arg Glu Arg Glu Val
145                 150                 155                 160

Ala Ala Lys Val Glu Tyr Leu Met Lys Met Asn Gly Ala Glu Lys Pro
                165                 170                 175

Ala Phe Asp Thr Ile Ile Ala Ser Gly His Arg Ser Ala Leu Pro His
            180                 185                 190

Gly Val Ala Ser Asp Lys Arg Ile Glu Arg Gly Asp Leu Val Val Ile
        195                 200                 205

Asp Leu Gly Ala Leu Tyr Asn His Tyr Asn Ser Asp Ile Thr Arg Thr
    210                 215                 220

Ile Val Val Gly Ser Pro Asn Glu Lys Gln Arg Glu Ile Tyr Glu Ile
225                 230                 235                 240

Val Leu Glu Ala Gln Lys Arg Ala Val Glu Ala Ala Lys Pro Gly Met
                245                 250                 255

Thr Ala Lys Glu Leu Asp Ser Ile Ala Arg Glu Ile Ile Lys Glu Tyr
            260                 265                 270
```

```
Gly Tyr Gly Asp Tyr Phe Ile His Ser Leu Gly His Gly Val Gly Leu
        275                 280                 285

Glu Ile His Glu Trp Pro Arg Ile Ser Gln Tyr Asp Glu Thr Val Leu
    290                 295                 300

Lys Glu Gly Met Val Ile Thr Ile Glu Pro Gly Ile Tyr Ile Pro Lys
305                 310                 315                 320

Leu Gly Gly Val Arg Ile Glu Asp Thr Val Leu Ile Thr Glu Asn Gly
                325                 330                 335

Ala Lys Arg Leu Thr Lys Thr Glu Arg Glu Leu Leu
            340                 345


<210> SEQ ID NO 8
<211> LENGTH: 298
<212> TYPE: PRT
<213> ORGANISM: Artificial Sequence
<220> FEATURE:
<223> OTHER INFORMATION: Synthetic

<400> SEQUENCE: 8

Met Ile Pro Ile Thr Thr Pro Val Gly Asn Phe Lys Val Trp Thr Lys
1               5                   10                  15

Arg Phe Gly Thr Asn Pro Lys Ile Lys Val Leu Leu Leu His Gly Gly
            20                  25                  30

Pro Ala Met Thr His Glu Tyr Met Glu Cys Phe Glu Thr Phe Phe Gln
        35                  40                  45

Arg Glu Gly Phe Glu Phe Tyr Glu Tyr Asp Gln Leu Gly Ser Tyr Tyr
    50                  55                  60

Ser Asp Gln Pro Thr Asp Glu Lys Leu Trp Asn Ile Asp Arg Phe Val
65                  70                  75                  80

Asp Glu Val Glu Gln Val Arg Lys Ala Ile His Ala Asp Lys Glu Asn
                85                  90                  95

Phe Tyr Val Leu Gly Asn Ser Trp Gly Gly Ile Leu Ala Met Glu Tyr
            100                 105                 110

Ala Leu Lys Tyr Gln Gln Asn Leu Lys Gly Leu Ile Val Ala Asn Met
        115                 120                 125

Met Ala Ser Ala Pro Glu Tyr Val Lys Tyr Ala Glu Val Leu Ser Lys
    130                 135                 140

Gln Met Lys Pro Glu Val Leu Ala Glu Val Arg Ala Ile Glu Ala Lys
145                 150                 155                 160

Lys Asp Tyr Ala Asn Pro Arg Tyr Thr Glu Leu Leu Phe Pro Asn Tyr
                165                 170                 175

Tyr Ala Gln His Ile Cys Arg Leu Lys Glu Trp Pro Asp Ala Leu Asn
            180                 185                 190

Arg Ser Leu Lys His Val Asn Ser Thr Val Tyr Thr Leu Met Gln Gly
        195                 200                 205

Pro Ser Glu Leu Gly Met Ser Ser Asp Ala Arg Leu Ala Lys Trp Asp
    210                 215                 220

Ile Lys Asn Arg Leu His Glu Ile Ala Thr Pro Thr Leu Met Ile Gly
225                 230                 235                 240

Ala Arg Tyr Asp Thr Met Asp Pro Lys Ala Met Glu Glu Gln Ser Lys
                245                 250                 255

Leu Val Gln Lys Gly Arg Tyr Leu Tyr Cys Pro Asn Gly Ser His Leu
            260                 265                 270

Ala Met Trp Asp Asp Gln Lys Val Phe Met Asp Gly Val Ile Lys Phe
        275                 280                 285
```

```
Ile Lys Asp Val Asp Thr Lys Ser Phe Asn
    290                 295


<210> SEQ ID NO 9
<211> LENGTH: 428
<212> TYPE: PRT
<213> ORGANISM: Artificial Sequence
<220> FEATURE:
<223> OTHER INFORMATION: Synthetic

<400> SEQUENCE: 9

His Met Ser Ser Pro Leu His Tyr Val Leu Asp Gly Ile His Cys Glu
1               5                   10                  15

Pro His Phe Phe Thr Val Pro Leu Asp His Gln Gln Pro Asp Asp Glu
            20                  25                  30

Glu Thr Ile Thr Leu Phe Gly Arg Thr Leu Cys Arg Lys Asp Arg Leu
        35                  40                  45

Asp Asp Glu Leu Pro Trp Leu Leu Tyr Leu Gln Gly Gly Pro Gly Phe
    50                  55                  60

Gly Ala Pro Arg Pro Ser Ala Asn Gly Gly Trp Ile Lys Arg Ala Leu
65                  70                  75                  80

Gln Glu Phe Arg Val Leu Leu Leu Asp Gln Arg Gly Thr Gly His Ser
                85                  90                  95

Thr Pro Ile His Ala Glu Leu Leu Ala His Leu Asn Pro Arg Gln Gln
            100                 105                 110

Ala Asp Tyr Leu Ser His Phe Arg Ala Asp Ser Ile Val Arg Asp Ala
        115                 120                 125

Glu Leu Ile Arg Glu Gln Leu Ser Pro Asp His Pro Trp Ser Leu Leu
    130                 135                 140

Gly Gln Ser Phe Gly Gly Phe Cys Ser Leu Thr Tyr Leu Ser Leu Phe
145                 150                 155                 160

Pro Asp Ser Leu His Glu Val Tyr Leu Thr Gly Gly Val Ala Pro Ile
                165                 170                 175

Gly Arg Ser Ala Asp Glu Val Tyr Arg Ala Thr Tyr Gln Arg Val Ala
            180                 185                 190

Asp Lys Asn Arg Ala Phe Phe Ala Arg Phe Pro His Ala Gln Ala Ile
        195                 200                 205

Ala Asn Arg Leu Ala Thr His Leu Gln Arg His Asp Val Arg Leu Pro
    210                 215                 220

Asn Gly Gln Arg Leu Thr Val Glu Gln Leu Gln Gln Gln Gly Leu Asp
225                 230                 235                 240

Leu Gly Ala Ser Gly Ala Phe Glu Glu Leu Tyr Tyr Leu Leu Glu Asp
                245                 250                 255

Ala Phe Ile Gly Glu Lys Leu Asn Pro Ala Phe Leu Tyr Gln Val Gln
            260                 265                 270

Ala Met Gln Pro Phe Asn Thr Asn Pro Val Phe Ala Ile Leu His Glu
        275                 280                 285

Leu Ile Tyr Cys Glu Gly Ala Ala Ser His Trp Ala Ala Glu Arg Val
    290                 295                 300

Arg Gly Glu Phe Pro Ala Leu Ala Trp Ala Gln Gly Lys Asp Phe Ala
305                 310                 315                 320

Phe Thr Gly Glu Met Ile Phe Pro Trp Met Phe Glu Gln Phe Arg Glu
                325                 330                 335

Leu Ile Pro Leu Lys Glu Ala Ala His Leu Leu Ala Glu Lys Ala Asp
            340                 345                 350
```

Trp Gly Pro Leu Tyr Asp Pro Val Gln Leu Ala Arg Asn Lys Val Pro
355 360 365

Val Ala Cys Ala Val Tyr Ala Glu Asp Met Tyr Val Glu Phe Asp Tyr
370 375 380

Ser Arg Glu Thr Leu Lys Gly Leu Ser Asn Ser Arg Ala Trp Ile Thr
385 390 395 400

Asn Glu Tyr Glu His Asn Gly Leu Arg Val Asp Gly Glu Gln Ile Leu
405 410 415

Asp Arg Leu Ile Arg Leu Asn Arg Asp Cys Leu Glu
420 425

<210> SEQ ID NO 10
<211> LENGTH: 310
<212> TYPE: PRT
<213> ORGANISM: Artificial Sequence
<220> FEATURE:
<223> OTHER INFORMATION: Synthetic

<400> SEQUENCE: 10

Met Tyr Glu Ile Lys Gln Pro Phe His Ser Gly Tyr Leu Gln Val Ser
1 5 10 15

Glu Ile His Gln Ile Tyr Trp Glu Glu Ser Gly Asn Pro Asp Gly Val
20 25 30

Pro Val Ile Phe Leu His Gly Gly Pro Gly Ala Gly Ala Ser Pro Glu
35 40 45

Cys Arg Gly Phe Phe Asn Pro Asp Val Phe Arg Ile Val Ile Ile Asp
50 55 60

Gln Arg Gly Cys Gly Arg Ser His Pro Tyr Ala Cys Ala Glu Asp Asn
65 70 75 80

Thr Thr Trp Asp Leu Val Ala Asp Ile Glu Lys Val Arg Glu Met Leu
85 90 95

Gly Ile Gly Lys Trp Leu Val Phe Gly Gly Ser Trp Gly Ser Thr Leu
100 105 110

Ser Leu Ala Tyr Ala Gln Thr His Pro Glu Arg Val Lys Gly Leu Val
115 120 125

Leu Arg Gly Ile Phe Leu Cys Arg Pro Ser Glu Thr Ala Trp Leu Asn
130 135 140

Glu Ala Gly Gly Val Ser Arg Ile Tyr Pro Glu Gln Trp Gln Lys Phe
145 150 155 160

Val Ala Pro Ile Ala Glu Asn Arg Arg Asn Arg Leu Ile Glu Ala Tyr
165 170 175

His Gly Leu Leu Phe His Gln Asp Glu Glu Val Cys Leu Ser Ala Ala
180 185 190

Lys Ala Trp Ala Asp Trp Glu Ser Tyr Leu Ile Arg Phe Glu Pro Glu
195 200 205

Gly Val Asp Glu Asp Ala Tyr Ala Ser Leu Ala Ile Ala Arg Leu Glu
210 215 220

Asn His Tyr Phe Val Asn Gly Gly Trp Leu Gln Gly Asp Lys Ala Ile
225 230 235 240

Leu Asn Asn Ile Gly Lys Ile Arg His Ile Pro Thr Val Ile Val Gln
245 250 255

Gly Arg Tyr Asp Leu Cys Thr Pro Met Gln Ser Ala Trp Glu Leu Ser
260 265 270

Lys Ala Phe Pro Glu Ala Glu Leu Arg Val Val Gln Ala Gly His Cys
275 280 285

```
Ala Phe Asp Pro Pro Leu Ala Asp Ala Leu Val Gln Ala Val Glu Asp
    290                 295                 300

Ile Leu Pro Arg Leu Leu
305                 310


<210> SEQ ID NO 11
<211> LENGTH: 891
<212> TYPE: PRT
<213> ORGANISM: Artificial Sequence
<220> FEATURE:
<223> OTHER INFORMATION: Synthetic

<400> SEQUENCE: 11

Met Gly Ser Ser His His His His His His Ser Ser Gly Glu Asn Leu
1               5                   10                  15

Tyr Phe Gln Gly His Met Thr Gln Gln Pro Gln Ala Lys Tyr Arg His
            20                  25                  30

Asp Tyr Arg Ala Pro Asp Tyr Gln Ile Thr Asp Ile Asp Leu Thr Phe
        35                  40                  45

Asp Leu Asp Ala Gln Lys Thr Val Val Thr Ala Val Ser Gln Ala Val
    50                  55                  60

Arg His Gly Ala Ser Asp Ala Pro Leu Arg Leu Asn Gly Glu Asp Leu
65                  70                  75                  80

Lys Leu Val Ser Val His Ile Asn Asp Glu Pro Trp Thr Ala Trp Lys
                85                  90                  95

Glu Glu Glu Gly Ala Leu Val Ile Ser Asn Leu Pro Glu Arg Phe Thr
            100                 105                 110

Leu Lys Ile Ile Asn Glu Ile Ser Pro Ala Ala Asn Thr Ala Leu Glu
        115                 120                 125

Gly Leu Tyr Gln Ser Gly Asp Ala Leu Cys Thr Gln Cys Glu Ala Glu
    130                 135                 140

Gly Phe Arg His Ile Thr Tyr Tyr Leu Asp Arg Pro Asp Val Leu Ala
145                 150                 155                 160

Arg Phe Thr Thr Lys Ile Ile Ala Asp Lys Ile Lys Tyr Pro Phe Leu
                165                 170                 175

Leu Ser Asn Gly Asn Arg Val Ala Gln Gly Glu Leu Glu Asn Gly Arg
            180                 185                 190

His Trp Val Gln Trp Gln Asp Pro Phe Pro Lys Pro Cys Tyr Leu Phe
        195                 200                 205

Ala Leu Val Ala Gly Asp Phe Asp Val Leu Arg Asp Thr Phe Thr Thr
    210                 215                 220

Arg Ser Gly Arg Glu Val Ala Leu Glu Leu Tyr Val Asp Arg Gly Asn
225                 230                 235                 240

Leu Asp Arg Ala Pro Trp Ala Met Thr Ser Leu Lys Asn Ser Met Lys
                245                 250                 255

Trp Asp Glu Glu Arg Phe Gly Leu Glu Tyr Asp Leu Asp Ile Tyr Met
            260                 265                 270

Ile Val Ala Val Asp Phe Phe Asn Met Gly Ala Met Glu Asn Lys Gly
        275                 280                 285

Leu Asn Ile Phe Asn Ser Lys Tyr Val Leu Ala Arg Thr Asp Thr Ala
    290                 295                 300

Thr Asp Lys Asp Tyr Leu Asp Ile Glu Arg Val Ile Gly His Glu Tyr
305                 310                 315                 320

Phe His Asn Trp Thr Gly Asn Arg Val Thr Cys Arg Asp Trp Phe Gln
                325                 330                 335
```

-continued

```
Leu Ser Leu Lys Glu Gly Leu Thr Val Phe Arg Asp Gln Glu Phe Ser
            340                 345                 350

Ser Asp Leu Gly Ser Arg Ala Val Asn Arg Ile Asn Asn Val Arg Thr
        355                 360                 365

Met Arg Gly Leu Gln Phe Ala Glu Asp Ala Ser Pro Met Ala His Pro
    370                 375                 380

Ile Arg Pro Asp Met Val Ile Glu Met Asn Asn Phe Tyr Thr Leu Thr
385                 390                 395                 400

Val Tyr Glu Lys Gly Ala Glu Val Ile Arg Met Ile His Thr Leu Leu
                405                 410                 415

Gly Glu Glu Asn Phe Gln Lys Gly Met Gln Leu Tyr Phe Glu Arg His
            420                 425                 430

Asp Gly Ser Ala Ala Thr Cys Asp Asp Phe Val Gln Ala Met Glu Asp
        435                 440                 445

Ala Ser Asn Val Asp Leu Ser His Phe Arg Arg Trp Tyr Ser Gln Ser
    450                 455                 460

Gly Thr Pro Ile Val Thr Val Lys Asp Asp Tyr Asn Pro Glu Thr Glu
465                 470                 475                 480

Gln Tyr Thr Leu Thr Ile Ser Gln Arg Thr Pro Ala Thr Pro Asp Gln
                485                 490                 495

Ala Glu Lys Gln Pro Leu His Ile Pro Phe Ala Ile Glu Leu Tyr Asp
            500                 505                 510

Asn Glu Gly Lys Val Ile Pro Leu Gln Lys Gly Gly His Pro Val Asn
        515                 520                 525

Ser Val Leu Asn Val Thr Gln Ala Glu Gln Thr Phe Val Phe Asp Asn
    530                 535                 540

Val Tyr Phe Gln Pro Val Pro Ala Leu Leu Cys Glu Phe Ser Ala Pro
545                 550                 555                 560

Val Lys Leu Glu Tyr Lys Trp Ser Asp Gln Gln Leu Thr Phe Leu Met
                565                 570                 575

Arg His Ala Arg Asn Asp Phe Ser Arg Trp Asp Ala Ala Gln Ser Leu
            580                 585                 590

Leu Ala Thr Tyr Ile Lys Leu Asn Val Ala Arg His Gln Gln Gly Gln
        595                 600                 605

Pro Leu Ser Leu Pro Val His Val Ala Asp Ala Phe Arg Ala Val Leu
    610                 615                 620

Leu Asp Glu Lys Ile Asp Pro Ala Leu Ala Ala Glu Ile Leu Thr Leu
625                 630                 635                 640

Pro Ser Val Asn Glu Met Ala Glu Leu Phe Asp Ile Ile Asp Pro Ile
                645                 650                 655

Ala Ile Ala Glu Val Arg Glu Ala Leu Thr Arg Thr Leu Ala Thr Glu
            660                 665                 670

Leu Ala Asp Glu Leu Leu Ala Ile Tyr Asn Ala Asn Tyr Gln Ser Glu
        675                 680                 685

Tyr Arg Val Glu His Glu Asp Ile Ala Lys Arg Thr Leu Arg Asn Ala
    690                 695                 700

Cys Leu Arg Phe Leu Ala Phe Gly Glu Thr His Leu Ala Asp Val Leu
705                 710                 715                 720

Val Ser Lys Gln Phe His Glu Ala Asn Asn Met Thr Asp Ala Leu Ala
                725                 730                 735

Ala Leu Ser Ala Ala Val Ala Ala Gln Leu Pro Cys Arg Asp Ala Leu
            740                 745                 750
```

Met Gln Glu Tyr Asp Asp Lys Trp His Gln Asn Gly Leu Val Met Asp
755 760 765

Lys Trp Phe Ile Leu Gln Ala Thr Ser Pro Ala Ala Asn Val Leu Glu
770 775 780

Thr Val Arg Gly Leu Leu Gln His Arg Ser Phe Thr Met Ser Asn Pro
785 790 795 800

Asn Arg Ile Arg Ser Leu Ile Gly Ala Phe Ala Gly Ser Asn Pro Ala
805 810 815

Ala Phe His Ala Glu Asp Gly Ser Gly Tyr Leu Phe Leu Val Glu Met
820 825 830

Leu Thr Asp Leu Asn Ser Arg Asn Pro Gln Val Ala Ser Arg Leu Ile
835 840 845

Glu Pro Leu Ile Arg Leu Lys Arg Tyr Asp Ala Lys Arg Gln Glu Lys
850 855 860

Met Arg Ala Ala Leu Glu Gln Leu Lys Gly Leu Glu Asn Leu Ser Gly
865 870 875 880

Asp Leu Tyr Glu Lys Ile Thr Lys Ala Leu Ala
885 890

<210> SEQ ID NO 12
<211> LENGTH: 889
<212> TYPE: PRT
<213> ORGANISM: Artificial Sequence
<220> FEATURE:
<223> OTHER INFORMATION: Synthetic

<400> SEQUENCE: 12

Pro Lys Ile His Tyr Arg Lys Asp Tyr Lys Pro Ser Gly Phe Ile Ile
1 5 10 15

Asn Gln Val Thr Leu Asn Ile Asn Ile His Asp Gln Glu Thr Ile Val
20 25 30

Arg Ser Val Leu Asp Met Asp Ile Ser Lys His Asn Val Gly Glu Asp
35 40 45

Leu Val Phe Asp Gly Val Gly Leu Lys Ile Asn Glu Ile Ser Ile Asn
50 55 60

Asn Lys Lys Leu Val Glu Gly Glu Glu Tyr Thr Tyr Asp Asn Glu Phe
65 70 75 80

Leu Thr Ile Phe Ser Lys Phe Val Pro Lys Ser Lys Phe Ala Phe Ser
85 90 95

Ser Glu Val Ile Ile His Pro Glu Thr Asn Tyr Ala Leu Thr Gly Leu
100 105 110

Tyr Lys Ser Lys Asn Ile Ile Val Ser Gln Cys Glu Ala Thr Gly Phe
115 120 125

Arg Arg Ile Thr Phe Phe Ile Asp Arg Pro Asp Met Met Ala Lys Tyr
130 135 140

Asp Val Thr Val Thr Ala Asp Lys Glu Lys Tyr Pro Val Leu Leu Ser
145 150 155 160

Asn Gly Asp Lys Val Asn Glu Phe Glu Ile Pro Gly Gly Arg His Gly
165 170 175

Ala Arg Phe Asn Asp Pro Pro Leu Lys Pro Cys Tyr Leu Phe Ala Val
180 185 190

Val Ala Gly Asp Leu Lys His Leu Ser Ala Thr Tyr Ile Thr Lys Tyr
195 200 205

Thr Lys Lys Lys Val Glu Leu Tyr Val Phe Ser Glu Glu Lys Tyr Val
210 215 220

-continued

```
Ser Lys Leu Gln Trp Ala Leu Glu Cys Leu Lys Lys Ser Met Ala Phe
225                 230                 235                 240

Asp Glu Asp Tyr Phe Gly Leu Glu Tyr Asp Leu Ser Arg Leu Asn Leu
                245                 250                 255

Val Ala Val Ser Asp Phe Asn Val Gly Ala Met Glu Asn Lys Gly Leu
            260                 265                 270

Asn Ile Phe Asn Ala Asn Ser Leu Leu Ala Ser Lys Lys Asn Ser Ile
        275                 280                 285

Asp Phe Ser Tyr Ala Arg Ile Leu Thr Val Val Gly His Glu Tyr Phe
    290                 295                 300

His Gln Tyr Thr Gly Asn Arg Val Thr Leu Arg Asp Trp Phe Gln Leu
305                 310                 315                 320

Thr Leu Lys Glu Gly Leu Thr Val His Arg Glu Asn Leu Phe Ser Glu
                325                 330                 335

Glu Met Thr Lys Thr Val Thr Thr Arg Leu Ser His Val Asp Leu Leu
            340                 345                 350

Arg Ser Val Gln Phe Leu Glu Asp Ser Ser Pro Leu Ser His Pro Ile
        355                 360                 365

Arg Pro Glu Ser Tyr Val Ser Met Glu Asn Phe Tyr Thr Thr Thr Val
    370                 375                 380

Tyr Asp Lys Gly Ser Glu Val Met Arg Met Tyr Leu Thr Ile Leu Gly
385                 390                 395                 400

Glu Glu Tyr Tyr Lys Lys Gly Phe Asp Ile Tyr Ile Lys Lys Asn Asp
                405                 410                 415

Gly Asn Thr Ala Thr Cys Glu Asp Phe Asn Tyr Ala Met Glu Gln Ala
            420                 425                 430

Tyr Lys Met Lys Lys Ala Asp Asn Ser Ala Asn Leu Asn Gln Tyr Leu
        435                 440                 445

Leu Trp Phe Ser Gln Ser Gly Thr Pro His Val Ser Phe Lys Tyr Asn
    450                 455                 460

Tyr Asp Ala Glu Lys Lys Gln Tyr Ser Ile His Val Asn Gln Tyr Thr
465                 470                 475                 480

Lys Pro Asp Glu Asn Gln Lys Glu Lys Lys Pro Leu Phe Ile Pro Ile
                485                 490                 495

Ser Val Gly Leu Ile Asn Pro Glu Asn Gly Lys Glu Met Ile Ser Gln
            500                 505                 510

Thr Thr Leu Glu Leu Thr Lys Glu Ser Asp Thr Phe Val Phe Asn Asn
        515                 520                 525

Ile Ala Val Lys Pro Ile Pro Ser Leu Phe Arg Gly Phe Ser Ala Pro
    530                 535                 540

Val Tyr Ile Glu Asp Gln Leu Thr Asp Glu Glu Arg Ile Leu Leu Leu
545                 550                 555                 560

Lys Tyr Asp Ser Asp Ala Phe Val Arg Tyr Asn Ser Cys Thr Asn Ile
                565                 570                 575

Tyr Met Lys Gln Ile Leu Met Asn Tyr Asn Glu Phe Leu Lys Ala Lys
            580                 585                 590

Asn Glu Lys Leu Glu Ser Phe Gln Leu Thr Pro Val Asn Ala Gln Phe
        595                 600                 605

Ile Asp Ala Ile Lys Tyr Leu Leu Glu Asp Pro His Ala Asp Ala Gly
    610                 615                 620

Phe Lys Ser Tyr Ile Val Ser Leu Pro Gln Asp Arg Tyr Ile Ile Asn
625                 630                 635                 640
```

```
Phe Val Ser Asn Leu Asp Thr Asp Val Leu Ala Asp Thr Lys Glu Tyr
                645                 650                 655

Ile Tyr Lys Gln Ile Gly Asp Lys Leu Asn Asp Val Tyr Tyr Lys Met
            660                 665                 670

Phe Lys Ser Leu Glu Ala Lys Ala Asp Asp Leu Thr Tyr Phe Asn Asp
        675                 680                 685

Glu Ser His Val Asp Phe Asp Gln Met Asn Met Arg Thr Leu Arg Asn
    690                 695                 700

Thr Leu Leu Ser Leu Leu Ser Lys Ala Gln Tyr Pro Asn Ile Leu Asn
705                 710                 715                 720

Glu Ile Ile Glu His Ser Lys Ser Pro Tyr Pro Ser Asn Trp Leu Thr
                725                 730                 735

Ser Leu Ser Val Ser Ala Tyr Phe Asp Lys Tyr Phe Glu Leu Tyr Asp
            740                 745                 750

Lys Thr Tyr Lys Leu Ser Lys Asp Asp Glu Leu Leu Leu Gln Glu Trp
        755                 760                 765

Leu Lys Thr Val Ser Arg Ser Asp Arg Lys Asp Ile Tyr Glu Ile Leu
    770                 775                 780

Lys Lys Leu Glu Asn Glu Val Leu Lys Asp Ser Lys Asn Pro Asn Asp
785                 790                 795                 800

Ile Arg Ala Val Tyr Leu Pro Phe Thr Asn Asn Leu Arg Arg Phe His
                805                 810                 815

Asp Ile Ser Gly Lys Gly Tyr Lys Leu Ile Ala Glu Val Ile Thr Lys
            820                 825                 830

Thr Asp Lys Phe Asn Pro Met Val Ala Thr Gln Leu Cys Glu Pro Phe
        835                 840                 845

Lys Leu Trp Asn Lys Leu Asp Thr Lys Arg Gln Glu Leu Met Leu Asn
    850                 855                 860

Glu Met Asn Thr Met Leu Gln Glu Pro Gln Ile Ser Asn Asn Leu Lys
865                 870                 875                 880

Glu Tyr Leu Leu Arg Leu Thr Asn Lys
                885
```

<210> SEQ ID NO 13
<211> LENGTH: 932
<212> TYPE: PRT
<213> ORGANISM: Artificial Sequence
<220> FEATURE:
<223> OTHER INFORMATION: Synthetic

<400> SEQUENCE: 13

```
Met Gly Ser Ser His His His His His His Ser Ser Gly Met Trp Leu
1               5                   10                  15

Ala Ala Ala Ala Pro Ser Leu Ala Arg Arg Leu Leu Phe Leu Gly Pro
            20                  25                  30

Pro Pro Pro Pro Leu Leu Leu Leu Val Phe Ser Arg Ser Ser Arg Arg
        35                  40                  45

Arg Leu His Ser Leu Gly Leu Ala Ala Met Pro Glu Lys Arg Pro Phe
    50                  55                  60

Glu Arg Leu Pro Ala Asp Val Ser Pro Ile Asn Tyr Ser Leu Cys Leu
65                  70                  75                  80

Lys Pro Asp Leu Leu Asp Phe Thr Phe Glu Gly Lys Leu Glu Ala Ala
                85                  90                  95

Ala Gln Val Arg Gln Ala Thr Asn Gln Ile Val Met Asn Cys Ala Asp
            100                 105                 110
```

-continued

```
Ile Asp Ile Ile Thr Ala Ser Tyr Ala Pro Glu Gly Asp Glu Glu Ile
        115                 120                 125

His Ala Thr Gly Phe Asn Tyr Gln Asn Glu Asp Glu Lys Val Thr Leu
    130                 135                 140

Ser Phe Pro Ser Thr Leu Gln Thr Gly Thr Gly Thr Leu Lys Ile Asp
145                 150                 155                 160

Phe Val Gly Glu Leu Asn Asp Lys Met Lys Gly Phe Tyr Arg Ser Lys
                165                 170                 175

Tyr Thr Thr Pro Ser Gly Glu Val Arg Tyr Ala Ala Val Thr Gln Phe
            180                 185                 190

Glu Ala Thr Asp Ala Arg Arg Ala Phe Pro Cys Trp Asp Glu Pro Ala
        195                 200                 205

Ile Lys Ala Thr Phe Asp Ile Ser Leu Val Val Pro Lys Asp Arg Val
    210                 215                 220

Ala Leu Ser Asn Met Asn Val Ile Asp Arg Lys Pro Tyr Pro Asp Asp
225                 230                 235                 240

Glu Asn Leu Val Glu Val Lys Phe Ala Arg Thr Pro Val Met Ser Thr
                245                 250                 255

Tyr Leu Val Ala Phe Val Val Gly Glu Tyr Asp Phe Val Glu Thr Arg
            260                 265                 270

Ser Lys Asp Gly Val Cys Val Arg Val Tyr Thr Pro Val Gly Lys Ala
        275                 280                 285

Glu Gln Gly Lys Phe Ala Leu Glu Val Ala Ala Lys Thr Leu Pro Phe
    290                 295                 300

Tyr Lys Asp Tyr Phe Asn Val Pro Tyr Pro Leu Pro Lys Ile Asp Leu
305                 310                 315                 320

Ile Ala Ile Ala Asp Phe Ala Ala Gly Ala Met Glu Asn Trp Gly Leu
                325                 330                 335

Val Thr Tyr Arg Glu Thr Ala Leu Leu Ile Asp Pro Lys Asn Ser Cys
            340                 345                 350

Ser Ser Ser Arg Gln Trp Val Ala Leu Val Val Gly His Glu Leu Ala
        355                 360                 365

His Gln Trp Phe Gly Asn Leu Val Thr Met Glu Trp Trp Thr His Leu
    370                 375                 380

Trp Leu Asn Glu Gly Phe Ala Ser Trp Ile Glu Tyr Leu Cys Val Asp
385                 390                 395                 400

His Cys Phe Pro Glu Tyr Asp Ile Trp Thr Gln Phe Val Ser Ala Asp
                405                 410                 415

Tyr Thr Arg Ala Gln Glu Leu Asp Ala Leu Asp Asn Ser His Pro Ile
            420                 425                 430

Glu Val Ser Val Gly His Pro Ser Glu Val Asp Glu Ile Phe Asp Ala
        435                 440                 445

Ile Ser Tyr Ser Lys Gly Ala Ser Val Ile Arg Met Leu His Asp Tyr
    450                 455                 460

Ile Gly Asp Lys Asp Phe Lys Lys Gly Met Asn Met Tyr Leu Thr Lys
465                 470                 475                 480

Phe Gln Gln Lys Asn Ala Ala Thr Glu Asp Leu Trp Glu Ser Leu Glu
                485                 490                 495

Asn Ala Ser Gly Lys Pro Ile Ala Ala Val Met Asn Thr Trp Thr Lys
            500                 505                 510

Gln Met Gly Phe Pro Leu Ile Tyr Val Glu Ala Glu Gln Val Glu Asp
        515                 520                 525
```

-continued

```
Asp Arg Leu Leu Arg Leu Ser Gln Lys Lys Phe Cys Ala Gly Gly Ser
    530                 535                 540

Tyr Val Gly Glu Asp Cys Pro Gln Trp Met Val Pro Ile Thr Ile Ser
545                 550                 555                 560

Thr Ser Glu Asp Pro Asn Gln Ala Lys Leu Lys Ile Leu Met Asp Lys
                565                 570                 575

Pro Glu Met Asn Val Val Leu Lys Asn Val Lys Pro Asp Gln Trp Val
            580                 585                 590

Lys Leu Asn Leu Gly Thr Val Gly Phe Tyr Arg Thr Gln Tyr Ser Ser
        595                 600                 605

Ala Met Leu Glu Ser Leu Leu Pro Gly Ile Arg Asp Leu Ser Leu Pro
    610                 615                 620

Pro Val Asp Arg Leu Gly Leu Gln Asn Asp Leu Phe Ser Leu Ala Arg
625                 630                 635                 640

Ala Gly Ile Ile Ser Thr Val Glu Val Leu Lys Val Met Glu Ala Phe
                645                 650                 655

Val Asn Glu Pro Asn Tyr Thr Val Trp Ser Asp Leu Ser Cys Asn Leu
            660                 665                 670

Gly Ile Leu Ser Thr Leu Leu Ser His Thr Asp Phe Tyr Glu Glu Ile
        675                 680                 685

Gln Glu Phe Val Lys Asp Val Phe Ser Pro Ile Gly Glu Arg Leu Gly
    690                 695                 700

Trp Asp Pro Lys Pro Gly Glu Gly His Leu Asp Ala Leu Leu Arg Gly
705                 710                 715                 720

Leu Val Leu Gly Lys Leu Gly Lys Ala Gly His Lys Ala Thr Leu Glu
                725                 730                 735

Glu Ala Arg Arg Arg Phe Lys Asp His Val Glu Gly Lys Gln Ile Leu
            740                 745                 750

Ser Ala Asp Leu Arg Ser Pro Val Tyr Leu Thr Val Leu Lys His Gly
        755                 760                 765

Asp Gly Thr Thr Leu Asp Ile Met Leu Lys Leu His Lys Gln Ala Asp
    770                 775                 780

Met Gln Glu Glu Lys Asn Arg Ile Glu Arg Val Leu Gly Ala Thr Leu
785                 790                 795                 800

Leu Pro Asp Leu Ile Gln Lys Val Leu Thr Phe Ala Leu Ser Glu Glu
                805                 810                 815

Val Arg Pro Gln Asp Thr Val Ser Val Ile Gly Gly Val Ala Gly Gly
            820                 825                 830

Ser Lys His Gly Arg Lys Ala Ala Trp Lys Phe Ile Lys Asp Asn Trp
        835                 840                 845

Glu Glu Leu Tyr Asn Arg Tyr Gln Gly Gly Phe Leu Ile Ser Arg Leu
    850                 855                 860

Ile Lys Leu Ser Val Glu Gly Phe Ala Val Asp Lys Met Ala Gly Glu
865                 870                 875                 880

Val Lys Ala Phe Phe Glu Ser His Pro Ala Pro Ser Ala Glu Arg Thr
                885                 890                 895

Ile Gln Gln Cys Cys Glu Asn Ile Leu Leu Asn Ala Ala Trp Leu Lys
            900                 905                 910

Arg Asp Ala Glu Ser Ile His Gln Tyr Leu Leu Gln Arg Lys Ala Ser
        915                 920                 925

Pro Pro Thr Val
    930
```

-continued

<210> SEQ ID NO 14
<211> LENGTH: 932
<212> TYPE: PRT
<213> ORGANISM: Artificial Sequence
<220> FEATURE:
<223> OTHER INFORMATION: Synthetic

<400> SEQUENCE: 14

```
Met Gly Ser Ser His His His His His His Ser Ser Gly Met Trp Leu
1               5                   10                  15

Ala Ala Ala Ala Pro Ser Leu Ala Arg Arg Leu Leu Phe Leu Gly Pro
            20                  25                  30

Pro Pro Pro Pro Leu Leu Leu Leu Val Phe Ser Arg Ser Ser Arg Arg
        35                  40                  45

Arg Leu His Ser Leu Gly Leu Ala Ala Met Pro Glu Lys Arg Pro Phe
    50                  55                  60

Glu Arg Leu Pro Ala Asp Val Ser Pro Ile Asn Tyr Ser Leu Cys Leu
65                  70                  75                  80

Lys Pro Asp Leu Leu Asp Phe Thr Phe Glu Gly Lys Leu Glu Ala Ala
                85                  90                  95

Ala Gln Val Arg Gln Ala Thr Asn Gln Ile Val Met Asn Cys Ala Asp
            100                 105                 110

Ile Asp Ile Ile Thr Ala Ser Tyr Ala Pro Glu Gly Asp Glu Glu Ile
        115                 120                 125

His Ala Thr Gly Phe Asn Tyr Gln Asn Glu Asp Glu Lys Val Thr Leu
    130                 135                 140

Ser Phe Pro Ser Thr Leu Gln Thr Gly Thr Gly Thr Leu Lys Ile Asp
145                 150                 155                 160

Phe Val Gly Glu Leu Asn Asp Lys Met Lys Gly Phe Tyr Arg Ser Lys
                165                 170                 175

Tyr Thr Thr Pro Ser Gly Glu Val Arg Tyr Ala Ala Val Thr Gln Phe
            180                 185                 190

Glu Ala Thr Asp Ala Arg Arg Ala Phe Pro Cys Trp Asp Glu Pro Ala
        195                 200                 205

Ile Lys Ala Thr Phe Asp Ile Ser Leu Val Val Pro Lys Asp Arg Val
    210                 215                 220

Ala Leu Ser Asn Met Asn Val Ile Asp Arg Lys Pro Tyr Pro Asp Asp
225                 230                 235                 240

Glu Asn Leu Val Glu Val Lys Phe Ala Arg Thr Pro Val Met Ser Thr
                245                 250                 255

Tyr Leu Val Ala Phe Val Val Gly Glu Tyr Asp Phe Val Glu Thr Arg
            260                 265                 270

Ser Lys Asp Gly Val Cys Val Arg Val Tyr Thr Pro Val Gly Lys Ala
        275                 280                 285

Glu Gln Gly Lys Phe Ala Leu Glu Val Ala Ala Lys Thr Leu Pro Phe
    290                 295                 300

Tyr Lys Asp Tyr Phe Asn Val Pro Tyr Pro Leu Pro Lys Ile Asp Leu
305                 310                 315                 320

Ile Ala Ile Ala Asp Phe Ala Ala Gly Ala Met Glu Asn Trp Gly Leu
                325                 330                 335

Val Thr Tyr Arg Glu Thr Ala Leu Leu Ile Asp Pro Lys Asn Ser Cys
            340                 345                 350

Ser Ser Ser Arg Gln Trp Val Ala Leu Val Val Gly His Val Leu Ala
        355                 360                 365
```

-continued

His Gln Trp Phe Gly Asn Leu Val Thr Met Glu Trp Trp Thr His Leu
370 375 380

Trp Leu Asn Glu Gly Phe Ala Ser Trp Ile Glu Tyr Leu Cys Val Asp
385 390 395 400

His Cys Phe Pro Glu Tyr Asp Ile Trp Thr Gln Phe Val Ser Ala Asp
405 410 415

Tyr Thr Arg Ala Gln Glu Leu Asp Ala Leu Asp Asn Ser His Pro Ile
420 425 430

Glu Val Ser Val Gly His Pro Ser Glu Val Asp Glu Ile Phe Asp Ala
435 440 445

Ile Ser Tyr Ser Lys Gly Ala Ser Val Ile Arg Met Leu His Asp Tyr
450 455 460

Ile Gly Asp Lys Asp Phe Lys Lys Gly Met Asn Met Tyr Leu Thr Lys
465 470 475 480

Phe Gln Gln Lys Asn Ala Ala Thr Glu Asp Leu Trp Glu Ser Leu Glu
485 490 495

Asn Ala Ser Gly Lys Pro Ile Ala Ala Val Met Asn Thr Trp Thr Lys
500 505 510

Gln Met Gly Phe Pro Leu Ile Tyr Val Glu Ala Glu Gln Val Glu Asp
515 520 525

Asp Arg Leu Leu Arg Leu Ser Gln Lys Lys Phe Cys Ala Gly Gly Ser
530 535 540

Tyr Val Gly Glu Asp Cys Pro Gln Trp Met Val Pro Ile Thr Ile Ser
545 550 555 560

Thr Ser Glu Asp Pro Asn Gln Ala Lys Leu Lys Ile Leu Met Asp Lys
565 570 575

Pro Glu Met Asn Val Val Leu Lys Asn Val Lys Pro Asp Gln Trp Val
580 585 590

Lys Leu Asn Leu Gly Thr Val Gly Phe Tyr Arg Thr Gln Tyr Ser Ser
595 600 605

Ala Met Leu Glu Ser Leu Leu Pro Gly Ile Arg Asp Leu Ser Leu Pro
610 615 620

Pro Val Asp Arg Leu Gly Leu Gln Asn Asp Leu Phe Ser Leu Ala Arg
625 630 635 640

Ala Gly Ile Ile Ser Thr Val Glu Val Leu Lys Val Met Glu Ala Phe
645 650 655

Val Asn Glu Pro Asn Tyr Thr Val Trp Ser Asp Leu Ser Cys Asn Leu
660 665 670

Gly Ile Leu Ser Thr Leu Leu Ser His Thr Asp Phe Tyr Glu Glu Ile
675 680 685

Gln Glu Phe Val Lys Asp Val Phe Ser Pro Ile Gly Glu Arg Leu Gly
690 695 700

Trp Asp Pro Lys Pro Gly Glu Gly His Leu Asp Ala Leu Leu Arg Gly
705 710 715 720

Leu Val Leu Gly Lys Leu Gly Lys Ala Gly His Lys Ala Thr Leu Glu
725 730 735

Glu Ala Arg Arg Arg Phe Lys Asp His Val Glu Gly Lys Gln Ile Leu
740 745 750

Ser Ala Asp Leu Arg Ser Pro Val Tyr Leu Thr Val Leu Lys His Gly
755 760 765

Asp Gly Thr Thr Leu Asp Ile Met Leu Lys Leu His Lys Gln Ala Asp
770 775 780

-continued

```
Met Gln Glu Glu Lys Asn Arg Ile Glu Arg Val Leu Gly Ala Thr Leu
785                 790                 795                 800

Leu Pro Asp Leu Ile Gln Lys Val Leu Thr Phe Ala Leu Ser Glu Glu
                805                 810                 815

Val Arg Pro Gln Asp Thr Val Ser Val Ile Gly Gly Val Ala Gly Gly
            820                 825                 830

Ser Lys His Gly Arg Lys Ala Ala Trp Lys Phe Ile Lys Asp Asn Trp
        835                 840                 845

Glu Glu Leu Tyr Asn Arg Tyr Gln Gly Gly Phe Leu Ile Ser Arg Leu
    850                 855                 860

Ile Lys Leu Ser Val Glu Gly Phe Ala Val Asp Lys Met Ala Gly Glu
865                 870                 875                 880

Val Lys Ala Phe Phe Glu Ser His Pro Ala Pro Ser Ala Glu Arg Thr
                885                 890                 895

Ile Gln Gln Cys Cys Glu Asn Ile Leu Leu Asn Ala Ala Trp Leu Lys
            900                 905                 910

Arg Asp Ala Glu Ser Ile His Gln Tyr Leu Leu Gln Arg Lys Ala Ser
        915                 920                 925

Pro Pro Thr Val
    930


<210> SEQ ID NO 15
<211> LENGTH: 864
<212> TYPE: PRT
<213> ORGANISM: Artificial Sequence
<220> FEATURE:
<223> OTHER INFORMATION: Synthetic

<400> SEQUENCE: 15

Met Ile Tyr Glu Phe Val Met Thr Asp Pro Lys Ile Lys Tyr Leu Lys
1               5                   10                  15

Asp Tyr Lys Pro Ser Asn Tyr Leu Ile Asp Glu Thr His Leu Ile Phe
            20                  25                  30

Glu Leu Asp Glu Ser Lys Thr Arg Val Thr Ala Asn Leu Tyr Ile Val
        35                  40                  45

Ala Asn Arg Glu Asn Arg Glu Asn Asn Thr Leu Val Leu Asp Gly Val
    50                  55                  60

Glu Leu Lys Leu Leu Ser Ile Lys Leu Asn Asn Lys His Leu Ser Pro
65                  70                  75                  80

Ala Glu Phe Ala Val Asn Glu Asn Gln Leu Ile Ile Asn Asn Val Pro
                85                  90                  95

Glu Lys Phe Val Leu Gln Thr Val Val Glu Ile Asn Pro Ser Ala Asn
            100                 105                 110

Thr Ser Leu Glu Gly Leu Tyr Lys Ser Gly Asp Val Phe Ser Thr Gln
        115                 120                 125

Cys Glu Ala Thr Gly Phe Arg Lys Ile Thr Tyr Tyr Leu Asp Arg Pro
    130                 135                 140

Asp Val Met Ala Ala Phe Thr Val Lys Ile Ile Ala Asp Lys Lys Lys
145                 150                 155                 160

Tyr Pro Ile Ile Leu Ser Asn Gly Asp Lys Ile Asp Ser Gly Asp Ile
                165                 170                 175

Ser Asp Asn Gln His Phe Ala Val Trp Lys Asp Pro Phe Lys Lys Pro
            180                 185                 190

Cys Tyr Leu Phe Ala Leu Val Ala Gly Asp Leu Ala Ser Ile Lys Asp
        195                 200                 205
```

-continued

```
Thr Tyr Ile Thr Lys Ser Gln Arg Lys Val Ser Leu Glu Ile Tyr Ala
    210                 215                 220

Phe Lys Gln Asp Ile Asp Lys Cys His Tyr Ala Met Gln Ala Val Lys
225                 230                 235                 240

Asp Ser Met Lys Trp Asp Glu Asp Arg Phe Gly Leu Glu Tyr Asp Leu
                245                 250                 255

Asp Thr Phe Met Ile Val Ala Val Pro Asp Phe Asn Ala Gly Ala Met
            260                 265                 270

Glu Asn Lys Gly Leu Asn Ile Phe Asn Thr Lys Tyr Ile Met Ala Ser
        275                 280                 285

Asn Lys Thr Ala Thr Asp Lys Asp Phe Glu Leu Val Gln Ser Val Val
    290                 295                 300

Gly His Glu Tyr Phe His Asn Trp Thr Gly Asp Arg Val Thr Cys Arg
305                 310                 315                 320

Asp Trp Phe Gln Leu Ser Leu Lys Glu Gly Leu Thr Val Phe Arg Asp
                325                 330                 335

Gln Glu Phe Thr Ser Asp Leu Asn Ser Arg Asp Val Lys Arg Ile Asp
            340                 345                 350

Asp Val Arg Ile Ile Arg Ser Ala Gln Phe Ala Glu Asp Ala Ser Pro
        355                 360                 365

Met Ser His Pro Ile Arg Pro Glu Ser Tyr Ile Glu Met Asn Asn Phe
    370                 375                 380

Tyr Thr Val Thr Val Tyr Asn Lys Gly Ala Glu Ile Ile Arg Met Ile
385                 390                 395                 400

His Thr Leu Leu Gly Glu Glu Gly Phe Gln Lys Gly Met Lys Leu Tyr
                405                 410                 415

Phe Glu Arg His Asp Gly Gln Ala Val Thr Cys Asp Asp Phe Val Asn
            420                 425                 430

Ala Met Ala Asp Ala Asn Asn Arg Asp Phe Ser Leu Phe Lys Arg Trp
        435                 440                 445

Tyr Ala Gln Ser Gly Thr Pro Asn Ile Lys Val Ser Glu Asn Tyr Asp
    450                 455                 460

Ala Ser Ser Gln Thr Tyr Ser Leu Thr Leu Glu Gln Thr Thr Leu Pro
465                 470                 475                 480

Thr Ala Asp Gln Lys Glu Lys Gln Ala Leu His Ile Pro Val Lys Met
                485                 490                 495

Gly Leu Ile Asn Pro Glu Gly Lys Asn Ile Ala Glu Gln Val Ile Glu
            500                 505                 510

Leu Lys Glu Gln Lys Gln Thr Tyr Thr Phe Glu Asn Ile Ala Ala Lys
        515                 520                 525

Pro Val Ala Ser Leu Phe Arg Asp Phe Ser Ala Pro Val Lys Val Glu
    530                 535                 540

His Lys Arg Ser Glu Lys Asp Leu Leu His Ile Val Lys Tyr Asp Asn
545                 550                 555                 560

Asn Ala Phe Asn Arg Trp Asp Ser Leu Gln Gln Ile Ala Thr Asn Ile
                565                 570                 575

Ile Leu Asn Asn Ala Asp Leu Asn Asp Glu Phe Leu Asn Ala Phe Lys
            580                 585                 590

Ser Ile Leu His Asp Lys Asp Leu Asp Lys Ala Leu Ile Ser Asn Ala
        595                 600                 605

Leu Leu Ile Pro Ile Glu Ser Thr Ile Ala Glu Ala Met Arg Val Ile
    610                 615                 620
```

```
Met Val Asp Asp Ile Val Leu Ser Arg Lys Asn Val Val Asn Gln Leu
625                 630                 635                 640

Ala Asp Lys Leu Lys Asp Asp Trp Leu Ala Val Tyr Gln Gln Cys Asn
                645                 650                 655

Asp Asn Lys Pro Tyr Ser Leu Ser Ala Glu Gln Ile Ala Lys Arg Lys
            660                 665                 670

Leu Lys Gly Val Cys Leu Ser Tyr Leu Met Asn Ala Ser Asp Gln Lys
        675                 680                 685

Val Gly Thr Asp Leu Ala Gln Gln Leu Phe Asp Asn Ala Asp Asn Met
    690                 695                 700

Thr Asp Gln Gln Thr Ala Phe Thr Glu Leu Leu Lys Ser Asn Asp Lys
705                 710                 715                 720

Gln Val Arg Asp Asn Ala Ile Asn Glu Phe Tyr Asn Arg Trp Arg His
                725                 730                 735

Glu Asp Leu Val Val Asn Lys Trp Leu Leu Ser Gln Ala Gln Ile Ser
            740                 745                 750

His Glu Ser Ala Leu Asp Ile Val Lys Gly Leu Val Asn His Pro Ala
        755                 760                 765

Tyr Asn Pro Lys Asn Pro Asn Lys Val Tyr Ser Leu Ile Gly Gly Phe
    770                 775                 780

Gly Ala Asn Phe Leu Gln Tyr His Cys Lys Asp Gly Leu Gly Tyr Ala
785                 790                 795                 800

Phe Met Ala Asp Thr Val Leu Ala Leu Asp Lys Phe Asn His Gln Val
                805                 810                 815

Ala Ala Arg Met Ala Arg Asn Leu Met Ser Trp Lys Arg Tyr Asp Ser
            820                 825                 830

Asp Arg Gln Ala Met Met Lys Asn Ala Leu Glu Lys Ile Lys Ala Ser
        835                 840                 845

Asn Pro Ser Lys Asn Val Phe Glu Ile Val Ser Lys Ser Leu Glu Ser
    850                 855                 860


<210> SEQ ID NO 16
<211> LENGTH: 366
<212> TYPE: PRT
<213> ORGANISM: Artificial Sequence
<220> FEATURE:
<223> OTHER INFORMATION: Synthetic

<400> SEQUENCE: 16

Met Gly Ser Ser His His His His His His Ser Ser Gly Met Glu Val
1               5                   10                  15

Arg Asn Met Val Asp Tyr Glu Leu Leu Lys Lys Val Val Glu Ala Pro
            20                  25                  30

Gly Val Ser Gly Tyr Glu Phe Leu Gly Ile Arg Asp Val Val Ile Glu
        35                  40                  45

Glu Ile Lys Asp Tyr Val Asp Glu Val Lys Val Asp Lys Leu Gly Asn
    50                  55                  60

Val Ile Ala His Lys Lys Gly Glu Gly Pro Lys Val Met Ile Ala Ala
65                  70                  75                  80

His Met Asp Gln Ile Gly Leu Met Val Thr His Ile Glu Lys Asn Gly
                85                  90                  95

Phe Leu Arg Val Ala Pro Ile Gly Gly Val Asp Pro Lys Thr Leu Ile
            100                 105                 110

Ala Gln Arg Phe Lys Val Trp Ile Asp Lys Gly Lys Phe Ile Tyr Gly
        115                 120                 125
```

```
Val Gly Ala Ser Val Pro Pro His Ile Gln Lys Pro Glu Asp Arg Lys
    130                 135                 140

Lys Ala Pro Asp Trp Asp Gln Ile Phe Ile Asp Ile Gly Ala Glu Ser
145                 150                 155                 160

Lys Glu Glu Ala Glu Asp Met Gly Val Lys Ile Gly Thr Val Ile Thr
                165                 170                 175

Trp Asp Gly Arg Leu Glu Arg Leu Gly Lys His Arg Phe Val Ser Ile
            180                 185                 190

Ala Phe Asp Asp Arg Ile Ala Val Tyr Thr Ile Leu Glu Val Ala Lys
        195                 200                 205

Gln Leu Lys Asp Ala Lys Ala Asp Val Tyr Phe Val Ala Thr Val Gln
    210                 215                 220

Glu Glu Val Gly Leu Arg Gly Ala Arg Thr Ser Ala Phe Gly Ile Glu
225                 230                 235                 240

Pro Asp Tyr Gly Phe Ala Ile Asp Val Thr Ile Ala Ala Asp Ile Pro
                245                 250                 255

Gly Thr Pro Glu His Lys Gln Val Thr His Leu Gly Lys Gly Thr Ala
            260                 265                 270

Ile Lys Ile Met Asp Arg Ser Val Ile Cys His Pro Thr Ile Val Arg
        275                 280                 285

Trp Leu Glu Glu Leu Ala Lys Lys His Glu Ile Pro Tyr Gln Leu Glu
    290                 295                 300

Ile Leu Leu Gly Gly Gly Thr Asp Ala Gly Ala Ile His Leu Thr Lys
305                 310                 315                 320

Ala Gly Val Pro Thr Gly Ala Leu Ser Val Pro Ala Arg Tyr Ile His
                325                 330                 335

Ser Asn Thr Glu Val Val Asp Glu Arg Asp Val Asp Ala Thr Val Glu
            340                 345                 350

Leu Met Thr Lys Ala Leu Glu Asn Ile His Glu Leu Lys Ile
        355                 360                 365


<210> SEQ ID NO 17
<211> LENGTH: 408
<212> TYPE: PRT
<213> ORGANISM: Artificial Sequence
<220> FEATURE:
<223> OTHER INFORMATION: Synthetic

<400> SEQUENCE: 17

Met Asp Ala Phe Thr Glu Asn Leu Asn Lys Leu Ala Glu Leu Ala Ile
1               5                   10                  15

Arg Val Gly Leu Asn Leu Glu Glu Gly Gln Glu Ile Val Ala Thr Ala
            20                  25                  30

Pro Ile Glu Ala Val Asp Phe Val Arg Leu Leu Ala Glu Lys Ala Tyr
        35                  40                  45

Glu Asn Gly Ala Ser Leu Phe Thr Val Leu Tyr Gly Asp Asn Leu Ile
    50                  55                  60

Ala Arg Lys Arg Leu Ala Leu Val Pro Glu Ala His Leu Asp Arg Ala
65                  70                  75                  80

Pro Ala Trp Leu Tyr Glu Gly Met Ala Lys Ala Phe His Glu Gly Ala
                85                  90                  95

Ala Arg Leu Ala Val Ser Gly Asn Asp Pro Lys Ala Leu Glu Gly Leu
            100                 105                 110

Pro Pro Glu Arg Val Gly Arg Ala Gln Gln Ala Gln Ser Arg Ala Tyr
        115                 120                 125
```

```
Arg Pro Thr Leu Ser Ala Ile Thr Glu Phe Val Thr Asn Trp Thr Ile
    130                 135                 140

Val Pro Phe Ala His Pro Gly Trp Ala Lys Ala Val Phe Pro Gly Leu
145                 150                 155                 160

Pro Glu Glu Glu Ala Val Gln Arg Leu Trp Gln Ala Ile Phe Gln Ala
                165                 170                 175

Thr Arg Val Asp Gln Glu Asp Pro Val Ala Ala Trp Glu Ala His Asn
            180                 185                 190

Arg Val Leu His Ala Lys Val Ala Phe Leu Asn Glu Lys Arg Phe His
        195                 200                 205

Ala Leu His Phe Gln Gly Pro Gly Thr Asp Leu Thr Val Gly Leu Ala
    210                 215                 220

Glu Gly His Leu Trp Gln Gly Gly Ala Thr Pro Thr Lys Lys Gly Arg
225                 230                 235                 240

Leu Cys Asn Pro Asn Leu Pro Thr Glu Glu Val Phe Thr Ala Pro His
                245                 250                 255

Arg Glu Arg Val Glu Gly Val Val Arg Ala Ser Arg Pro Leu Ala Leu
            260                 265                 270

Ser Gly Gln Leu Val Glu Gly Leu Trp Ala Arg Phe Glu Gly Gly Val
        275                 280                 285

Ala Val Glu Val Gly Ala Glu Lys Gly Glu Glu Val Leu Lys Lys Leu
    290                 295                 300

Leu Asp Thr Asp Glu Gly Ala Arg Arg Leu Gly Glu Val Ala Leu Val
305                 310                 315                 320

Pro Ala Asp Asn Pro Ile Ala Lys Thr Gly Leu Val Phe Phe Asp Thr
                325                 330                 335

Leu Phe Asp Glu Asn Ala Ala Ser His Ile Ala Phe Gly Gln Ala Tyr
            340                 345                 350

Ala Glu Asn Leu Glu Gly Arg Pro Ser Gly Glu Glu Phe Arg Arg Arg
        355                 360                 365

Gly Gly Asn Glu Ser Met Val His Val Asp Trp Met Ile Gly Ser Glu
    370                 375                 380

Glu Val Asp Val Asp Gly Leu Leu Glu Asp Gly Thr Arg Val Pro Leu
385                 390                 395                 400

Met Arg Arg Gly Arg Trp Val Ile
                405
```

<210> SEQ ID NO 18
<211> LENGTH: 362
<212> TYPE: PRT
<213> ORGANISM: Artificial Sequence
<220> FEATURE:
<223> OTHER INFORMATION: Synthetic

<400> SEQUENCE: 18

```
Met Ala Lys Leu Asp Glu Thr Leu Thr Met Leu Lys Ala Leu Thr Asp
1               5                   10                  15

Ala Lys Gly Val Pro Gly Asn Glu Arg Glu Ala Arg Asp Val Met Lys
            20                  25                  30

Thr Tyr Ile Ala Pro Tyr Ala Asp Glu Val Thr Thr Asp Gly Leu Gly
        35                  40                  45

Ser Leu Ile Ala Lys Lys Glu Gly Lys Ser Gly Gly Pro Lys Val Met
    50                  55                  60

Ile Ala Gly His Leu Asp Glu Val Gly Phe Met Val Thr Gln Ile Asp
65                  70                  75                  80
```

```
Asp Lys Gly Phe Ile Arg Phe Gln Thr Leu Gly Gly Trp Trp Ser Gln
                85                  90                  95

Val Met Leu Ala Gln Arg Val Thr Ile Val Thr Lys Lys Gly Asp Ile
            100                 105                 110

Thr Gly Val Ile Gly Ser Lys Pro Pro His Ile Leu Pro Ser Glu Ala
        115                 120                 125

Arg Lys Lys Pro Val Glu Ile Lys Asp Met Phe Ile Asp Ile Gly Ala
    130                 135                 140

Thr Ser Arg Glu Glu Ala Met Glu Trp Gly Val Arg Pro Gly Asp Met
145                 150                 155                 160

Ile Val Pro Tyr Phe Glu Phe Thr Val Leu Asn Asn Glu Lys Met Leu
                165                 170                 175

Leu Ala Lys Ala Trp Asp Asn Arg Ile Gly Cys Ala Val Ala Ile Asp
            180                 185                 190

Val Leu Lys Gln Leu Lys Gly Val Asp His Pro Asn Thr Val Tyr Gly
        195                 200                 205

Val Gly Thr Val Gln Glu Glu Val Gly Leu Arg Gly Ala Arg Thr Ala
    210                 215                 220

Ala Gln Phe Ile Gln Pro Asp Ile Ala Phe Ala Val Asp Val Gly Ile
225                 230                 235                 240

Ala Gly Asp Thr Pro Gly Val Ser Glu Lys Glu Ala Met Gly Lys Leu
                245                 250                 255

Gly Ala Gly Pro His Ile Val Leu Tyr Asp Ala Thr Met Val Ser His
            260                 265                 270

Arg Gly Leu Arg Glu Phe Val Ile Glu Val Ala Glu Glu Leu Asn Ile
        275                 280                 285

Pro His His Phe Asp Ala Met Pro Gly Val Gly Thr Asp Ala Gly Ala
    290                 295                 300

Ile His Leu Thr Gly Ile Gly Val Pro Ser Leu Thr Ile Ala Ile Pro
305                 310                 315                 320

Thr Arg Tyr Ile His Ser His Ala Ala Ile Leu His Arg Asp Asp Tyr
                325                 330                 335

Glu Asn Thr Val Lys Leu Leu Val Glu Val Ile Lys Arg Leu Asp Ala
            340                 345                 350

Asp Lys Val Lys Gln Leu Thr Phe Asp Glu
        355                 360


<210> SEQ ID NO 19
<211> LENGTH: 490
<212> TYPE: PRT
<213> ORGANISM: Artificial Sequence
<220> FEATURE:
<223> OTHER INFORMATION: Synthetic

<400> SEQUENCE: 19

Met Glu Asp Lys Val Trp Ile Ser Met Gly Ala Asp Ala Val Gly Ser
1               5                   10                  15

Leu Asn Pro Ala Leu Ser Glu Ser Leu Leu Pro His Ser Phe Ala Ser
            20                  25                  30

Gly Ser Gln Val Trp Ile Gly Glu Val Ala Ile Asp Glu Leu Ala Glu
        35                  40                  45

Leu Ser His Thr Met His Glu Gln His Asn Arg Cys Gly Gly Tyr Met
    50                  55                  60

Val His Thr Ser Ala Gln Gly Ala Met Ala Ala Leu Met Met Pro Glu
65                  70                  75                  80
```

-continued

```
Ser Ile Ala Asn Phe Thr Ile Pro Ala Pro Ser Gln Gln Asp Leu Val
                85                  90                  95

Asn Ala Trp Leu Pro Gln Val Ser Ala Asp Gln Ile Thr Asn Thr Ile
            100                 105                 110

Arg Ala Leu Ser Ser Phe Asn Asn Arg Phe Tyr Thr Thr Thr Ser Gly
        115                 120                 125

Ala Gln Ala Ser Asp Trp Leu Ala Asn Glu Trp Arg Ser Leu Ile Ser
    130                 135                 140

Ser Leu Pro Gly Ser Arg Ile Glu Gln Ile Lys His Ser Gly Tyr Asn
145                 150                 155                 160

Gln Lys Ser Val Val Leu Thr Ile Gln Gly Ser Glu Lys Pro Asp Glu
                165                 170                 175

Trp Val Ile Val Gly Gly His Leu Asp Ser Thr Leu Gly Ser His Thr
            180                 185                 190

Asn Glu Gln Ser Ile Ala Pro Gly Ala Asp Asp Asp Ala Ser Gly Ile
        195                 200                 205

Ala Ser Leu Ser Glu Ile Ile Arg Val Leu Arg Asp Asn Asn Phe Arg
    210                 215                 220

Pro Lys Arg Ser Val Ala Leu Met Ala Tyr Ala Ala Glu Glu Val Gly
225                 230                 235                 240

Leu Arg Gly Ser Gln Asp Leu Ala Asn Gln Tyr Lys Ala Gln Gly Lys
                245                 250                 255

Lys Val Val Ser Val Leu Gln Leu Asp Met Thr Asn Tyr Arg Gly Ser
            260                 265                 270

Ala Glu Asp Ile Val Phe Ile Thr Asp Tyr Thr Asp Ser Asn Leu Thr
        275                 280                 285

Gln Phe Leu Thr Thr Leu Ile Asp Glu Tyr Leu Pro Glu Leu Thr Tyr
    290                 295                 300

Gly Tyr Asp Arg Cys Gly Tyr Ala Cys Ser Asp His Ala Ser Trp His
305                 310                 315                 320

Lys Ala Gly Phe Ser Ala Ala Met Pro Phe Glu Ser Lys Phe Lys Asp
                325                 330                 335

Tyr Asn Pro Lys Ile His Thr Ser Gln Asp Thr Leu Ala Asn Ser Asp
            340                 345                 350

Pro Thr Gly Asn His Ala Val Lys Phe Thr Lys Leu Gly Leu Ala Tyr
        355                 360                 365

Val Ile Glu Met Ala Asn Ala Gly Ser Ser Gln Val Pro Asp Asp Ser
    370                 375                 380

Val Leu Gln Asp Gly Thr Ala Lys Ile Asn Leu Ser Gly Ala Arg Gly
385                 390                 395                 400

Thr Gln Lys Arg Phe Thr Phe Glu Leu Ser Gln Ser Lys Pro Leu Thr
                405                 410                 415

Ile Gln Thr Tyr Gly Gly Ser Gly Asp Val Asp Leu Tyr Val Lys Tyr
            420                 425                 430

Gly Ser Ala Pro Ser Lys Ser Asn Trp Asp Cys Arg Pro Tyr Gln Asn
        435                 440                 445

Gly Asn Arg Glu Thr Cys Ser Phe Asn Asn Ala Gln Pro Gly Ile Tyr
    450                 455                 460

His Val Met Leu Asp Gly Tyr Thr Asn Tyr Asn Asp Val Ala Leu Lys
465                 470                 475                 480

Ala Ser Thr Gln His His His His His His
                485                 490
```

<210> SEQ ID NO 20
<211> LENGTH: 494
<212> TYPE: PRT
<213> ORGANISM: Artificial Sequence
<220> FEATURE:
<223> OTHER INFORMATION: Synthetic

<400> SEQUENCE: 20

```
Met Glu Asp Lys Val Trp Ile Ser Ile Gly Ser Asp Ala Ser Gln Thr
1               5                   10                  15

Val Lys Ser Val Met Gln Ser Asn Ala Arg Ser Leu Leu Pro Glu Ser
            20                  25                  30

Leu Ala Ser Asn Gly Pro Val Trp Val Gly Gln Val Asp Tyr Ser Gln
        35                  40                  45

Leu Ala Glu Leu Ser His His Met His Glu Asp His Gln Arg Cys Gly
    50                  55                  60

Gly Tyr Met Val His Ser Ser Pro Glu Ser Ala Ile Ala Ala Ser Asn
65                  70                  75                  80

Met Pro Gln Ser Leu Val Ala Phe Ser Ile Pro Glu Ile Ser Gln Gln
                85                  90                  95

Asp Thr Val Asn Ala Trp Leu Pro Gln Val Asn Ser Gln Ala Ile Thr
            100                 105                 110

Gly Thr Ile Thr Ser Leu Thr Ser Phe Ile Asn Arg Phe Tyr Thr Thr
        115                 120                 125

Thr Ser Gly Ala Gln Ala Ser Asp Trp Leu Ala Asn Glu Trp Arg Ser
    130                 135                 140

Leu Ser Ala Ser Leu Pro Asn Ala Ser Val Arg Gln Val Ser His Phe
145                 150                 155                 160

Gly Tyr Asn Gln Lys Ser Val Val Leu Thr Ile Thr Gly Ser Glu Lys
                165                 170                 175

Pro Asp Glu Trp Ile Val Leu Gly Gly His Leu Asp Ser Thr Ile Gly
            180                 185                 190

Ser His Thr Asn Glu Gln Ser Val Ala Pro Gly Ala Asp Asp Asp Ala
        195                 200                 205

Ser Gly Ile Ala Ser Val Thr Glu Ile Ile Arg Val Leu Ser Glu Asn
    210                 215                 220

Asn Phe Gln Pro Lys Arg Ser Ile Ala Phe Met Ala Tyr Ala Ala Glu
225                 230                 235                 240

Glu Val Gly Leu Arg Gly Ser Gln Asp Leu Ala Asn Gln Tyr Lys Ala
                245                 250                 255

Glu Gly Lys Gln Val Ile Ser Ala Leu Gln Leu Asp Met Thr Asn Tyr
            260                 265                 270

Lys Gly Ser Val Glu Asp Ile Val Phe Ile Thr Asp Tyr Thr Asp Ser
        275                 280                 285

Asn Leu Thr Thr Phe Leu Ser Gln Leu Val Asp Glu Tyr Leu Pro Ser
    290                 295                 300

Leu Thr Tyr Gly Phe Asp Thr Cys Gly Tyr Ala Cys Ser Asp His Ala
305                 310                 315                 320

Ser Trp His Lys Ala Gly Phe Ser Ala Ala Met Pro Phe Glu Ala Lys
                325                 330                 335

Phe Asn Asp Tyr Asn Pro Met Ile His Thr Pro Asn Asp Thr Leu Gln
            340                 345                 350

Asn Ser Asp Pro Thr Ala Ser His Ala Val Lys Phe Thr Lys Leu Gly
        355                 360                 365
```

-continued

```
Leu Ala Tyr Ala Ile Glu Met Ala Ser Thr Thr Gly Gly Thr Pro Pro
    370                 375                 380

Pro Thr Gly Asn Val Leu Lys Asp Gly Val Pro Val Asn Gly Leu Ser
385                 390                 395                 400

Gly Ala Thr Gly Ser Gln Val His Tyr Ser Phe Glu Leu Pro Ala Gln
                405                 410                 415

Lys Asn Leu Gln Ile Ser Thr Ala Gly Gly Ser Gly Asp Val Asp Leu
            420                 425                 430

Tyr Val Ser Phe Gly Ser Glu Ala Thr Lys Gln Asn Trp Asp Cys Arg
        435                 440                 445

Pro Tyr Arg Asn Gly Asn Asn Glu Val Cys Thr Phe Ala Gly Ala Thr
    450                 455                 460

Pro Gly Thr Tyr Ser Ile Met Leu Asp Gly Tyr Arg Gln Phe Ser Gly
465                 470                 475                 480

Val Thr Leu Lys Ala Ser Thr Gln His His His His His His
                485                 490


<210> SEQ ID NO 21
<211> LENGTH: 877
<212> TYPE: PRT
<213> ORGANISM: Artificial Sequence
<220> FEATURE:
<223> OTHER INFORMATION: Synthetic

<400> SEQUENCE: 21

Met Thr Gln Gln Pro Gln Ala Lys Tyr Arg His Asp Tyr Arg Ala Pro
1               5                   10                  15

Asp Tyr Thr Ile Thr Asp Ile Asp Leu Asp Phe Ala Leu Asp Ala Gln
            20                  25                  30

Lys Thr Thr Val Thr Ala Val Ser Lys Val Lys Arg Gln Gly Thr Asp
        35                  40                  45

Val Thr Pro Leu Ile Leu Asn Gly Glu Asp Leu Thr Leu Ile Ser Val
    50                  55                  60

Ser Val Asp Gly Gln Ala Trp Pro His Tyr Arg Gln Gln Asp Asn Thr
65                  70                  75                  80

Leu Val Ile Glu Gln Leu Pro Ala Asp Phe Thr Leu Thr Ile Val Asn
                85                  90                  95

Asp Ile His Pro Ala Thr Asn Ser Ala Leu Glu Gly Leu Tyr Leu Ser
            100                 105                 110

Gly Glu Ala Leu Cys Thr Gln Cys Glu Ala Glu Gly Phe Arg His Ile
        115                 120                 125

Thr Tyr Tyr Leu Asp Arg Pro Asp Val Leu Ala Arg Phe Thr Thr Arg
    130                 135                 140

Ile Val Ala Asp Lys Ser Arg Tyr Pro Tyr Leu Leu Ser Asn Gly Asn
145                 150                 155                 160

Arg Val Gly Gln Gly Glu Leu Asp Asp Gly Arg His Trp Val Lys Trp
                165                 170                 175

Glu Asp Pro Phe Pro Lys Pro Ser Tyr Leu Phe Ala Leu Val Ala Gly
            180                 185                 190

Asp Phe Asp Val Leu Gln Asp Lys Phe Ile Thr Arg Ser Gly Arg Glu
        195                 200                 205

Val Ala Leu Glu Ile Phe Val Asp Arg Gly Asn Leu Asp Arg Ala Asp
    210                 215                 220

Trp Ala Met Thr Ser Leu Lys Asn Ser Met Lys Trp Asp Glu Thr Arg
225                 230                 235                 240
```

-continued

```
Phe Gly Leu Glu Tyr Asp Leu Asp Ile Tyr Met Ile Val Ala Val Asp
                245                 250                 255

Phe Phe Asn Met Gly Ala Met Glu Asn Lys Gly Leu Asn Val Phe Asn
            260                 265                 270

Ser Lys Tyr Val Leu Ala Lys Ala Glu Thr Ala Thr Asp Lys Asp Tyr
        275                 280                 285

Leu Asn Ile Glu Ala Val Ile Gly His Glu Tyr Phe His Asn Trp Thr
    290                 295                 300

Gly Asn Arg Val Thr Cys Arg Asp Trp Phe Gln Leu Ser Leu Lys Glu
305                 310                 315                 320

Gly Leu Thr Val Phe Arg Asp Gln Glu Phe Ser Ser Asp Leu Gly Ser
                325                 330                 335

Arg Ser Val Asn Arg Ile Glu Asn Val Arg Val Met Arg Ala Ala Gln
            340                 345                 350

Phe Ala Glu Asp Ala Ser Pro Met Ala His Ala Ile Arg Pro Asp Lys
        355                 360                 365

Val Ile Glu Met Asn Asn Phe Tyr Thr Leu Thr Val Tyr Glu Lys Gly
    370                 375                 380

Ser Glu Val Ile Arg Met Met His Thr Leu Leu Gly Glu Gln Gln Phe
385                 390                 395                 400

Gln Ala Gly Met Arg Leu Tyr Phe Glu Arg His Asp Gly Ser Ala Ala
                405                 410                 415

Thr Cys Asp Asp Phe Val Gln Ala Met Glu Asp Val Ser Asn Val Asp
            420                 425                 430

Leu Ser Leu Phe Arg Arg Trp Tyr Ser Gln Ser Gly Thr Pro Leu Leu
        435                 440                 445

Thr Val His Asp Asp Tyr Asp Val Glu Lys Gln Gln Tyr His Leu Phe
    450                 455                 460

Val Ser Gln Lys Thr Leu Pro Thr Ala Asp Gln Pro Glu Lys Leu Pro
465                 470                 475                 480

Leu His Ile Pro Leu Asp Ile Glu Leu Tyr Asp Ser Lys Gly Asn Val
                485                 490                 495

Ile Pro Leu Gln His Asn Gly Leu Pro Val His His Val Leu Asn Val
            500                 505                 510

Thr Glu Ala Glu Gln Thr Phe Thr Phe Asp Asn Val Ala Gln Lys Pro
        515                 520                 525

Ile Pro Ser Leu Leu Arg Glu Phe Ser Ala Pro Val Lys Leu Asp Tyr
    530                 535                 540

Pro Tyr Ser Asp Gln Gln Leu Thr Phe Leu Met Gln His Ala Arg Asn
545                 550                 555                 560

Glu Phe Ser Arg Trp Asp Ala Ala Gln Ser Leu Leu Ala Thr Tyr Ile
                565                 570                 575

Lys Leu Asn Val Ala Lys Tyr Gln Gln Gln Gln Pro Leu Ser Leu Pro
            580                 585                 590

Ala His Val Ala Asp Ala Phe Arg Ala Ile Leu Leu Asp Glu His Leu
        595                 600                 605

Asp Pro Ala Leu Ala Ala Gln Ile Leu Thr Leu Pro Ser Glu Asn Glu
    610                 615                 620

Met Ala Glu Leu Phe Thr Thr Ile Asp Pro Gln Ala Ile Ser Thr Val
625                 630                 635                 640

His Glu Ala Ile Thr Arg Cys Leu Ala Gln Glu Leu Ser Asp Glu Leu
                645                 650                 655
```

```
Leu Ala Val Tyr Val Ala Asn Met Thr Pro Val Tyr Arg Ile Glu His
            660                 665                 670

Gly Asp Ile Ala Lys Arg Ala Leu Arg Asn Thr Cys Leu Asn Tyr Leu
        675                 680                 685

Ala Phe Gly Asp Glu Glu Phe Ala Asn Lys Leu Val Ser Leu Gln Tyr
    690                 695                 700

His Gln Ala Asp Asn Met Thr Asp Ser Leu Ala Ala Leu Ala Ala Ala
705                 710                 715                 720

Val Ala Ala Gln Leu Pro Cys Arg Asp Glu Leu Leu Ala Ala Phe Asp
                725                 730                 735

Val Arg Trp Asn His Asp Gly Leu Val Met Asp Lys Trp Phe Ala Leu
            740                 745                 750

Gln Ala Thr Ser Pro Ala Ala Asn Val Leu Val Gln Val Arg Thr Leu
        755                 760                 765

Leu Lys His Pro Ala Phe Ser Leu Ser Asn Pro Asn Arg Thr Arg Ser
    770                 775                 780

Leu Ile Gly Ser Phe Ala Ser Gly Asn Pro Ala Ala Phe His Ala Ala
785                 790                 795                 800

Asp Gly Ser Gly Tyr Gln Phe Leu Val Glu Ile Leu Ser Asp Leu Asn
                805                 810                 815

Thr Arg Asn Pro Gln Val Ala Ala Arg Leu Ile Glu Pro Leu Ile Arg
            820                 825                 830

Leu Lys Arg Tyr Asp Ala Gly Arg Gln Ala Leu Met Arg Lys Ala Leu
        835                 840                 845

Glu Gln Leu Lys Thr Leu Asp Asn Leu Ser Gly Asp Leu Tyr Glu Lys
    850                 855                 860

Ile Thr Lys Ala Leu Ala Ala His His His His His His
865                 870                 875


<210> SEQ ID NO 22
<211> LENGTH: 489
<212> TYPE: PRT
<213> ORGANISM: Artificial Sequence
<220> FEATURE:
<223> OTHER INFORMATION: Synthetic

<400> SEQUENCE: 22

Met Glu Glu Lys Val Trp Ile Ser Ile Gly Gly Asp Ala Thr Gln Thr
1               5                   10                  15

Ala Leu Arg Ser Gly Ala Gln Ser Leu Leu Pro Glu Asn Leu Ile Asn
            20                  25                  30

Gln Thr Ser Val Trp Val Gly Gln Val Pro Val Ser Glu Leu Ala Thr
        35                  40                  45

Leu Ser His Glu Met His Glu Asn His Gln Arg Cys Gly Gly Tyr Met
    50                  55                  60

Val His Pro Ser Ala Gln Ser Ala Met Ser Val Ser Ala Met Pro Leu
65                  70                  75                  80

Asn Leu Asn Ala Phe Ser Ala Pro Glu Ile Thr Gln Gln Thr Thr Val
                85                  90                  95

Asn Ala Trp Leu Pro Ser Val Ser Ala Gln Gln Ile Thr Ser Thr Ile
            100                 105                 110

Thr Thr Leu Thr Gln Phe Lys Asn Arg Phe Tyr Thr Thr Ser Thr Gly
        115                 120                 125

Ala Gln Ala Ser Asn Trp Ile Ala Asp His Trp Arg Ser Leu Ser Ala
    130                 135                 140
```

-continued

```
Ser Leu Pro Ala Ser Lys Val Glu Gln Ile Thr His Ser Gly Tyr Asn
145                 150                 155                 160

Gln Lys Ser Val Met Leu Thr Ile Thr Gly Ser Glu Lys Pro Asp Glu
                165                 170                 175

Trp Val Val Ile Gly Gly His Leu Asp Ser Thr Leu Gly Ser Arg Thr
            180                 185                 190

Asn Glu Ser Ser Ile Ala Pro Gly Ala Asp Asp Asp Ala Ser Gly Ile
        195                 200                 205

Ala Gly Val Thr Glu Ile Ile Arg Leu Leu Ser Glu Gln Asn Phe Arg
    210                 215                 220

Pro Lys Arg Ser Ile Ala Phe Met Ala Tyr Ala Ala Glu Glu Val Gly
225                 230                 235                 240

Leu Arg Gly Ser Gln Asp Leu Ala Asn Arg Phe Lys Ala Glu Gly Lys
                245                 250                 255

Lys Val Met Ser Val Met Gln Leu Asp Met Thr Asn Tyr Gln Gly Ser
            260                 265                 270

Arg Glu Asp Ile Val Phe Ile Thr Asp Tyr Thr Asp Ser Asn Phe Thr
        275                 280                 285

Gln Tyr Leu Thr Gln Leu Leu Asp Glu Tyr Leu Pro Ser Leu Thr Tyr
    290                 295                 300

Gly Phe Asp Thr Cys Gly Tyr Ala Cys Ser Asp His Ala Ser Trp His
305                 310                 315                 320

Ala Val Gly Tyr Pro Ala Ala Met Pro Phe Glu Ser Lys Phe Asn Asp
                325                 330                 335

Tyr Asn Pro Asn Ile His Ser Pro Gln Asp Thr Leu Gln Asn Ser Asp
            340                 345                 350

Pro Thr Gly Phe His Ala Val Lys Phe Thr Lys Leu Gly Leu Ala Tyr
        355                 360                 365

Val Val Glu Met Gly Asn Ala Ser Thr Pro Pro Thr Pro Ser Asn Gln
    370                 375                 380

Leu Lys Asn Gly Val Pro Val Asn Gly Leu Ser Ala Ser Arg Asn Ser
385                 390                 395                 400

Lys Thr Trp Tyr Gln Phe Glu Leu Gln Glu Ala Gly Asn Leu Ser Ile
                405                 410                 415

Val Leu Ser Gly Gly Ser Gly Asp Ala Asp Leu Tyr Val Lys Tyr Gln
            420                 425                 430

Thr Asp Ala Asp Leu Gln Gln Tyr Asp Cys Arg Pro Tyr Arg Ser Gly
        435                 440                 445

Asn Asn Glu Thr Cys Gln Phe Ser Asn Ala Gln Pro Gly Arg Tyr Ser
    450                 455                 460

Ile Leu Leu His Gly Tyr Asn Asn Tyr Ser Asn Ala Ser Leu Val Ala
465                 470                 475                 480

Asn Ala Gln His His His His His His
                485
```

<210> SEQ ID NO 23
<211> LENGTH: 488
<212> TYPE: PRT
<213> ORGANISM: Artificial Sequence
<220> FEATURE:
<223> OTHER INFORMATION: Synthetic

<400> SEQUENCE: 23

```
Met Glu Asp Lys Lys Val Trp Ile Ser Ile Gly Ala Asp Ala Gln Gln
1               5                   10                  15
```

```
Thr Ala Leu Ser Ser Gly Ala Gln Pro Leu Leu Ala Gln Ser Val Ala
            20                  25                  30

His Asn Gly Gln Ala Trp Ile Gly Glu Val Ser Glu Ser Glu Leu Ala
        35                  40                  45

Ala Leu Ser His Glu Met His Glu Asn His His Arg Cys Gly Gly Tyr
    50                  55                  60

Ile Val His Ser Ser Ala Gln Ser Ala Met Ala Ala Ser Asn Met Pro
65                  70                  75                  80

Leu Ser Arg Ala Ser Phe Ile Ala Pro Ala Ile Ser Gln Gln Ala Leu
                85                  90                  95

Val Thr Pro Trp Ile Ser Gln Ile Asp Ser Ala Leu Ile Val Asn Thr
            100                 105                 110

Ile Asp Arg Leu Thr Asp Phe Pro Asn Arg Phe Tyr Thr Thr Thr Ser
        115                 120                 125

Gly Ala Gln Ala Ser Asp Trp Ile Lys Gln Arg Trp Gln Ser Leu Ser
    130                 135                 140

Ala Gly Leu Ala Gly Ala Ser Val Thr Gln Ile Ser His Ser Gly Tyr
145                 150                 155                 160

Asn Gln Ala Ser Val Met Leu Thr Ile Glu Gly Ser Glu Ser Pro Asp
                165                 170                 175

Glu Trp Val Val Val Gly Gly His Leu Asp Ser Thr Ile Gly Ser Arg
            180                 185                 190

Thr Asn Glu Gln Ser Ile Ala Pro Gly Ala Asp Asp Asp Ala Ser Gly
        195                 200                 205

Ile Ala Ala Val Thr Glu Val Ile Arg Val Leu Ala Gln Asn Asn Phe
    210                 215                 220

Gln Pro Lys Arg Ser Ile Ala Phe Val Ala Tyr Ala Ala Glu Glu Val
225                 230                 235                 240

Gly Leu Arg Gly Ser Gln Asp Val Ala Asn Gln Phe Lys Gln Ala Gly
                245                 250                 255

Lys Asp Val Arg Gly Val Leu Gln Leu Asp Met Thr Asn Tyr Gln Gly
            260                 265                 270

Ser Ala Glu Asp Ile Val Phe Ile Thr Asp Tyr Thr Asp Asn Gln Leu
        275                 280                 285

Thr Gln Tyr Leu Thr Gln Leu Leu Asp Glu Tyr Leu Pro Thr Leu Asn
    290                 295                 300

Tyr Gly Phe Asp Thr Cys Gly Tyr Ala Cys Ser Asp His Ala Ser Trp
305                 310                 315                 320

His Gln Val Gly Tyr Pro Ala Ala Met Pro Phe Glu Ala Lys Phe Asn
                325                 330                 335

Asp Tyr Asn Pro Asn Ile His Thr Pro Gln Asp Thr Leu Ala Asn Ser
            340                 345                 350

Asp Ser Glu Gly Ala His Ala Ala Lys Phe Thr Lys Leu Gly Leu Ala
        355                 360                 365

Tyr Thr Val Glu Leu Ala Asn Ala Asp Ser Ser Pro Asn Pro Gly Asn
    370                 375                 380

Glu Leu Lys Leu Gly Glu Pro Ile Asn Gly Leu Ser Gly Ala Arg Gly
385                 390                 395                 400

Asn Glu Lys Tyr Phe Asn Tyr Arg Leu Asp Gln Ser Gly Glu Leu Val
                405                 410                 415
```

```
Ile Arg Thr Tyr Gly Gly Ser Gly Asp Val Asp Leu Tyr Val Lys Ala
            420                 425                 430

Asn Gly Asp Val Ser Thr Gly Asn Trp Asp Cys Arg Pro Tyr Arg Ser
        435                 440                 445

Gly Asn Asp Glu Val Cys Arg Phe Asp Asn Ala Thr Pro Gly Asn Tyr
    450                 455                 460

Ala Val Met Leu Arg Gly Tyr Arg Thr Tyr Asp Asn Val Ser Leu Ile
465                 470                 475                 480

Val Glu His His His His His His
                485


<210> SEQ ID NO 24
<211> LENGTH: 308
<212> TYPE: PRT
<213> ORGANISM: Artificial Sequence
<220> FEATURE:
<223> OTHER INFORMATION: Synthetic

<400> SEQUENCE: 24

Gly Met Pro Pro Ile Thr Gln Gln Ala Thr Val Thr Ala Trp Leu Pro
1               5                   10                  15

Gln Val Asp Ala Ser Gln Ile Thr Gly Thr Ile Ser Ser Leu Glu Ser
            20                  25                  30

Phe Thr Asn Arg Phe Tyr Thr Thr Thr Ser Gly Ala Gln Ala Ser Asp
        35                  40                  45

Trp Ile Ala Ser Glu Trp Gln Phe Leu Ser Ala Ser Leu Pro Asn Ala
    50                  55                  60

Ser Val Lys Gln Val Ser His Ser Gly Tyr Asn Gln Lys Ser Val Val
65                  70                  75                  80

Met Thr Ile Thr Gly Ser Glu Ala Pro Asp Glu Trp Ile Val Ile Gly
                85                  90                  95

Gly His Leu Asp Ser Thr Ile Gly Ser His Thr Asn Glu Gln Ser Val
            100                 105                 110

Ala Pro Gly Ala Asp Asp Asp Ala Ser Gly Ile Ala Ala Val Thr Glu
        115                 120                 125

Val Ile Arg Val Leu Ser Glu Asn Asn Phe Gln Pro Lys Arg Ser Ile
    130                 135                 140

Ala Phe Met Ala Tyr Ala Ala Glu Glu Val Gly Leu Arg Gly Ser Gln
145                 150                 155                 160

Asp Leu Ala Asn Gln Tyr Lys Ser Glu Gly Lys Asn Val Val Ser Ala
                165                 170                 175

Leu Gln Leu Asp Met Thr Asn Tyr Lys Gly Ser Ala Gln Asp Val Val
            180                 185                 190

Phe Ile Thr Asp Tyr Thr Asp Ser Asn Phe Thr Gln Tyr Leu Thr Gln
        195                 200                 205

Leu Met Asp Glu Tyr Leu Pro Ser Leu Thr Tyr Gly Phe Asp Thr Cys
    210                 215                 220

Gly Tyr Ala Cys Ser Asp His Ala Ser Trp His Asn Ala Gly Tyr Pro
225                 230                 235                 240

Ala Ala Met Pro Phe Glu Ser Lys Phe Asn Asp Tyr Asn Pro Arg Ile
                245                 250                 255

His Thr Thr Gln Asp Thr Leu Ala Asn Ser Asp Pro Thr Gly Ser His
            260                 265                 270

Ala Lys Lys Phe Thr Gln Leu Gly Leu Ala Tyr Ala Ile Glu Met Gly
        275                 280                 285
```

```
Ser Ala Thr Gly Asp Thr Pro Thr Pro Gly Asn Gln Leu Glu His His
    290                 295                 300

His His His His
305


<210> SEQ ID NO 25
<211> LENGTH: 354
<212> TYPE: PRT
<213> ORGANISM: Artificial Sequence
<220> FEATURE:
<223> OTHER INFORMATION: Synthetic

<400> SEQUENCE: 25

Met Val Asp Trp Glu Leu Met Lys Lys Ile Ile Glu Ser Pro Gly Val
1               5                   10                  15

Ser Gly Tyr Glu His Leu Gly Ile Arg Asp Leu Val Val Asp Ile Leu
            20                  25                  30

Lys Asp Val Ala Asp Glu Val Lys Ile Asp Lys Leu Gly Asn Val Ile
        35                  40                  45

Ala His Phe Lys Gly Ser Ala Pro Lys Val Met Val Ala Ala His Met
    50                  55                  60

Asp Lys Ile Gly Leu Met Val Asn His Ile Asp Lys Asp Gly Tyr Leu
65                  70                  75                  80

Arg Val Val Pro Ile Gly Gly Val Leu Pro Glu Thr Leu Ile Ala Gln
                85                  90                  95

Lys Ile Arg Phe Phe Thr Glu Lys Gly Glu Arg Tyr Gly Val Val Gly
            100                 105                 110

Val Leu Pro Pro His Leu Arg Arg Glu Ala Lys Asp Gln Gly Gly Lys
        115                 120                 125

Ile Asp Trp Asp Ser Ile Ile Val Asp Val Gly Ala Ser Ser Arg Glu
    130                 135                 140

Glu Ala Glu Glu Met Gly Phe Arg Ile Gly Thr Ile Gly Glu Phe Ala
145                 150                 155                 160

Pro Asn Phe Thr Arg Leu Ser Glu His Arg Phe Ala Thr Pro Tyr Leu
                165                 170                 175

Asp Asp Arg Ile Cys Leu Tyr Ala Met Ile Glu Ala Ala Arg Gln Leu
            180                 185                 190

Gly Glu His Glu Ala Asp Ile Tyr Ile Val Ala Ser Val Gln Glu Glu
        195                 200                 205

Ile Gly Leu Arg Gly Ala Arg Val Ala Ser Phe Ala Ile Asp Pro Glu
    210                 215                 220

Val Gly Ile Ala Met Asp Val Thr Phe Ala Lys Gln Pro Asn Asp Lys
225                 230                 235                 240

Gly Lys Ile Val Pro Glu Leu Gly Lys Gly Pro Val Met Asp Val Gly
                245                 250                 255

Pro Asn Ile Asn Pro Lys Leu Arg Gln Phe Ala Asp Glu Val Ala Lys
            260                 265                 270

Lys Tyr Glu Ile Pro Leu Gln Val Glu Pro Ser Pro Arg Pro Thr Gly
        275                 280                 285

Thr Asp Ala Asn Val Met Gln Ile Asn Arg Glu Gly Val Ala Thr Ala
    290                 295                 300

Val Leu Ser Ile Pro Ile Arg Tyr Met His Ser Gln Val Glu Leu Ala
305                 310                 315                 320

Asp Ala Arg Asp Val Asp Asn Thr Ile Lys Leu Ala Lys Ala Leu Leu
                325                 330                 335
```

Glu Glu Leu Lys Pro Met Asp Phe Thr Pro Leu Glu His His His His
340 345 350

His His

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Asp Tyr Arg Ala Gly Pro
1 5

<210> SEQ ID NO 27
<211> LENGTH: 6
<212> TYPE: PRT
<213> ORGANISM: Artificial Sequence
<220> FEATURE:
<223> OTHER INFORMATION: Synthetic

<400> SEQUENCE: 27

Leu Phe Trp Val Met Cys
1 5

<210> SEQ ID NO 28
<211> LENGTH: 7
<212> TYPE: PRT
<213> ORGANISM: Artificial Sequence
<220> FEATURE:
<223> OTHER INFORMATION: Synthetic

<400> SEQUENCE: 28

Arg Glu Pro Ile Leu Gln Asn
1 5

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Ile Leu Ser Thr Glu Pro
1 5

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Asp Ala Gly Met Cys Val
1 5

<210> SEQ ID NO 31
<211> LENGTH: 7
<212> TYPE: PRT
<213> ORGANISM: Artificial Sequence
<220> FEATURE:
<223> OTHER INFORMATION: Synthetic -continued

```
<400> SEQUENCE: 31

Ser Pro Ile Gln Arg Tyr Pro
1               5


<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

Gln Trp Cys Val Arg Glu
1               5


<210> SEQ ID NO 33
<211> LENGTH: 6
<212> TYPE: PRT
<213> ORGANISM: Artificial Sequence
<220> FEATURE:
<223> OTHER INFORMATION: Synthetic

<400> SEQUENCE: 33

Trp Val Asp Tyr Glu Arg
1               5
```